(12) United States Patent
Brown et al.

(10) Patent No.: US 7,687,526 B2
(45) Date of Patent: Mar. 30, 2010

(54) BENZO-FUSED COMPOUNDS FOR USE IN TREATING METABOLIC DISORDERS

(75) Inventors: Sean P. Brown, San Francisco, CA (US);
Paul Dransfield, San Francisco, CA (US); Jonathan B. Houze, San Mateo, CA (US); Jinqian Liu, Palo Alto, CA (US); Jiwen Liu, Foster City, CA (US); Zhihua Ma, San Mateo, CA (US); Julio C. Medina, San Carlos, CA (US); Vatee Pattaropong, Burlingame, CA (US); Michael J. Schmitt, Oakland, CA (US); Rajiv Sharma, Fremont, CA (US); Yingcai Wang, Fremont, CA (US)

(73) Assignee: Amgen Inc., Thousand Oaks, CA (US)

( * ) Notice: Subject to any disclaimer, the term of this patent is extended or adjusted under 35 U.S.C. 154(b) by 113 days.

(21) Appl. No.: 11/900,014

(22) Filed: Sep. 6, 2007

(65) Prior Publication Data

US 2008/0119511 A1    May 22, 2008

Related U.S. Application Data

(60) Provisional application No. 60/843,262, filed on Sep. 7, 2006.

(51) Int. Cl.
  *A61K 31/4192*    (2006.01)
  *A61K 31/192*    (2006.01)
  *C07D 249/04*    (2006.01)
  *C07C 59/13*    (2006.01)

(52) U.S. Cl. .................. 514/359; 514/569; 548/255; 562/490

(58) Field of Classification Search ................. 514/359, 514/569; 548/255; 562/490
See application file for complete search history.

(56) References Cited

U.S. PATENT DOCUMENTS

| | | | |
|---|---|---|---|
| 3,507,881 A | 4/1970 | Sandberg et al. | |
| 4,760,089 A | 7/1988 | Chambers et al. | |
| 6,037,367 A | 3/2000 | Christensen, IV et al. | |
| 6,506,757 B1 | 1/2003 | Tajima et al. | |
| 6,620,832 B2 | 9/2003 | Eastwood | |
| 6,645,939 B1 | 11/2003 | Durette et al. | |
| 6,710,063 B1 | 3/2004 | Chao et al. | |
| 6,723,740 B2 | 4/2004 | Chao et al. | |
| 6,875,780 B2 | 4/2005 | Auerbach et al. | |
| 6,939,875 B2 | 9/2005 | Auerbach et al. | |
| 6,964,983 B2 | 11/2005 | Auerbach et al. | |
| 7,338,960 B2 | 3/2008 | Bell et al. | |
| 7,345,068 B2 | 3/2008 | Endou et al. | |
| 2004/0058965 A1 | 3/2004 | Momose et al. | |
| 2005/0089866 A1 | 4/2005 | Hinuma et al. | |
| 2005/0119256 A1 | 6/2005 | Endo et al. | |
| 2006/0003344 A1 | 1/2006 | Houseknecht et al. | |
| 2006/0004012 A1 | 1/2006 | Akerman et al. | |
| 2006/0270724 A1 | 11/2006 | Houze et al. | |
| 2007/0066647 A1* | 3/2007 | Akerman et al. | ............ 514/310 |
| 2007/0244155 A1 | 10/2007 | Sharma et al. | |
| 2007/0265332 A1 | 11/2007 | Ge et al. | |
| 2008/0090840 A1 | 4/2008 | Beck et al. | |

FOREIGN PATENT DOCUMENTS

| | | |
|---|---|---|
| AU | A 27141/77 | 1/1979 |
| AU | A 52306/93 | 6/1994 |
| CA | 2111035 | 11/1994 |
| DE | 199 4 1 567 A1 | 4/2000 |
| EP | 0 250 264 | 12/1987 |
| EP | 0 414 289 | 2/1994 |
| EP | 1 357 115 A1 | 10/2003 |
| EP | 1 380 562 | 1/2004 |
| EP | 1 535 915 A1 | 6/2005 |
| EP | 1 559 422 A1 | 8/2005 |
| EP | 1 630 152 A1 | 3/2006 |
| JP | 10316641 | 2/1998 |
| JP | 2001242165 | 9/2001 |
| JP | 2002003368 | 1/2002 |
| WO | WO 93/23040 | 11/1993 |
| WO | WO 93/23041 | 11/1993 |
| WO | WO 95/01326 | 1/1995 |
| WO | WO 95/01348 | 1/1995 |
| WO | WO 97/12867 | 4/1997 |

(Continued)

OTHER PUBLICATIONS

Wu and Farrelly, Toxicology 236:1-6, 2007.*

(Continued)

*Primary Examiner*—Yong Chu
(74) *Attorney, Agent, or Firm*—Bernard Friedrichsen

(57) ABSTRACT

The present invention provides compounds useful, for example, for treating metabolic disorders in a subject. Such compounds have the general formula I:

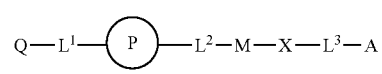

where the definitions of the variables

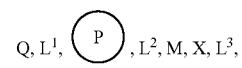

and A are provided herein. The present invention also provides compositions that include, and methods for using, the compounds in preparing medicaments and for treating metabolic disorders such as, for example, type II diabetes.

18 Claims, No Drawings

FOREIGN PATENT DOCUMENTS

| | | |
|---|---|---|
| WO | WO 99/11255 | 3/1999 |
| WO | WO 01/00603 | 1/2001 |
| WO | WO 01/36351 | 5/2001 |
| WO | WO 01/36365 | 5/2001 |
| WO | WO 02/057783 | 7/2002 |
| WO | WO 02/062774 | 8/2002 |
| WO | WO 00/63196 | 10/2002 |
| WO | WO 02/100403 | 12/2002 |
| WO | WO 03/074050 | 9/2003 |
| WO | WO 03/099793 | 12/2003 |
| WO | WO 2004/000315 | 12/2003 |
| WO | WO 2004/092117 | 10/2004 |
| WO | WO 2004/106276 | 12/2004 |
| WO | WO 2005/051890 | 6/2005 |
| WO | WO 2005/058848 | 6/2005 |
| WO | WO 2005/063725 | 7/2005 |
| WO | WO 2005/063729 | 7/2005 |
| WO | WO 2005/087710 | 9/2005 |
| WO | WO 2006/001092 | 1/2006 |
| WO | WO 2006/011615 | 2/2006 |
| WO | WO 2006/083612 | 8/2006 |
| WO | WO 2006/083781 | 8/2006 |
| WO | WO 2007/123225 | 11/2007 |
| WO | WO 2007/131619 | 11/2007 |
| WO | WO 2007/131620 | 11/2007 |
| WO | WO 2007/131622 | 11/2007 |

OTHER PUBLICATIONS

Vippagunta et al., Advanced Drug Delivery Reviews, p. 1.*
Preliminary STN search_1900014.*
Vippagunta et al., Advanced Drug Delivery Reviews, p. 3, 2001.*
Preliminary STN search_11900014, 2009.*
Bachmann, W. E. et al., "The Synthesis of an Analog of the Sex Hormones," *J. Am. Chem. Soc.*, 64, 94-97 (1942).
Berthelot et al., "Synthesis and Pharmacological Evaluation of γ-Aminobutyric Acid Analogues. New Ligand for GABA$_B$ Sites," *J. Med. Chem.*, 30, 743-746 (1987).
Boyle, Thomas F. et al., "Applications of the Spiroannulation of Tetralins with Alkynes; Towards New Anti-Estrogenic Compounds," *J. Chem. Soc. Perkin Trans. I: Organic and Bioorganic Chem.*, 18, 2707-2711 (1997).
Briscoe et al., "The Orphan G Protein-Coupled Receptor GPR40 is Activated by Medium and Long Chain Fatty Acids," *J. of Biol. Chem.*, 278(13), 11303-11311 (2003).
Briscoe, C. P. et al., "Pharmacological Regulation of Insulin Secretion in MIN6 Cells Through the Fatty Acid Receptor GPR40: Identification of Agonist and Antagonist Small Molecules," *Brit. J. of Pharmacology*, 148, 619-628 (2006).
Burnop, V.C.E. et al., "Fused Carbon Rings. Part XIX. Experiments on the Synthesis of Tetracyclic Compounds of the Sexual Hormonal Type," *J. Chem. Soc.*, 727-735 (1940).
Chatterjee, A., et al., "Studies on Nucleophilic Ring Opening of Some Epoxides in Polar Protic Solvents," *Tetrahedron*, 33, 85-94 (1977).
Ray, Chhanda et al., "Synthesis of some angularly cyclopentanone fused hydrophenanthrene and hydrofluorene derivatives by acid-catalyzed intramolecular C-alkylation of γ, δ-unsaturated α'-diazomethyl ketones," *Synthetic Commun.*, 21(10-11), 1223-1242 (1991).
Collins, David J. et al., "The Structure and Function of Oestrogens. IX*. Synthesis of the trans Isomer of 5,5,10b-Trimtehyl-4b,5,6,10b,11,12-hexahydrocvhrysene-2,8-diol," *Aust. J. Chem.*, 41, 735-744 (1988).
Deb, Soumitra et al., "A Stereocontrolled Synthesis of (1'RS,2'SR)-3-oxo-3',4'-dihydrospiro[cyclopentane-1,1'(2'H)-naphthalen]-2-yl Acetic Acid and its Methoxy Derivatives," *J. Chem. Res. Synops.*, 12, 406 (1985).

DeWolf et al., "Inactivation of Dopamine β-Hydroxylase by β-Ethynyltyramine: Kinetic Characterization and Covalent Modification of an Active Site Peptide," *Biochemistry*, 28, 3833-3842 (1989).
Egan, R. W. et al., "Naphthalenes as Inhibitors of Myeloperoxidase: Direct and Indirect Mechanisms of Inhibition," *Agents and Actions*, 29¾ 266-276 (1990).
Frey et al., "Total Synthesis of Pentacyclic Diterpenoid Tropone Hainanolidol," *Aust. J. Chemistry*, 53, 819-830 (2000).
Galemmo et al., "The Development of a Novel Series of (Quinolin-2-ylmethoxy) phenyl-Containing Compounds as High-Affinity Leukotriene Receptor Antagonists. 3. Structural Variation of the Acidic Side Chain to Give Antagonists of Enhanced Potency," *J. Med. Chem.*, 33, 2828-2841 (1990).
Garrido, D. M., et al., "Synthesis and Activity of Small Molecule GPR40 Agonists," *Bioorg. and Med. Chem. Lett.*, 16, 1840-1845 (2006).
Ghosal, Probir Kumar, et al., "Stereospecific Synthesis of 9bβ-Carbomethoxy-7-methoxy-2,3,3aα,4,5,9bβ-Hexahydro-1H-Benz[e]-Inden-2-one; An Intermediate Towards Physiologically Active Compounds," *Tet. Lett.*, 17, 1463-1464 (1977).
Guthrie, R. W. et al., "Synthesis in the Series of Diterpene Alkaloids VI. A Simple Synthesis of Atisine," *Tet. Lett.*, 38, 4645-4654 (1966).
Haigh et al., "Non-thiazolidinedione Antihyperglycaemic Agents. Part 3: The Effects of Stereochemistry on the Potency of α-Methoxy-β-phenylpropanoic Acids," *Bioorg. & Med. Chem.*, 7, 821-830 (1999).
Hares, Owen et al., "Sythetic Studies of Tricyclospirodienones: Model Chemistry for Novel Mimics of Steroid Substrates," *J. Chem. Soc. Perkin Trans. I: Organic and Bioorganic Chem.*, 13, 1481-1492 (1993).
Iizuka et al., "β-Substituted Phenethylamines as High Affinity Mechanism-Based Inhibitors of Dopamine β-Hydroxylase," *J. Med. Chem.*, 31, 704-706 (1988).
Ishikawa et al., "Actions of the Novel Oral Antidiabetic Agent HQL-975 in Insulin-Resistant Non-Insulin—Dependent Diabetes Mellitus Model Animals," *Diabetes Res. and Clin. Pract.*, 41, 101-111 (1998).
Ishikawa et al., "Effects of the Novel Oral Antidiabetic Agent HQL-975 on Glucose and Lipid Metabolism in Diabetic db/db Mice," *Arzneim. Forsch. Drug Res.*, 48(3), 245-250 (1998).
Itoh et al., "Free Fatty Acids Regulate Insulin Secretion from Pancreatic β Cells Through GPR40," *Nature*, 422, 173-176 (2003).
Johns, William F. et al., "Total Synthesis of Estrajervatetraene," *J. Org. Chem.*, 44(6), 958-961 (1979).
Kolasa et al., "Symmetrical Bis (heteroarylmethoxyphenyl) alkylcarboxylic Acids as Inhibitors of Leukotriene Biosynthesis," *J. Med. Chem.*, 43, 3322-3334 (2000).
Kotarsky et al., "A Human Cell Surface Receptor Activated by Free Fatty Acids and Thiazolidinedione Drugs", *Biochemical and Biophysical Research Communications*, 301, 406-410 (2003).
Kuchar et al., "Benzyloxyarylaliphatic Acids: Synthesis and Quantitative Relations Between Structure and Antiinflammatory Activity," *Collection Czechoslovak Chem, Commun.*, 47, 2514-2524 (1982).
Kuchar et al., "The Effects of Lopophilicity on the Inhibition of Denaturation of Serum Albumin and on the Activation of Fibrinolysis Observed with a Serixes of Benzyloxyarylaliphatic Acids," *Collection Czechoslovak Chem, Commun.*, 48, 1077-1088 (1983).
Lin, Llnus S. et al., "The Discovery of Acylated β-Amino Acids as Potent and Orally Bioavailable VLA-4 Antagonists," *Bioorganic and Medicinal Chem. Lett.*, 12, 611-614 (2002).
Liu et al., "Synthesis and Biological Activity of L-Tyrosine-based PPARγ Agonists with Reduced Molecular Weight," *Bioorg. & Med. Chem. Lett.*, 11, 3111-3113 (2001).
Nilsson, N. E. et al., "Identification of a Free Fatty Acid Receptor, FFA$_2$R, Expressed on Leukocytes and Activated by Short-Chain Fatty Acids," *Biochemical and Biophysical Research Communication*, 303 1047-1052 (2003).
Oliver et al., "A Selective Peroxisome Proliferator-Activated Receptor δ Agonist Promotes Reverse Cholesterol Transport," *PNAS*, 98(9), 5306-5311 (2001).

Poitout, Vincent, "The Ins and Outs of Fatty Acids on the Pancreatic β Cells," *Trends in Endocrinology and Metabolism*, 14(5), 201-203 (2003).

Sandberg, Rune et al., "N-Aminoalkylsuccinimides as Local Anaesthetics," *Acta Pharmaceutica Suecica*, 17(4) 169-176 (1980).

Sanyal, Utpal et al., "A Novel Synthesis of a Tricyclo $(7.5.0^{1,5}.0^{1,9})$ Tetradecane Ring System Related to Gascardic Acid," *Tet. Lett.*, 25, 2187-2190 (1978).

Sarma, Aluru Sudarsana et al., "Synthetic Studies on Terpenoids. Parts XVIII. Stereocontrolled Synthesis of (+/−)-1,2,3,4,4a,9,10,10aα-Octahydro-1α-methylenephenanthrene-1β,4aβ-dicarboxylic acid and the 7-Methoxy Analog: A Potential Intermediate for Diterpinoid Synthesis," *J. Chem. Soc. Perkin Trans. I: Organic and Bioorganic Chem.*, 7, 722-727 (1976).

Sawzdargo et al., "A Cluster of Four Novel Human G Protein-Coupled Receptor Genes Occurring in Close Proximity to CD22 Gene on Chromosome 19q13.1", *Biochemical and Biophysical Research Communications*, 239, 543-547 (1997).

Shaw et al., "Enantioselective Synthesis of (+)-(2S, 3S)-3-Ethyltyrosine," *Tetrahedron Letters*, 31(35), 5081-84 (1990).

Shiotani, Shunsaku et al., "Synthesis of 1,3-Bridged 1,2,3,4,5,6-Hexahydro-2,6-methano-3-benzazocine Derivatives," *Chem. Pharm. Bull.*, 28(6), 1928-1931 (1980).

Waid et al., "Constrained Amino Acids. An Approach to the Synthesis of 3-Substituted Prolines," *Tetrahedron Letters*, 37(24), 4091-4094 (1996).

Kao et al., "One-Pot Synthesis of the Hydroximoyl Chlorides and [3.3.0] Bicyclic Compounds from the Reactions of β-Nitrostyrenese with Stabilized Nucleophiles," *Tetrahedron*, 54(46), 13997-14014 (1998).

Booth, C. J. et al., "The Synthesis and Transition Temperatures of Novel Low Molar Mass Chosesteric materials Derives from (R)-2-(4-Hydroxyphenoxy)propanoic Acid," *Mol. Cryst. Liq. Cryst.*, vol. 210, pp. 31-57 (1992).

Booth, C. J. et al., "The Influence of the Liquid Crystalline Core Geometry on the Mesogenicity of Novel Chiral 2-(4-Substituted-phenoxy)propanonitriles," *Liquid Crystals*, vol. 16(6), pp. 925-940, (1994).

McKeown, S.C. et al., "Solid Phase Synthesis and SAR of Small Molecule Agonists for the GPR40 Receptor," *Bioorg. & Med. Chem. Lett.*, 17, pp. 1584-1589 (2007).

Song, F. et al., "Synthesis and Biological Evaluation of 3-Aryl-3-(4-phenoxy)-propionic Acid as a Novel Series of G Protein-Coupled REceptor 40 Agonists," *J. Med. Chem.* 50 pp. 2807-2817 (2007).

Houze, J. et al., "Beta-substituted Carboxylic Acids as Potent, Bioavailable Agonists of GPR40", 234th ACS National Meeting Boston, MA Aug. 19-23, 2007.

International Search Report and Written Opinion for Copending PCT/US2007/019662 (WO 2008/030618) mailed on Jan. 28, 2008.

* cited by examiner

BENZO-FUSED COMPOUNDS FOR USE IN TREATING METABOLIC DISORDERS

1. CROSS REFERENCES TO RELATED APPLICATIONS

This application claims the benefit of U.S. Provisional Application No. 60/843,262, filed on Sep. 7, 2006, which is hereby incorporated by reference in its entirety and for all purposes as if fully set forth herein.

2. FIELD OF THE INVENTION

The present invention relates to compounds capable of modulating the G-protein-coupled receptor GPR40, compositions comprising the compounds, and methods for their use for controlling insulin levels in vivo and for the treatment of conditions such as type II diabetes, hypertension, ketoacidosis, obesity, glucose intolerance, and hypercholesterolemia and related disorders associated with abnormally high or low plasma lipoprotein, triglyceride or glucose levels.

3. BACKGROUND OF THE INVENTION

The production of insulin is central to the regulation of carbohydrate and lipid metabolism. Insulin imbalances lead to conditions such as type II diabetes mellitus, a serious metabolic disease that afflicts around 5% of the population in Western Societies and over 150 million people worldwide. Insulin is secreted from pancreatic β cells in response to elevated plasma glucose which is augmented by the presence of fatty acids. The recent recognition of the function of the G-protein coupled receptor GPR40 in modulating insulin secretion has provided insight into regulation of carbohydrate and lipid metabolism in vertebrates, and further provided targets for the development of therapeutic agents for disorders such as obesity, diabetes, cardiovascular disease and dyslipidemia.

GPR40 is a member of the gene superfamily of G-protein coupled receptors ("GPCRs"). GPCRs are membrane proteins characterized as having seven putative transmembrane domains that respond to a variety of molecules by activating intra-cellular signaling pathways critical to a diversity of physiological functions. GPR40 was first identified as an orphan receptor (i.e., a receptor without a known ligand) from a human genomic DNA fragment. Sawzdargo et al. (1997) *Biochem. Biophys. Res. Commun.* 239: 543-547. GPR40 is highly expressed in pancreatic β cells and insulin-secreting cell lines. GPR40 activation is linked to modulation of the $G_q$ family of intra-cellular signaling proteins and concomitant induction of elevated calcium levels. It has been recognized that fatty acids serve as ligands for GPR40, and that fatty acids regulate insulin secretion through GPR40. Itoh et al. (2003) *Nature* 422:173-176; Briscoe et al. (2003) *J. Biol. Chem.* 278:11303-11311; Kotarsky et al. (2003) *Biochem. Biophys. Res. Commun.* 301: 406-410.

Various documents have disclosed compounds reportedly having activity with respect to GPR40. For example, WO 2004/041266 and EP 1559422 disclose compounds that purportedly act as GPR40 receptor function regulators. WO 2004/106276 and EP 1630152 are directed to condensed ring compounds that purportedly possess GPR40 receptor function modulating action. More recently, WO 2005/086661, U.S. Patent Publication No. 2006/0004012, US Patent Publication No. 2006/0270724, and US Patent Publication No. 2007/0066647 disclose compounds useful for modulating insulin levels in subjects and useful for treating type II diabetes.

Although a number of compounds have been disclosed that reportedly modulate GPR40 activity, the prevalence of type II diabetes, obesity, hypertension, cardiovascular disease and dyslipidemia underscores the need for new therapies to effectively treat or prevent these conditions.

4. SUMMARY OF THE INVENTION

Provided herein are compounds, pharmaceutical compositions and methods useful for treating or preventing a condition or disorder such as type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer or edema.

In one aspect, the present invention provides a compound having the formula I or a pharmaceutically acceptable salt, solvate, stereoisomer, or prodrug thereof; or a tautomer or a pharmaceutically acceptable salt, solvate, stereoisomer, or prodrug thereof; or a mixture thereof:

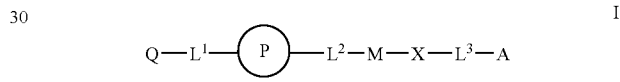

where Q, $L^1$, P, $L^2$, M, X, $L^3$, and A are defined below.

Q is hydrogen, aryl, heteroaryl, ($C_1$-$C_6$)alkyl, or ($C_2$-$C_6$)heteroalkyl.

In certain embodiments, Q is hydrogen, aryl, or heteroaryl.

In certain embodiments, Q is a substituted or unsubstituted phenyl.

$L^1$ is a bond, ($C_1$-$C_4$)alkylene, ($C_2$-$C_4$)heteroalkylene, O, S(O)$_k$, N(R$^a$), C(O)—($C_5$-$C_7$)heterocycloalkylene, ($C_1$-$C_4$)alkylene-SO$_2$N(R$^b$), ($C_1$-$C_4$)alkylene-N(R$^b$)SO$_2$, or C(O)N (R$^b$).

In certain embodiments, $L^1$ is a bond. In some such embodiments, Q is H.

represents an optionally substituted benzo-fused ($C_5$-$C_8$)cycloalkane ring comprising a benzene ring fused to a ($C_5$-$C_8$) cycloalkane ring, an optionally substituted heterobenzo-fused ($C_5$-$C_8$)cycloalkane ring comprising a six-membered heteroaryl ring comprising 1 or 2 N atoms fused to a ($C_5$-$C_8$) cycloalkane ring, or a heteroaryl-fused ($C_5$-$C_8$)cycloalkane ring comprises a five-membered heteroaryl ring comprising 1 or 2 heteroatoms fused to a ($C_5$-$C_8$)cycloalkane ring, wherein the benzene ring of the benzo-fused ($C_5$-$C_8$)cycloalkane ring, the heteroaryl ring of the heterobenzo-fused ($C_5$-$C_8$)cycloalkane ring, or the heteroaryl ring of the heteroaryl-fused ($C_5$-

$C_8$)cycloalkane ring is bonded to $L^2$ or M, if $L^2$ is a bond. In some embodiments, (P)

is a benzo-fused $(C_5$-$C_8)$cycloalkane ring. In some embodiments, (P)

is a substituted benzo-fused $(C_5$-$C_8)$cycloalkane ring. In some embodiments, (P)

is an unsubstituted benzo-fused $(C_5$-$C_8)$cycloalkane ring. In some embodiments, (P)

is a heterobenzo-fused $(C_5$-$C_8)$cycloalkane ring. In some such embodiments, the heteroaryl ring of the heterobenzo-fused $(C_5$-$C_8)$cycloalkane ring comprises 1 N atom. In other such embodiments, the heteroaryl ring of the heterobenzo-fused $(C_5$-$C_8)$cycloalkane ring comprises 2 N atoms. In some embodiments, (P)

is a substituted heterobenzo-fused $(C_5$-$C_8)$cycloalkane ring. In some embodiments, (P)

is an unsubstituted heterobenzo-fused $(C_5$-$C_8)$cycloalkane ring. In some embodiments, (P)

is a heteroaryl-fused $(C_5$-$C_8)$cycloalkane ring. In some such embodiments, the heteroaryl ring of the heteroaryl-fused $(C_5$-$C_8)$cycloalkane ring comprises 1 N atom. In some embodiment the heteroaryl ring of the heteroaryl-fused $(C_5$-$C_8)$cycloalkane ring comprises 1 N atom and either 1 O atom or 1 S atom. In other such embodiments, the heteroaryl ring of the heteroaryl-fused $(C_5$-$C_8)$cycloalkane ring comprises 2 N atoms. In some embodiments, (P)

is a substituted heteroaryl-fused $(C_5$-$C_8)$cycloalkane ring. In some embodiments, (P)

is an unsubstituted heteroaryl-fused $(C_5$-$C_8)$cycloalkane ring. In some embodiments, the $(C_5$-$C_8)$cycloalkane ring of the benzo-fused $(C_5$-$C_8)$cycloalkane ring, the heterobenzo-fused $(C_5$-$C_8)$cycloalkane ring, or the heteroaryl-fused $(C_5$-$C_8)$cycloalkane ring of (P)

comprises 0-3 heteroatoms selected from O, N, or S. In some such embodiments, the cycloalkane ring comprises 1 or 2 heteroatom ring members selected from O or N, and in some embodiments 1 heteroatom ring member, selected from O or N. In some such embodiments, the cycloalkane comprises 0 heteroatom ring atoms such that each of the cycloalkane ring members of the benzo-fused $(C_5$-$C_8)$cycloalkane, the heterobenzo-fused $(C_5$-$C_8)$cycloalkane, or the heteroaryl-fused $(C_5$-$C_8)$cycloalkane ring is a carbon atom. In some such embodiments, (P)

is selected from the group consisting of dihydroindene (i.e., indane or a benzo-cyclopentyl ring), tetrahydronaphthalene (i.e., a benzo-cyclohexyl ring), tetrahydrobenzo[7]annulene (i.e., a benzo-cycloheptyl ring), and hexahydrobenzo[8]annulene (i.e., a benzo-cyclooctyl ring). In some embodiments, (P)

is a heteroaryl-fused $(C_5$-$C_8)$cycloalkane ring and the heteroaryl of the heteroaryl-fused $(C_5$-$C_8)$cycloalkane ring is selected from pyrrole, furan, thiophene, imidazole, thiazole, or oxazole.

$L^2$ is a bond, $(C_1$-$C_6)$alkylene, $(C_2$-$C_6)$heteroalkylene, oxymethylene, O, $S(O)_k$, $N(R^a)$, $C(O)N(R^b)$, $SO_2N(R^b)$, $(C_1$-$C_4)$alkylene-$C(O)N(R^b)$, $(C_1$-$C_4)$alkylene-$N(R^b)C(O)$, $(C_2$-$C_4)$alkenylene-$C(O)N(R^b)$, $(C_2$-$C_4)$alkenylene-$N(R^b)C(O)$, $(C_1$-$C_4)$alkylene-$SO_2N(R^b)$, $(C_2$-$C_4)$alkenylene-$N(R^b)SO_2$, $(C_2$-$C_4)$alkenylene-$SO_2N(R^b)$, or $(C_2$-$C_4)$alkenylene-$N(R^b)SO_2$. In some embodiments, $L^2$ is selected from $(C_1$-$C_6)$alkylene, $(C_2$-$C_6)$heteroalkylene, oxymethylene, O, or $S(O)_k$. In some embodiments, $L^2$ is selected from —$CH_2$—, substituted oxymethylene, or O. In some embodiments, $L^2$ is selected from —$CH_2$—O— or —$CH(CH_3)$—O—. In some embodiments, $L^2$ is selected from —$CH_2$—O— or an alkyl-substituted oxymethylene. In certain embodiments, $L^2$ is O or $S(O)_k$.

M is an aromatic ring, a heteroaromatic ring, ($C_5$-$C_8$)cycloalkylene, aryl($C_1$-$C_4$)alkylene or heteroaryl($C_1$-$C_4$)alkylene. In certain embodiments where M is an aromatic ring, the term aromatic includes aryl. In other embodiments where M is a heteroaromatic ring, the term heteroaromatic includes heteroaryl. In some embodiments, M is an aromatic ring or is a heteroaromatic ring. In certain embodiments, M is a monocyclic aromatic or is a monocyclic heteroaromatic ring. In some embodiments, M is an unsubstituted monocyclic aromatic ring or is an unsubstituted monocyclic heteroaromatic ring. In certain embodiments, M is a substituted benzene ring. In other embodiments, M is an unsubstituted benzene ring. In some embodiments, M is a heteroaromatic ring comprising six ring members. In some such embodiments, the heteroaromatic ring comprises 1 or 2 N atoms. In some such embodiments, the heteroaromatic ring comprises 1 N atom, and in other such embodiments, the heteroaromatic ring comprises 2 N atoms.

X is $CR^1R^{1'}$, $N(R^{1''})$, O, or $S(O)_k$, where the subscript k is 0, 1, or 2. In some embodiments X is a $CR^1R^{1'}$.

In certain embodiments, M is a substituted or unsubstituted benzene ring and X is para to $L^2$.

$L^3$ is a ($C_1$-$C_5$)alkylene, or ($C_2$-$C_5$)heteroalkylene. In some embodiments, $L^3$ is a ($C_1$-$C_5$)alkylene or is a ($C_2$-$C_5$)heteroalkylene. In certain embodiments, $L^3$ is ($C_1$-$C_3$)alkylene. In some embodiments, $L^3$ is methylene. In certain embodiments, $L^3$ is a methylene substituted with a monocyclic aryl or monocyclic heteroaryl.

A is —$CO_2H$, tetrazol-5-yl, —$SO_3H$, —$PO_3H_2$, —$SO_2NH_2$, —$C(O)NHSO_2CH_3$, —CHO, thiazolidinedionyl, hydroxyphenyl, or pyridyl. In some embodiments, A is —$CO_2H$, tetrazol-5-yl, —$SO_3H$, —$PO_3H_2$, —$SO_2NH_2$, —$C(O)NHSO_2CH_3$, thiazolidinedionyl, hydroxyphenyl, or pyridyl. In certain embodiments, A is —$CO_2H$ or a salt thereof. In some embodiments, A is —$CO_2H$ or an alkyl ester thereof. In some embodiments, A is a $C_1$-$C_6$ alkyl ester such as a methyl, ethyl, propyl, butyl, pentyl, or hexyl ester.

$R^a$ is hydrogen, ($C_1$-$C_6$)alkyl, aryl($C_1$-$C_3$)alkyl, or ($C_2$-$C_6$)heteroalkyl. In certain embodiments, $R^a$ is ($C_1$-$C_6$)alkyl or ($C_2$-$C_6$)heteroalkyl.

$R^b$ is hydrogen, ($C_1$-$C_6$)alkyl, or ($C_2$-$C_6$)heteroalkyl.

$R^1$ is cyano, aryl, heteroaryl, a heterocycloalkyl, ($C_2$-$C_8$)alkenyl, ($C_3$-$C_8$)alkenyl, ($C_2$-$C_8$)alkynyl, ($C_3$-$C_8$)alkynyl, or —$C(O)NR^2R^3$. In any of the embodiments described herein, the heterocycle of the heterocycloalkyl $R^1$ group may be a saturated or unsaturated heterocycle comprising from 5-7 ring members of which from 1-4 are heteroatoms selected from O, S, or N with the balance of the ring members being C. In some embodiments, $R^1$ is a group other than a group of the following formula:

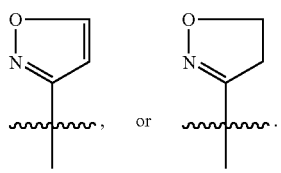

In certain embodiments, $R^1$ is selected from ($C_2$-$C_8$)alkynyl, aryl, heteroaryl, heterocycloalkyl, or —$C(O)NR^2R^3$. In some embodiments, $R^1$ is selected from aryl, heteroaryl, heterocycloalkyl, ($C_2$-$C_8$)alkenyl, ($C_3$-$C_8$)alkenyl, ($C_2$-$C_8$)alkynyl, or ($C_3$-$C_8$)alkynyl. In other embodiments, $R^1$ is selected from $R^1$ is selected from heteroaryl or heterocycloalkyl. In some such embodiments, $R^1$ is selected from a substituted or unsubstituted imidazolyl, triazolyl, tetrazolyl, oxazolyl, isoxazolyl, dihydroisoxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; isoxazol-3-yl; pyrimidin-5-yl; tetrazol-5-yl; oxazol-2-yl; or dihydroisoxazol-3-yl. In some such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; isoxazol-3-yl; pyrimidin-5-yl; 1-methyl-1H-tetrazol-5-yl; oxazol-2-yl; or 4,5-dihydroisoxazol-3-yl. In certain embodiments, $R^1$ is selected from the group consisting of prop-1-ynyl, phenyl, or a substituted or unsubstituted imidazolyl, triazolyl, tetrazolyl, oxazolyl, isoxazolyl, dihydroisoxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; pyrimidin-5-yl; tetrazol-5-yl; or oxazol-2-yl. In some such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; pyrimidin-5-yl; 1-methyl-1H-tetrazol-5-yl; or oxazol-2-yl. In certain embodiments, $R^1$ is selected from the group consisting of prop-1-ynyl, phenyl, or a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl.

$R^{1'}$ is hydrogen, cyano, aryl, heteroaryl, ($C_1$-$C_8$)alkyl, ($C_2$-$C_8$)alkenyl, or ($C_2$-$C_8$)alkynyl. In some embodiments, $R^{1'}$ is hydrogen or methyl. In some such embodiments, $R^{1'}$ is hydrogen.

$R^{1''}$ is hydrogen, aryl, heteroaryl, ($C_1$-$C_8$)alkyl, ($C_2$-$C_8$) alkenyl, ($C_2$-$C_8$)alkynyl, or ($C_3$-$C_8$)cycloalkyl.

$R^2$ and $R^3$ are independently selected from hydrogen, aryl, heteroaryl, ($C_1$-$C_8$)alkyl, ($C_2$-$C_8$)heteroalkyl, ($C_3$-$C_8$)cycloalkyl, or ($C_3$-$C_8$)heterocycloalkyl. Optionally, $R^2$ and $R^3$ are combined to form a 4-, 5-, 6- or 7-membered ring containing the nitrogen atom to which they are attached comprising from 0 to 2 additional heteroatoms selected from N, O, or S. The ring formed by combining $R^2$ and $R^3$ may be a saturated, unsaturated, or aromatic ring.

The subscript k is, in each instance, independently selected from 0, 1, or 2. In some embodiments, k is 0.

In certain embodiments, the compound of the present invention is a pharmaceutically acceptable salt, solvate, stereoisomer, or prodrug of the compound of formula I; or a tautomer, or a pharmaceutically acceptable salt, solvate, stereoisomer, or prodrug of the tautomer; or a mixture thereof.

In certain embodiments, the present invention provides a compound having the formula II or a pharmaceutically acceptable salt, solvate, stereoisomer, or prodrug thereof; or a tautomer, or a pharmaceutically acceptable salt, solvate, stereoisomer, or prodrug thereof; or a mixture thereof:

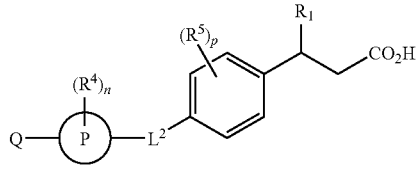

II where Q is selected from hydrogen, aryl, or heteroaryl; $L^2$ is selected from $(C_1-C_6)$alkylene, $(C_2-C_6)$heteroalkylene, oxymethylene, O, or $S(O)_k$; $R^1$ is selected from $(C_2-C_8)$alkynyl, aryl, heteroaryl, heterocycloalkyl, or —C(O)NR$^2$R$^3$; $R^2$ and $R^3$ are independently selected from hydrogen or $(C_1-C_4)$alkyl; $R^4$ is independently selected from substituted $(C_1-C_6)$alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R''', —NR'—SO$_2$NR"R''', —NR"CO$_2$R', —NH—C(NH$_2$)=NH, —NR'C(NH$_2$)=NH, —NH—C(NH$_2$)=NR', —SiR'R" R''', —S(O)R', —SO$_2$R', —SO$_2$NR'R", —NR" SO$_2$R, —CN, —(C$_2$-C$_5$)alkynyl, —(C$_2$-C$_5$)alkenyl, or —NO$_2$, where R', R" and R''' each independently refer to hydrogen, unsubstituted $(C_1-C_8)$alkyl or heteroalkyl, unsubstituted aryl, aryl substituted with one to three halogens, unsubstituted alkyl, alkoxy or thioalkoxy groups, halo$(C_1-C_4)$alkyl, or aryl-$(C_1-C_4)$alkyl groups; $R^5$ is independently selected from $(C_1-C_6)$alkyl, halogen, $(C_1-C_6)$alkoxy, cyano, or nitro; the subscript k is 0, 1 or 2; the subscript n is 0, 1, 2, 3, 4, 5, 6, 7, 8, 9, 10, 11, 12, 13, or 14; and the subscript p is 0, 1, 2, 3, or 4. In some such embodiments, $R^4$ is independently selected from $(C_1-C_6)$alkyl, halogen, $(C_1-C_6)$alkoxy, cyano, or nitro. In certain embodiments,

is a benzo-fused $(C_5-C_8)$cycloalkane ring selected from substituted or unsubstituted dihydroindene, tetrahydronaphthalene, tetrahydrobenzo[7]annulene, or hexahydrobenzo[8]annulene. In certain embodiments, $R^1$ is selected from 1-propynyl, substituted or unsubstituted phenyl, heteroaryl, or heterocycloalkyl. In some such embodiments, $R^1$ is selected from substituted or unsubstituted heteroaryl, or heterocycloalkyl. In some such embodiments, $R^1$ is selected from a substituted or unsubstituted imidazolyl, triazolyl, tetrazolyl, oxazolyl, isoxazolyl, dihydroisoxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; isoxazol-3-yl; pyrimidin-5-yl; tetrazol-5-yl; oxazol-2-yl; or dihydroisoxazol-3-yl. In some such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; isoxazol-3-yl; pyrimidin-5-yl; 1-methyl-1H-tetrazol-5-yl; oxazol-2-yl; or 4,5-dihydroisoxazol-3-yl. In certain embodiments, the subscript p is 0. In some such embodiments, $R^1$ is selected from a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; pyrimidin-5-yl; tetrazol-5-yl; or oxazol-2-yl. In some such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; pyrimidin-5-yl; 1-methyl-1H-tetrazol-5-yl; or oxazol-2-yl.

It will be apparent that, in certain embodiments of formula II, the carbon with a bond to $R^1$ is a chiral carbon. Thus, in certain embodiments, the present invention provides a compound having formula IIIA or IIIB or a pharmaceutically acceptable salt, solvate, or prodrug thereof; or a tautomer, or a pharmaceutically acceptable salt, solvate, or prodrug thereof; or a mixture thereof:

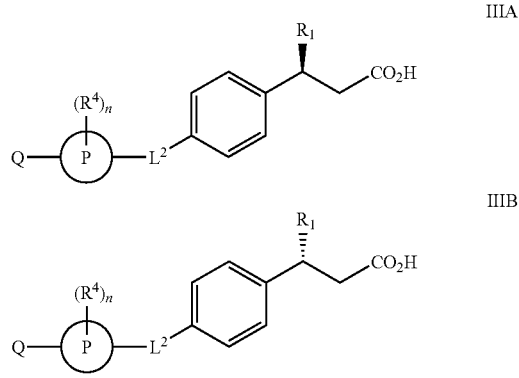

where the variables can have any of the values in any of the embodiments described above.

In some embodiments, the compound of formula II comprises a stereomerically pure S-enantiomer. In other embodiments, the compound of formula II comprises a stereomerically pure R-enantiomer. In yet other embodiments, the compound of formula II comprises a mixture of S- and R-enantiomers.

In certain embodiments, the compound of the present invention is a pharmaceutically acceptable salt, solvate, stereoisomer, or prodrug of the compound of formula II; or a tautomer, or a pharmaceutically acceptable salt, solvate, stereoisomer, or prodrug thereof; or a mixture thereof.

In some embodiments of formula II, IIIA, and IIIB, the hydrogen on the carboxylic group in formula II is replaced with an alkyl group to form an ester. For example, the compound of the present invention can be a methyl or ethyl ester of the compound of formula II.

In certain embodiments of the compound of formula I, the compound has the formula IV or is a pharmaceutically acceptable salt, solvate, stereoisomer, or prodrug thereof; or a tautomer, or a pharmaceutically acceptable salt, solvate, stereoisomer, or prodrug thereof; or a mixture thereof:

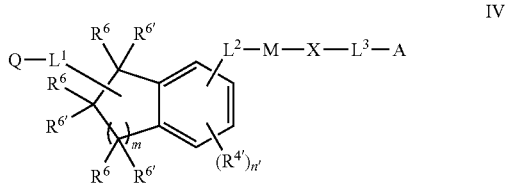

IV where $R^{4'}$ is independently selected from substituted $(C_1-C_6)$alkyl, —R', —OR', =O, =NR', =N—OR', —NR'R", —SR', halogen, —OC(O)R', —C(O)R', —CO$_2$R', —CONR'R'', —OC(O)NR'R'', —NR''C(O)R', —NR'—C(O)NR''R''', —NR'—SO$_2$NR''R''', —NR''CO$_2$R', —NH—C(NH$_2$)=NH, —NR'C(NH$_2$)=NH, —NH—C(NH$_2$)=NR', —SiR'R''R''', —S(O)R', —SO$_2$R', —SO$_2$NR'R'', —NR''SO$_2$R, —CN, —(C$_2$-C$_5$)alkynyl, —(C$_2$-C$_5$)alkenyl, or —NO$_2$, where R', R'' and R''' each independently refer to hydrogen, unsubstituted (C$_1$-C$_8$)alkyl or heteroalkyl, unsubstituted aryl, aryl substituted with one to three halogens, unsubstituted alkyl, alkoxy or thioalkoxy groups, halo(C$_1$-C$_4$)alkyl, or aryl-(C$_1$-C$_4$)alkyl groups; one of R$^6$ and R$^{6'}$ is L$^1$ or Q, if L$^1$ is a bond, and the others of R$^6$ and R$^{6'}$ are independently selected from H, (C$_1$-C$_6$)alkyl, halogen, (C$_1$-C$_6$) alkoxy, cyano, or nitro, or one of R$^6$ and one of R$^{6'}$ on adjacent or non-adjacent carbon atoms, or on the same carbon atom, may join together to form a C$_5$-C$_8$ cycloalkane ring, or two of R$^6$ or two of R$^{6'}$, on adjacent or non-adjacent carbon atoms, may join together to form a C$_5$-C$_8$ cycloalkane ring; the subscript n' is 0, 1, 2, or 3; and the subscript m is 1, 2, 3, or 4.

In some embodiments, the compound of formula IV comprises a stereomerically pure S-enantiomer. In other embodiments, the compound of formula IV comprises a stereomerically pure R-enantiomer. In yet other embodiments, the compound of formula IV comprises a mixture of S- and R-enantiomers.

In some embodiments, the compound of formula IV has the formula V:

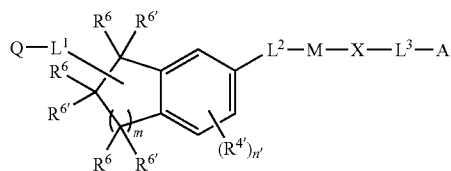

V or is a pharmaceutically acceptable salt, solvate, stereoisomer or prodrug thereof; or a tautomer, or a pharmaceutically acceptable salt, solvate, stereoisomer, or prodrug thereof; or a mixture thereof.

In some embodiments, the compound of formula IV or V, the compound has the formula VI:

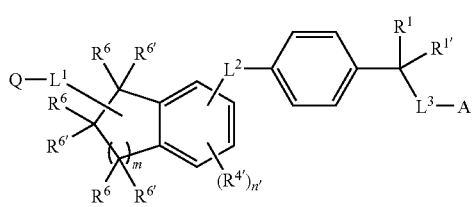

VI or is a pharmaceutically acceptable salt, solvate, stereoisomer or prodrug thereof; or a tautomer, or a pharmaceutically acceptable salt, solvate, stereoisomer, or prodrug thereof; or a mixture thereof.

It will be apparent that, in certain embodiments of formula VI, the carbon with a bond to R$^1$ is a chiral carbon. Thus, in certain embodiments, the present invention provides a compound having formula VIA or VIB or a pharmaceutically acceptable salt, solvate, or prodrug thereof or a tautomer, or a pharmaceutically acceptable salt, solvate, or prodrug thereof; or a mixture thereof:

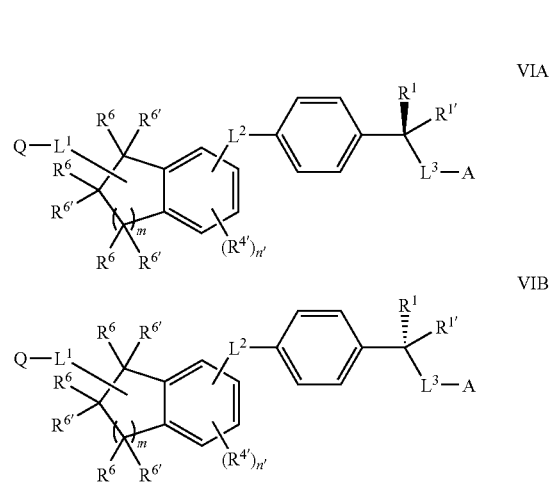

where the variables can have any of the values in any of the embodiments described above.

In some embodiments, the compound of formula VI comprises a stereomerically pure S-enantiomer. In other embodiments, the compound of formula VI comprises a stereomerically pure R-enantiomer. In yet other embodiments, the compound of formula VI comprises a mixture of S- and R-enantiomers.

In certain embodiments, the compound of the present invention is a pharmaceutically acceptable salt, solvate, stereoisomer, or prodrug of the compound of formula II; or a tautomer, or a pharmaceutically acceptable salt, solvate, stereoisomer, or prodrug thereof; or a mixture thereof.

In some embodiments of formula IV, V, VI, VIA, and VIB, A is —CO$_2$H or is a salt thereof. In some embodiments, the hydrogen on the carboxylic group of A is replaced with an alkyl group to form an ester. For example, the compound of the present invention can be a methyl or ethyl ester of the compound of formula IV, V, VI, VIA, or VIB.

In some embodiments of the compounds of formula IV, V, VI, VIA, and VIB, the subscript m is 1 or 2.

In some embodiments of the compounds of formula IV, V, VI, VIA, and VIB, the subscript m is 1 or 2; the subscript n' is 0; L$^1$ is a bond; L$^2$ is selected from —CH$_2$—O—, substituted oxymethylene, or O; R$^1$ is selected from aryl, heteroaryl, heterocycloalkyl, (C$_2$-C$_8$)alkenyl, (C$_3$-C$_8$)alkenyl, (C$_2$-C$_8$) alkynyl, or (C$_3$-C$_8$)alkynyl; R$^{1'}$ is H; and A is —CO$_2$H.

In some embodiments of the compounds of formula IV, V, VI, VIA, and VIB, Q is H; L$^3$ is CH$_2$; and L$^2$ is —CH$_2$—O— or —CH(CH$_3$)—O—.

In some embodiments of the compounds of formula IV, V, VI, VIA, and VIB, R$^6$ and R$^{6'}$ are independently selected from H and (C$_1$-C$_6$)alkyl and at least two of R$^6$ and R$^{6'}$ are (C$_1$-C$_6$) alkyl. In some such embodiments, R$^6$ and R$^{6'}$ are independently selected from H and methyl and at least two of R$^6$ and R$^{6'}$ are methyl groups. In some such embodiments, two of R$^6$ and R$^{6'}$ are methyl groups. In some embodiments, R$^6$ and R$^{6'}$ are independently selected from H and methyl and at least four of R$^6$ and R$^{6'}$ are methyl groups. In some such embodiments, R$^6$ and R$^{6'}$ are independently selected from H and methyl and four of R$^6$ and R$^{6'}$ are methyl groups.

In some embodiments of the compounds of formula I, II, III, IIIA, IIIB, IV, V, VI, VIA, and VIB, R$^1$ is selected from heteroaryl or heterocycloalkyl. In some such embodiments, R$^1$ is selected from a substituted or unsubstituted imidazolyl, triazolyl, tetrazolyl, oxazolyl, isoxazolyl, dihydroisoxazolyl, pyrazolyl, pyrrolyl, thiazolyl, thiophenyl, furanyl, thiadiazolyl, pyridyl, or pyrimidinyl. In certain such embodiments, R$^1$ is selected from a substituted or unsubstituted imidazol-2-yl;

1,2,4-triazol-3-yl; 1,2,3-triazol-4-yl; imidazol-5-yl; oxazol-5-yl; isoxazol-3-yl; pyrimidin-5-yl; tetrazol-5-yl; oxazol-2-yl; or dihydroisoxazol-3-yl. In still further such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; isoxazol-3-yl; pyrimidin-5-yl; 1-methyl-1H-tetrazol-5-yl; oxazol-2-yl; or 4,5-dihydroisoxazol-3-yl. In some such embodiments, $R^1$ is selected from a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl. In certain such embodiments, $R^1$ is selected from a substituted or unsubstituted imidazol-2-yl; 1,2,4-triazol-3-yl; 1,2,3-triazol-4-yl; imidazol-5-yl; oxazol-5-yl; pyrimidin-5-yl; tetrazol-5-yl; or oxazol-2-yl. In still further such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; pyrimidin-5-yl; 1-methyl-1H-tetrazol-5-yl; oxazol-2-yl.

In certain embodiments, the compound has the formula VIIA, VIIB, VIIC, or VIID:

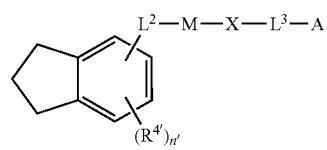

VIIA

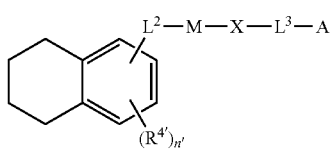

VIIB

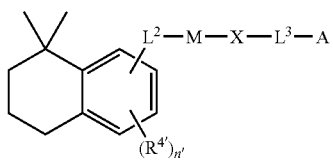

VIIC

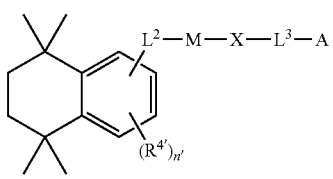

VIID or a pharmaceutically acceptable salt, solvate, or prodrug thereof; or a tautomer or a pharmaceutically acceptable salt, solvate, or prodrug thereof; or a mixture thereof.

In certain embodiments, the compound of formula VIIA, VIIB, VIIC, or VIID, has the formula VIIIA, VIIIB, VIIIC, or VIIID:

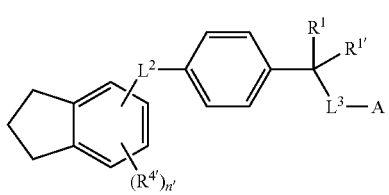

VIIIA

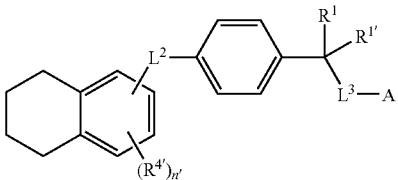

VIIIB

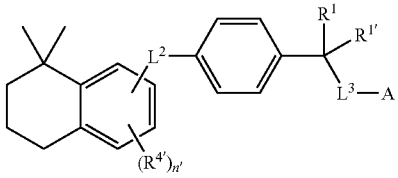

VIIIC

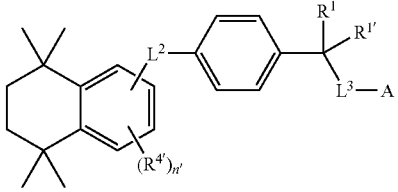

VIIID or a pharmaceutically acceptable salt, solvate, or prodrug thereof; or a tautomer or a pharmaceutically acceptable salt, solvate, or prodrug thereof; or a mixture thereof.

In certain embodiments, the compound of formula VIIIA, VIIIB, VIIC, or VIIID, has the formula IXA, IXB, IXC, or IXD:

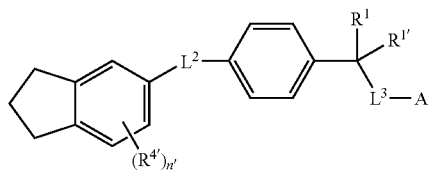

IXA

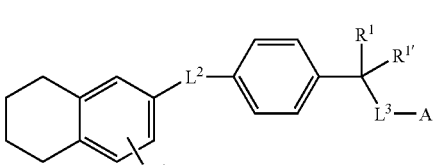

IXB

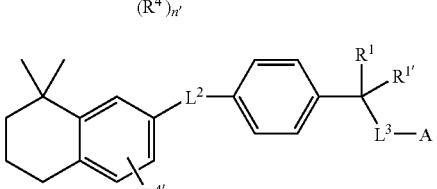

IXC

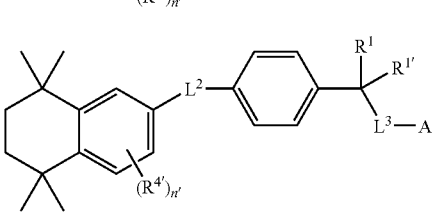

IXD or a pharmaceutically acceptable salt, solvate, or prodrug thereof; or a tautomer or a pharmaceutically acceptable salt, solvate, or prodrug thereof; or a mixture thereof.

In certain embodiments of the compound of formula VIIA, VIIB, VIIC, VIID, VIIIA, VIIIB, VIIIC, VIIID, IXA, IXB, IXC, or IXD, $L^2$ is —$CH_2$—O— or an alkyl-substituted oxymethylene; the subscript n' is 0; $R^1$ is ($C_2$-$C_3$)alkynyl, heteroaryl, or heterocycloalkyl; $R^{1'}$ is H; and A is —$CO_2$H. In some such embodiments, $R^1$ is selected from a substituted or unsubstituted imidazolyl, triazolyl, tetrazolyl, oxazolyl, isoxazolyl, dihydroisoxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; isoxazol-3-yl; pyrimidin-5-yl; tetrazol-5-yl; oxazol-2-yl; or dihydroisoxazol-3-yl. In still further such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; isoxazol-3-yl; pyrimidin-5-yl; 1-methyl-1H-tetrazol-5-yl; oxazol-2-yl; or 4,5-dihydroisoxazol-3-yl. In some such embodiments, $R^1$ is selected from a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; pyrimidin-5-yl; tetrazol-5-yl; or oxazol-2-yl. In still further such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; pyrimidin-5-yl; 1-methyl-1H-tetrazol-5-yl; or oxazol-2-yl. In some embodiments, the compound is a compound of formula VIIA. In some embodiments, the compound is a compound of formula VIIB. In some embodiments, the compound is a compound of formula VIIC. In some embodiments, the compound is a compound of formula VIID. In some embodiments, the compound is a compound of formula VIIIA. In some embodiments, the compound is a compound of formula VIIIB. In some embodiments, the compound is a compound of formula VIIIC. In some embodiments, the compound is a compound of formula VIIID. In some embodiments, the compound is a compound of formula IXA. In some embodiments, the compound is a compound of formula IXB. In some embodiments, the compound is a compound of formula IXC. In some embodiments, the compound is a compound of formula IXD.

In certain embodiments, the compound of formula IXA, IXB, IXC, or IXD, has the formula XA, XB, XC, or XD:

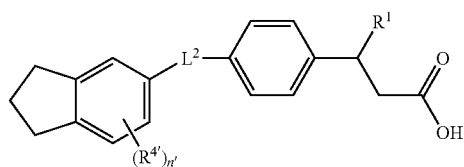

XA

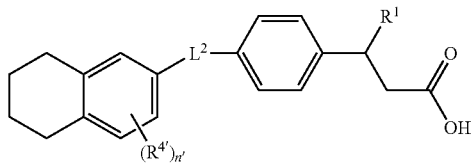

XB

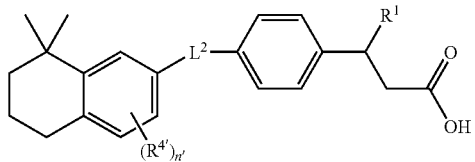

XC

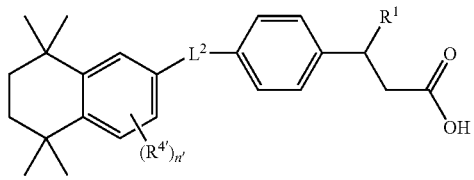

XD or a pharmaceutically acceptable salt, solvate, or prodrug thereof; or a tautomer or a pharmaceutically acceptable salt, solvate, or prodrug thereof; or a mixture thereof.

In certain embodiments of the compound of formula XA, XB, XC, or XD, $L^2$ is —$CH_2$—O— or an alkyl-substituted oxymethylene; the subscript n' is 0; $R^1$ is ($C_2$-$C_3$)alkynyl, heteroaryl, or heterocycloalkyl; and $R^{1'}$ is H. In some such embodiments, $R^1$ is selected from a substituted or unsubstituted imidazolyl, triazolyl, tetrazolyl, oxazolyl, isoxazolyl, dihydroisoxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; isoxazol-3-yl; pyrimidin-5-yl; tetrazol-5-yl; oxazol-2-yl; or dihydroisoxazol-3-yl. In still further such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; isoxazol-3-yl; pyrimidin-5-yl; 1-methyl-1H-tetrazol-5-yl; oxazol-2-yl; or 4,5-dihydroisoxazol-3-yl. In some such embodiments, $R^1$ is selected from a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; pyrimidin-5-yl; tetrazol-5-yl; or oxazol-2-yl. In still further such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; pyrimidin-5-yl; 1-methyl-1H-tetrazol-5-yl; or oxazol-2-yl. In some embodiments, the compound is a compound of formula XA. In some embodiments, the compound is a compound of formula XB. In some embodiments, the compound is a compound of formula XC. In some embodiments, the compound is a compound of formula XD.

The compounds of the invention include pharmaceutically acceptable salts, solvates, stereoisomers, and prodrugs thereof, and tautomers and pharmaceutically acceptable salts, solvates, stereoisomers, and prodrugs thereof, and mixtures thereof. In some embodiments, the compounds are pharmaceutically acceptable salts. In other embodiments, the compounds are prodrugs such as esters of a carboxylic acid.

In certain embodiments of the compound of formula I, the compound has the formula of any one of XIa-XIm or is a pharmaceutically acceptable salt, solvate, stereoisomer, or prodrug thereof; or a tautomer, or a pharmaceutically acceptable salt, solvate, stereoisomer, or prodrug thereof; or a mixture thereof:

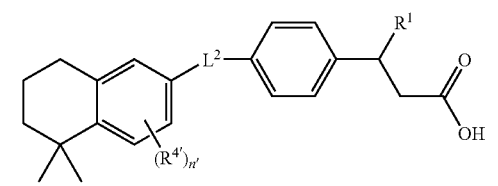
XIa

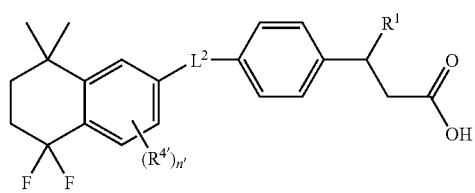
XIb

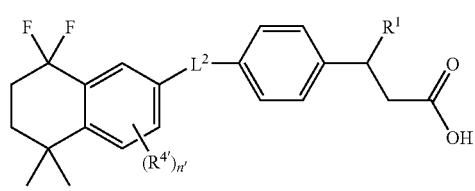
XIc

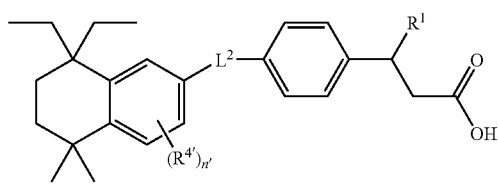
XId

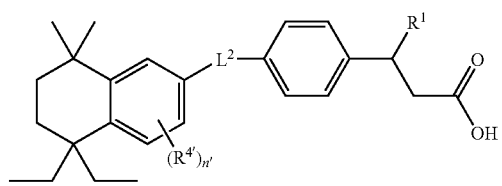
XIe

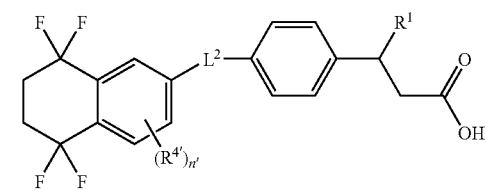
XIf

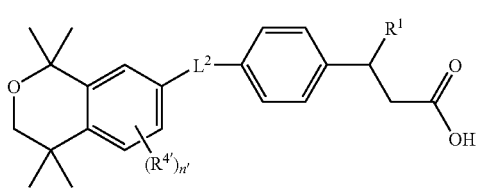
XIg

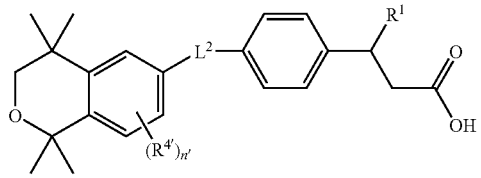
XIh

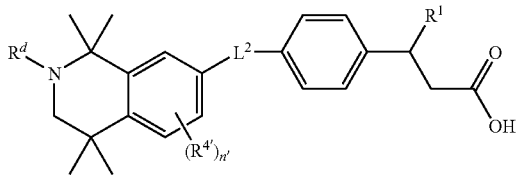
XIi

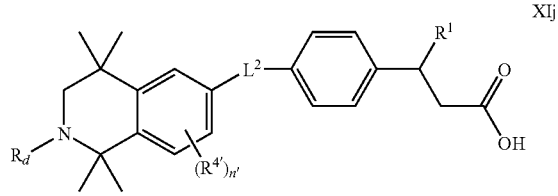
XIj

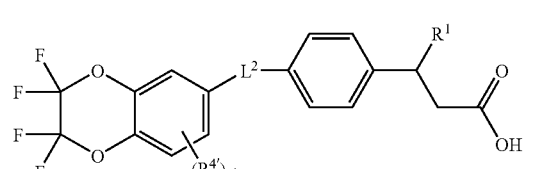
XIk

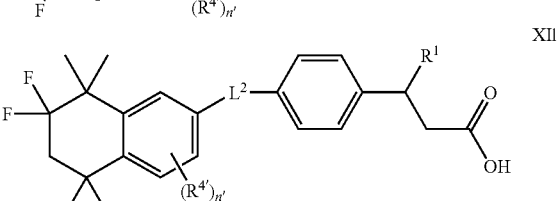
XIl

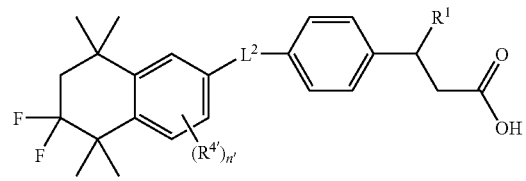
XIm where $R^{4'}$ is independently selected from substituted ($C_1$-$C_6$) alkyl, —R', —OR', =O, =NR', =N—OR', —NR'R", —SR', halogen, —OC(O)R', —C(O)R', —CO$_2$R', —CONR"R'", —OC(O)NR'R", —NR"C(O)R', —NR'—C(O)NR"R'", —NR'—SO$_2$NR"R'", —NR"CO$_2$R', —NH—C(NH$_2$)=NH, —NR'C(NH$_2$)=NH, —NH—C(NH$_2$)=NR', —SiR'R"R'", —S(O)R', —SO$_2$R', —SO$_2$NR'R", —NR"SO$_2$R, —CN, —(C$_2$-C$_5$)alkynyl, —(C$_2$-C$_5$)alkenyl, or —NO$_2$, where R', R" and R'" each independently refer to hydrogen, unsubstituted (C$_1$-C$_8$)alkyl or heteroalkyl, unsubstituted aryl, aryl substituted with one to three halogens, unsubstituted alkyl, alkoxy or thioalkoxy groups, halo(C$_1$-C$_4$)alkyl, or aryl-(C$_1$-C$_4$)alkyl groups; the subscript n' is 0, 1, 2, or 3; and $R^d$ is selected from optionally substituted C$_1$-C$_6$ alkyl or optionally substituted aryl.

In some embodiments, the compound of any one of formula XIa-XIm comprises a stereomerically pure S-enantiomer. In other embodiments, the compound comprises a stereomerically pure R-enantiomer. In yet other embodiments, the compound comprises a mixture of S- and R-enantiomers.

In certain embodiments of the compound of formula I, the compound has the formula of any one of XIIa-XIIm or is a pharmaceutically acceptable salt, solvate, stereoisomer, or prodrug thereof; or a tautomer, or a pharmaceutically acceptable salt, solvate, stereoisomer, or prodrug thereof; or a mixture thereof:

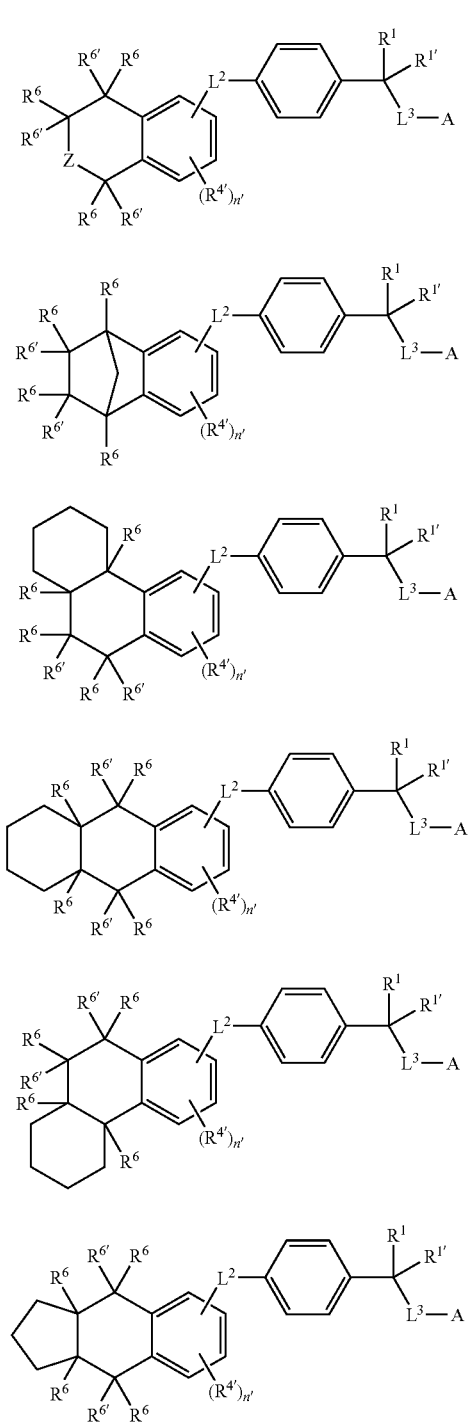

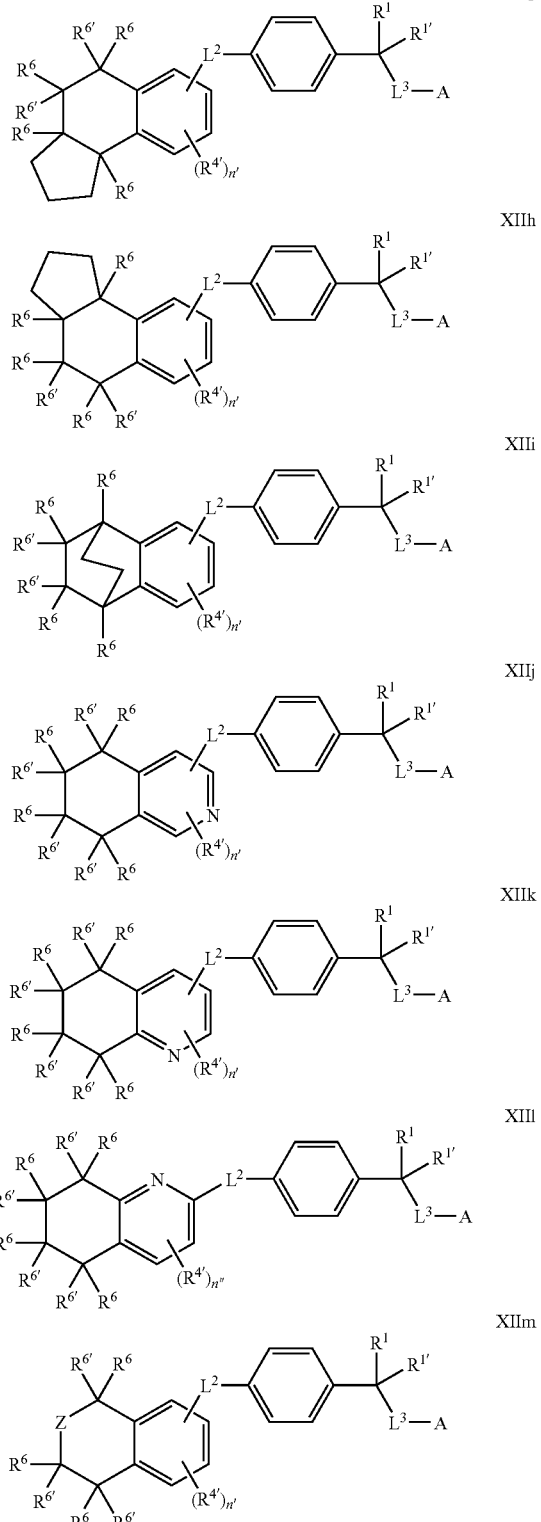

where $R^{4'}$ is independently selected from substituted $(C_1\text{-}C_6)$ alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R''', —NR'—SO$_2$NR"R''', —NR"CO$_2$R', —NH—C(NH$_2$)=NH, —NR'C(NH$_2$)=NH, —NH—C(NH$_2$)=NR', —SiR'R"R'", —S(O)R', —SO₂R', —SO₂NR'R", —NR" SO₂R, —CN, —(C₂-C₅)alkynyl, —(C₂-C₅)alkenyl, or —NO₂, where R', R" and R'" each independently refer to hydrogen, unsubstituted (C₁-C₈)alkyl or heteroalkyl, unsubstituted aryl, aryl substituted with one to three halogens, unsubstituted alkyl, alkoxy or thioalkoxy groups, halo(C₁-C₄)alkyl, or aryl-(C₁-C₄)alkyl groups; R⁶ and R⁶' are independently selected from H, (C₁-C₆)alkyl, halogen, (C₁-C₆)alkoxy, cyano, or nitro; Z is selected from O, NR$^d$, or S; R$^d$ is selected from optionally substituted C₁-C₆ alkyl or optionally substituted aryl; the subscript n' is 0, 1, 2, or 3; and the subscript n" is 0, 1, or 2.

In some embodiments, the compound of any one of formula XIIa-XIIm comprises a stereomerically pure S-enantiomer. In other embodiments, the compound comprises a stereomerically pure R-enantiomer. In yet other embodiments, the compound comprises a mixture of S- and R-enantiomers.

In another aspect, the invention provides pharmaceutical compositions comprising a pharmaceutically acceptable carrier, diluent, or excipient, and a compound of any of the embodiments of the invention.

In another aspect, the invention provides methods for treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, hypertension, cancer, and edema. Such methods include administering to a subject in need thereof, a therapeutically effective amount of a compound of any of the embodiments. In some such embodiments, the disease or condition is type II diabetes. In some embodiments, a compound of any of the embodiments is administered with combination with a second therapeutic agent. In some such embodiments, the second therapeutic agent is metformin or is a thiazolidinedione. The second therapeutic agent may be administered before, during, or after administration of the compound of any of the embodiments.

In another aspect, the invention provides methods for treating or preventing a disease or condition responsive to the modulation of GPR40. Such methods include administering to a subject in need thereof, a therapeutically effective amount of a compound of any of the embodiments.

In another aspect, the invention provides methods for treating or preventing a disease or condition mediated, regulated, or influenced by pancreatic β cells. Such methods include administering to a subject in need thereof, a therapeutically effective amount of a compound of any of the embodiments.

In another aspect, the invention provides methods for modulating GPR40 function in a cell. Such methods include contacting a cell with a compound of formula any of the embodiments.

In another aspect, the invention provides methods for modulating GPR40 function. Such methods include contacting GPR40 with a compound of any of the embodiments.

In another aspect, the invention provides methods for modulating circulating insulin concentration in a subject. Such methods include administering a compound of any of the embodiments to the subject. In some such embodiments, the circulating insulin concentration is increased in the subject after administration whereas in other such embodiments, the circulating insulin concentration is decreased in the subject after administration.

In another aspect, the invention provides the use of a compound of any of the embodiments for treating a disease or condition or for preparing a medicament for treating a disease or condition where the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. In some such embodiments, the disease or condition is type II diabetes. The compounds of the invention may also be used to prepare medicaments that include a second therapeutic agent such as metformin or a thiazolidinedione.

In another aspect, the invention provides the use of a compound of any of the embodiments for modulating GPR40 or for use in the preparation of a medicament for modulating GPR40.

In another aspect, the invention provides a therapeutic composition that includes a compound of any of the embodiments and a second therapeutic agent such as those described herein, for example, metformin or a thiazolidinedione, as a combined preparation for simultaneous, separate, or sequential use in the treatment of a disease or condition mediated by GPR40. In some such embodiments, the disease or condition is type II diabetes. In some embodiments, the compound of any of the embodiments and the second therapeutic agent are provided as a single composition, whereas in other embodiments they are provided separately as parts of a kit.

In one aspect, the invention provides a method of synthesizing a compound of formula XV as shown in Scheme 2. The method includes: reacting a compound of formula XIII with a compound of formula XIV to produce the compound of formula XV, wherein the compounds of formula XIII, XIV, and XV have the following structures:

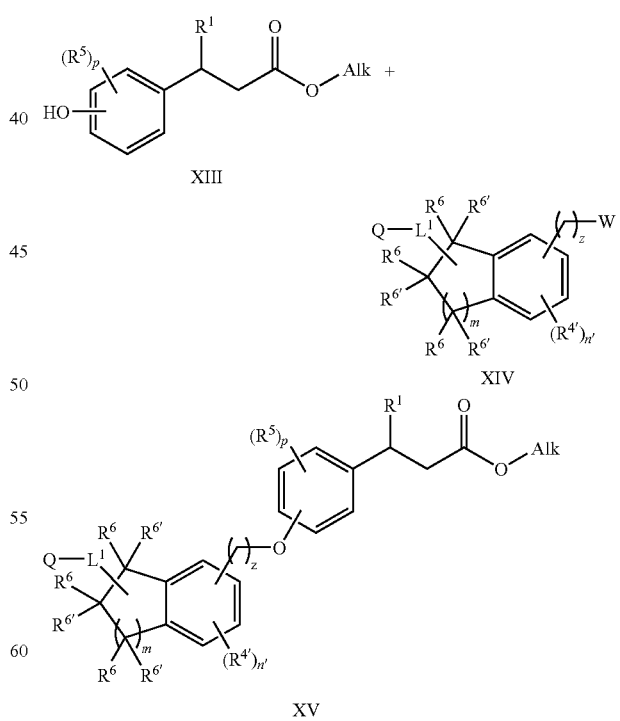

wherein, Alk is a straight or branched chain alkyl group having from 1 to 8 carbon atoms; R¹ is selected from cyano, aryl, heteroaryl, heterocycloalkyl, (C₂-C₈)alkenyl, (C₃-C₈)

alkenyl, $(C_2-C_8)$alkynyl, $(C_3-C_8)$alkynyl, or $-C(O)NR^2R^3$; $R^2$ and $R^3$ are independently selected from hydrogen, aryl, heteroaryl, $(C_1-C_8)$alkyl, $(C_2-C_8)$heteroalkyl, $(C_3-C_8)$cycloalkyl, or $(C_3-C_8)$heterocycloalkyl; optionally, $R^2$ and $R^3$ are combined to form a 4-, 5-, 6- or 7-membered ring containing the nitrogen atom to which they are attached comprising from 0 to 2 additional heteroatoms selected from N, O, or S; and; $R^5$ is independently selected from $(C_1-C_6)$alkyl, halogen, $(C_1-C_6)$alkoxy, cyano, or nitro; p is selected from 0, 1, 2, 3, or 4; z is selected from 1, 2, or 3; $R^{4'}$ is independently selected from substituted $(C_1-C_6)$alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R'", —NR'—SO$_2$NR"R'", —NR"CO$_2$R', —NH—C(NH$_2$)=NH, —NR'C(NH$_2$)=NH, —NH—C(NH$_2$)=NR', —SiR'R"R'", —S(O)R', —SO$_2$R', —SO$_2$NR'R", —NR"SO$_2$R, —CN, —(C$_2$-C$_5$)alkynyl, —(C$_2$-C$_5$)alkenyl, or —NO$_2$, wherein R', R" and R'" are each independently selected from hydrogen, unsubstituted $(C_1-C_8)$alkyl or heteroalkyl, unsubstituted aryl, aryl substituted with one to three halogens, unsubstituted alkyl, alkoxy or thioalkoxy groups, halo$(C_1-C_4)$alkyl, or aryl-$(C_1-C_4)$alkyl groups; n' is 0, 1, 2, or 3; m is 1, 2, 3, or 4; one of $R^6$ and $R^{6'}$ is $L^1$ or Q, if $L^1$ is a bond, and the others of $R^6$ and $R^{6'}$ are independently selected from H, $(C_1-C_6)$alkyl, halogen, $(C_1-C_6)$alkoxy, cyano, or nitro, wherein one of $R^6$ and one of $R^{6'}$ on adjacent or non-adjacent carbon atoms, or on the same carbon atom may join together to form a $C_5-C_8$ cycloalkane ring, or two of $R^6$ or two of $R^{6'}$, on adjacent or non-adjacent carbon atoms, may join together to form a $C_5-C_8$ cycloalkane ring; $L^1$ is selected from a bond, $(C_1-C_4)$alkylene, $(C_2-C_4)$ heteroalkylene, O, $S(O)_k$, $N(R^a)$, $C(O)$—$(C_5-C_7)$heterocycloalkylene, $(C_1-C_4)$alkylene-SO$_2$N(R$^b$), $(C_1-C_4)$alkylene-N(R$^b$)SO$_2$, or C(O)N(R$^b$); $R^a$ is selected from hydrogen, $(C_1-C_6)$alkyl, aryl$(C_1-C_3)$alkyl, or $(C_2-C_6)$heteroalkyl; $R^b$ is selected from hydrogen, $(C_1-C_6)$alkyl, or $(C_2-C_6)$heteroalkyl; Q is selected from hydrogen, aryl, heteroaryl, $(C_1-C_6)$alkyl, or $(C_2-C_6)$heteroalkyl; W is a leaving group; and further wherein, the compounds of formula XIII and XV can be a mixture of compounds having the R and S stereochemistry at the carbon bonded to $R^1$, can have the R stereochemistry at the carbon bonded to $R^1$, or can have the S stereochemistry at the carbon bonded to $R^1$.

In some embodiments, W is selected from OH or a halogen. In some such embodiments, W is OH and a phosphine selected from a trialkylphosphine, a dialkylarylphosphine, a alkyldiarylphosphine, or a triarylphosphine and an azodicarboxylate are used to react the compound of formula XIII with the compound of formula XIV. In other such embodiments, W is a halogen selected from Br or Cl, and a base is used to react the compound of formula XXII with the compound of formula XXIII. In some embodiments, W is selected from OH, a halogen, OTs, OMs, or OTf, where OTs is tosylate, OMs is mesylate, and OTf is triflate and Ts is p-toluenesulfonyl, Ms is methanesulfonyl, and Tf is trifluoromethanesulfonyl.

In some embodiments, Alk is selected from methyl or ethyl.

In some embodiments, m is 1 or 2.

In some embodiments, n' is 0

In some embodiments, z is 1.

In some embodiments, the method further includes removing the Alk group of the compound of formula XV to form a compound of formula XVI or a salt thereof, and the compound of formula XVI has the following structure:

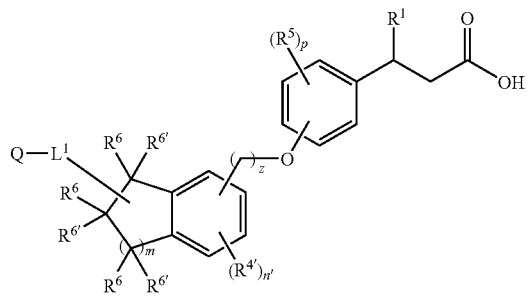

wherein the variables have the definitions provided with respect to the compounds of any of the embodiments of formula XIII, XIV, and XV. In some such embodiments, the compound of formula XV is reacted in the presence of a hydroxide base to produce the compound of formula XVI. In some such embodiments, the hydroxide base is selected from LiOH, NaOH, KOH, or Ca(OH)$_2$.

Other objects, features and advantages of the invention will become apparent to those skilled in the art from the following description and claims.

5. DETAILED DESCRIPTION OF THE INVENTION

5.1 Abbreviations and Definitions

The terms "treat", "treating" and "treatment", as used herein, are meant to include alleviating or abrogating a condition or disease and/or its attendant symptoms. The terms "prevent", "preventing" and "prevention", as used herein, refer to a method of delaying or precluding the onset of a condition or disease and/or its attendant symptoms, barring a subject from acquiring a condition or disease, or reducing a subject's risk of acquiring a condition or disease.

The term "therapeutically effective amount" refers to that amount of the compound that will elicit the biological or medical response of a tissue, system, or subject that is being sought. The term "therapeutically effective amount" includes that amount of a compound that, when administered, is sufficient to prevent development of, or alleviate to some extent, one or more of the symptoms of the condition or disorder being treated in a subject. The therapeutically effective amount in a subject will vary depending on the compound, the disease and its severity, and the age, weight, etc., of the subject to be treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "modulate", "modulation" and the like refer to the ability of a compound to increase or decrease the function or activity of GPR40 either directly or indirectly. Inhibitors are compounds that, for example, bind to, partially or totally block stimulation, decrease, prevent, delay activation, inactivate, desensitize, or down regulate signal transduction, such as, for instance, antagonists. Activators are compounds that, for example, bind to, stimulate, increase, activate, facilitate, enhance activation, sensitize or up regulate signal transduction, such as agonists for instance. Modulation may occur in vitro or in vivo.

As used herein, the phrases "GPR40-mediated condition or disorder", "disease or condition mediated by GPR40", and the like refer to a condition or disorder characterized by inappropriate, for example, less than or greater than normal, GPR40 activity. A GPR40-mediated condition or disorder may be completely or partially mediated by inappropriate GPR40 activity. However, a GPR40-mediated condition or disorder is one in which modulation of GPR40 results in some effect on the underlying condition or disease (e.g., a GPR40 modulator results in some improvement in patient well-being in at least some patients). Exemplary GPR40-mediated conditions and disorders include cancer and metabolic disorders, e.g., diabetes, type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, ketoacidosis, hypoglycemia, thrombotic disorders, metabolic syndrome, syndrome X and related disorders, e.g., cardiovascular disease, atherosclerosis, kidney disease, nephropathy, diabetic neuropathy, diabetic retinopathy, sexual dysfunction, dermatopathy, dyspepsia, and edema.

The term "alkyl", by itself or as part of another substituent, means, unless otherwise stated, a straight or branched chain, or cyclic hydrocarbon radical, or combination thereof, which is fully saturated, having the number of carbon atoms designated (e.g., $C_1$-$C_{10}$ means one to ten carbons). Examples of alkyl groups include methyl, ethyl, n-propyl, isopropyl, n-butyl, t-butyl, isobutyl, sec-butyl, cyclohexyl, (cyclohexyl)methyl, cyclopropyl, cyclopropylmethyl, and homologs and isomers of, for example, n-pentyl, n-hexyl, n-heptyl, n-octyl, and the like.

The term "alkenyl", by itself or as part of another substituent, means a straight or branched chain, or cyclic hydrocarbon radical, or combination thereof, which may be mono- or polyunsaturated, having the number of carbon atoms designated (i.e., $C_2$-$C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl), and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more triple bonds. Examples of alkynyl groups include ethynyl, 1- and 3-propynyl, 3-butynyl, and higher homologs and isomers thereof.

The term "alkylene" by itself or as part of another substituent means a divalent radical derived from alkyl, as exemplified by —$CH_2CH_2CH_2CH_2$—. Typically, an alkyl (or alkylene) group will have from 1 to 24 carbon atoms, with those groups having 12 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups. The alkyl groups of a dialkylamino may be the same or different.

The term "heteroalkyl," by itself or in combination with another term, means, unless otherwise stated, a stable straight or branched chain, or cyclic hydrocarbon radical, or combinations thereof, consisting of carbon atoms and from one to three heteroatoms selected from the group consisting of O, N, and S, and wherein the nitrogen and sulfur atoms may optionally be oxidized, and the nitrogen heteroatom may optionally be quaternized. The heteroatom(s) O, N, and S may be placed at any position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, and —$CH_2$—CH=N—$OCH_3$. Up to two heteroatoms may be consecutive, such as, for example, —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group is an, oxyalkyl group. For instance, ($C_2$-$C_5$)oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2OH$, and the like.

The term "heteroalkylene" by itself or as part of another substituent means a divalent radical derived from heteroalkyl, as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied. Heteroalkylene groups such as oxymethyl groups (—$CH_2$—O—) may be substituted or unsubstituted. In some embodiments, heteroalkylene groups may be substituted with an alkyl group. For example, the carbon atom of an oxymethylene group may be substituted with a methyl group in a group of formula —$CH(CH_3)$—O—.

The terms "cycloalkyl" and "heterocycloalkyl," by themselves or in combination with other terms, represent, unless otherwise stated, cyclic versions of "alkyl" and "heteroalkyl," respectively. Thus, the terms "cycloalkyl" and "heterocycloalkyl" are meant to be included in the terms "alkyl" and "heteroalkyl," respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, 4,5-dihydroisoxazol-3-yl, and the like. The term "heterocycloalkyl" includes fully saturated compounds such as piperidine and compounds with partial saturation that are not aromatic. Examples of such groups include, but are not limited to, an imidazole, oxazole, or isoxazole which has been partially hydrogenated so that it only contains one double bond.

The term "cycloalkylene" and "heterocycloalkylene," by themselves or in combination with other terms, represent, unless otherwise stated, cyclic versions of "alkylene" and "heteroalkylene," respectively. Thus, the terms "cycloalkylene" and "heterocycloalkylene" are meant to be included in the terms "alkylene" and "heteroalkylene," respectively. Additionally, for heterocycloalkylene, one or more heteroatoms can occupy positions at which the heterocycle is attached to the remainder of the molecule. Typically, a cycloalkylene or heterocycloalkylene will have from 3 to 9 atoms forming the ring, more typically, 4 to 7 atoms forming the ring, and even more typically, 5 or 6 atoms will form the cycloalkylene or heterocycloalkylene ring.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo ($C_1$-$C_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatoms selected from the group consisting of N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, dibenzofuryl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, 2-benzoxazolyl, 5-benzoxazolyl, benzo[c][1,2,5]oxadiazolyl, purinyl, 2-benzimidazolyl, 5-indolyl, 1H-indazolyl, carbazolyl, α-carbolinyl, β-carbolinyl, γ-carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl, and 8-quinolyl.

Preferably, the term "aryl" refers to a phenyl or naphthyl group which is unsubstituted or substituted. Preferably, the term "heteroaryl" refers to a pyrrolyl, pyrazolyl, imidazolyl, pyrazinyl, oxazolyl, oxadiazolyl, isoxazolyl, thiazolyl, furyl, thienyl (thiophenyl), pyridyl, pyrimidyl, benzothiazolyl, purinyl, benzimidazolyl, indolyl, isoquinolyl, triazolyl, tetrazolyl, quinoxalinyl, or quinolyl group which is unsubstituted or substituted.

For brevity, the term "aryl" when used in combination with other terms (e.g., aryloxy, arylalkoxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). As another example, the term "aryl($C_1$-$C_4$)alkoxy" is mean to include radicals in which an aryl group is attached to an alkyl group having 1 to 4 carbon atoms that is bonded to an O which is attached to the rest of the molecule. Examples include substituted and unsubstituted phenylmethoxy, phenylethoxy, phenylpropoxy, pyridylmethoxy, and the like.

Each of the above terms (e.g., "alkyl," "heteroalkyl," "aryl" and "heteroaryl") is meant to include both substituted and unsubstituted forms of the indicated radical, unless otherwise indicated. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —OC(O)R', —C(O)R', —$CO_2$R', —CONR'R", —OC(O)NR'R", —NR"C(O)R', —NR'—C(O)NR"R''', —NR'—$SO_2$NR"R''', —NR"$CO_2$R', —NH—C($NH_2$)=NH, —NR'C($NH_2$)=NH, —NH—C($NH_2$)=NR', —SiR'R"R''', —S(O)R', —$SO_2$R', —$SO_2$NR'R", —NR"$SO_2$R, —CN, —($C_2$-$C_5$)alkynyl, —($C_2$-$C_5$)alkenyl, and —$NO_2$, in a number ranging from zero to three, with those groups having zero, one or two substituents being particularly preferred. Other suitable substituents include aryl and heteroaryl groups. R', R" and R''' each independently refer to hydrogen, unsubstituted ($C_1$-$C_8$)alkyl and heteroalkyl, unsubstituted aryl, aryl substituted with one to three halogens, unsubstituted alkyl, alkoxy or thioalkoxy groups, halo($C_1$-$C_4$)alkyl, or aryl-($C_1$-$C_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl.

Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —$CF_3$ and —$CH_2CF_3$).

Preferred substituents for the alkyl and heteroalkyl radicals are selected from: —OR', =O, —NR'R", —SR', halogen, —OC(O)R', —C(O)R', —$CO_2$R', —CONR'R", —OC(O)NR'R", —NR"C(O)R', —NR"$CO_2$R', —NR'—$SO_2$NR"R''', —S(O)R', —$SO_2$R', —$SO_2$NR'R", —NR"$SO_2$R, —CN, —($C_2$-$C_5$)alkynyl, —($C_2$-$C_5$)alkenyl and —$NO_2$, where R' and R" are as defined above. Further preferred substituents are selected from: —OR', =O, —NR'R", halogen, —OC(O)R', —$CO_2$R', —CONR'R", —OC(O)NR'R", —NR"C(O)R', —NR"$CO_2$R', —NR'—$SO_2$NR"R''', —$SO_2$R', —$SO_2$NR'R", —NR"$SO_2$R, —CN, —($C_2$-$C_5$)alkynyl, —($C_2$-$C_5$)alkenyl, and —$NO_2$.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R''', —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, ($C_1$-$C_8$)alkyl and heteroalkyl, unsubstituted aryl and heteroaryl, (unsubstituted aryl)-($C_1$-$C_4$)alkyl, (unsubstituted aryl)oxy-($C_1$-$C_4$)alkyl, —($C_2$-$C_5$)alkynyl, and —($C_2$-$C_5$)alkenyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$—, or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'—, or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl. Otherwise, R' is as defined above.

As used herein, the term "benzo-fused cycloalkane ring" is meant to include bicyclic structures in which benzene is fused with a cycloalkane (or cycloheteroalkane). To illustrate, in some embodiments, "benzo-fused cycloalkane ring" includes the following structures:

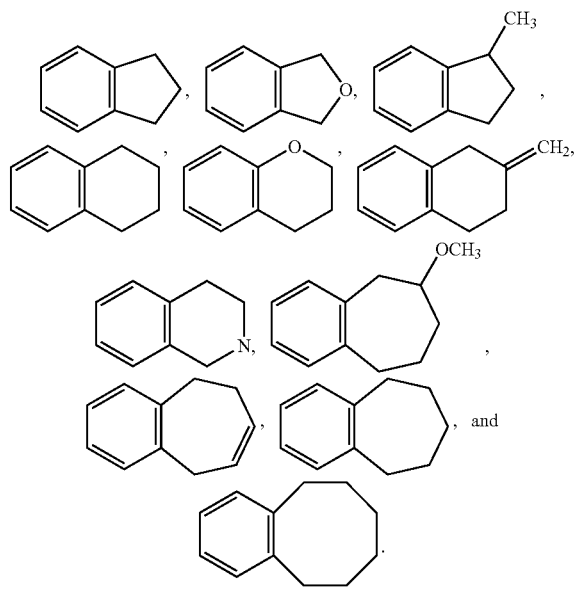

As used herein, the term "heterobenzo-fused (C$_5$-C$_8$)cycloalkane ring" has the same meaning as "benzo-fused (C$_5$-C$_8$) cycloalkane ring" except the benzene of the benzo-fused (C$_5$-C$_8$)cycloalkane ring is replaced with a six-membered heteroaryl ring comprising 1 or 2 nitrogen (N) atoms. As indicated in the structures shown above, the (C$_5$-C$_8$)cycloalkane of benzo-fused (C$_5$-C$_8$)cycloalkane rings and heterobenzo-fused (C$_5$-C$_8$)cycloalkane ring may include only carbon atoms, but may also include one or more heteroatoms. Such heteroatoms typically are selected from O, N, or S.

As used herein, the term "heteroatom" is meant to include oxygen (O), nitrogen (N), and sulfur (S).

The term "pharmaceutically acceptable salt" is meant to include a salt of the active compound which is prepared with relatively nontoxic acids or bases, depending on the particular substituents found on the compound described herein. When a compound of the invention contains relatively acidic functionalities, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound of the invention contains relatively basic functionalities, an acid addition salt can be obtained by contacting the neutral form of such compound with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galacturonic acids and the like (see, for example, Berge et al. (1977) *J. Pharm. Sci.* 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein, "solvate" refers to a compound of the present invention or a salt thereof, that further includes a stoichiometric or non-stoichiometric amount of solvent bound by non-covalent intermolecular forces. Where the solvent is water, the solvate is a hydrate.

Certain compounds of the invention may exist in multiple crystalline or amorphous forms. In general, all physical forms are equivalent for the uses contemplated by the invention and are intended to be within the scope of the invention.

As known by those skilled in the art, certain compounds of the invention may exist in one or more tautomeric forms. Because one chemical structure may only be used to represent one tautomeric form, it will be understood that convenience, referral to a compound of a given structural formula includes tautomers of the structure represented by the structural formula.

Certain compounds of the invention possess asymmetric carbon atoms (optical centers) or double bonds; the racemates, enantiomers, diastereomers, geometric isomers and individual isomers are all intended to be encompassed within the scope of the invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al. (1997) *Tetrahedron* 33:2725; Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, 1N, 1972).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., GPR40 assay reagents, and diagnostic agents, e.g., in vivo imaging agents. All isotopic variations of the compounds of the invention, whether radioactive or not, are intended to be encompassed within the scope of the invention.

5.2 Embodiments of the Invention

In one aspect, a class of compounds that modulates GPR40 is described herein. Depending on the biological environment (e.g., cell type, pathological condition of the subject, etc.), these compounds can modulate, e.g., activate or inhibit, the actions of GPR40. By modulating GPR40, the compounds find use as therapeutic agents capable of regulating insulin levels in a subject. The compounds find use as therapeutic agents for modulating diseases and conditions responsive to modulation of GPR40 and/or mediated by GPR40 and/or mediated by pancreatic β cells. As noted above, examples of such diseases and conditions include diabetes, obesity, hyperglycemia, glucose intolerance, insulin resistance, cancer, hyperinsulinemia, hypercholesterolemia, hypertension, hyperlipoproteinemia, hyperlipidemia, hypertriglylceridemia, dyslipidemia, ketoacidosis, hypoglycemia, metabolic syndrome, syndrome X, cardiovascular disease, atherosclerosis, kidney disease, nephropathy, thrombotic disorders, diabetic neuropathy, diabetic retinopathy, dermatopathy, dyspepsia and edema. Additionally, the compounds are useful for the treatment and/or prevention of complications of these diseases and disorders (e.g., type II diabetes, sexual dysfunction, dyspepsia and so forth).

While the compounds of the invention are believed to exert their effects by interacting with GPR40, the mechanism of action by which the compounds act is not a limiting embodiment of the invention.

Compounds contemplated by the invention include, but are not limited to, the exemplary compounds provided herein.

5.2.1 Compounds

In one aspect, the present invention provides a compound having the formula I or a pharmaceutically acceptable salt, solvate, stereoisomer, or prodrug thereof; or a tautomer or a pharmaceutically acceptable salt, solvate, stereoisomer, or prodrug thereof; or a mixture thereof:

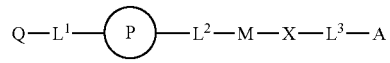

I where Q, $L^1$, P, $L^2$, M, X, $L^3$, and A are defined below.

Q is hydrogen, aryl, heteroaryl, ($C_1$-$C_6$)alkyl, or ($C_2$-$C_6$)heteroalkyl.

In certain embodiments, Q is hydrogen, aryl, or heteroaryl.

In certain embodiments, Q is a substituted or unsubstituted phenyl.

$L^1$ is a bond, ($C_1$-$C_4$)alkylene, ($C_2$-$C_4$)heteroalkylene, O, S(O)$_k$, N(R$^a$), C(O)—($C_5$-$C_7$)heterocycloalkylene, ($C_1$-$C_4$)alkylene-SO$_2$N(R$^b$), ($C_1$-$C_4$)alkylene-N(R$^b$)SO$_2$, or C(O)N(R$^b$).

In certain embodiments, $L^1$ is a bond. In some such embodiments, Q is H.

represents an optionally substituted benzo-fused ($C_5$-$C_8$) cycloalkane ring comprising a benzene ring fused to a ($C_5$-$C_8$)cycloalkane ring, an optionally substituted heterobenzo-fused ($C_5$-$C_8$)cycloalkane ring comprising a six-membered heteroaryl ring comprising 1 or 2 N atoms fused to a ($C_5$-$C_8$) cycloalkane ring, or a heteroaryl-fused ($C_5$-$C_8$)cycloalkane ring comprises a five-membered heteroaryl ring comprising 1 or 2 N heteroatoms, generally selected from O, N, and S, fused to a ($C_5$-$C_8$)cycloalkane ring, wherein the benzene ring of the benzo-fused $(C_5-C_8)$cycloalkane ring, the heteroaryl ring of the heterobenzo-fused $(C_5-C_8)$cycloalkane ring, or the heteroaryl ring of the heteroaryl-fused $(C_5-C_8)$cycloalkane ring is bonded to $L^2$ or M, if $L^2$ is a bond. In some embodiments, (P)

is a benzo-fused $(C_5-C_8)$cycloalkane ring. In some embodiments, (P)

is a substituted benzo-fused $(C_5-C_8)$cycloalkane ring. In some embodiments, (P)

is an unsubstituted benzo-fused $(C_5-C_8)$cycloalkane ring. In some embodiments, (P)

is a heterobenzo-fused $(C_5-C_8)$cycloalkane ring. In some such embodiments, the heteroaryl ring of the heterobenzo-fused $(C_5-C_8)$cycloalkane ring comprises 1 N atom. For example, the heteroaryl ring of the heterobenzo-fused $(C_5-C_8)$cycloalkane ring may be a pyridine ring. In other such embodiments, the heteroaryl ring of the heterobenzo-fused $(C_5-C_8)$cycloalkane ring comprises 2 N atoms. For example, the heteroaryl ring of the heterobenzo-fused $(C_5-C_8)$cycloalkane ring may be a pyrimidine, pyrazine, or pyridazine ring. In some embodiments, (P)

is a substituted heterobenzo-fused $(C_5-C_8)$cycloalkane ring. In some embodiments, (P)

is an unsubstituted heterobenzo-fused $(C_5-C_8)$cycloalkane ring. In some embodiments, (P)

is a heteroaryl-fused $(C_5-C_8)$cycloalkane ring. In some such embodiments, the heteroaryl ring of the heteroaryl-fused $(C_5-C_8)$cycloalkane ring comprises 1 N atom. In some embodiment the heteroaryl ring of the heteroaryl-fused $(C_5-C_8)$cycloalkane ring comprises 1 N atom and either 1 O atom or 1 S atom. In other such embodiments, the heteroaryl ring of the heteroaryl-fused $(C_5-C_8)$cycloalkane ring comprises 2 N atoms. In some embodiments, (P)

is a substituted heteroaryl-fused $(C_5-C_8)$cycloalkane ring. In some embodiments, (P)

is an unsubstituted heteroaryl-fused $(C_5-C_8)$cycloalkane ring. In some embodiments, the $(C_5-C_8)$cycloalkane ring of the benzo-fused $(C_5-C_8)$cycloalkane ring, the heterobenzo-fused $(C_5-C_8)$cycloalkane ring, or the heteroaryl-fused $(C_5-C_8)$cycloalkane ring of (P)

comprises 0-3 heteroatoms selected from O, N, or S. In some such embodiments, the cycloalkane ring comprises 1 or 2 heteroatom ring members selected from O or N, and in some embodiments 1 heteroatom ring member, selected from O or N. In some such embodiments, the cycloalkane comprises 0 heteroatom ring atoms such that each of the cycloalkane ring members of the benzo-fused $(C_5-C_8)$cycloalkane, the heterobenzo-fused $(C_5-C_8)$cycloalkane, or the heteroaryl-fused $(C_5-C_8)$cycloalkane ring is a carbon atom. In some such embodiments, (P)

is selected from the group consisting of dihydroindene (i.e., indane or a benzo-cyclopentyl ring), tetrahydronaphthalene (i.e., a benzo-cyclohexyl ring), tetrahydrobenzo[7]annulene (i.e., a benzo-cycloheptyl ring), and hexahydrobenzo[8]annulene (i.e., a benzo-cyclooctyl ring). In some embodiments, (P)

is a heteroaryl-fused $(C_5-C_8)$cycloalkane ring and the heteroaryl of the heteroaryl-fused $(C_5-C_8)$cycloalkane ring is selected from pyrrole, furan, thiophene, imidazole, thiazole, or oxazole.

$L^2$ is a bond, $(C_1-C_6)$alkylene, $(C_2-C_6)$heteroalkylene, oxymethylene, O, $S(O)_k$, $N(R^a)$, $C(O)N(R^b)$, $SO_2N(R^b)$, $(C_1-C_4)$alkylene-$C(O)N(R^b)$, $(C_1-C_4)$alkylene-$N(R^b)C(O)$, $(C_2-C_4)$alkenylene-$C(O)N(R^b)$, $(C_2-C_4)$alkenylene-$N(R^b)C(O)$, $(C_1-C_4)$alkylene-$SO_2N(R^b)$, $(C_1-C_4)$alkylene-$N(R^b)SO_2$, $(C_2-C_4)$alkenylene-$SO_2N(R^b)$, or $(C_2-C_4)$alkenylene-$N(R^b)SO_2$. In some embodiments, $L^2$ is selected from $(C_1-C_6)$alkylene, $(C_2-C_6)$heteroalkylene, oxymethylene, O, or $S(O)_k$. In some embodiments, $L^2$ is selected from —$CH_2$—O—, substituted oxymethylene, or O. In some embodiments, $L^2$ is selected from —CH₂—O— or —CH(CH₃)—O—. In some embodiments, L² is selected from —CH₂—O— or an alkyl-substituted oxymethylene. In certain embodiments, L² is O or S(O)$_k$.

M is an aromatic ring, a heteroaromatic ring, (C₅-C₈)cycloalkylene, aryl(C₁-C₄)alkylene or heteroaryl(C₁-C₄)alkylene. In certain embodiments where M is an aromatic ring, the term aromatic includes aryl. In other embodiments where M is a heteroaromatic ring, the term heteroaromatic includes heteroaryl. In some embodiments, M is an aromatic ring or is a heteroaromatic ring. In certain embodiments, M is a monocyclic aromatic or is a monocyclic heteroaromatic ring. In some embodiments, M is an unsubstituted monocyclic aromatic ring or is an unsubstituted monocyclic heteroaromatic ring. In certain embodiments, M is a substituted benzene ring. In other embodiments, M is an unsubstituted benzene ring. In some embodiments, M is a heteroaromatic ring comprising six ring members. In some such embodiments, the heteroaromatic ring comprises 1 or 2 N atoms. In some such embodiments, the heteroaromatic ring comprises 1 N atom, and in other such embodiments, the heteroaromatic ring comprises 2 N atoms.

X is CR¹R¹', N(R¹''), O, or S(O)$_k$, where the subscript k is 0, 1, or 2. In some embodiments X is a CR¹R¹'.

In certain embodiments, M is a substituted or unsubstituted benzene ring and X is para to L².

L³ is a (C₁-C₅)alkylene, or (C₂-C₅)heteroalkylene. In some embodiments, L³ is a (C₁-C₅)alkylene or is a (C₂-C₅)heteroalkylene. In certain embodiments, L³ is (C₁-C₃)alkylene. In some embodiments, L³ is methylene. In certain embodiments, L³ is a methylene substituted with a monocyclic aryl or monocyclic heteroaryl.

A is —CO₂H, tetrazol-5-yl, —SO₃H, —PO₃H₂, —SO₂NH₂, —C(O)NHSO₂CH₃, —CHO, thiazolidinedionyl, hydroxyphenyl, or pyridyl. In some embodiments, A is —CO₂H, tetrazol-5-yl, —SO₃H, —PO₃H₂, —SO₂NH₂, —C(O)NHSO₂CH₃, thiazolidinedionyl, hydroxyphenyl, or pyridyl In certain embodiments, A is —CO₂H or a salt thereof. In some embodiments, A is —CO₂H or an alkyl ester thereof. In some such embodiments, A is a C₁-C₆ alkyl ester such as a methyl, ethyl, propyl, butyl, pentyl, or hexyl ester.

Rᵃ is hydrogen, (C₁-C₆)alkyl, aryl(C₁-C₃)alkyl, or (C₂-C₆)heteroalkyl. In certain embodiments, Rᵃ is (C₁-C₆)alkyl or (C₂-C₆)heteroalkyl.

Rᵇ is hydrogen, (C₁-C₆)alkyl, or (C₂-C₆)heteroalkyl. R¹ is cyano, aryl, heteroaryl, a heterocycloalkyl, (C₂-C₈)alkenyl, (C₃-C₈)alkenyl, (C₂-C₈)alkynyl, (C₃-C₈)alkynyl, or —C(O)NR²R³. In some embodiments, R¹ is a group other than a group of the following formula:

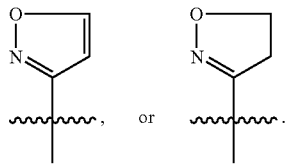

In any of the embodiments described herein, the heterocycle of the heterocycloalkyl R¹ group may be a saturated or unsaturated heterocycle comprising from 5-7 ring members of which from 1-4 are heteroatoms selected from O, S, or N with the balance of the ring members being C. In certain embodiments, R¹ is selected from (C₂-C₈)alkynyl, aryl, heteroaryl, heterocycloalkyl, or —C(O)NR²R³. In some embodiments, R¹ is selected from aryl, heteroaryl, heterocycloalkyl, (C₂-C₈)alkenyl, (C₃-C₈)alkenyl, (C₂-C₈)alkynyl, or (C₃-C₈)alkynyl. In other embodiments, R¹ is selected from heteroaryl or heterocycloalkyl. In some embodiments, R¹ is selected from a substituted or unsubstituted imidazolyl, triazolyl, tetrazolyl, oxazolyl, isoxazolyl, dihydroisoxazolyl, pyrazolyl, pyrrolyl, thiazolyl, thiophenyl, furanyl, thiadiazolyl, pyridyl, or pyrimidinyl. In some such embodiments, R¹ is selected from a substituted or unsubstituted imidazol-2-yl; 1,2,4-triazol-3-yl; 1,2,3-triazol-4-yl; imidazol-5-yl; oxazol-5-yl; isoxazol-3-yl; pyrimidin-5-yl; tetrazol-5-yl; oxazol-2-yl; or dihydroisoxazol-3-yl. In some such embodiments, R¹ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; isoxazol-3-yl; pyrimidin-5-yl; 1-methyl-1H-tetrazol-5-yl; oxazol-2-yl; or 4,5-dihydroisoxazol-3-yl. In certain embodiments, R¹ is selected from the group consisting of prop-1-ynyl, phenyl, or a substituted or unsubstituted imidazolyl, triazolyl, tetrazolyl, oxazolyl, isoxazolyl, dihydroisoxazolyl, pyrazolyl, pyrrolyl, thiazolyl, thiophenyl, furanyl, thiadiazolyl, pyridyl, or pyrimidinyl. In some such embodiments, R¹ is selected from a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl. In some such embodiments, R¹ is selected from a substituted or unsubstituted imidazol-2-yl; 1,2,4-triazol-3-yl; 1,2,3-triazol-4-yl; imidazol-5-yl; oxazol-5-yl; pyrimidin-5-yl; tetrazol-5-yl; or oxazol-2-yl. In some such embodiments, R¹ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; pyrimidin-5-yl; 1-methyl-1H-tetrazol-5-yl; or oxazol-2-yl. In certain embodiments, R¹ is selected from the group consisting of prop-1-ynyl, phenyl, or a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl. In some embodiments, R¹ is a (C₂-C₈)alkenyl or a (C₃-C₈)alkenyl group that may optionally be substituted with groups such as aryl or heteroaryl. For example, in some embodiments, R¹ may be a an alkenyl group such as, but not limited to, the E and Z forms, where applicable, of one of the following: —CH=CH₂, —CH₂—CH=CH₂, —CH=CH—CH₃, —CH₂—CH₂—CH=CH₂, —CH₂—CH=CH—CH₃, —CH=CH—CH₂—CH₃, —C(CH₃)=CH₂, —CH(CH₃)—CH=CH₂, —CH₂—C(CH₃)=CH₂, —CH(CH₃)—CH₂—CH=CH₂, —CH₂—CH(CH₃)—CH=CH₂, —CH₂—CH₂—C(CH₃)=CH₂, —CH(CH₃)—CH=CH—CH₃, —CH₂—C(CH₃)=CH—CH₃, —CH₂—CH=C(CH₃)—CH₃, —C(CH₃)=CH—CH₂—CH₃, —CH=C(CH₃)—CH₂—CH₃, —CH=CH—CH(CH₃)—CH₃. Such R¹ alkenyl groups may optionally be substituted with one or more aryl group such as a benzene. For example, in some embodiments, the R¹ group may be a group such as a —CH=CH—CH₂CH₂-Phenyl group.

R¹' is hydrogen, cyano, aryl, heteroaryl, (C₁-C₈)alkyl, (C₂-C₈)alkenyl, or (C₂-C₈)alkynyl. In some embodiments, R¹' is hydrogen or methyl. In some such embodiments, R¹' is hydrogen.

R¹'' is hydrogen, aryl, heteroaryl, (C₁-C₈)alkyl, (C₂-C₈)alkenyl, (C₂-C₈)alkynyl, or (C₃-C₈)cycloalkyl.

R² and R³ are independently selected from hydrogen, aryl, heteroaryl, (C₁-C₈)alkyl, (C₂-C₈)heteroalkyl, (C₃-C₈)cycloalkyl, or (C₃-C₈)heterocycloalkyl. Optionally, R² and R³ are combined to form a 4-, 5-, 6- or 7-membered ring containing the nitrogen atom to which they are attached comprising from 0 to 2 additional heteroatoms selected from N, O, or S. The ring formed by combining $R^2$ and $R^3$ may be a saturated, unsaturated, or aromatic ring.

The subscript k is, in each instance, independently selected from 0, 1, or 2. In some embodiments, k is 0.

In certain embodiments, the compound of the present invention is a pharmaceutically acceptable salt, solvate, stereoisomer, or prodrug of the compound of formula I; or a tautomer, or a pharmaceutically acceptable salt, solvate, stereoisomer, or prodrug of the tautomer; or a mixture thereof.

In certain embodiments, the present invention provides a compound having the formula II or a pharmaceutically acceptable salt, solvate, stereoisomer, or prodrug thereof; or a tautomer, or a pharmaceutically acceptable salt, solvate, stereoisomer, or prodrug thereof; or a mixture thereof:

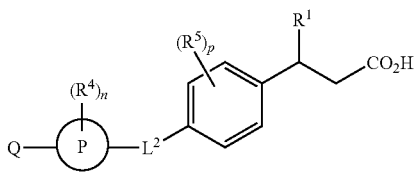

II where Q is selected from hydrogen, aryl, or heteroaryl; $L^2$ is selected from $(C_1\text{-}C_6)$alkylene, $(C_2\text{-}C_6)$heteroalkylene, oxymethylene, O, or $S(O)_k$; $R^1$ is selected from $(C_2\text{-}C_8)$alkynyl, aryl, heteroaryl, heterocycloalkyl, or —$C(O)NR^2R^3$; $R^2$ and $R^3$ are independently selected from hydrogen or $(C_1\text{-}C_4)$ alkyl; $R^4$ is independently selected from substituted $(C_1\text{-}C_6)$ alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R"', —NR'-SO$_2$NR"R"', —NR"CO$_2$R', —NH—C(NH$_2$)=NH, —NR'C(NH$_2$)=NH, —NH—C(NH$_2$)=NR', —SiR'R"R"', —S(O)R', —SO$_2$R', —SO$_2$NR'R", —NR"SO$_2$R, —CN, —(C$_2$-C$_5$)alkynyl, —(C$_2$-C$_5$)alkenyl, or —NO$_2$, where R', R" and R"' each independently refer to hydrogen, unsubstituted $(C_1\text{-}C_8)$alkyl or heteroalkyl, unsubstituted aryl, aryl substituted with one to three halogens, unsubstituted alkyl, alkoxy or thioalkoxy groups, halo$(C_1\text{-}C_4)$alkyl, or aryl-$(C_1\text{-}C_4)$alkyl groups; $R^5$ is independently selected from $(C_1\text{-}C_6)$alkyl, halogen, $(C_1\text{-}C_6)$alkoxy, cyano, or nitro; the subscript k is 0, 1, or 2; the subscript n is 0, 1, 2, 3, 4, 5, 6, 7, 8, 9, 10, 11, 12, 13, or 14; and the subscript p is 0, 1, 2, 3, or 4. In some such embodiments, $R^4$ is independently selected from $(C_1\text{-}C_6)$alkyl, halogen, $(C_1\text{-}C_6)$alkoxy, cyano, or nitro. In certain embodiments,

is a benzo-fused $(C_5\text{-}C_8)$cycloalkane ring selected from substituted or unsubstituted dihydroindene, tetrahydronaphthalene, tetrahydrobenzo[7]annulene, or hexahydrobenzo[8]annulene. In certain embodiments, $R^1$ is selected from 1-propynyl, substituted or unsubstituted phenyl, heteroaryl, or heterocycloalkyl. In some such embodiments, $R^1$ is selected from substituted or unsubstituted heteroaryl, or heterocycloalkyl. In some such embodiments, $R^1$ is selected from a substituted or unsubstituted imidazolyl, triazolyl, tetrazolyl, oxazolyl, isoxazolyl, dihydroisoxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; isoxazol-3-yl; pyrimidin-5-yl; tetrazol-5-yl; oxazol-2-yl; or dihydroisoxazol-3-yl. In some such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; isoxazol-3-yl; pyrimidin-5-yl; 1-methyl-1H-tetrazol-5-yl; oxazol-2-yl; or 4,5-dihydroisoxazol-3-yl. In some such embodiments, $R^1$ is selected from a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; pyrimidin-5-yl; tetrazol-5-yl; or oxazol-2-yl. In some such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; pyrimidin-5-yl; 1-methyl-1H-tetrazol-5-yl; or oxazol-2-yl. In certain embodiments, the subscript p is 0.

It will be apparent that, in certain embodiments of formula II, the carbon with a bond to $R^1$ is a chiral carbon. Thus, in certain embodiments, the present invention provides a compound having formula IIIA or IIIB or a pharmaceutically acceptable salt, solvate, or prodrug thereof or a tautomer, or a pharmaceutically acceptable salt, solvate, or prodrug thereof; or a mixture thereof:

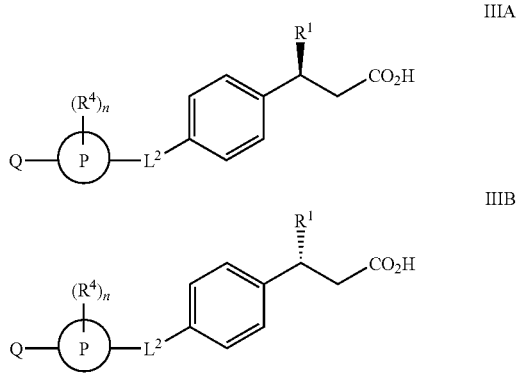

where the variables can have any of the values in any of the embodiments described above.

In some embodiments, the compound of formula II comprises a stereomerically pure S-enantiomer. In other embodiments, the compound of formula II comprises a stereomerically pure R-enantiomer. In yet other embodiments, the compound of formula II comprises a mixture of S- and R-enantiomers.

In certain embodiments, the compound of the present invention is a pharmaceutically acceptable salt, solvate, stereoisomer, or prodrug of the compound of formula II; or a tautomer, or a pharmaceutically acceptable salt, solvate, stereoisomer, or prodrug thereof; or a mixture thereof.

In some embodiments of formula II, IIIA, and IIIB, the hydrogen on the carboxylic group in formula II is replaced with an alkyl group to form an ester. For example, the compound of the present invention can be a methyl or ethyl ester of the compound of formula II.

In certain embodiments of the compound of formula I, the compound has the formula IV or is a pharmaceutically acceptable salt, solvate, stereoisomer, or prodrug thereof; or a tautomer, or a pharmaceutically acceptable salt, solvate, stereoisomer, or prodrug thereof; or a mixture thereof:

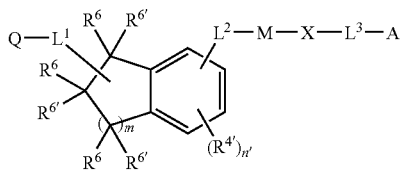

IV where $R^{4'}$ is independently selected from substituted ($C_1$-$C_6$) alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R''', —NR'—SO$_2$NR"R''', —NR"CO$_2$R', —NH—C(NH$_2$)=NH, —NR'C(NH$_2$)=NH, —NH—C(NH$_2$)=NR', —SiR'R"R''', —S(O)R', —SO$_2$R', —SO$_2$NR'R", —NR"SO$_2$R, —CN, —(C$_2$-C$_5$)alkynyl, —(C$_2$-C$_5$)alkenyl, or —NO$_2$, where R', R" and R''' each independently refer to hydrogen, unsubstituted (C$_1$-C$_8$)alkyl or heteroalkyl, unsubstituted aryl, aryl substituted with one to three halogens, unsubstituted alkyl, alkoxy or thioalkoxy groups, halo(C$_1$-C$_4$)alkyl, or aryl-(C$_1$-C$_4$)alkyl groups; one of $R^6$ and $R^{6'}$ is $L^1$ or Q, if $L^1$ is a bond, and the others of $R^6$ and $R^{6'}$ are independently selected from H, (C$_1$-C$_6$)alkyl, halogen, (C$_1$-C$_6$) alkoxy, cyano, or nitro, or one of $R^6$ and one of $R^{6'}$ on adjacent or non-adjacent carbon atoms, or on the same carbon atom, may join together to form a C$_5$-C$_8$ cycloalkane ring, or two of $R^6$ or two of $R^{6'}$, on adjacent or non-adjacent carbon atoms, may join together to form a C$_5$-C$_8$ cycloalkane ring; the subscript n' is 0, 1, 2, or 3; and the subscript m is 1, 2, 3, or 4.

In some embodiments, the compound of formula IV comprises a stereomerically pure S-enantiomer. In other embodiments, the compound of formula IV comprises a stereomerically pure R-enantiomer. In yet other embodiments, the compound of formula IV comprises a mixture of S- and R-enantiomers.

In some embodiments, the compound of formula IV has the formula V:

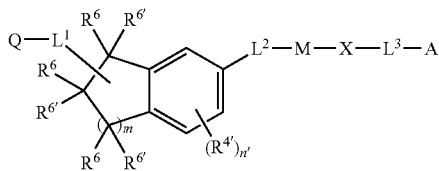

V or is a pharmaceutically acceptable salt, solvate, stereoisomer or prodrug thereof; or a tautomer, or a pharmaceutically acceptable salt, solvate, stereoisomer, or prodrug thereof; or a mixture thereof.

In some embodiments, the compound of formula IV or V, the compound has the formula VI:

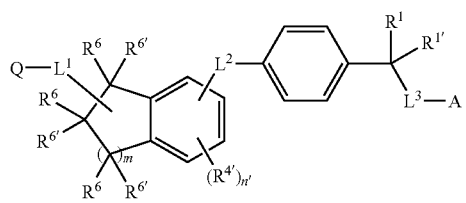

VI or is a pharmaceutically acceptable salt, solvate, stereoisomer or prodrug thereof; or a tautomer, or a pharmaceutically acceptable salt, solvate, stereoisomer, or prodrug thereof; or a mixture thereof.

It will be apparent that, in certain embodiments of formula VI, the carbon with a bond to $R^1$ is a chiral carbon. Thus, in certain embodiments, the present invention provides a compound having formula VIA or VIB or a pharmaceutically acceptable salt, solvate, or prodrug thereof or a tautomer, or a pharmaceutically acceptable salt, solvate, or prodrug thereof; or a mixture thereof:

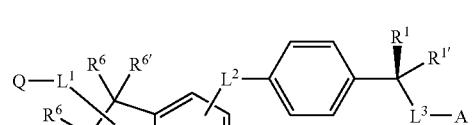

VIA

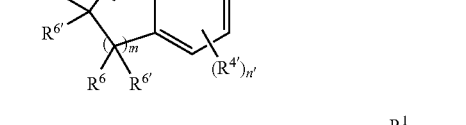

VIB

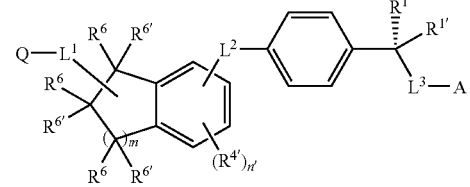

where the variables can have any of the values in any of the embodiments described above.

In some embodiments, the compound of formula VI comprises a stereomerically pure S-enantiomer. In other embodiments, the compound of formula VI comprises a stereomerically pure R-enantiomer. In yet other embodiments, the compound of formula VI comprises a mixture of S- and R-enantiomers.

In certain embodiments, the compound of the present invention is a pharmaceutically acceptable salt, solvate, stereoisomer, or prodrug of the compound of formula II; or a tautomer, or a pharmaceutically acceptable salt, solvate, stereoisomer, or prodrug thereof; or a mixture thereof.

In some embodiments of formula IV, V, VI, VIA, and VIB, A is —CO$_2$H or is a salt thereof. In some embodiments, the hydrogen on the carboxylic group of A is replaced with an alkyl group to form an ester. For example, the compound of the present invention can be a methyl or ethyl ester of the compound of formula IV, V, VI, VIA, or VIB.

In some embodiments of the compounds of formula IV, V, VI, VIA, and VIB, the subscript m is 1 or 2.

In some embodiments of the compounds of formula IV, V, VI, VIA, and VIB, the subscript m is 1 or 2; the subscript n' is 0; $L^1$ is a bond; $L^2$ is selected from —CH$_2$—O—, substituted oxymethylene, or O; $R^1$ is selected from aryl, heteroaryl, heterocycloalkyl, (C$_2$-C$_8$)alkenyl, (C$_3$-C$_8$)alkenyl, (C$_2$-C$_8$) alkynyl, or (C$_3$-C$_8$)alkynyl; $R^{1'}$ is H; and A is —CO$_2$H.

In some embodiments of the compounds of formula IV, V, VI, VIA, and VIB, Q is H; $L^3$ is CH$_2$; and $L^2$ is —CH$_2$—O— or —CH(CH$_3$)—O—.

In some embodiments of the compounds of formula IV, V, VI, VIA, and VIB, $R^6$ and $R^{6'}$ are independently selected from H and (C$_1$-C$_6$)alkyl and at least two of $R^6$ and $R^{6'}$ are (C$_1$-C$_6$) alkyl. In some such embodiments, $R^6$ and $R^{6'}$ are independently selected from H and methyl and at least two of $R^6$ and $R^{6'}$ are methyl groups. In some such embodiments, two of $R^6$ and $R^{6'}$ are methyl groups. In some embodiments, $R^6$ and $R^{6'}$ are independently selected from H and methyl and at least four of $R^6$ and $R^{6'}$ are methyl groups. In some such embodiments, $R^6$ and $R^{6'}$ are independently selected from H and methyl and four of $R^6$ and $R^{6'}$ are methyl groups.

In some embodiments of the compounds of formula I, II, III, IIIA, IIIB, IV, V, VI, VIA, and VIB, $R^1$ is selected from heteroaryl or heterocycloalkyl. In some such embodiments, $R^1$ is selected from a substituted or unsubstituted imidazolyl, triazolyl, tetrazolyl, oxazolyl, isoxazolyl, dihydroisoxazolyl, pyrazolyl, pyrrolyl, thiazolyl, thiophenyl, furanyl, thiadiazolyl, pyridyl, or pyrimidinyl. In certain such embodiments, $R^1$ is selected from a substituted or unsubstituted imidazol-2-yl; 1,2,4-triazol-3-yl; 1,2,3-triazol-4-yl; imidazol-5-yl; oxazol-5-yl; isoxazol-3-yl; pyrimidin-5-yl; tetrazol-5-yl; oxazol-2-yl; or dihydroisoxazol-3-yl. In still further such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; isoxazol-3-yl; pyrimidin-5-yl; 1-methyl-1H-tetrazol-5-yl; oxazol-2-yl; or 4,5-dihydroisoxazol-3-yl. In some such embodiments, $R^1$ is selected from a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl. In certain such embodiments, $R^1$ is selected from a substituted or unsubstituted imidazol-2-yl; 1,2,4-triazol-3-yl; 1,2,3-triazol-4-yl; imidazol-5-yl; oxazol-5-yl; pyrimidin-5-yl; tetrazol-5-yl; or oxazol-2-yl. In still further such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; pyrimidin-5-yl; 1-methyl-1H-tetrazol-5-yl; or oxazol-2-yl.

In certain embodiments, the compound has the formula VIIA, VIIB, VIIC, or VIID:

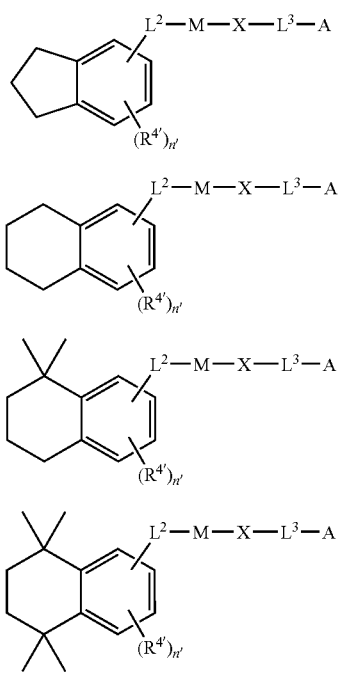

or a pharmaceutically acceptable salt, solvate, or prodrug thereof; or a tautomer or a pharmaceutically acceptable salt, solvate, or prodrug thereof; or a mixture thereof.

In certain embodiments, the compound of formula VIIA, VIIB, VIIC, or VIID, has the formula VIIIA, VIIIB, VIIIC, or VIIID:

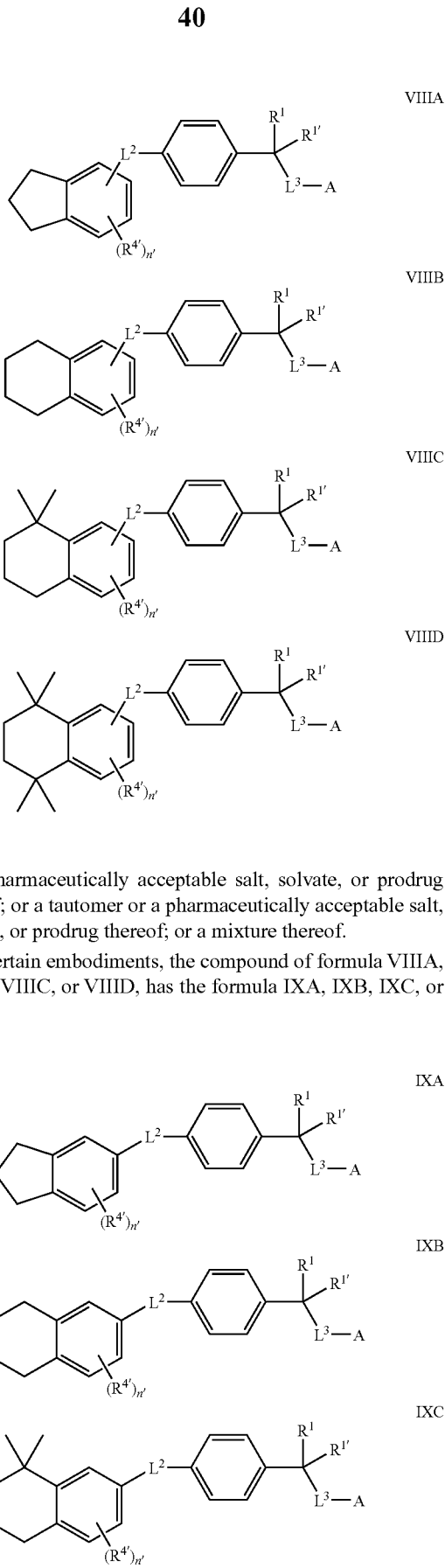

or a pharmaceutically acceptable salt, solvate, or prodrug thereof; or a tautomer or a pharmaceutically acceptable salt, solvate, or prodrug thereof; or a mixture thereof.

In certain embodiments, the compound of formula VIIIA, VIIIB, VIIIC, or VIIID, has the formula IXA, IXB, IXC, or IXD:

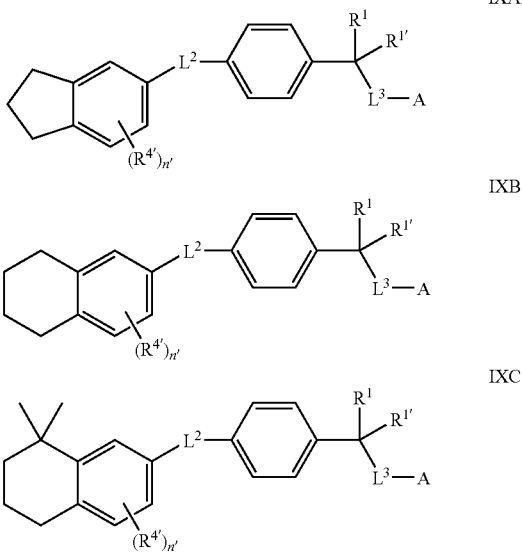

-continued

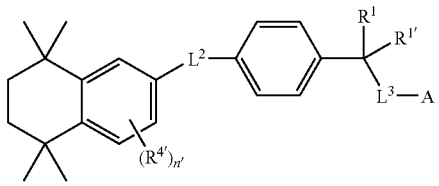
IXD

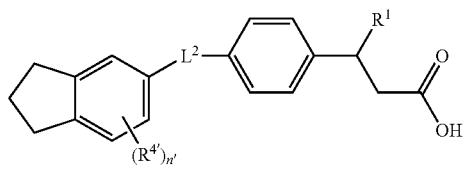
XA

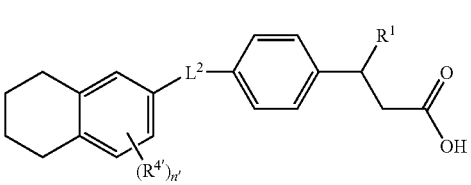
XB

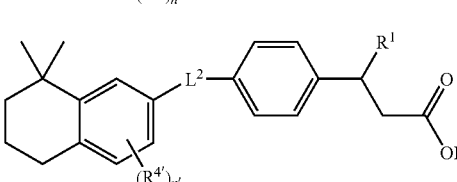
XC

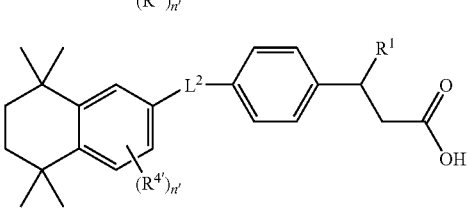
XD or a pharmaceutically acceptable salt, solvate, or prodrug thereof; or a tautomer or a pharmaceutically acceptable salt, solvate, or prodrug thereof; or a mixture thereof.

In certain embodiments of the compound of formula VIIA, VIIB, VIIC, VIID, VIIIA, VIIIB, VIIIC, VIIID, IXA, IXB, IXC, or IXD, $L^2$ is —$CH_2$—O— or an alkyl-substituted oxymethylene; the subscript n' is 0; $R^1$ is $(C_2-C_3)$alkynyl, heteroaryl, or heterocycloalkyl; $R^{1'}$ is H; and A is —$CO_2H$. In some such embodiments, $R^1$ is selected from a substituted or unsubstituted imidazolyl, triazolyl, tetrazolyl, oxazolyl, isoxazolyl, dihydroisoxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; isoxazol-3-yl; pyrimidin-5-yl; tetrazol-5-yl; oxazol-2-yl; or dihydroisoxazol-3-yl. In still further such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; isoxazol-3-yl; pyrimidin-5-yl; 1-methyl-1H-tetrazol-5-yl; oxazol-2-yl; or 4,5-dihydroisoxazol-3-yl. In some such embodiments, $R^1$ is selected from a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; pyrimidin-5-yl; tetrazol-5-yl; or oxazol-2-yl. In still further such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; pyrimidin-5-yl; 1-methyl-1H-tetrazol-5-yl; or oxazol-2-yl. In some embodiments, the compound is a compound of formula VIIA. In some embodiments, the compound is of formula VIIB. In some embodiments, the compound is a compound of formula VIIC. In some embodiments, the compound is a compound of formula VIID. In some embodiments, the compound is a compound of formula VIIIA. In some embodiments, the compound is a compound of formula VIIIB. In some embodiments, the compound is a compound of formula VIIIC. In some embodiments, the compound is a compound of formula VIIID. In some embodiments, the compound is a compound of formula IXA. In some embodiments, the compound is a compound of formula IXB. In some embodiments, the compound is a compound of formula IXC. In some embodiments, the compound is a compound of formula IXD.

In certain embodiments, the compound of formula IXA, IXB, IXC, or IXD, has the formula XA, XB, XC, or XD:

or a pharmaceutically acceptable salt, solvate, or prodrug thereof; or a tautomer or a pharmaceutically acceptable salt, solvate, or prodrug thereof; or a mixture thereof.

In certain embodiments of the compound of formula XA, XB, XC, or XD, $L^2$ is —$CH_2$—O— or an alkyl-substituted oxymethylene; the subscript n' is 0; $R^1$ is $(C_2-C_3)$alkynyl, heteroaryl, or heterocycloalkyl; and $R^{1'}$ is H. In some such embodiments, $R^1$ is selected from a substituted or unsubstituted imidazolyl, triazolyl, tetrazolyl, oxazolyl, isoxazolyl, dihydroisoxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; isoxazol-3-yl; pyrimidin-5-yl; tetrazol-5-yl; oxazol-2-yl; or dihydroisoxazol-3-yl. In still further such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; isoxazol-3-yl; pyrimidin-5-yl; 1-methyl-1H-tetrazol-5-yl; oxazol-2-yl; or 4,5-dihydroisoxazol-3-yl. In some such embodiments, $R^1$ is selected from a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl. In some such embodiments, $R^1$ is selected from a substituted or unsubstituted imidazol-2-yl; 1,2,4-triazol-3-yl; 1,2,3-triazol-4-yl; imidazol-5-yl; oxazol-5-yl; pyrimidin-5-yl; tetrazol-5-yl; or oxazol-2-yl. In still further such embodiments, $R^1$ is selected from a substituted or unsubstituted 1-methyl-1H-imidazol-2-yl; 2-methyl-2H-1,2,4-triazol-3-yl; 4-methyl-4H-1,2,4-triazol-3-yl; 3-methyl-3H-1,2,3-triazol-4-yl; 1-methyl-1H-imidazol-5-yl; oxazol-5-yl; pyrimidin-5-yl; 1-methyl-1H-tetrazol-5-yl; or oxazol-2-yl. In some embodiments, the compound is a compound of formula XA. In some embodiments, the compound is a compound of formula XB. In some embodiments, the compound is a compound of formula XC. In some embodiments, the compound is a compound of formula XD.

In certain embodiments of the compound of formula I, the compound has the formula of any one of XIa-XIm or is a pharmaceutically acceptable salt, solvate, stereoisomer, or prodrug thereof; or a tautomer, or a pharmaceutically acceptable salt, solvate, stereoisomer, or prodrug thereof; or a mixture thereof:

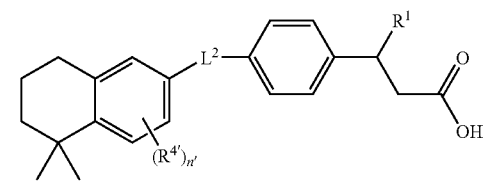
XIa

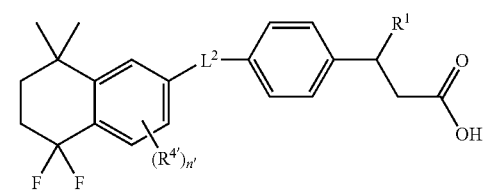
XIb

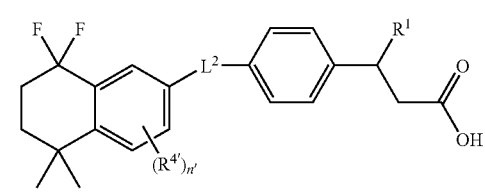
XIc

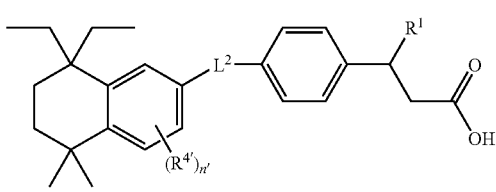
XId

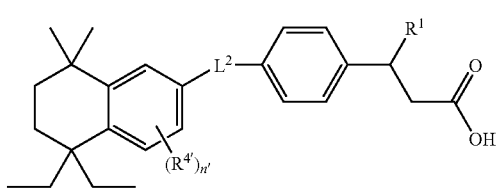
XIe

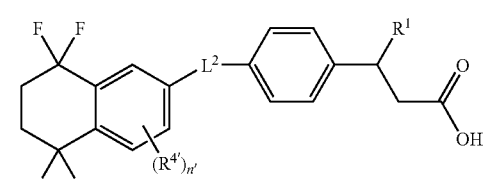
XIf

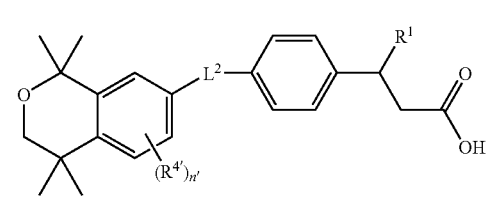
XIg

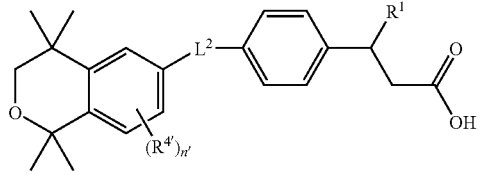
XIh

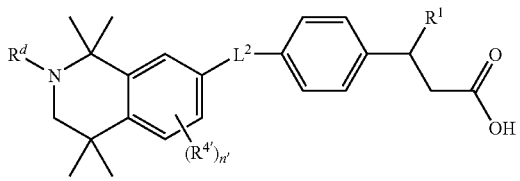
XIi

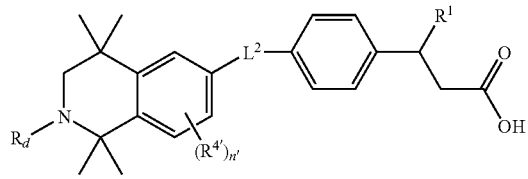
XIj

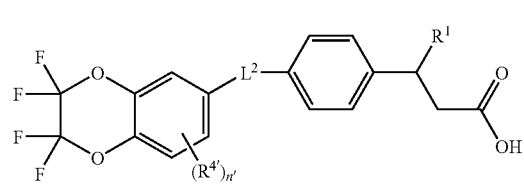
XIk

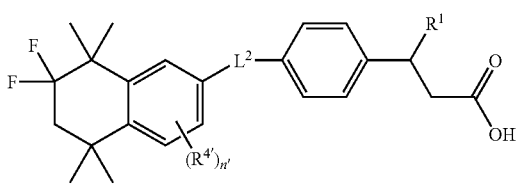
XIl

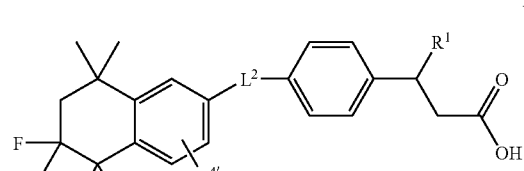
XIm where $R^{4'}$ is independently selected from substituted ($C_1$-$C_6$) alkyl, —R', —OR', =O, =NR', =N—OR', —NR'R", —SR', halogen, —OC(O)R', —C(O)R', —CO$_2$R', —CONR"R''', —OC(O)NR'R", —NR"C(O)R', —NR'—C(O)NR"R''', —NR'—SO$_2$NR"R''', —NR"CO$_2$R', —NH—C(NH$_2$)=NH, —NR'C(NH$_2$)=NH, —NH—C(NH$_2$)=NR', —SiR'R"R''', —S(O)R', —SO$_2$R', —SO$_2$NR'R", —NR"SO$_2$R, —CN, —(C$_2$-C$_5$)alkynyl, —(C$_2$-C$_5$)alkenyl, or —NO$_2$, where R', R" and R''' each independently refer to hydrogen, unsubstituted (C$_1$-C$_8$)alkyl or heteroalkyl, unsubstituted aryl, aryl substituted with one to three halogens, unsubstituted alkyl, alkoxy or thioalkoxy groups, halo(C$_1$-C$_4$)alkyl, or aryl-C$_4$)alkyl groups; the subscript n' is 0, 1, 2, or 3; and $R^d$ is selected from optionally substituted C$_1$-C$_6$ alkyl or optionally substituted aryl.

In some embodiments, the compound of any one of formula XIa-XIm comprises a stereomerically pure S-enantiomer. In other embodiments, the compound comprises a stereomerically pure R-enantiomer. In yet other embodiments, the compound comprises a mixture of S- and R-enantiomers.

In certain embodiments of the compound of formula I, the compound has the formula of any one of XIIa-XIIm or is a pharmaceutically acceptable salt, solvate, stereoisomer, or prodrug thereof; or a tautomer, or a pharmaceutically acceptable salt, solvate, stereoisomer, or prodrug thereof; or a mixture thereof:

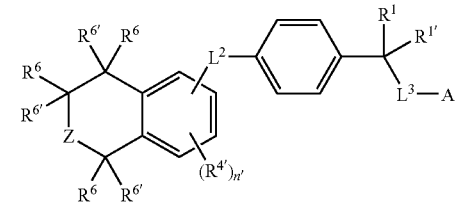

XIIa

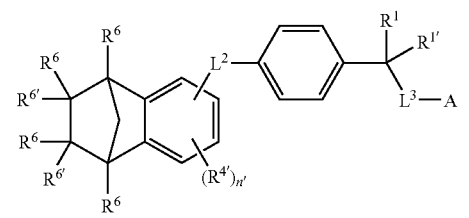

XIIb

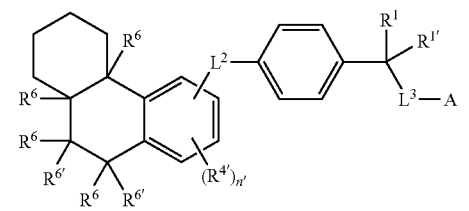

XIIc

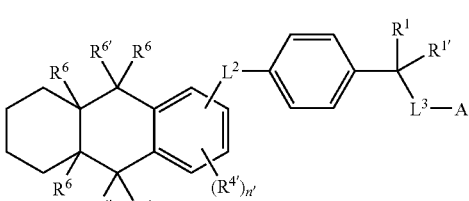

XIId

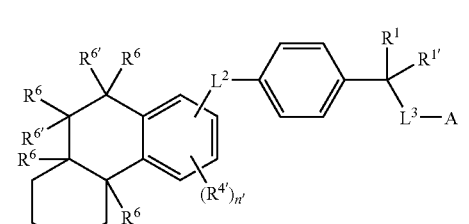

XIIe

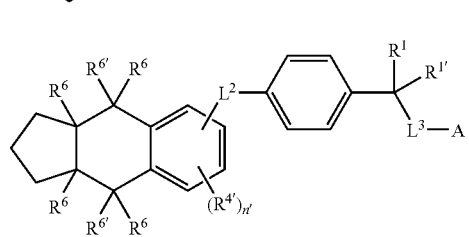

XIIf

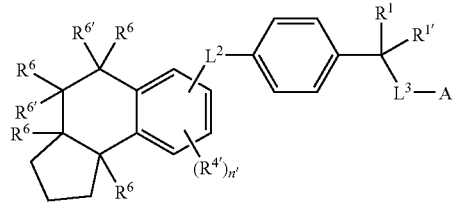

XIIg

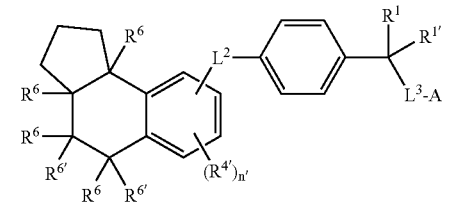

XIIh

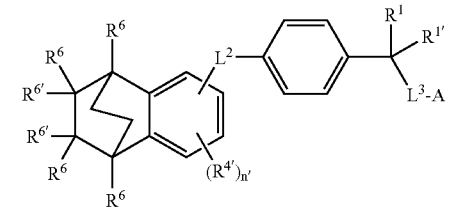

XIIi

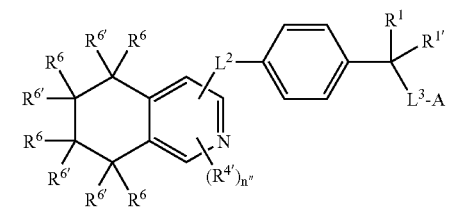

XIIj

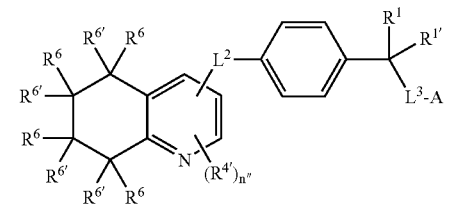

XIIk

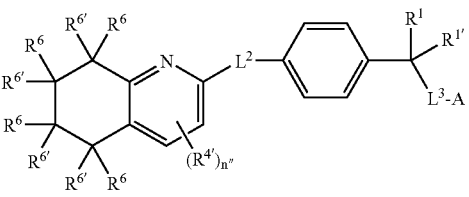

XIIl

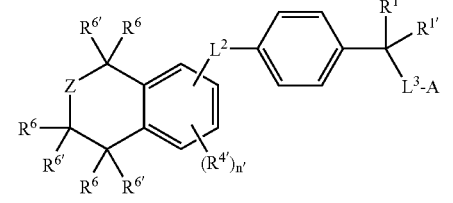

XIIm where $R^{4'}$ is independently selected from substituted ($C_1$-$C_6$) alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)

NR"R'", —NR'—SO$_2$NR"R'", —NR"CO$_2$R', —NH—C(NH$_2$)=NH, —NR'C(NH$_2$)=NH, —NH—C(NH$_2$)=NR', —SiR'R"R'", —S(O)R', —SO$_2$R', —SO$_2$NR"R", —NR"SO$_2$R, —CN, —(C$_2$-C$_5$)alkynyl, —(C$_2$-C$_5$)alkenyl, or —NO$_2$, where R', R" and R'" each independently refer to hydrogen, unsubstituted (C$_1$-C$_8$)alkyl or heteroalkyl, unsubstituted aryl, aryl substituted with one to three halogens, unsubstituted alkyl, alkoxy or thioalkoxy groups, halo(C$_1$-C$_4$)alkyl, or aryl-(C$_1$-C$_4$)alkyl groups; R$^6$ and R$^{6'}$ are independently selected from H, (C$_1$-C$_6$)alkyl, halogen, (C$_1$-C$_6$) alkoxy, cyano, or nitro; Z is selected from O, NR$^d$, or S; R$^d$ is selected from optionally substituted C$_1$-C$_6$ alkyl or optionally substituted aryl; the subscript n' is 0, 1, 2, or 3; and the subscript n" is 0, 1, or 2.

In some embodiments, the compound of any one of formula XIIa-XIIm comprises a stereomerically pure S-enantiomer. In other embodiments, the compound comprises a stereomerically pure R-enantiomer. In yet other embodiments, the compound comprises a mixture of S- and R-enantiomers.

5.2.2 Preparation of the Compounds

The compounds of the invention can be prepared by a variety of synthetic or semisynthetic techniques. Scheme 1 provides a general synthetic scheme for exemplary compounds of the invention utilizing ester A where the variables Q, L$^1$, P, R$^4$, n, and R$^1$ have any of the values described above with respect to any of the embodiments, W is a OH or a halogen such as, but not limited to a Cl, Br, or I, and Alk is a straight or branched chain alkyl group having from 1-8 carbon atoms. It will be understood that the phenolic OH group of A can be replaced with an SH and reacted with a compound where W is a halogen to produce the analogous S-containing derivative to the compounds shown. The methods and examples provided below provide syntheses of A bearing different exemplary R$^1$ groups. Additional examples for the synthesis of esters of formula A are described in described in WO 2005/086661 and US 2006/0004012 which are both hereby incorporated by reference in their entireties and for all purposes as if fully set forth herein. Further relevant synthetic routes for related compounds are also described in WO 2005/086661 and US 2006/0004012. Appropriate starting materials can be prepared by techniques known or apparent to those of skill in the art or the starting materials may be commercially available. One of skill in the art will understand that the synthetic routes can be modified to use different starting materials or alternative reagents and that suitable adjustments in conditions (e.g., temperatures, solvents, etc.) can be made to accomplish the desired transformations. Additionally, one of skill in the art will recognize that protecting groups may be necessary for the preparation of certain compounds and will be aware of those conditions compatible with a selected protecting group. Examples of such protecting groups include, for example, those set forth in Protective Groups in Organic Synthesis, Greene, T. W.; Wuts, P. G. M., John Wiley & Sons, New York, N.Y., (3rd Edition, 1999). Accordingly, the exemplary methods and the examples described herein are illustrative of the present invention and are not to be construed as limiting the scope thereof.

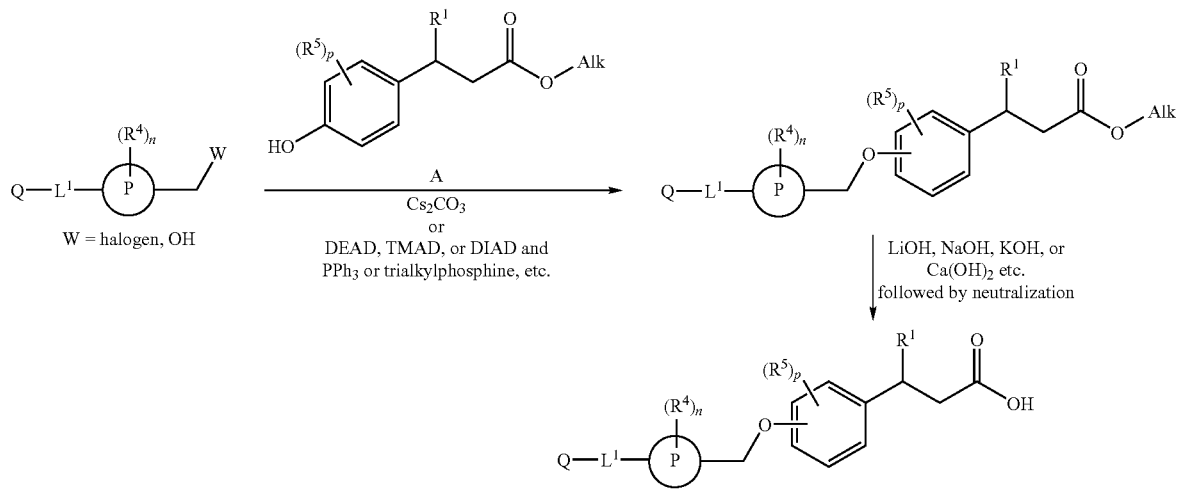

Scheme 1

Scheme 2 shows a general synthetic route that can be used to prepare compounds of formula XV and XVI, and salts thereof. In the compound of formula XIII and XV, Alk is a straight or branched chain alkyl group having from 1 to 8 carbon atoms. Examples of such groups include methyl, ethyl, propyl, butyl, pentyl, hexyl, heptyl, octyl, i-propyl, s-butyl, t-butyl groups, and the like. In some embodiments, Alk is a methyl or ethyl group. In the compounds of formula XIII, XV and XVI, R$^1$ is any of the R$^1$ groups described herein. For example, R$^1$ may be selected from cyano, aryl, heteroaryl, heterocycloalkyl, (C$_2$-C$_8$)alkenyl, (C$_3$-C$_8$)alkenyl, (C$_2$-C$_8$)alkynyl, (C$_3$-C$_8$)alkynyl, or —C(O)NR$^2$R$^3$ where R$^2$ and R$^3$ have the same values as set forth with respect to any of the compounds of any of the embodiments set forth herein. In the compounds of formula XIII, XV and XVI, R$^5$ is independently selected from (C$_1$-C$_6$)alkyl, halogen, (C$_1$-C$_6$) alkoxy, cyano, or nitro, and p is selected from 0, 1, 2, 3, or 4. In the compounds of formula XIII, XIV, XV, and XVI, R$^{4'}$ is independently selected from substituted (C$_1$-C$_6$)alkyl, —R', —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R'", —NR'—SO$_2$NR"R'", —NR"CO$_2$R', —NH—C(NH$_2$)=NH, —NR'C(NH$_2$)=NH, —NH—C(NH$_2$)=NR', —SiR'R"R'", —S(O)R', —SO$_2$R', —SO$_2$NR'R", —NR"SO$_2$R, —CN, —(C$_2$-C$_5$) alkynyl, —(C$_2$-C$_5$)alkenyl, or —NO$_2$, where R', R" and R'"

are each independently selected from hydrogen, unsubstituted ($C_1$-$C_8$)alkyl or heteroalkyl, unsubstituted aryl, aryl substituted with one to three halogens, unsubstituted alkyl, alkoxy or thioalkoxy groups, halo($C_1$-$C_4$)alkyl, or aryl-($C_1$-$C_4$)alkyl groups; m is selected from 1, 2, 3, or 4; n' is selected from 0, 1, 2, or 3; one of $R^6$ and $R^{6'}$ is $L^1$ or Q, if $L^1$ is a bond, and the others of $R^6$ and $R^{6'}$ are independently selected from H, ($C_1$-$C_6$)alkyl, halogen, ($C_1$-$C_6$)alkoxy, cyano, or nitro, wherein one of $R^6$ and one of $R^{6'}$ on adjacent or non-adjacent carbon atoms, or on the same carbon atom may join together to form a $C_5$-$C_8$ cycloalkane ring, or two of $R^6$ or two of $R^{6'}$, on adjacent or non-adjacent carbon atoms, may join together to form a $C_5$-$C_8$ cycloalkane ring, z is selected from 1, 2, or 3, $L^1$ is selected from a bond, ($C_1$-$C_4$)alkylene, ($C_2$-$C_4$)heteroalkylene, O, $S(O)_k$, $N(R^a)$, $C(O)$—($C_5$-$C_7$)heterocycloalkylene, ($C_1$-$C_4$)alkylene-$SO_2N(R^b)$, ($C_1$-$C_4$)alkylene-N($R^b$)$SO_2$, or $C(O)N(R^b)$, $R^a$ is selected from hydrogen, ($C_1$-$C_6$)alkyl, aryl($C_1$-$C_3$)alkyl, or ($C_2$-$C_6$)heteroalkyl, $R^b$ is selected from hydrogen, ($C_1$-$C_6$)alkyl, or ($C_2$-$C_6$)heteroalkyl, and Q is selected from hydrogen, aryl, heteroaryl, ($C_1$-$C_6$)alkyl, or ($C_2$-$C_6$)heteroalkyl. In the compound of formula XIV, W represents a leaving group such as a halogen like Br or Cl or OH. Coupling of a compound of formula XIV with a compound of formula XIII may be accomplished using different procedures. For example, when W is a halogen such as Br, Cl, or I (conveniently synthesized from the other two using the Finkelstein reaction as known to those skilled in the art), then a compound of formula XIII may be coupled with a compound of formula XIV by reacting the two in the presence of any appropriate base such as, but not limited to, $Cs_2CO_3$ in an appropriate solvent such as, but not limited to DMF. When W is an OH, then a compound of formula XIII may be coupled with a compound of formula XIV using an azodicarboxylate such as DEAD, TMAD, or DIAD in combination with a suitable phosphine such as a trialkylphosphine, a triarylphosphine, an alkyldiarylphosphine, or a dialkylarylphosphine. This highly flexible approach allows a large number of compounds of formula XV to be synthesized and then converted to compounds of formula XVI by removal of the ester functionality. Conversion of a compound of formula XV to a compound of formula XVI may be accomplished by reacting the compound of formula XV with a base such as a metal hydroxide base such as, but not limited to, LiOH, NaOH, KOH, Ca(OH)$_2$, or the like. Those skilled in the art will recognize that the carbon atom bonded to $R^1$ in compounds of formula XIII, XV, and XVI is a chiral center. In accordance with the method described above, XIII, XV, and XVI may be a mixture of the R and S enantiomers, may be the R enantiomer, or may be the S enantiomer. Therefore, in some embodiments each of the compounds of formula XIII, XV, and XVI are a mixture of the R and S enantiomers. In other embodiments, each of the compounds of formula XIII, XV, and XVI are the R enantiomer. In other embodiments, each of the compounds of formula XIII, XV, and XVI are the R enantiomer.

Scheme 2

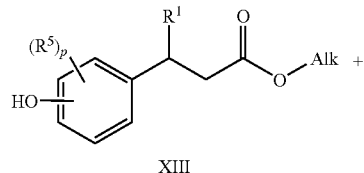

XIII

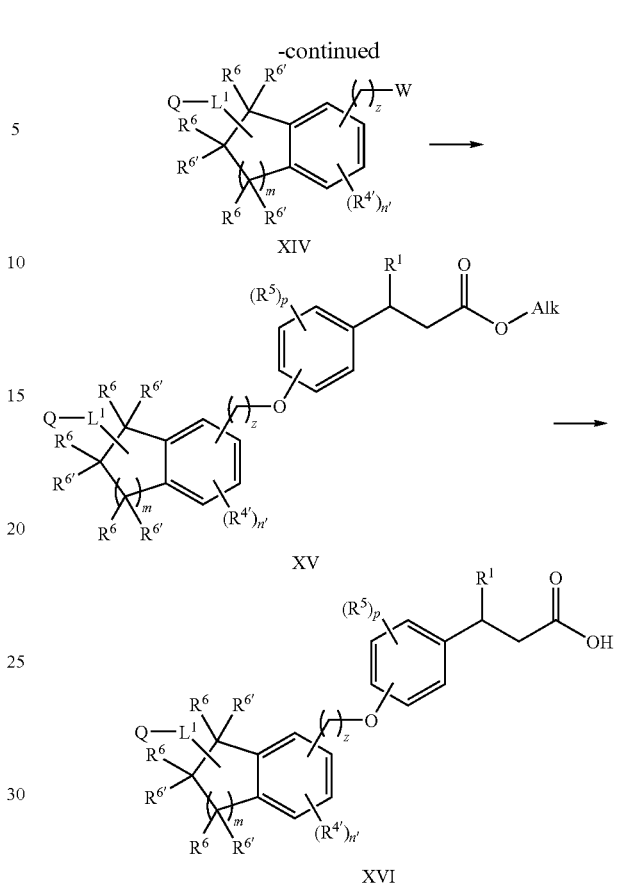

In one aspect, the invention provides a method of synthesizing a compound of formula XV as shown in Scheme 2. The method includes: reacting a compound of formula XIII with a compound of formula XIV to produce the compound of formula XV, wherein the compounds of formula XIII, XIV, and XV have the following structures:

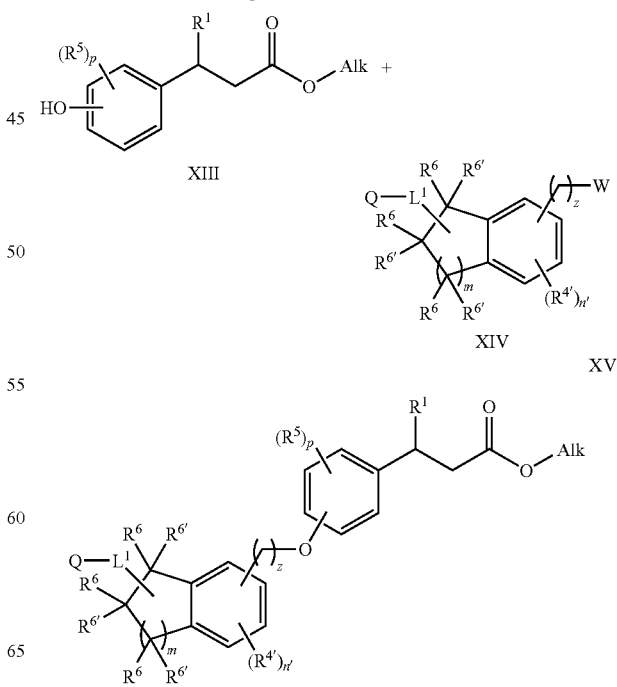

wherein, Alk is a straight or branched chain alkyl group having from 1 to 8 carbon atoms; $R^1$ is selected from cyano, aryl, heteroaryl, heterocycloalkyl, $(C_2-C_8)$alkenyl, $(C_3-C_8)$alkenyl, $(C_2-C_8)$alkynyl, $(C_3-C_8)$alkynyl, or $-C(O)NR^2R^3$; $R^2$ and $R^3$ are independently selected from hydrogen, aryl, heteroaryl, $(C_1-C_8)$alkyl, $(C_2-C_8)$heteroalkyl, $(C_3-C_8)$cycloalkyl, or $(C_3-C_8)$heterocycloalkyl; optionally, $R^2$ and $R^3$ are combined to form a 4-, 5-, 6- or 7-membered ring containing the nitrogen atom to which they are attached comprising from 0 to 2 additional heteroatoms selected from N, O, or S; and; $R^5$ is independently selected from $(C_1-C_6)$alkyl, halogen, $(C_1-C_6)$alkoxy, cyano, or nitro; p is selected from 0, 1, 2, 3, or 4; z is selected from 1, 2, or 3; $R^{4'}$ is independently selected from substituted $(C_1-C_6)$alkyl, —R', —OR', =O, =NR', =N—OR', —NR'R'', —SR', halogen, —OC(O)R', —C(O)R', —CO$_2$R', —CONR'R'', —OC(O)NR'R'', —NR''C(O)R', —NR'—C(O)NR''R''', —NR'—SO$_2$NR''R''', —NR''CO$_2$R', —NH—C(NH$_2$)=NH, —NR'C(NH$_2$)=NH, —NH—C(NH$_2$)=NR', —SiR'R''R''', —S(O)R', —SO$_2$R', —SO$_2$NR'R'', —NR''SO$_2$R, —CN, —(C$_2$-C$_5$)alkynyl, —(C$_2$-C$_5$)alkenyl, or —NO$_2$, wherein R', R'' and R''' are each independently selected from hydrogen, unsubstituted $(C_1-C_8)$alkyl or heteroalkyl, unsubstituted aryl, aryl substituted with one to three halogens, unsubstituted alkyl, alkoxy or thioalkoxy groups, halo$(C_1-C_4)$alkyl, or aryl-$(C_1-C_4)$alkyl groups; n' is 0, 1, 2, or 3; m is 1, 2, 3, or 4; one of $R^6$ and $R^{6'}$ is $L^1$ or Q, if $L^1$ is a bond, and the others of $R^6$ and $R^{6'}$ are independently selected from H, $(C_1-C_6)$alkyl, halogen, $(C_1-C_6)$alkoxy, cyano, or nitro, wherein one of $R^6$ and one of $R^{6'}$ on adjacent or non-adjacent carbon atoms, or on the same carbon atom may join together to form a $C_5-C_8$ cycloalkane ring, or two of $R^6$ or two of $R^{6'}$, on adjacent or non-adjacent carbon atoms, may join together to form a $C_5-C_8$ cycloalkane ring; $L^1$ is selected from a bond, $(C_1-C_4)$alkylene, $(C_2-C_4)$heteroalkylene, O, S(O)$_k$, N(R$^a$), C(O)—(C$_5$-C$_7$)heterocycloalkylene, $(C_1-C_4)$alkylene-SO$_2$N(R$^b$), $(C_1-C_4)$alkylene-N(R$^b$)SO$_2$, or C(O)N(R$^b$); R$^a$ is selected from hydrogen, $(C_1-C_6)$alkyl, aryl$(C_1-C_3)$alkyl, or $(C_2-C_6)$heteroalkyl; R$^b$ is selected from hydrogen, $(C_1-C_6)$alkyl, or $(C_2-C_6)$heteroalkyl; Q is selected from hydrogen, aryl, heteroaryl, $(C_1-C_6)$alkyl, or $(C_2-C_6)$heteroalkyl; W is a leaving group; and further wherein, the compounds of formula XIII and XV can be a mixture of compounds having the R and S stereochemistry at the carbon bonded to $R^1$, can have the R stereochemistry at the carbon bonded to $R^1$, or can have the S stereochemistry at the carbon bonded to $R^1$.

In some embodiments, W is selected from OH, a halogen, an OTs, an OMs, or an OTf where OTs represents the tosylate (Ts is p-toluenesulfonyl) OMs represents mesylate (Ms is methanesulfonyl), and OTf represents triflate (Tf is trifluoromethanesulfonyl). In some such embodiments, W is OH and a phosphine selected from a trialkylphosphine, a dialkylarylphosphine, a alkyldiarylphosphine, or a triarylphosphine and an azodicarboxylate are used to react the compound of formula XIII with the compound of formula XIV. In other such embodiments, W is a halogen selected from Br or Cl, and a base is used to react the compound of formula XXII with the compound of formula XXIII.

In some embodiments, Alk is selected from methyl or ethyl.

In some embodiments, m is 1 or 2.
In some embodiments, n' is 0
In some embodiments, z is 1.
In some embodiments, the method further includes removing the Alk group of the compound of formula XV to form a compound of formula XVI or a salt thereof, and the compound of formula XVI has the following structure:

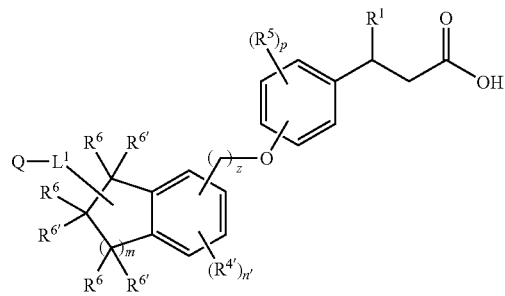

wherein the variables have the definitions provided with respect to the compounds of any of the embodiments of formula XIII, XIV, and XV. In some such embodiments, the compound of formula XV is reacted in the presence of a hydroxide base to produce the compound of formula XVI. In some such embodiments, the hydroxide base is selected from LiOH, NaOH, KOH, or Ca(OH)$_2$.

5.2.3 Compositions

In another aspect, the invention provides pharmaceutical compositions suitable for pharmaceutical use comprising one or more compounds of the invention and a pharmaceutically acceptable carrier, excipient, or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are, water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The pharmaceutical compositions and methods of the invention may further comprise other therapeutically active compounds, as noted herein, useful in the treatment of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

5.2.4 Methods of Use

In another aspect, the invention provides methods of treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema, comprising administering to a subject in need thereof a therapeutically effective amount of a compound or composition of the invention.

In one embodiment, the disease or condition is type II diabetes.

In another aspect, the present invention provides a method for treating a disease or condition responsive to the modulation of GPR40 comprising administering to a subject in need thereof a therapeutically effective amount of a compound or composition of the invention.

In some embodiments, the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In certain embodiments, the disease or condition is type II diabetes.

In some embodiments, the disease or condition is obesity.

In some embodiments, the disease or condition is hypertension.

In some embodiments of administering the compounds or compositions of the invention, the compound or composition is administered orally.

In other embodiments, the compound or composition is administered parenterally.

In other embodiments, the compound or composition is administered in combination with a second therapeutic agent.

In other embodiments, the second therapeutic agent is an insulin sensitizing agent, such as metformin or a thiazolidinedione, for example.

In another aspect, the invention provides methods of treating or preventing a disease or disorder responsive to modulation of GPR40 comprising administering to a subject having such a disease or disorder, a therapeutically effective amount of one or more of the subject compounds or compositions.

In yet another aspect, the invention provides methods of treating or preventing a GPR40-mediated condition, disease or disorder comprising administering to a subject having such a condition, disease or disorder, a therapeutically effective amount of one or more of the subject compounds or compositions.

In yet another aspect, the invention provides methods of modulating GPR40 comprising contacting a cell with one or more of the subject compounds or compositions.

For example, in some embodiments, a cell that constitutively expresses GPR40 is contacted with one or more of the subject compounds or compositions.

In certain embodiments, a cell to be contacted can be made to express or overexpress GPR40, for example, by expressing GPR40 from heterologous nucleic acid introduced into the cell or, as another example, by upregulating the expression of GPR40 from nucleic acid endogenous to the cell.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment or prevention type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema or other conditions or disorders associated with GPR40, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day. For oral administration, the compositions are preferably provided in the form of tablets containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. Such other agents, or drugs, may be administered, by a route and in an amount commonly used therefore, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

The compounds of the invention may be used in combination with a second therapeutic agent such as those described herein. Thus, in some embodiments, therapeutic compositions are provided that include a compound of the invention and a second therapeutic agent as a combined preparation for simultaneous, separate or sequential use in the treatment of a subject with a disease or condition mediated by GPR40. In some embodiments, therapeutic compositions are provided that include a compound of the invention and a second therapeutic agent as a combined preparation for simultaneous, separate or sequential use in the prophylactic treatment of a subject at risk for a disease or condition mediated by GPR40.

In some such embodiments, the components are provided as a single composition. In other embodiments, the compound and the second therapeutic agent are provided separately as parts of a kit.

Examples of other therapeutic agents that may be combined with a compound of the invention, either administered separately or in the same pharmaceutical compositions, include, but are not limited to: (a) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acyl-CoA-cholesterol acyltransferase (ACAT) inhibitors such as melinamide), HMG-CoA synthase inhibitors, squalene epoxidase inhibitors and squalene synthetase inhibitors; (b) antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat); and (c) antidiabetic agents such as insulin and insulin mimetics, sulfonylureas (e.g., glyburide, meglinatide), biguanides, e.g., metformin (GLUCOPHAGE®), α-glucosidase inhibitors (acarbose), insulin sensitizers, e.g., thiazolidinone compounds, rosiglitazone (AVANDIA®), troglitazone (REZULIN®), ciglitazone, pioglitazone (ACTOS®) and englitazone, DPP-IV inhibitors, e.g., vildagliptin (Galvus®), sitagliptin (Januvia™), and GLP-I analogs, e.g., exenatide (Byetta®). In some embodiments, a compound of the invention may be administered along with a DPP-IV inhibitor or a GLP-I analog.

The weight ratio of the compound of the invention to the second active ingredient may be varied and will depend upon the effective dose of each ingredient. Generally, an effective dose of each will be used. Combinations of a compound of the invention and other active ingredients will generally also be within the aforementioned range, but in each case, an effective dose of each active ingredient should be used.

In another aspect, the present invention provides a method for modulating circulating insulin concentration in a subject, comprising administering a compound or composition of the invention.

In some embodiments, the insulin concentration is increased.

In other embodiments, the insulin concentration is decreased.

The following examples are offered by way of illustration and are not intended to limit the scope of the invention. Those of skill in the art will readily recognize a variety of noncritical parameters that could be modified to yield essentially similar results.

6. EXAMPLES

Unless otherwise stated, all compounds were obtained from commercial sources or were prepared using the methods and experimental procedures described herein. Various procedures are also set forth in published U.S. Patent Application No. 2006/0004012 which is hereby incorporated by reference in its entirety and for all purposes as if set forth herein. The following abbreviations are used to refer to various reagents, solvents, experimental procedures, or analytical techniques that are described in the examples:

ACN Acetonitrile
AcOH Acetic Acid
DCM Dichloromethane
DEAD Diethyl azodicarboxylate
DIBALH Diisobutylaluminum Hydride
DMF N,N'-Dimethyl Formamide
DMSO Dimethyl Sulfoxide
ESI Electrospray Ionization
EtOAc EtOAc
EtOH Ethanol
HPLC High Performance Liquid Chromatography
HSA Human Serum Albumin
i-ProH 2-Propanol
LDA Lithium Diisopropylamide
MeOH Methanol
MS Mass Spectrometry
NBS N-Bromosuccinimide
n-BuLi n-Butyllithium
NMR Nuclear Magnetic Resonance
n-ProH 1-Propanol
PCC Pyridinium Chlorochromate
PDC Pyridinium Dichromate
PPTS Pyridinium p-Toluenesulfonate
t-BuOH t-Butanol
TEA Triethlamine
TFA Trifluoroacetic Acid
THF Tetrahydrofuran
THP Tetrahydropyran
TLC Thin Layer Chromatography
TMAD N,N,N',N'-Tetramethylazodicarboxamide
SPA Scintilliation Proximity Assay

6.1

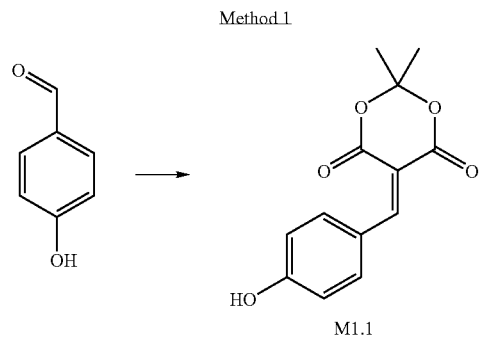

5-(4-Hydroxy-benzylidene)-2,2-dimethyl-[1,3]dioxane-4,6-dione (M1.1). Condensation with Meldrum's acid was carried out according to the method of Bigi et. al. (2001) *Tetrahedron Lett.* 42:5203-5205. A 2 L pear-shaped flask was charged with 4-hydroxybenzaldehyde (50 g, 409 mmol) and water (400 mL). The flask was placed in a water bath at 75° C., and Meldrum's acid (62 g, 430 mmol) was added as a slurry in 400 mL of water. The reaction mixture was agitated for 2 hours and cooled in an ice bath for 2 hours. The product was collected by filtration and rinsed with cold water. After drying thoroughly, adduct M1.1 was obtained as a fine yellow powder. MS ESI (pos.) m/e: 519.0 (2M+Na). $^1$H NMR (500 MHz) (DMSO-$d_6$) δ 9.75 (br s, 1H); 8.27 (s, 1H); 8.24 (d, 2H, J=10 Hz); 6.98 (d, 2H, J=10 Hz); 1.76 (s, 6H).

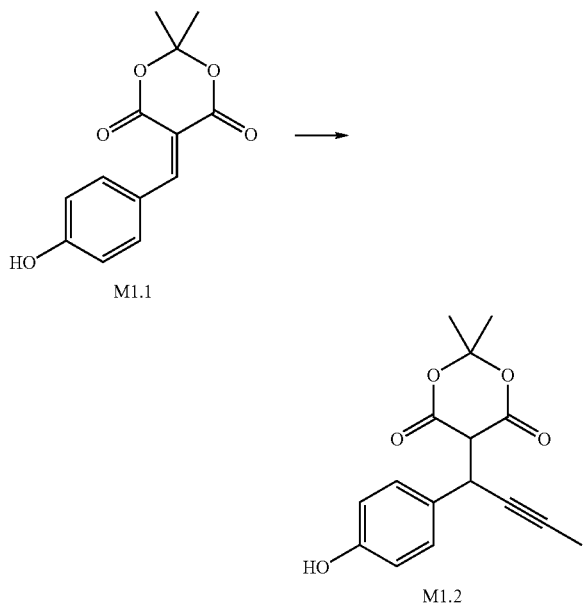

M1.1

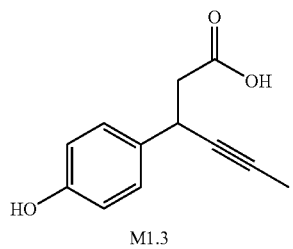

M1.3

(+/−)-3-(4-Hydroxy-phenyl)-hex-4-ynoic acid (M1.3). A 1 L round-bottom flask was charged with compound M1.2 (37 g), diethyl ketone (160 mL), and water (80 mL). The suspension was heated at reflux for 48 hours. After cooling, the aqueous layer was saturated with NaCl(s) and separated. The organic layer was dried over MgSO$_4$, filtered, and concentrated to a light brown oil, which was crystallized from hot EtOAc:hexanes (1:2). After collecting and drying, the product was obtained as an off-white powder. MS ESI (pos.) m/e: 205.1 (M+H); 227.1 (M+Na). $^1$H NMR (500 MHz) (DMSO-d$_6$) δ 12.2 (s, 1H); 9.27 (s, 1H); 7.12 (d, 2H, J=8.5 Hz); 6.67 (d, 2H, J=8.6 Hz); 3.87 (m, 1H); 2.54 (m, 2H); 1.82 (d, 3H, J=2.4 Hz).

(+/−)-5-[1-(4-Hydroxy-phenyl)-but-2-ynyl]-2,2-dimethyl-[1,3]dioxane-4,6-dione (M1.2). An oven-dried 3 L 3-neck flask was equipped with a mechanical stirrer, a nitrogen inlet, and a nitrogen outlet and placed in a room-temperature water bath. After purging with nitrogen for 20 minutes, a solution of 1-propynylmagnesium bromide in THF (0.5 N, 600 mL) was added by cannula. In a separate oven-dried and nitrogen-flushed 500 mL round-bottom flask, compound M1.1 (35 g, 142 mmol) was dissolved in anhydrous THF (350 mL) with gentle warming. The solution of M1.1 was added over 15 minutes. Over the course of the addition, the reaction mixture changed to a thick, yellow suspension. After the addition was complete, the reaction mixture was stirred for 15 minutes, quenched with aqueous NH$_4$Cl (0.6 N, 750 mL), and diluted with hexanes (800 mL). The layers were separated, and the organic layer was discarded. The aqueous layer was acidified to pH 2 with saturated aqueous KHSO$_4$ and extracted with EtOAc (2×400 mL). The combined extracts were washed with saturated brine, dried over MgSO$_4$, filtered, and concentrated to a light yellow solid. MS ESI (pos.) m/e: 599.0 (2M+Na). $^1$H NMR (500 MHz) (acetone-d$_6$) δ 8.26 (s, 1H); 7.39 (d, 2H, J=8.5 Hz); 6.76 (d, 2H, J=8.4 Hz); 4.73 (br s, 1H); 4.46 (d, 1H, J=2.4 Hz); 1.82 (s, 3H); 1.81 (s, 3H); 1.64 (s, 3H).

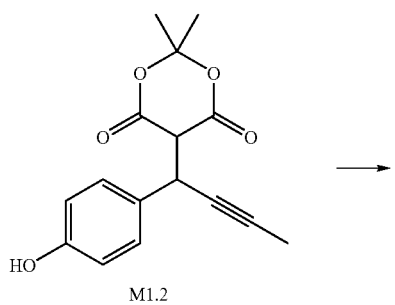

M1.2

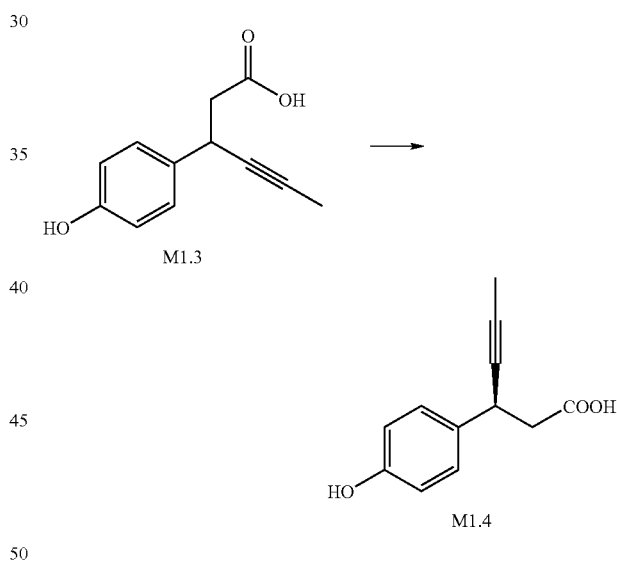

(3S)-3-(4-Hydroxy-phenyl)-hex-4-ynoic acid (M1.4). A 5 L round-bottom flask was charged with compound M1.3 (66.4 g, 325 mmol) and 2-propanol (1 L) and heated to 70° C. (1S,2R)-1-Amino-2-indanol (46.1 g, 309 mmol) was dissolved in 2-propanol (1 L) with gentle warming. The solution of amine was added to the dissolved carboxylic acid and the resulting solution was allowed to cool to room temperature. After 16 hours, the crystals were collected and dried. The salt was re-suspended in 2 L of 2-propanol and dissolved by heating to reflux. After allowing to cool to room temperature, the salt was collected after 16 hours. A small sample of the salt was decomposed with aqueous acid and the free carboxylic acid was analyzed by chiral HPLC (Daicel ChiralPAK AD-H column, eluant: 0.1% TFA in 90:10 hexanes:2-propanol) and was found to have 75% ee. The salt was re-suspended in 1.5

L of 2-propanol and dissolved by heating to reflux. After allowing to cool to room temperature, the salt was collected after 16 hours. This material was found to have 96% ee by chiral HPLC. This material was suspended in EtOAc (300 mL) and water (100 mL). Saturated aqueous KHSO$_4$ (100 mL) was added with vigorous mixing. After two clear layers were obtained, the layers were separated, and the aqueous layer was extracted with EtOAc (100 mL). The combined extracts were washed with saturated brine, dried over MgSO$_4$, filtered, and concentrated to a light yellow oil, which crystallized on drying in vacuo. Compound M1.4 was obtained as an off-white solid.

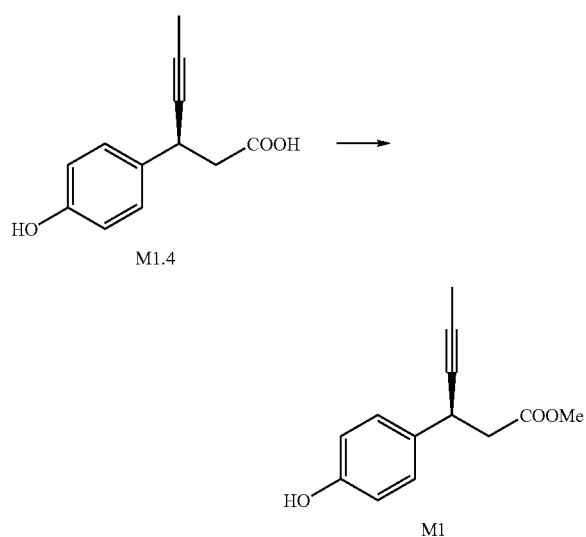

(3S)-3-(4-Hydroxy-phenyl)-hex-4-ynoic acid methyl ester (M1). Phenol M1.4 (23.5 g, 115 mmol) was dissolved in acetone (230 mL) and treated with KHCO$_3$ (11.5 g, 115 mmol). After 15 minutes, methyl iodide (5 mL, 80 mmol) was added, and the reaction was stirred at 40° C. for 14 hours. An additional portion of methyl iodide (3 mL, 48 mmol) was added and heating was continued for 24 hours. Potassium salts were removed by filtration and thoroughly rinsed with acetone. The filtrate was concentrated to an oil, which was filtered through a 1 cm plug of silica gel. Elution with 2.5% MeOH in DCM followed by concentration provided phenol M1 as a light yellow oil. MS ESI (pos.) m/e: 219.1 (M+H); 241.1 (M+Na). $^1$H NMR (500 MHz) (acetone-d$_6$) δ 8.2 (br s, 1H); 7.20 (d, 2H, J=9.5 Hz); 6.77 (d, 2H, J=9.0 Hz); 3.98 (m, 1H); 3.60 (s, 3H); 2.65 (m, 2H); 1.78 (d, 3H, J=2.5 Hz).

6.2

Method 2

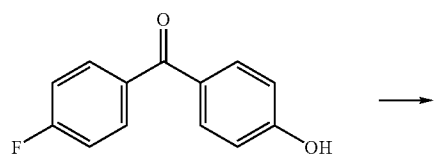

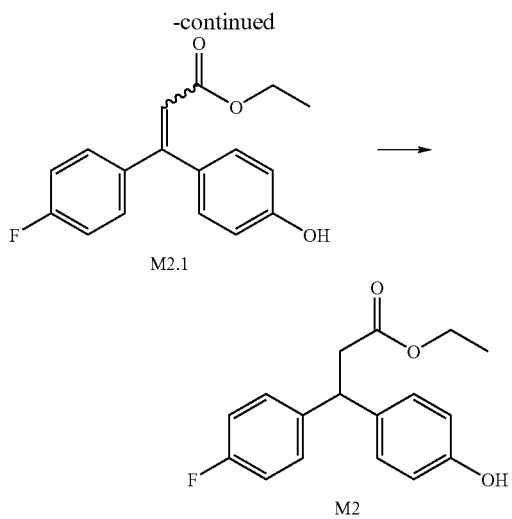

Ethyl 3-(4-fluoro-phenyl)-3-(4-hydroxy-phenyl)-acrylate (M2.1). A solution of lithium hexamethyldisilazide (23.1 mL, 1 M in THF) was added to a stirred solution of ethyl (trimethylsilyl)acetate (2.53 mL, 13.9 mmol) in THF (15 mL) in 10 minutes at −78° C. The reaction mixture was further stirred at this temperature for 20 minutes. A solution of (4-fluoro-phenyl)-(4-hydroxy-phenyl)-methanone (2 g, 9.2 mmol) in THF (30 mL) was slowly added to the reaction mixture. The reaction mixture was brought to 0° C. over 5 hours. The reaction mixture was quenched with saturated NH$_4$Cl solution, extracted into EtOAc and washed with dilute NH$_4$Cl solution. The organic layer was dried over magnesium sulfate. The solvent was removed under vacuum, and the resulting product was flash chromatographed on silica gel, giving M2.1 as an oil.

(+/−)-3-(4-Fluoro-phenyl)-3-(4-hydroxy-phenyl)-propionic acid ethyl ester (M2). A solution of M2.1 (385 mg) in EtOH (12 mL) and EtOAc (10 mL) was stirred with 10% Pd—C (50 mg) under a hydrogen atmosphere at room temperature for 3 hours. The reaction mixture was filtered and concentrated to provide M2.

6.3 Method 3

Starting from (4-hydroxy-phenyl)-phenyl-methanone, compound M3 was prepared according to methods analogous to those described in Method 2.

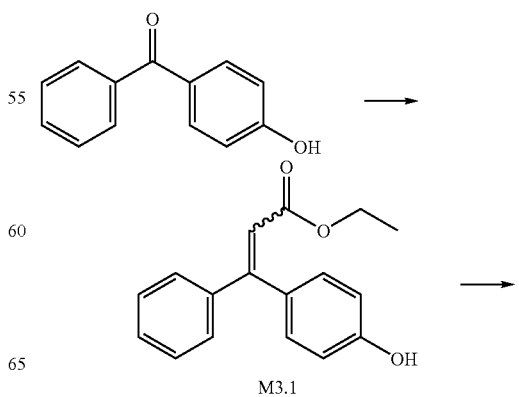

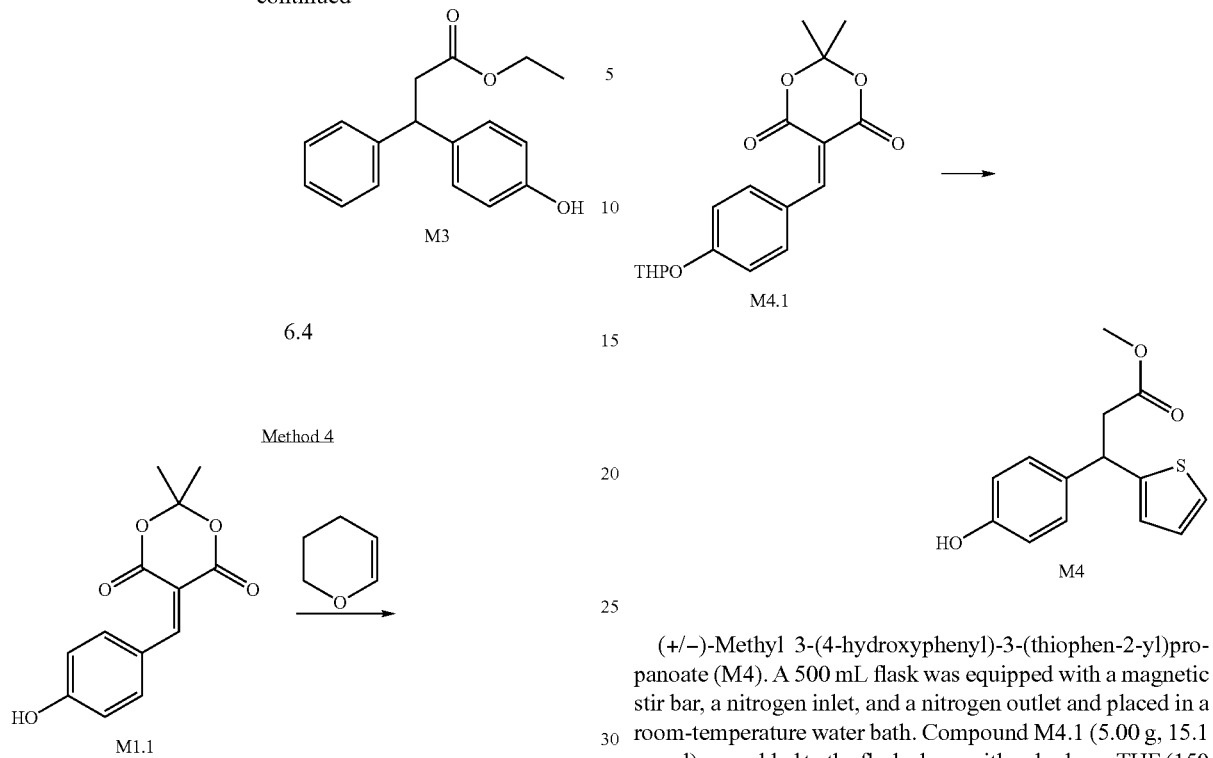

2,2-Dimethyl-5-[4-(tetrahydro-pyran-2-yloxy)-benzylidene]-[1,3]dioxane-4,6-dione (M4.1). Protection of the phenol with dihydropyran was carried out based on the method described in Miyashita et al. (1977) *J. Org. Chem.* 42:3772. Compound M1.1 (500 g, 2 mol) was dissolved in DCM (4 L). 3,4-Dihydro-2H-pyran (250 g, 3 mol) was added to the suspension followed by PPTS (5 g, 20 mmol). The reaction mixture was then heated at a gentle reflux (3.5 hours). The reaction was concentrated under reduced pressure to ~2 L of volume. 1 L of acetone was then added, and 2 L of solvent were removed under reduced pressure. 1 L of acetone was added, and 1 L of solvent was removed under reduced pressure. 0.5 L of acetone was added, and 0.5 L of solvent was removed under reduced pressure. The resulting slurry of very fine, light yellow crystals was filtered and rinsed sequentially with two 500 mL portions of acetone. The product was dried in a vacuum oven at 50° C. until no further solvent collected in the traps. Compound M4.1 was obtained as fine, light yellow crystals. MS ESI (pos.) m/e: 355.1 (M+Na). $^1$H NMR (400 MHz) (DMSO-$d_6$) δ 8.29 (s, 1H); 8.18 (d, 2H, J=8.9 Hz); 7.13 (d, 2H, J=8.9 Hz); 5.67 (m, 1H); 3.70 (m, 1H); 3.60 (m, 1H). 1.9-1.5 (m, 12H).

(+/−)-Methyl 3-(4-hydroxyphenyl)-3-(thiophen-2-yl)propanoate (M4). A 500 mL flask was equipped with a magnetic stir bar, a nitrogen inlet, and a nitrogen outlet and placed in a room-temperature water bath. Compound M4.1 (5.00 g, 15.1 mmol) was added to the flask along with anhydrous THF (150 mL). After purging with nitrogen for 30 minutes, a solution of thiophene-2-yl-magnesium bromide in THF (1 M, 18.1 mL) was added by cannula. After the addition was complete, the reaction mixture was stirred for 1.5 hours and quenched with aqueous NH$_4$Cl (1 M, 100 mL), and diluted with EtOAc (100 mL). The aqueous layer was acidified to pH ~2 with concentrated HCl and extracted with EtOAc (150 mL×2). The extract was washed with brine and concentrated. The residue was dissolved in 100 mL of 10:1 DMF:water and heated to 100° C. for 8 hours. The reaction was cooled, diluted with 500 mL water, and extracted with EtOAc (150 mL×3). The organic layer was dried with MgSO$_4$, filtered, and concentrated on a rotary evaporator. The residue was dissolved in MeOH (200 mL), 5 drops of concentrated H$_2$SO$_4$ were added, and the solution was refluxed for 24 hours. The solution was concentrated to a residue on a rotary evaporator and flash column chromatographed with 30% EtOAc/hexanes as the eluant. The fractions were combined and concentrated to afford M4 as a viscous oil.

6.5

Method 5

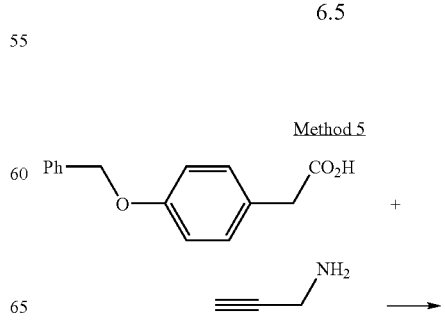

-continued

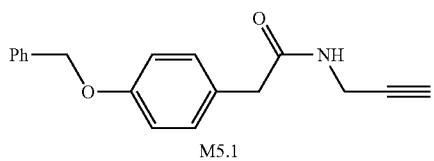
M5.1

2-(4-(Benzyloxy)phenyl)-N-(prop-2-ynyl)acetamide (M5.1). A mixture of 4-(benzyloxy)phenylacetic acid (20.7 mmol), 1-hydroxybenzotrizole hydrate (37 mmol), 1-(3-dimethylaminopropyl)-3-ethylcarbodiimide (37 mmol), propargylamine (20.7 mmol) and N-methylmorpholine (62 mmol) in DMF (60 mL) were stirred at room temperature overnight. The reaction mixture was diluted with EtOAc (400 mL), washed with 1N HCl, water, saturated Na$_2$CO$_3$ solution, and brine, and dried over Na$_2$SO$_4$. After removing solvent under reduced pressure, the residue was triturated with DCM. Compound M5.1 was obtained as a white solid after filtration and drying. LC-MS ESI (pos.) m/e: 280 (M+H).

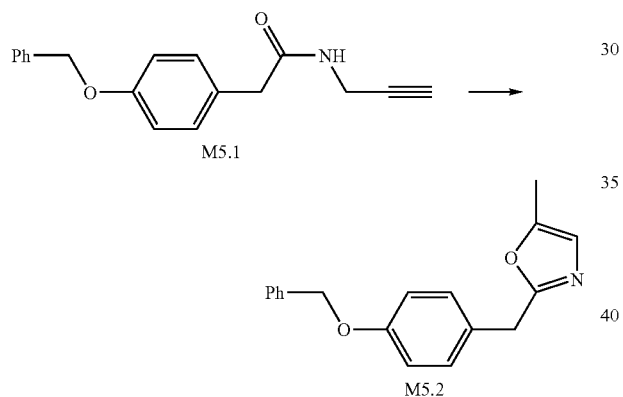

2-(4-Benzyloxy)benzyl)-5-methyl oxazole (M5.2). A mixture of compound M5.1 (10.1 mmol) and AuCl$_3$ (1 mmol) in DCM (100 mL) was stirred at room temperature overnight. Additional DCM (100 mL) was added, and the reaction mixture was washed with NaHCO$_3$ solution and saturated brine. After drying over Na$_2$SO$_4$ and concentration under reduced pressure, the residue was column chromatographed (1:2 EtOAc:hexanes) to obtain compound M5.2. LC-MS ESI (pos.) m/e: 280 (M+H).

-continued

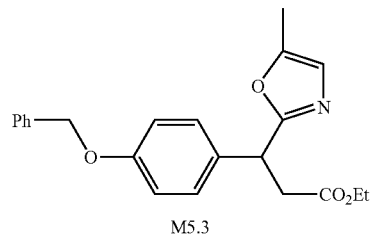
M5.3

(+/−)-Ethyl 3-(4-(benzyloxy)phenyl)-3-(5-methyloxazol-2-yl)propanoate (M5.3). To a solution of 2-(4-(benzyloxy)benzyl)-5-methyloxazole (M5.2) (3.23 mmol) in THF (25 mL) at −78° C., was added dropwise LDA (4.5 mmol). The mixture was stirred for 18 minutes, followed by addition of ethyl bromoacetate (4.5 mmol). It was allowed to warm to room temperature for 3 hours, followed by addition of water, which was extracted with EtOAc. The extract was washed with brine and dried over Na$_2$SO$_4$ using standard work up conditions. Column chromatography (1/3 EtOAc/hexane) of the residue afforded compound M5.3. MS ESI (pos.) m/e: 366 (M+H).

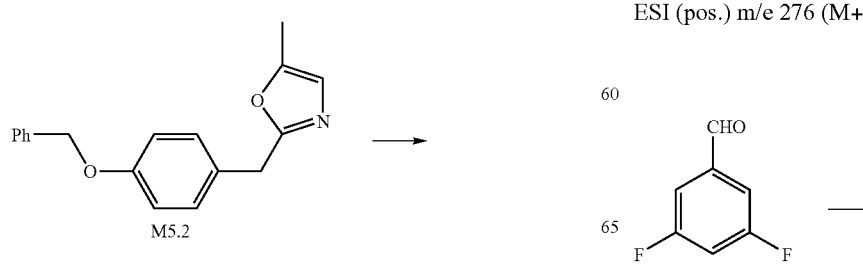

(+/−)-Ethyl 3-(4-hydroxyphenyl)-3-(5-methyloxazol-2-yl)propanoate (M5). A mixture of ethyl 3-(4-(benzyloxy)phenyl)-3-(5-methyloxazol-2-yl)propanoate (M5.3) (2.47 mmol) and Pd—C (270 mg) in EtOH was stirred under hydrogen atmosphere at room temperature for 4 hours. The Pd—C was removed by filtration through silica gel eluting with EtOH. After concentration, product M5 was obtained. MS ESI (pos.) m/e 276 (M+H).

Method 6

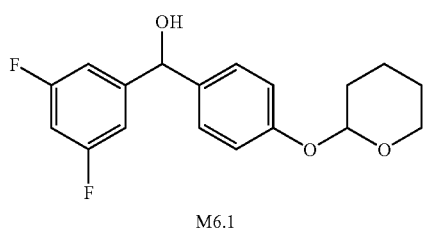

M6.1

(+/−) (3,5-Difluorophenyl)(4-(tetrahydro-2H-pyran-2-yloxy)phenyl)methanol (M6.1). 4-(2-Tetrahydro-2H-pyran-oxy)phenylmagnesium bromide (0.5 M in THF, 35 mL, 17.5 mmol) was added to a solution of 3,5-difluorobenzaldehyde (1.95 g, 13.7 mmol) in THF (50 mL) slowly via syringe at −78° C. The reaction mixture was stirred at this temperature for 3 hours and then quenched with saturated NH₄Cl (aqueous). The mixture was extracted with EtOAc (60 mL×2), and the combined organic layers were dried over Na₂SO₄, filtered, and concentrated under reduced pressure to provide a colorless oil (3.9 g) as product M6.1, which was used directly in the next step.

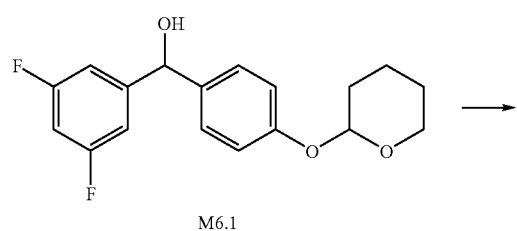

M6.1

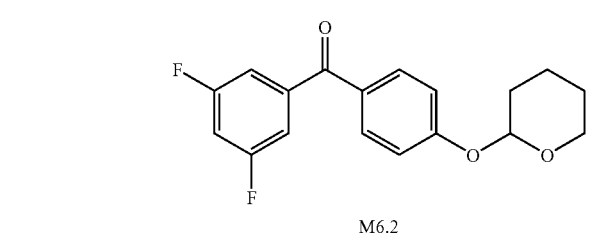

M6.2

(+/−)-(3,5-Difluorophenyl)(4-(tetrahydro-2H-pyran-2-yloxy)phenyl)methanone (M6.2). PDC (8.5 g, 22.6 mmol) was added to the solution of M6.1 (3.9 g, 13.7 mmol) in DCM (100 mL) at 0° C. in several portions. The mixture was stirred at 0° C. for 1 hour and at room temperature for 6 hours. Silica gel (about 20 g) was added to the reaction mixture and the resulting slurry was filtered through a pad of silica gel to remove most of the inorganic chemicals. The solid was washed with DCM until no further product remained on the silica gel (monitored by TLC). The combined organic solvent was washed with water and saturated brine, dried over Na₂SO₄, filtered, and concentrated under reduced pressure to provide an oily residue, which was flash chromatographed (silica gel, 0-30% EtOAc in hexane), generating product ketone M6.2 as light yellow oil. MS ESI (pos.) m/e: 319 (M+H).

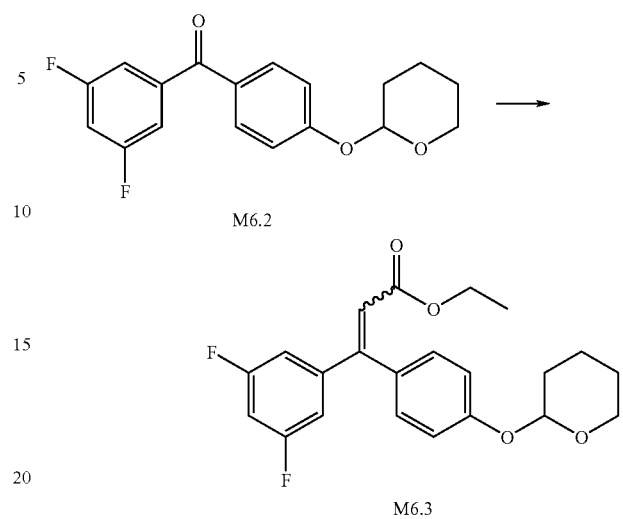

M6.2

M6.3

(Z/E)-Ethyl 3-(3,5-difluorophenyl)-3-(4-(tetrahydro-2H-pyran-2-yloxy)phenyl)acrylate (M6.3). Ethyl (trimethylsilyl) acetate (2.63 g/3.0 mL in 20 mL THF) was added to lithium hexamethyldisilazide (1 M in THF, 17.6 mL) at −78° C. slowly via syringe. The mixture was stirred at the same temperature for 1 hour, and the solution of ketone M6.2 (4.3 g, 13.5 mmol) in anhydrous THF (25 mL) was added slowly via syringe. The reaction mixture was further stirred at this temperature for 2 hours. The reaction temperature was then allowed to rise to −20° C. in 6 hours. The reaction mixture was quenched with saturated NH₄Cl (aqueous) at this temperature, extracted with EtOAc (2×100 mL) and dried over Na₂SO₄. After filtration, the solvent was removed under reduced pressure and M6.3 was obtained as light yellow oil (including some ethyl (trimethylsilyl)acetate), which was used directly in the next step. MS ESI (pos.) m/e: 389 (M+H).

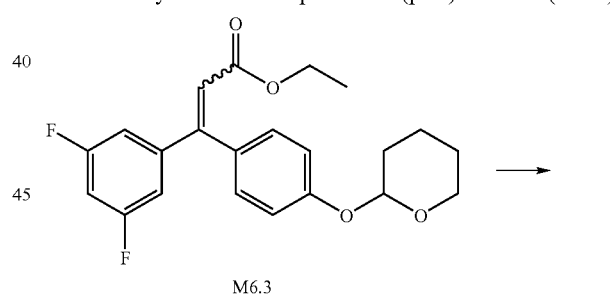

M6.3

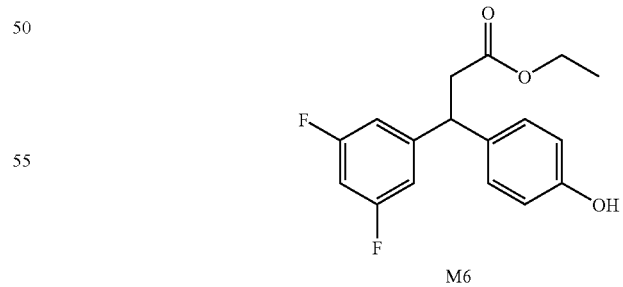

M6

(+/−)-Ethyl 3-(3,5-difluorophenyl)-3-(4-hydroxyphenyl) propanoate (M6). A solution of olefin M6.3 (5.4 g, 13.5 mmol) in EtOH (80 mL) was stirred with 10% Pd—C (1.5 g, 1.4 mmol) under a hydrogen atmosphere (provided by a balloon) overnight at room temperature. The reaction mixture was filtered through a short silica gel pad and stirred with AcOH (14 mL) at room temperature for 4 hours. The reaction mixture was concentrated under reduced pressure to provide a yellow oily residue, which was re-dissolved in DCM (150 mL) and washed with water, saturated NaHCO₃, water, and brine, and dried over Na₂SO₄. After filtration, the solvent was removed under reduced pressure, and the residue was flash chromatographed (silica gel, 0-40% EtOAc in hexane as eluant). The product M6 was obtained as the (+/−)ethyl ester. MS ESI (pos.) m/e: 307 (M+H).

6.7

Method 7

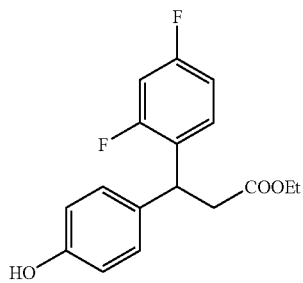

M7

(+/−)-Ethyl 3-(2,4-difluoro-phenyl)-3-(4-hydroxy-phenyl) propanoate (M7). Compound M7 was prepared by a method analogous to that for M6.

6.8

Method 8

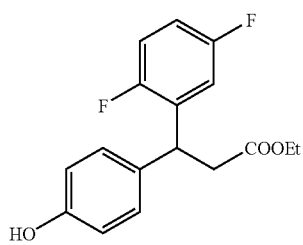

M8

(+/−)-Ethyl 3-(2,5-difluoro-phenyl)-3-(4-hydroxy-phenyl) propanoate (8). Compound M8 was prepared by a method analogous to that for M6.

6.9

Method 9

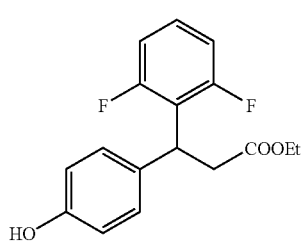

M9

(+/−)-Ethyl 3-(2,6-difluoro-phenyl)-3-(4-hydroxy-phenyl) propanoate (M9). Compound M9 was prepared by a method analogous to that for M6.

6.10

Method 10

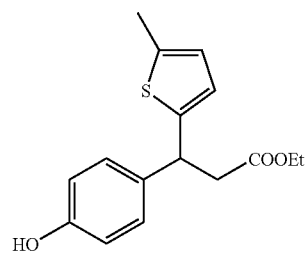

M10

(+/−)-Ethyl 3-(4-hydroxy-phenyl)-3-(5-methyl-thiophen-2-yl) propanoate (M10). Compound M10 was prepared by a method analogous to that for M6.

6.11

Method 11

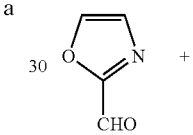

M11.1

(+/−)-Oxazol-2-yl(4-(tetrahydro-2H-pyran-2-yloxy)phenyl)methanol (M11.1). 4-(2-Tetrahydro-3-H-pyranoxy)phenylmagnesium bromide (6.7 mmol) in THF (0.5 M) was added dropwise to a solution of oxazole-2-carbaldehyde (5.15 mmol) in THF (8 mL). After it was stirred at room temperature for 2.5 hours, the reaction was quenched with water and extracted with EtOAc (200 mL). The organic phase was washed with brine, dried over anhydrous sodium sulfate, filtered, and concentrated under reduced pressure. The residue was column chromatographed (silica gel, 1:2 EtOAc/hexane). Compound M11.1 was obtained. MS ESI (pos.) m/e: 276 (M+H). ¹H NMR (400 MHz) (DMSO-d₆) δ 8.02 (s, 1H); 7.31 (d, J=8.7 Hz, 2H); 7.14 (s, 1H); 6.97-7.01 (m, 2H); 6.27 (d, J=5 Hz, 1H); 5.74 (d, J=5 Hz, 1H); 5.44 (s, 1H); 3.74 (m, 1H); 3.52 (M, 1H); 1.72-1.81 (m, 3H); 1.52-1.60 (m, 4H).

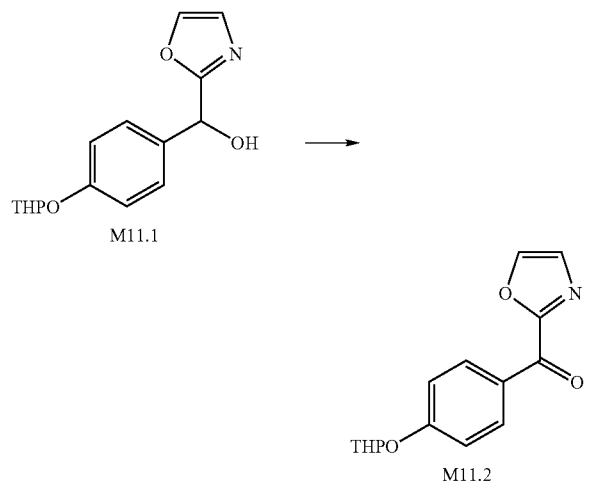

(+/−)-Oxazol-2-yl(4-(tetrahydro-2H-pyran-2-yloxy)phenyl)methanone (M11.2). PCC (14.5 mmol, 20% w/w on silica gel) was added to a solution of M11.1 (2.91 mmol) in DCM (20 mL). After it was stirred at room temperature for 1 hour, the reaction mixture was column chromatographed (silica gel, 1:2 EtOAc/hexane). Compound M11.2 was obtained. MS ESI (pos.) m/e: 296.0 (M+23). $^1$H NMR (500 MHz) (DMSO-$d_6$) δ 8.52 (s, 1H); 8.43 (d, J=9 Hz, 2H); 7.67 (s, 1H); 7.23 (d, J=9 Hz, 2H); 5.71 (m, 1H); 3.74-3.76 (m, 1H); 3.62-3.65 (m, 1H); 1.88-1.91 (m, 2H); 1.81-1.82 (m, 1H); 1.59-1.67 (m, 3H).

(E/Z)-Methyl 3-(oxazol-2-yl)-3-(4-(tetrahydro-2H-pyran-2-yloxy)phenyl)acrylate (M11.3). Lithium bis(trimethylsilyl) amide (3.46 mmol, 1 M in THF) was added dropwise to a solution of methyl trimethylsilylacetate (3.46 mmol) in THF (5 mL) at −78° C. After it was stirred at −78° C. for 20 minutes, a solution of M11.2 (2.16 mmol) in THF (9 mL) was added dropwise, and the temperature was maintained at −78° C. for 1.5 hours. The reaction was quenched with water and extracted with EtOAc. The organic phase was washed with brine, dried over anhydrous sodium sulfate, filtered, and concentrated under reduced pressure. The residue was column chromatographed (silica gel, 1:1 EtOAc/hexane) and compound M11.3 was obtained. MS ESI (pos.) m/e 330.1 (M+H).

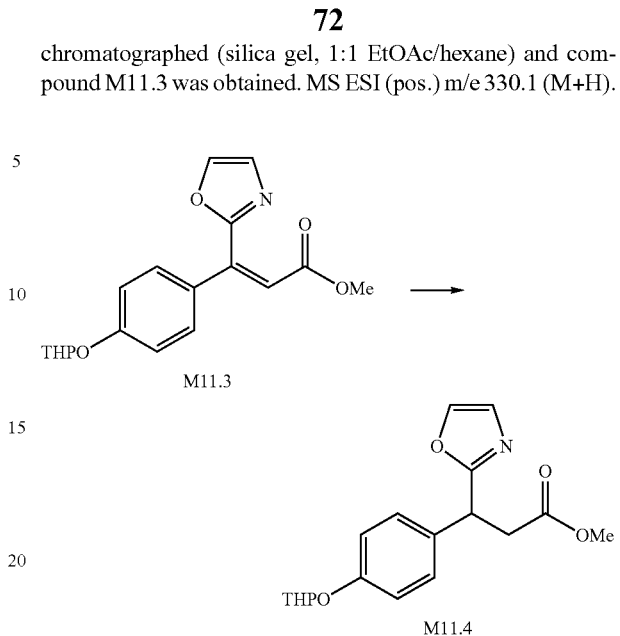

(+/−)-Methyl 3-(oxazol-2-yl)-3-(4-(tetrahydro-2H-pyran-2-yloxy)phenyl)propanoate (M11.4). A mixture of M11.3 (2.55 mmol) and Pd—C (440 mg) in MeOH was stirred under hydrogen at room temperature for 30 minutes. The Pd—C was removed by filtration through silica gel eluting with EtOAc. After concentration, the residue was column chromatographed (silica gel, 1:1 EtOAc/hexane) and compound M11.4 was obtained. MS ESI (pos.) m/e 332.2 (M+H).

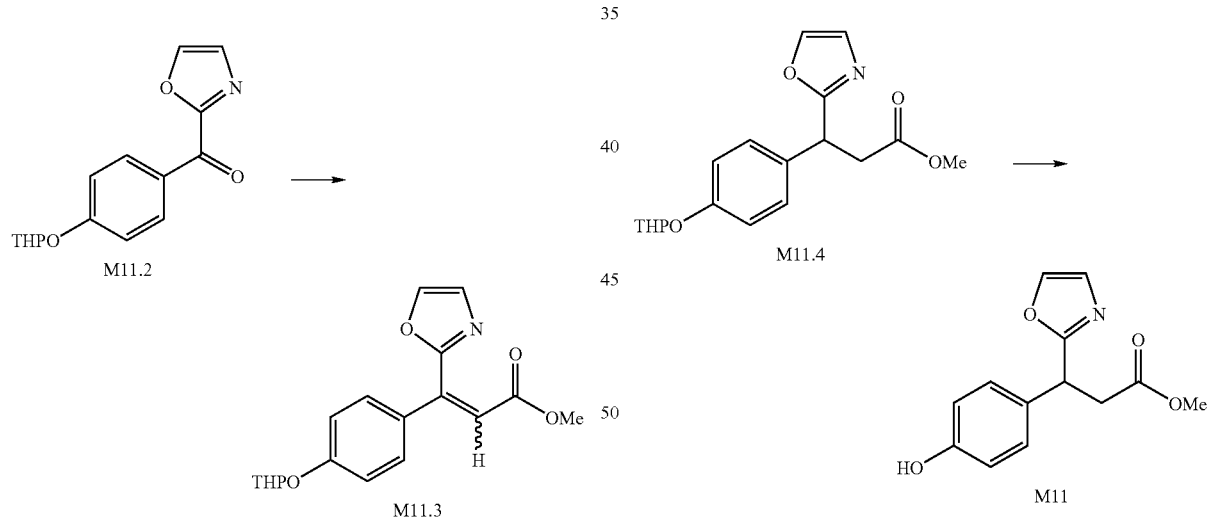

(+/−)-Methyl 3-(4-hydroxyphenyl)-3-(oxazol-2-yl)propanoate (M11). A mixture of M11.4 (2.1 mmol), p-toluenesulfonic acid monohydrate (0.57 mmol) in MeOH (15 mL) was stirred at room temperature for 1.5 hours. After it was quenched with NaHCO$_3$ (aqueous) solution, MeOH was removed by rotary evaporator. The residue was extracted with EtOAc, and the combined organic phase was washed with brine, dried over anhydrous sodium sulfate, and filtered through short plug of silica gel. After removing solvent, compound M11 was obtained. MS ESI (pos.) m/e 248.1 (M+H). $^1$H NMR (500 MHz) (DMSO-$d_6$) δ 9.04 (s, 1H); 7.99 (s, 1H);

7.14 (s, 1H); 7.05 (m, 2H); 6.72 (m, 2H); 4.49-4.52 (m, 1H); 3.57 (s, 1H); 3.22-3.27 (m, 1H); 2.89-2.94 (m, 1H).

6.12

Method 12

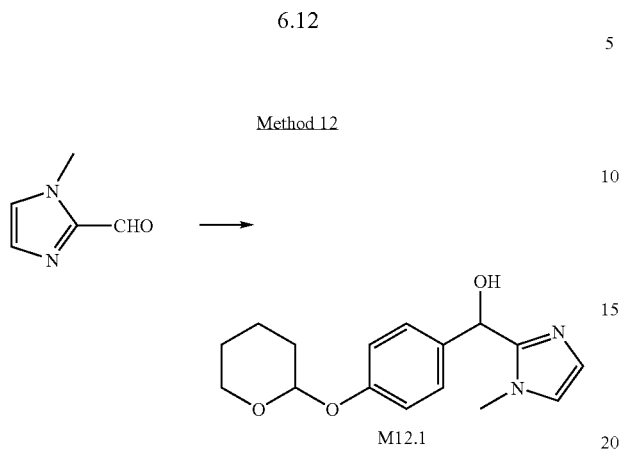

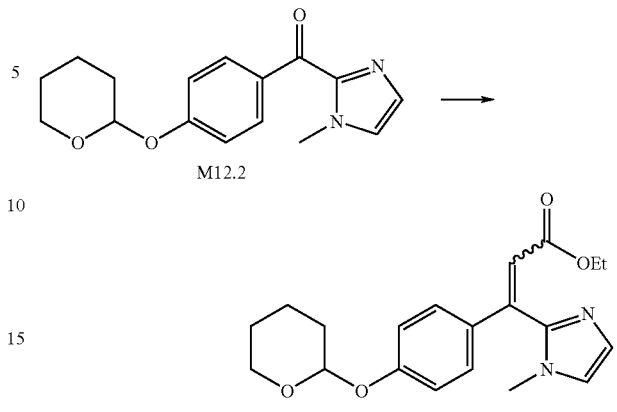

(Z/E)-Ethyl 3-(1-methyl-1H-imidazol-2-yl)-3-(4-(tetrahydro-2H-pyran-2-yloxy)phenyl)acrylate (M12.3). A solution of lithium hexamethyldisilazide (1 M in THF, 64 mL) was added slowly to a stirred solution of ethyl (trimethylsilyl) acetate (9.9 g, 61.5 mmol) and ketone M12.2 (16 g, 55.9 mmol) in anhydrous THF (60 mL) via syringe at −78° C. The reaction mixture was stirred at this temperature for 2 hours. The reaction temperature was allowed to rise to −20° C. over 6 hours. The reaction mixture was quenched with saturated NH$_4$Cl (aq) at this temperature, extracted with EtOAc (2×150 mL), and dried over Na$_2$SO$_4$. After filtration, the solvent was removed under reduced pressure to afford M12.3 as a colorless oil (21 g, including some ethyl (trimethylsilyl)acetate), which was used directly in the next step. LC-MS ESI (pos.) m/e: 357 (M+H).

(1-Methyl-1H-imidazol-2-yl)(4-(tetrahydro-2H-pyran-2-yloxy)phenyl)methanol (M12.1). 4-(2-Tetrahydro-2H-pyranoxy)phenylmagnesium bromide (0.5 M in THF, 160 mL, 80 mmol) was added slowly to a solution of 1-methyl-2-imidazolecarboxaldehyde (8 g, 72.7 mmol) in THF (100 mL) via syringe at −78° C. The reaction mixture was stirred at this temperature for 3 hours and quenched with saturated NH$_4$Cl (aq). The mixture was extracted with EtOAc (2×100 mL), and the combined organic extracts were dried over Na$_2$SO$_4$, filtered, and concentrated under reduced pressure to afford M12.1 as a colorless oil (21 g), which was used directly in the next step.

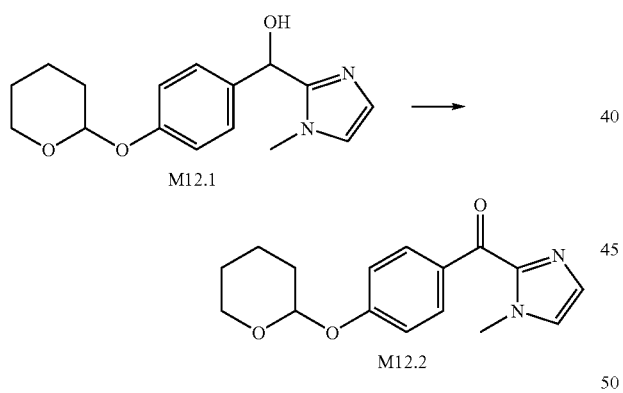

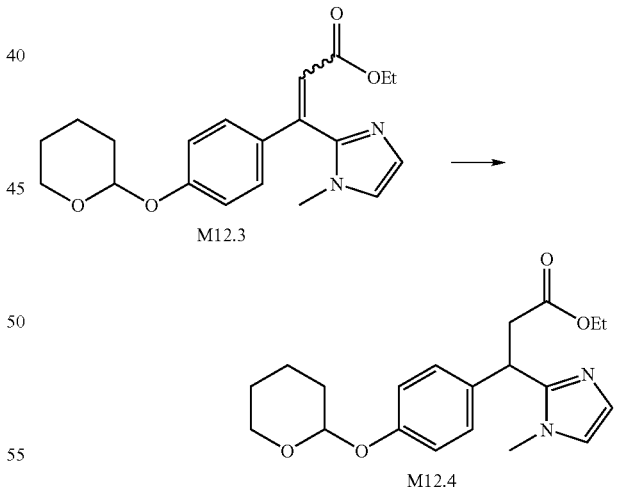

(1-Methyl-1H-imidazol-2-yl)(4-(tetrahydro-2H-pyran-2-yloxy)phenyl)methanone (M12.2). PDC (36 g, 95.7 mmol) was added to a solution of M12.1 (21 g, 72.7 mmol) in DCM (100 mL) at 0° C. in several portions. The mixture was stirred at 0° C. for 1 hour and at room temperature for 6 hours. Silica gel (75 g) was added to the reaction mixture, and the resulting slurry was filtered through a pad of silica gel. The solid was washed with DCM (200 mL). The filtrate was washed with water and saturated brine, dried over Na$_2$SO$_4$, filtered and concentrated under reduced pressure to give an oily residue, which was flash chromatographed (silica gel, 0-30% EtOAc in hexane) to afford ketone M12.2 as yellow solid (16 g). $^1$H NMR (500 MHz) (CDCl$_3$) δ 8.33-8.35 (m, 2H); 7.10-7.29 (m, 4H); 5.56 (t, J=3.0 Hz, 1H); 4.08 (s, 3H); 3.85-3.90 (m, 1H); 3.61-3.65 (m, 1H); 2.03 (m, 1H); 1.90-1.91 (m, 2H); 1.69-1.74 (m, 2H); 1.61-1.64 (m, 1H).

(+/−)-Ethyl 3-(1-methyl-1H-imidazol-2-yl)-3-(4-(tetrahydro-2H-pyran-2-yloxy)phenyl)propanoate (M12.4). A solution of olefin M12.3 (21 g, 55.9 mmol) in EtOH (200 mL) was stirred with 10% Pd—C (2.1 g, 2 mmol) under a hydrogen atmosphere (provided by a balloon) at room temperature overnight. The reaction mixture was filtered through a silica gel pad and concentrated to provide protected ester M12.4 as an off-white oil (21 g), which was used directly in the next step. LC-MS ESI (pos.) m/e: 359 (M+H).

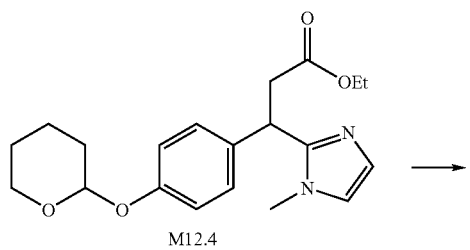

M12.4

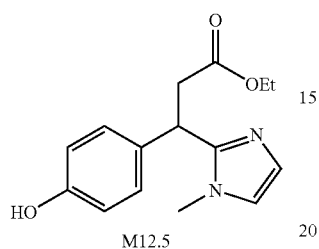

M12.5

(+/−)-Ethyl 3-(4-hydroxyphenyl)-3-(1-methyl-1H-imidazol-2-yl)propanoate (M12.5). TFA (21 mL) was added to a solution of protected ester M12.4 (21 g) in dry DCM (210 mL) with caution at 0° C. The mixture was brought to room temperature over 4 hours. The reaction mixture was concentrated under reduced pressure to provide a yellow oily residue, which was re-dissolved in DCM (200 mL) and washed with water, saturated NaHCO$_3$, water and brine, and dried over Na$_2$SO$_4$. After filtration, the solvent was removed under reduced pressure, and the product was crystallized in EtOAc-hexane. The mother liquid was concentrated and flash chromatographed (silica gel, 50% EtOAc in hexane as eluant). The product, (±)-ethyl 3-(4-hydroxyphenyl)-3-(1-methyl-1H-imidazol-2-yl)propanoate (M12.5) was obtained as a colorless crystal (combined yield 11 g). LC-MS ESI (pos.) m/e: 275 (M+H). $^1$H NMR (500 MHz) (CDCl$_3$) δ 9.28 (s, 1H); 6.98-7.00 (m, 3H); 6.65-6.77 (m, 3H); 4.41 (dd, J=9.0, 3.0 Hz, 1H); 3.96 (q, J=7.0, 2H); 3.39 (s, 3H); 3.19 (dd, J=16.0, 7.0 Hz, 1H); 2.78 (dd, J=16.0, 6.5 Hz, 1H); 1.80 (t, J=7.0 Hz, 3H).

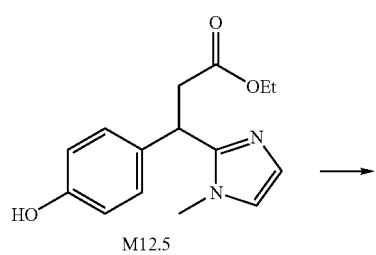

M12.5

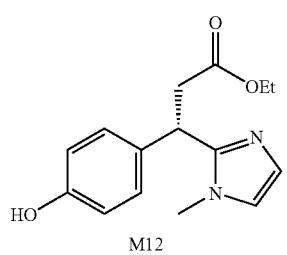

M12

(S)-Ethyl 3-(4-hydroxyphenyl)-3-(1-methyl-1H-imidazol-2-yl)propanoate (M12). Racemic compound M12.5 was separated on a preparatory chiral HPLC with CHIRALPAK AD column, using 11% i-PrOH in hexane as eluant. Eluant containing the peak with greater retention time was concentrated and compound M12 was obtained as colorless crystals. The enantiomer of M12 was also obtained. The absolute configuration was assigned by analogy to other GPR40 agonist compounds.

6.13

Method 13

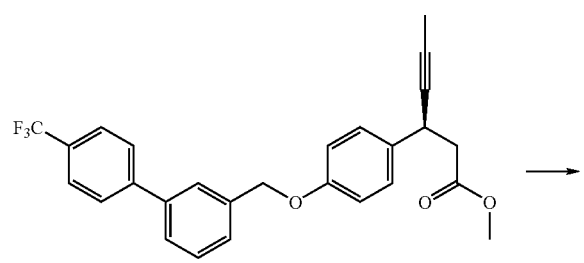

M13.1

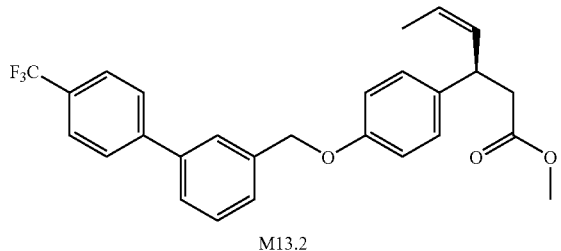

M13.2

Methyl ester (M13.2). Compound M13.1 (5.5 g, 12.16 mmol, prepared as described in US 2006/0004012 which is hereby incorporated by reference) was dissolved in 100 mL of EtOAc and quinoline (2 mL, 1.093 g/mL, 16.93 mmol) was added. Nitrogen was bubbled through the solution for 5 minutes. 500 mg of Lindlar's catalyst was added, and a hydrogen balloon was attached. After 8 hours, the mixture was filtered through a plug of silica with EtOAc. The organic layer was washed with 2 N HCl (aq) (2×50 mL), saturated NaHCO$_3$ (aq) (1×50 mL), brine (1×50 mL) and dried with MgSO$_4$. The organic layer was filtered and concentrated under reduced pressure. The material was chromatographed on silica with 10% EtOAc/hexane to afford M13.2 (5.1 g, 11.22 mmol) as a colorless oil. MS ESI (pos.) m/e: 455.0 (M+H)$^+$.

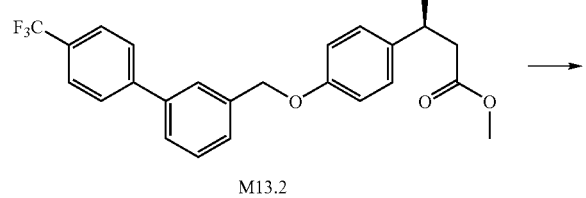

M13.2

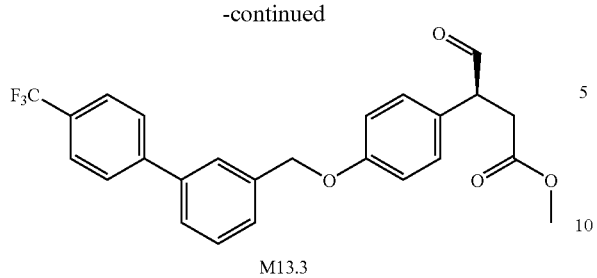

M13.3

Aldehyde (M13.3). Alkene M13.2 (5.1 g, 11.22 mmol) was dissolved in 100 mL of 4:1 (1,2-dioxane/water), and 2,6-lutidine (2.61 mL, 0.920 g/mL, 22.44 mmol) was added. Next, 1.2 g of a 3.4% $OsO_4$ in t-BuOH (0.22 mmol) solution was added dropwise over 5 minutes. $NaIO_4$ (9.6 g, 44.88 mmol) in 25 mL of water was added. The internal reaction temperature did not rise above 30° C. After 8 hours at room temperature, the reaction mixture was diluted with 500 mL of DCM, the layers were separated, and the organic layer was washed with 0.5 M $HCl_{(aq)}$ (2×50 mL), saturated $NaHCO_3$ (aq) (1×50 mL), 5% sodium sulfite (aq) (1×50 mL), and brine. The organic layer was dried with $Na_2SO_4$, filtered, and concentrated under reduced pressure. The residue was flashed on silica with 30% EtOAc/hexanes to afford M13.3 (4.0 g, 9.09 mmol) as a yellow oil. MS ESI (pos.) m/e: 443.4 $(M+H)^+$.

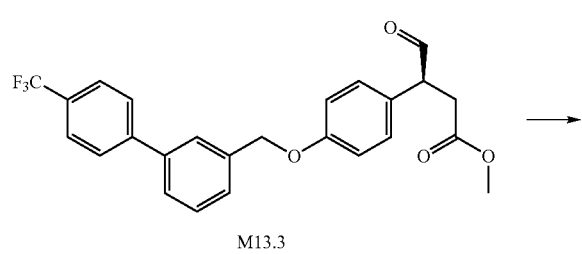

M13.3

M13.4

Acid (M13.4). Aldehyde M13.3 (2.32 g, 5.25 mmol) was dissolved in 20 mL of ACN. To this was added $KH_2PO_4$ (178 mg, 1.31 mmol) in 5 mL of water. The solution was cooled to −5° C. and 30% $H_2O_2$ (aq) (714 mg, 6.30 mmol) was added. $NaClO_2$ (712 mg, 7.88 mmol) was dissolved in 5 mL of water and added via syringe pump over 3 hours while maintaining a temperature below 0° C. After the addition of the $NaClO_2$ solution, the mixture was stirred for 1 hour. 300 mL of DCM was added, and the pH of the aqueous layer was adjusted to 2 with 2 N HCl (aq). The aqueous layer was extracted with DCM (2×100 mL), and the combined organic extracts were washed with 5% sodium sulfite (aq) (1×50 mL), and brine. The organic layer was dried with $NaSO_4$, filtered, and concentrated under reduced pressure. The residue was chromatographed on silica with 50% EtOAc/hexanes to afford M13.4 (2.12 g, 4.62 mmol) as a colorless oil. MS ESI (pos.) m/e: 459.3 $(M+H)^+$.

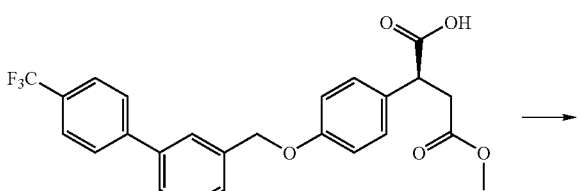

M13.4

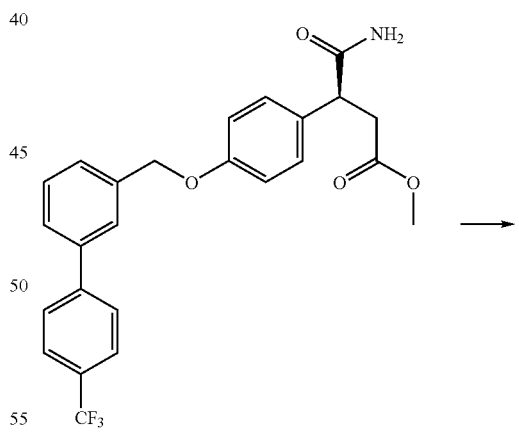

M13.5

Amide (M13.5). Acid M13.4 (6.0 g, 13.1 mmol) was dissolved in 100 mL of DCM. To this was added 1-hydroxybenzotriazole hydrate (3.7 g, 27.5 mmol), N-(3-dimethylaminopropyl)-N'-ethylcarbondiimide hydrochloride (5.0 g, 26.2 mmol), and 2 M ammonia in n-PrOH (14 mL, 26.2 mmol). The reaction was stirred for 8 hours and diluted with 500 mL of EtOAc. The organic layer was washed with 2N HCl (aq) (2×75 mL), $NaHCO_3$ (aq) (1×75 mL), and brine (1×75 mL) and dried with $MgSO_4$ and filtered. The organic layer was concentrated under reduced pressure, and the residue was flashed through silica with 25% EtOAc/DCM. The combined fractions were concentrated under reduced pressure to afford M13.5 (5.3 g, 11.5 mmol) as a colorless oil.

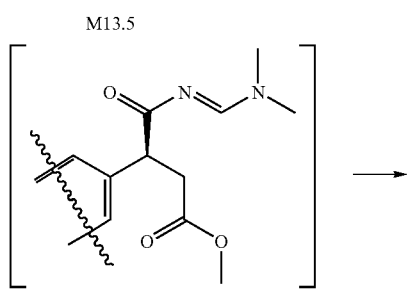

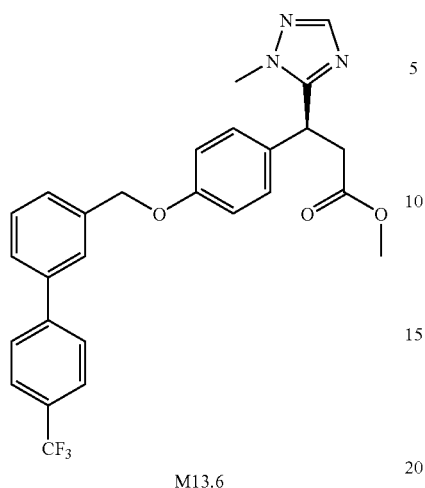

M13.6

(S)-3-(2-Methyl-2H-1,2,4-triazol-3-yl)-3-[4-(4'-trifluoromethyl-biphenyl-3-ylmethoxy)-phenyl]-propionic acid (M13.6). Amide M13.5 (6.48 g, 14.2 mmol) was dissolved in 7 mL of N,N-dimethylformamide dimethyl acetal (119.17 MW, 0.894 g/mL, 52.6 mmol). The solution was gradually heated to 80° C. over 30 minutes. The mixture was allowed to cool to 35° C., and the sample was concentrated under reduced pressure. The residue was dissolved in 20 mL of AcOH followed by careful addition of methylhydrazine (5 mL, 0.866 g/mL, 94.0 mmol) over 5 minutes (the acid/base exotherm was used to run the reaction). The temperature increased to 65° C., and an oil bath at 80° C. was used to finish the reaction. The total heating time was 45 minutes. The reaction was allowed to come to room temperature, and was diluted with 500 mL of DCM. The organic layer was washed with water (3×100 mL), brine (1×100 mL), dried with Na$_2$SO$_4$, filtered, and concentrated to a residue. The material was flashed on silica with 10% ACN/DCM to afford methyltriazole M13.6 (4.3 g, 8.7 mmol) as a yellow oil. MS ESI (pos.) m/e: 496.5 (M+H)$^+$.

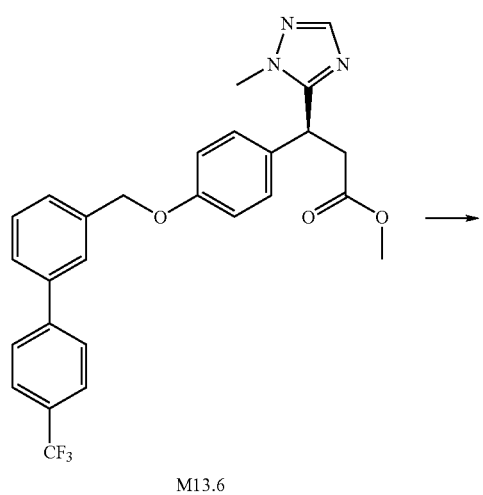

M13.6

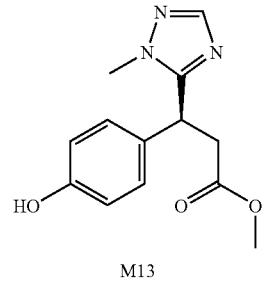

M13

(S)-Methyl 3-(4-hydroxyphenyl)-3-(2-methyl-2H-1,2,4-triazol-3-yl)propanoate (M13). Methyltriazole M13.6 (2.78 g, 5.61 mmol) was dissolved in 50 mL of EtOAc, and nitrogen was bubbled through the solution for 5 minutes. 1 g of palladium on carbon (5 wt. %, wet contains 50% water) was added, and a hydrogen balloon was attached. After 8 hours, the mixture was filtered through a plug of silica with 10% MeOH in EtOAc. The organic layer was concentrated under reduced pressure and partitioned between ACN (100 mL) and hexane (50 mL). The ACN layer was washed with hexane (4×50 mL). The ACN layer was concentrated under reduced pressure to afford (S)-methyl 3-(4-hydroxyphenyl)-3-(2-methyl-2H-1,2,4-triazol-3-yl)propanoate M13 (1.30 g, 4.99 mmol) as a colorless oil. MS ESI (pos.) m/e: 262.4 (M+H)$^+$.

6.14

Method 14

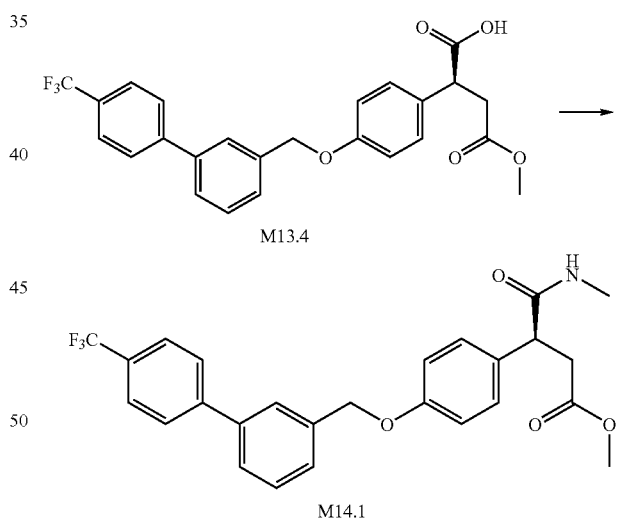

Methylamide (M14.1). Acid M13.4 (6.0 g, 13.1 mmol), prepared as described above, was dissolved in 100 mL of DCM. To this mixture was added 1-hydroxybenzotriazole hydrate (3.7 g, 27.5 mmol), N-(3-dimethylaminopropyl)-N'-ethylcarbondiimide hydrochloride (5.0 g, 26.2 mmol), and 2 M methylamine in THF (14 mL, 26.2 mmol). The reaction was stirred for 8 hours, diluted with 500 mL of EtOAc, and the organic layer was washed with 2N HCl (aq) (2×75 mL), NaHCO$_3$ (aq) (1×75 mL), brine (1×75 mL) and dried with MgSO$_4$ and filtered. The organic layer was concentrated under reduced pressure, and the residue was flashed through silica with 15% EtOAc/DCM. The combined fractions were concentrated under reduced pressure to afford M14.1 (4.2 g, 11.5 mmol) as a colorless oil. MS ESI (pos.) m/e: 472.3 (M+H)+.

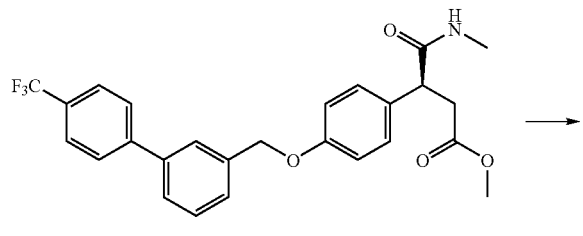

M14.1

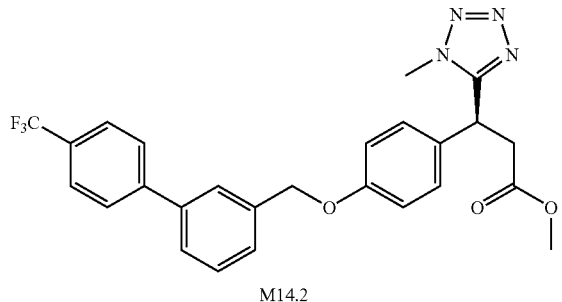

M14.2

(S)-3-(1-Methyl-1H-tetrazol-5-yl)-3-[4-(4'-trifluoromethyl-biphenyl-3-ylmethoxy)-phenyl]-propionic acid (M14.2). Methylamide M14.1 (2.15 g, 4.59 mmol) was dissolved in 50 mL of ACN. NaN$_3$ (900 mg, 13.8 mmol) was added followed by the dropwise addition of Tf$_2$O (5.2 g, 18.4 mmol). The temperature rose to 34° C. The reaction was stirred for 12 hours and diluted with 250 mL of DCM. The organic layer was washed with NaHCO$_3$ (aq) (2×50 mL), brine (1×50 mL) and dried with MgSO$_4$ and filtered. The organic layer was concentrated under reduced pressure, and the residue was flashed through silica with 15% EtOAc/DCM. The combined fractions were concentrated under reduced pressure to afford methyltetrazole M14.2 (1.52 g, 3.07 mmol) as a colorless oil. MS ESI (pos.) m/e: 497.4 (M+H)+.

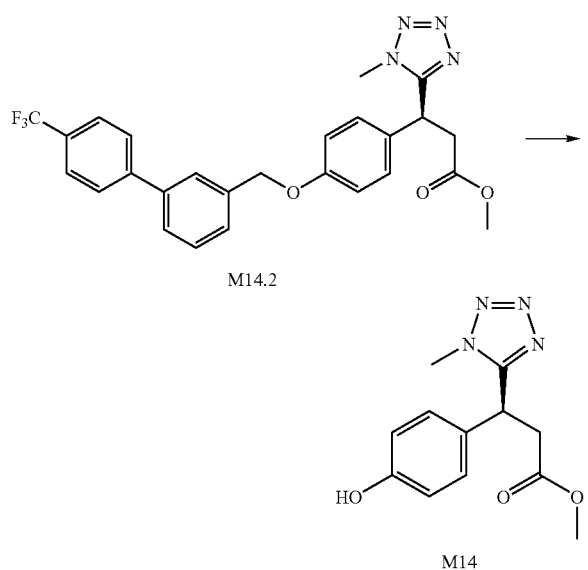

M14.2

M14

(S)-Methyl 3-(4-hydroxyphenyl)-3-(1-methyl-1H-tetrazol-5-yl)propanoate (M14). Methyltetrazole M14.2 (413 mg, 0.833 mmol) was dissolved in 5 mL of EtOAc and nitrogen was bubbled through the solution for 5 minutes. Palladium on carbon (200 mg, 5 wt. %, wet contains 50% water) was added, and a hydrogen balloon was attached. After 8 hours, the mixture was filtered through a plug of silica with 10% MeOH in EtOAc. The organic layer was concentrated under reduced pressure and partitioned between ACN (10 mL) and hexane (5 mL). The ACN layer was washed with hexane (4×5 mL). The ACN layer was concentrated under reduced pressure to afford (S)-methyl 3-(4-hydroxyphenyl)-3-(1-methyl-1H-tetrazol-5-yl)propanoate (M14) (203 mg, 0.775 mmol) as a colorless oil.

Method 15

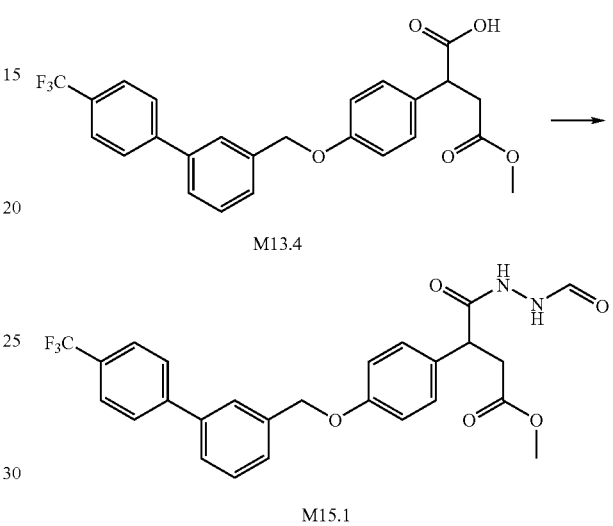

M13.4

M15.1

Formic hydrazide (M15.1). Acid M13.4 (10 mmol) is dissolved in 100 mL of DCM. To this is added 1-hydroxybenzotriazole hydrate (20 mmol), N-(3-dimethylaminopropyl)-N'-ethylcarbondiimide hydrochloride (20 mmol), and formic hydrazide (12 mmol). The reaction is stirred for 8 hours and diluted with 500 mL of EtOAc. The organic layer is washed with 2 N HCl (aq) (2×75 mL), NaHCO$_3$ (aq) (1×75 mL), and brine (1×75 mL) and dried with MgSO$_4$ and filtered. The organic layer is concentrated under reduced pressure, and the residue is purified on silica. The combined fractions are concentrated under reduced pressure to afford M15.1.

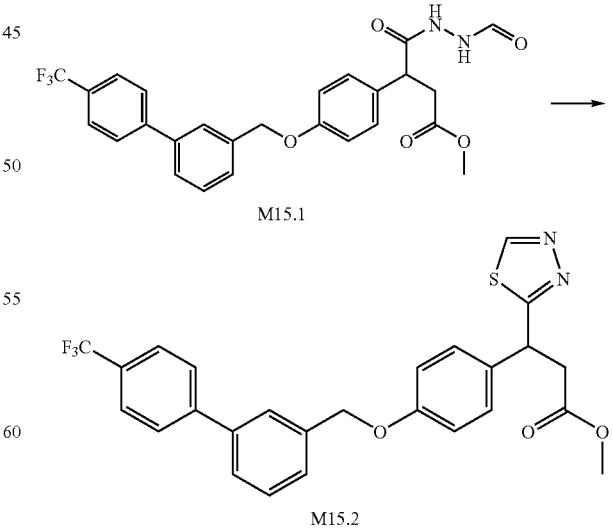

M15.1

M15.2

Thiadiazole (M15.2). Formic hydrazide M15.1 (9 mmol) is dissolved in THF (100 mL) and Lawesson's Reagent (18 mmol) is added. The mixture is stirred for 24 hours and then is concentrated to a residue. The residue is purified on silica gel to afford M15.2.

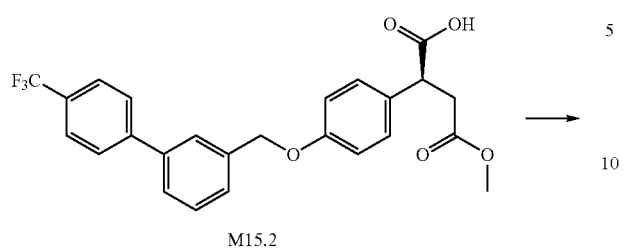

M15.2

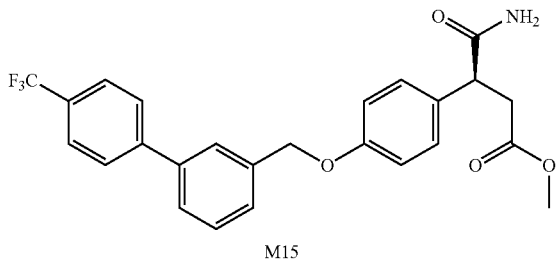

M15

Thiadiazole Phenol (M15). Thiadiazole M15.2 (8 mmol) is dissolved in EtOAc (100 mL) and Pd/C (18 mmol) is added under nitrogen atmosphere. A hydrogen balloon is attached and the mixture is stirred for 24 hours and then is filtered and concentrated to a residue. The residue is purified on silica gel to afford M15.

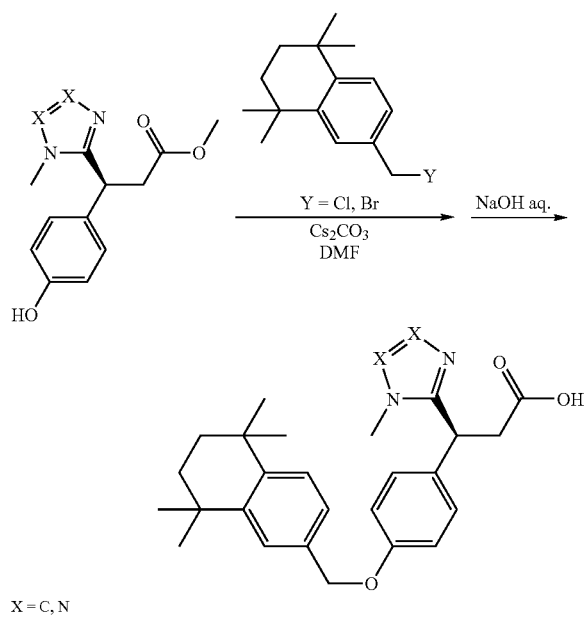

X = C, N

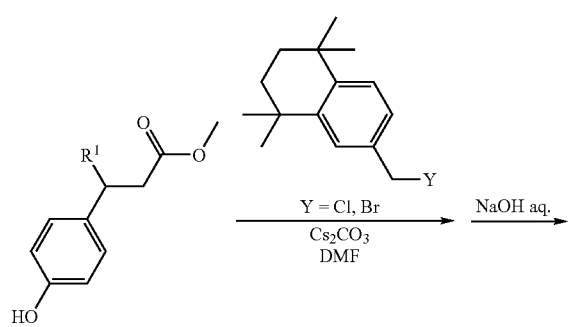

-continued

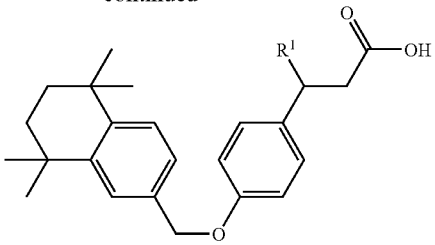

6.15.1 General Procedure A

Reaction of the Various Headgroups with 6-Halomethyl-1, 1,4,4-Tetramethyl-1,2,3, 4-Tetrahydro-naphthalene A mixture of phenol (0.18 mmol), 6-halomethyl-1,1,4,4-tetramethyl-1, 2,3,4-tetrahydro-naphthalene (0.2 mmol) or another benzyl chloride or benzyl bromide compound, and cesium carbonate (0.27 mmol) in DMF (2 mL), was/is stirred at room temperature overnight. The reaction mixture was/is diluted with water and extracted into DCM. The separated DCM layer was/is washed with water. The residue obtained after concentration was/is dissolved into THF and MeOH (1 mL each) and treated with 2 M NaOH solution (0.45 mL, 0.9 mmol). The resulting solution was/is further stirred for 16-48 hours at room temperature. The reaction mixture was/is concentrated, and the residue was/is dissolved in a mixture of DMF/ACN (1:4, 5 mL) containing TFA (67 µL, 0.9 mmol). This solution was/is filtered and purified by preparatory HPLC. The solvent was/is evaporated by freeze-drying to provide the desired product generally as a white amorphous solid.

6.16 Example 1

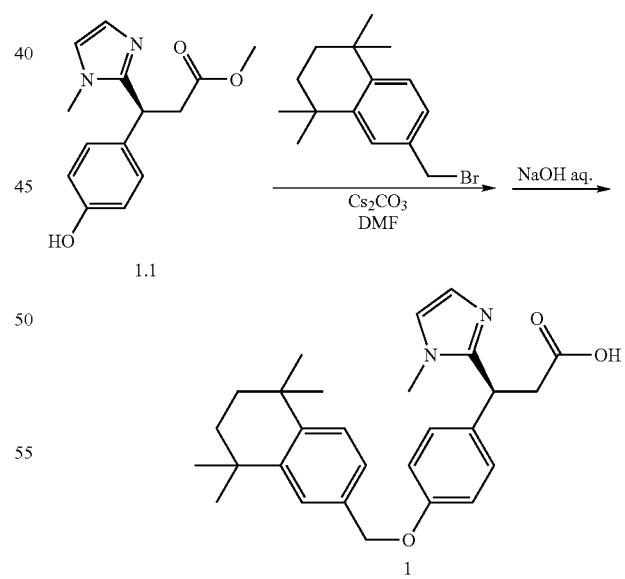

(S)-3-(1-Methyl-1H-imidazol-2-yl)-3-[4-(5,5,8,8-tetramethyl-5,6,7,8-tetrahydro-naphthalen-2-ylmethoxy)-phenyl]-propionic acid (1). Compound 1 was obtained from compound 1.1 (M12) (see Method 12) using the general procedure A. MS ESI (neg.) M/E: 445 (M−H). $^1$HNMR (DMSO-$d_6$) δ 7.65 (s, 1H), 7.6 (s, 1H), 7.3 (overlapping m, 2H), 7.20 (d, 2H), 7.1 (d, 1H), 7.0 (d, 2H), 5.0 (s, 2H), 4.85 (m, 1H), 3.8 (s, 1H), 3.1 (dd, 1H), 1.6 (s, 4H), 1.2 (s, 12H).

6.17 Example 2

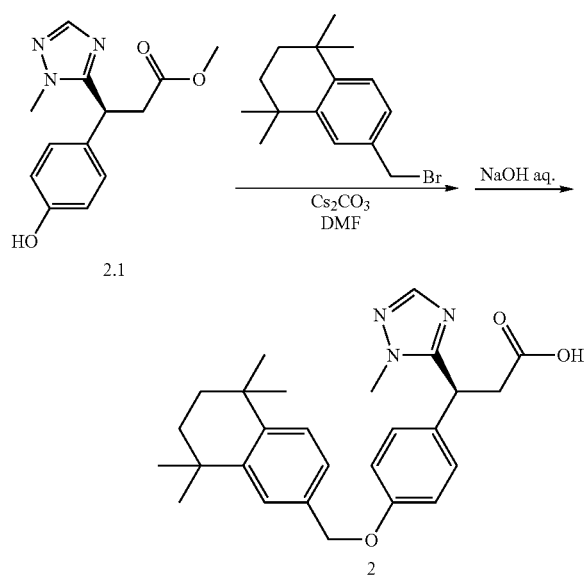

(S)-3-(2-Methyl-2H-[1,2,4]triazol-3-yl)-3-[4-(5,5,8,8-tetramethyl-5,6,7,8-tetrahydro-naphthalen-2-ylmethoxy)-phenyl]-propionic acid (2). Compound 2 was obtained from compound 2.1 (M13) by following the general procedure A. MS ESI (neg.) M/E: 446 (M−H). $^1$HNMR (DMSO-d$_6$) δ 7.75 (s, 1H), 7.2 (m, 2H), 7.12 (s, 2H), 7.08 (d, 1H), 6.85 (d, 2H), 4.9 (s, 2H), 4.5 (m, 1H), 3.6 (s, 3H), 3.1 (dd, 1H), 2.7 (dd, 1H), 1.55 (s, 4H), 1.15 (s, 12H).

6.18 Example 3

This example illustrates the preparation of (S)-3-(3-methyl-3H-1,2,3-triazol-4-yl)-3-(4-((5,5,8,8-tetramethyl-5,6,7,8-tetrahydronaphthalen-2-yl)methoxy) phenyl)propanoic acid (3).

1-methyl-1H-1,2,3-triazole (3.1). A mixture of 2-(trimethylsilyl)-2H-1, 2,3-triazole (179 mmol), MeI (179 mmol), and TBAF on silica gel (16.3 mmol) in ACN (200 mL), was refluxed for 4 hours. After cooling to room temperature, the mixture was concentrated with silica gel and chromatographed (silica gel, 5:95 MeOH/DCM). The fractions containing product were collected, concentrated, and distilled under vacuum to give desired product 1.1 (7.5 g, 90 mmol, b.p.=97° C. at 3 mmHg). MS ESI (pos.) m/e 83.9 (M+H).

(4-(Benzyloxy)phenyl)(3-methyl-3H-1,2,3-triazol-4-yl) methanol (3.2). A solution of n-BuLi (11.6 mL, 1.6 M, 18.6 mmol) in hexane was added dropwise to a solution of 3.1 (1.29 g, 15.5 mmol) in THF (75 mL) at −40° C. After stirring at −40° C. for 2 hours, 4-(benzyloxy)benzaldehyde was added at −40° C., and the reaction was warmed to room temperature. The reaction was quenched saturated NH$_4$Cl (aq) after 3 hours of stirring and then extracted with EtOAc. The organic phase was washed with water and brine, dried over anhydrous sodium sulfate, filtered, and concentrated under reduced pressure. The residue 3.2 was used in the next reaction without further purification. MS ESI (pos.) m/e 296.2 (M+H).

(4-(Benzyloxy)phenyl)(3-methyl-3H-1,2,3-triazol-4-yl) methanone (3.3). Dess-Martin periodinane (8 g, 19 mmol) was added to a solution of 3.2 (~15.5 mmol) in DCM (80 mL). After 1 hour, the reaction mixture was concentrated with silica gel and chromatographed (silica gel, 1:2 EtOAc/hexane) to obtain compound 3.3 (4.3 g, 14.7 mmol). MS ESI (pos.) m/e: 294.1 (M+H).

-continued

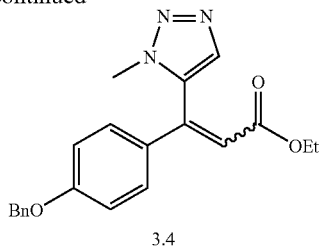
3.4

Ethyl 3-(4-(benzyloxy)phenyl)-3-(3-methyl-3H-1,2,3-triazol-4-yl)acrylate (3.4). To a solution of lithium bis(trimethylsilyl)amide (22 mmol, 1 m in THF) was added ethyl trimethylsilylacetate (31.5 mmol) dropwise at −78° C. After 20 minutes at −78° C., a solution of 3.3 (14.7 mmol) in THF (50 mL) was added dropwise, and the reaction was maintained at −78° C. for 4 hours. The reaction was quenched with saturated NH$_4$Cl (aq) and warmed to room temperature. The mixture was extracted with EtOAc (500 mL), dried over anhydrous sodium sulfate, filtered, and concentrated with silica gel under reduced pressure. The residue was chromatographed (silica gel, 1:1 EtOAc/hexane) to afford compound 3.4 (5.1 g, 14 mmol). MS ESI (pos.) m/e 364.1 (M+H).

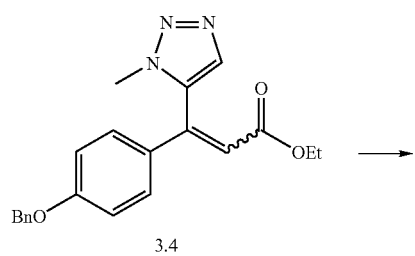
3.4

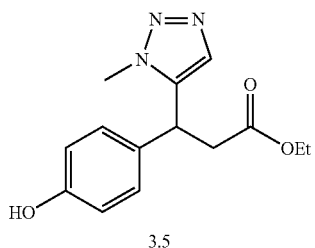
3.5

Ethyl 3-(4-hydroxyphenyl)-3-(3-methyl-3H-1,2,3-triazol-4-yl) propanoate (3.5). 3.4 was dissolved in EtOH and stirred with Pd—C (1.48 g, 0.7 mmol) under hydrogen at room temperature for 3 hours. The Pd—C was removed by filtration through celite with EtOAc as eluant. After concentration, the residue was chromatographed (silica gel, 1:1 EtOAc/hexane) to afford compound 3.5 (3.28 g, 12 mmol). MS ESI (pos.) m/e 276.1 (M+H).

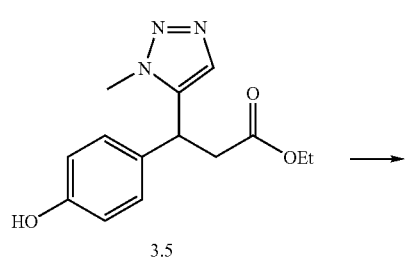
3.5

-continued

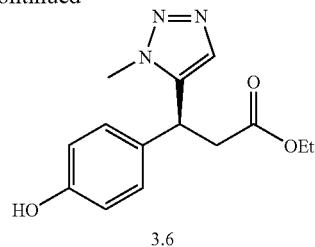
3.6

(S)-ethyl 3-(4-hydroxyphenyl)-3-(3-methyl-3H-1,2,3-triazol-4-yl) propanoate (3.6). Racemic compound 3.5 (3.28 g, 12 mmol) was separated on a semi-preparatory chiral CHIRALCEL OJ-H column (30×250 mm), using 30% i-PrOH hexane as eluant. Eluant containing the peak with less retention time was concentrated and compound 3.6 (1.5 g, 5.45 mmol) was obtained as off-white solid. The absolute configuration was assigned by analogy to other GPR40 agonist compounds. MS ESI (pos.) m/e 276.1 (M+H).

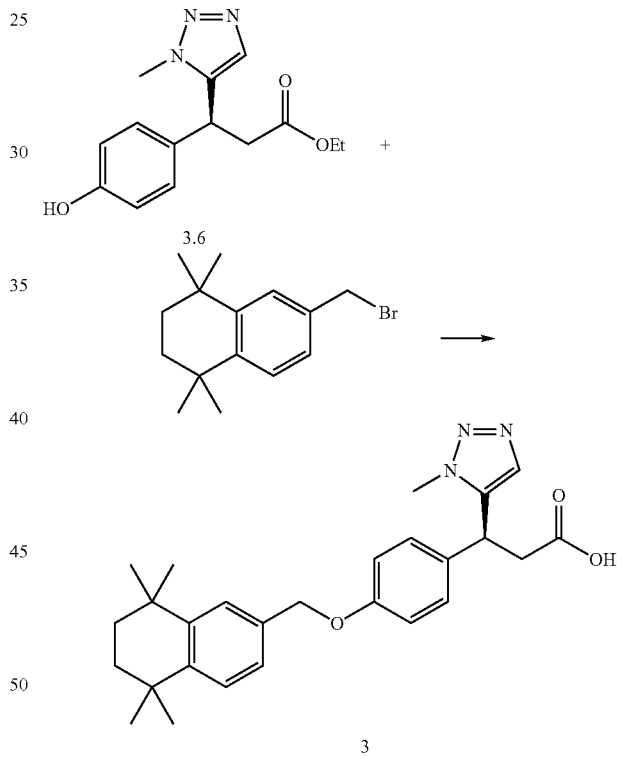
3

(S)-3-(3-methyl-3H-1,2,3-triazol-4-yl)-3-(4-((5,5,8,8-tetramethyl-5,6,7,8-tetrahydronaphthalen-2-yl)methoxy)phenyl)propanoic acid (3). A mixture of 3.6 (0.15 mmol), 6-(bromomethyl)-1,1,4,4-tetramethyl-1,2,3,4-tetrahydronaphthalene (0.18 mmol) and cesium carbonate (0.2 mmol) in DMF (2 mL), was stirred at room temperature for 16 hours. To the reaction mixture was added LiOH in water (1 mL, 1N solution), and the resulting mixture was stirred at 50° C. for 3 hours. The mixture was filtered and purified by reverse phase HPLC to give 3 (26 mg, 0.06 mmol) after lyophilization. MS ESI (pos.) m/e 448.3 (M+H). $^1$H NMR (500 MHz) (CDCl$_3$) δ 7.95 (1H, s), 7.71 (1H, s), 7.33-7.36 (2H, m), 7.20 (1H, dd, J=7.9, 1.5 Hz), 7.07 (2H, d, J=8.5

Hz), 6.97 (2H, d, J=8.9 Hz), 4.98 (2H, s), 4.51-4.55 (1H, m), 3.86 (3H, s), 3.11-3.17 (1H, m), 3.01-3.07 (1H, m), 1.72 (4H, s), 1.31 (6H, s) 1.30 (6H, s).

6.19 Example 4

This example illustrates the preparation of (S)-3-(1-methyl-1H-imidazol-5-yl)-3-(4-((5,5,8,8-tetramethyl-5,6,7,8-tetrahydronaphthalen-2-yl)methoxy)phenyl)propanoic acid (4).

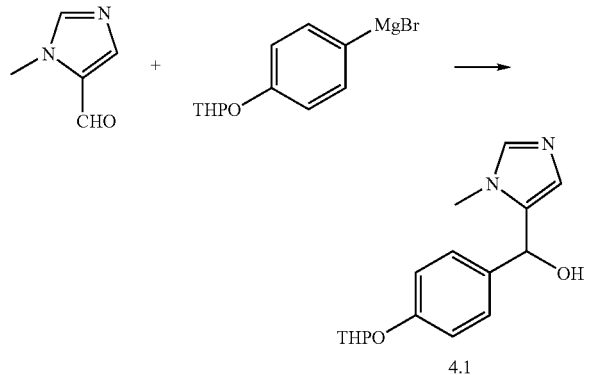

(1-Methyl-1H-imidazol-5-yl)(4-(tetrahydro-2H-pyran-2-yloxy)phenyl)methanol (4.1). 4-(2-Tetrahydro-3H-pyranoxy)phenylmagnesium bromide (110 mL, 0.5 M in THF, 55 mmol) was added dropwise to a solution of 1-methyl-1H-imidazole-5-carbaldehyde (4.7 g, 50 mmol) in THF (790 mL) at −78° C. After stirring −78° C. for 2 hours, the reaction was quenched with saturated NH₄Cl (aq) and warmed to room temperature. The mixture was extracted with EtOAc (500 mL), and the organic phase was washed with water and brine, dried over anhydrous sodium sulfate, filtered, and concentrated under reduced pressure to give 14 g of the crude product 4.1, which was used in the next reaction without further purification.

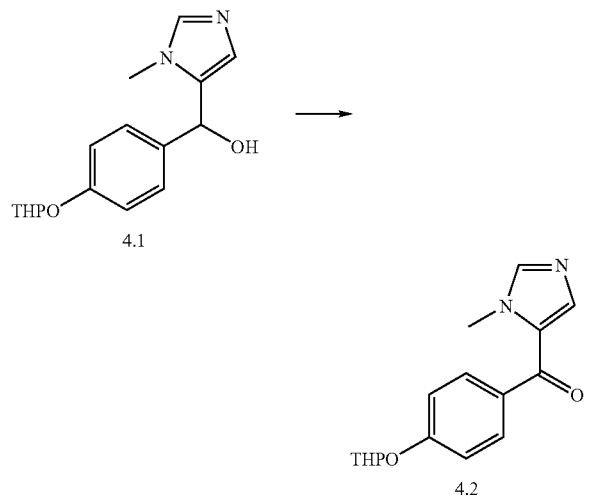

(1-Methyl-1H-imidazol-5-yl)(4-(tetrahydro-2H-pyran-2-yloxy)phenyl)methanone (4.2). Dess-Martin periodinane (21 g, 50 mmol) was added to a solution of 4.1 (14 g crude, ~50 mmol) in DCM (200 mL). After 1 hour, the reaction mixture was concentrated with silica gel and chromatographed (silica gel, 1:2 EtOAc/hexane) to provide compound 4.2 (3.3 g, 11.5 mmol). MS ESI (pos.) m/e: 287.1 (M+H).

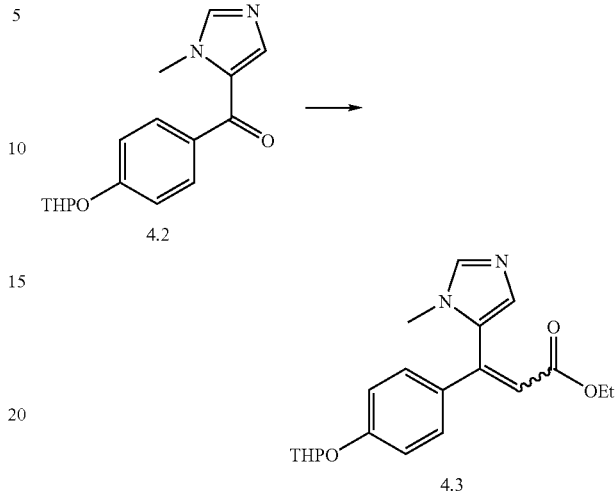

Ethyl 3-(1-methyl-1H-imidazol-5-yl)-3-(4-(tetrahydro-2H-pyran-2-yloxy)phenyl)acrylate (4.3). To a solution of lithium bis(trimethylsilyl)amide (6.8 mmol, 1 M in THF) was added ethyl trimethylsilylacetate (6.5 mmol) dropwise at −78° C. After 20 minutes at −78° C., a solution of 4.2 (5.9 mmol) in THF (20 mL) was added dropwise. The reaction was maintained at −78° C. for 3 hours and at −45° C. for 2 hours. The reaction was quenched with saturated NH₄Cl (aq) at 0° C. and warmed to room temperature. The mixture was extracted with EtOAc (500 mL), dried over anhydrous sodium sulfate, filtered, and concentrated under reduced pressure to afford crude 4.3 (2.49 g). MS ESI (pos.) m/e 357.2 (M+H).

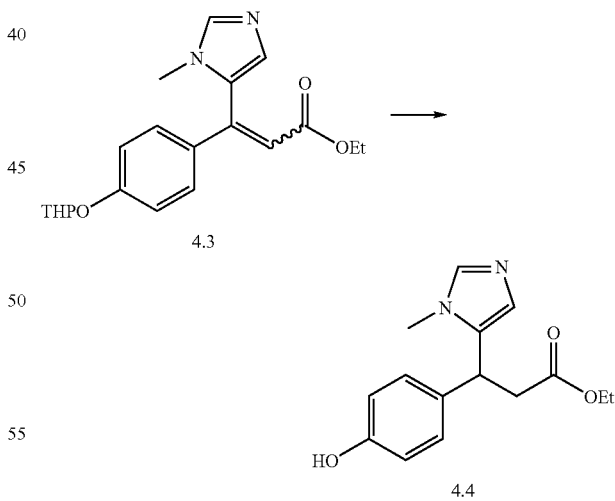

Ethyl 3-(4-hydroxyphenyl)-3-(1-methyl-1H-imidazol-5-yl)propanoate (4.4). The crude 4.3 was dissolved in EtOH (50 mL), stirred with Pd—C (1.48 g, 0.7 mmol) under hydrogen at room temperature for 60 hours. The Pd—C was removed by filtration through celite with EtOAc as eluant. After concentration, the residue was treated with TFA (2 mL) in dry DCM (20 mL) at room temperature for 2 hours. The reaction mixture was concentrated then redissolved in DCM, washed with water, washed with saturated NaHCO₃, dried over Na$_2$SO$_4$, and concentrated under reduced pressure. The residue was chromatographed (silica gel, 1:1 EtOAc/hexane) to afford compound 4.4 (700 mg, 2.6 mmol). MS ESI (pos.) m/e 275.2 (M+H).

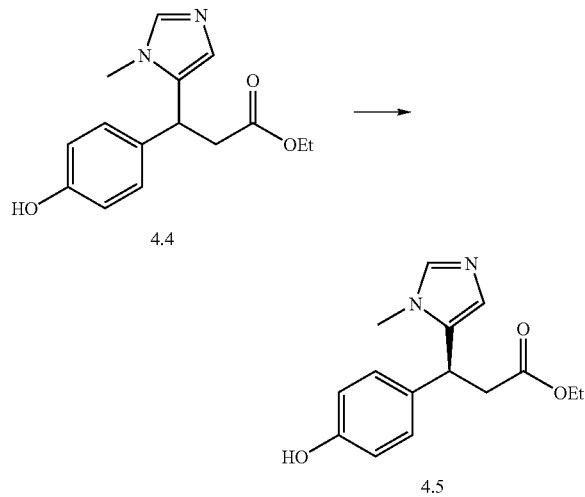

(S)-ethyl 3-(4-hydroxyphenyl)-3-(1-methyl-1H-imidazol-5-yl)propanoate (4.5). Racemic compound 4.4 (680 mg, 2.5 mmol) was separated on a semi-preparatory chiral CHIRAL-CEL OJ-H column (30×250 mm), using 15% i-PrOH in hexane as eluant. Eluant containing the peak with less retention time was concentrated and compound 4.5 (300 mg, 1.1 mmol) was obtained as off-white solid. The absolute configuration was assigned by analogy to other GPR40 agonist compounds. MS ESI (pos.) m/e 275.2 (M+H).

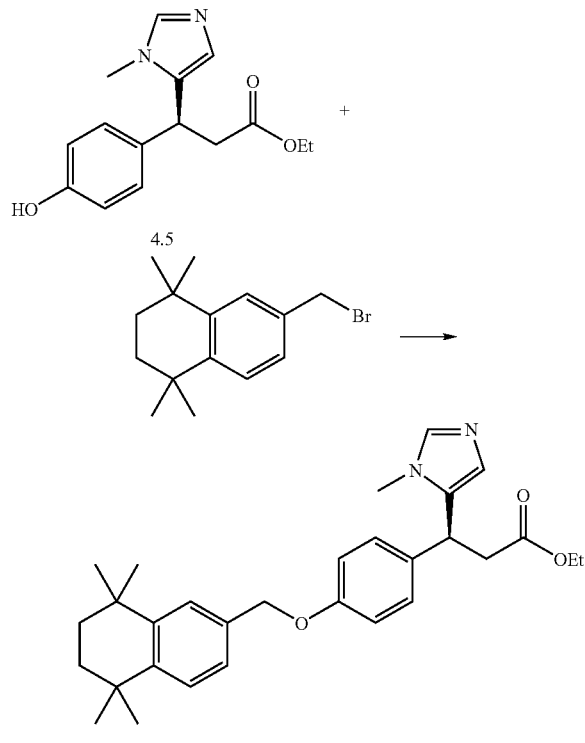

(S)-3-(1-methyl-1H-imidazol-5-yl)-3-(4-((5,5,8,8-tetramethyl-5,6,7,8-tetrahydronaphthalen-2-yl)methoxy)phenyl)propanoic acid (4). A mixture of 4.5 (0.15 mmol), 6-(bromomethyl)-1,1,4,4-tetramethyl-1,2,3,4-tetrahydronaphthalene (0.18 mmol) and cesium carbonate (0.2 mmol) in DMF (2 mL), was stirred at room temperature for 16 hours. To the reaction mixture was added LiOH in water (1 mL, 1N solution), and the reaction was stirred at 50° C. for 3 hours. The mixture was filtered and purified by reverse phase HPLC to give 4 (35 mg, 0.08 mmol) after lyophilization. MS ESI (pos.) m/e 447.3 (M+H). $^1$H NMR (500 MHz) (CDCl$_3$) δ 8.64 (1 H, s), 7.59 (1 H, s), 7.33-7.36 (2 H, m), 7.20 (1 H, dd, J=7.9, 1.8 Hz), 7.08 (2 H, d, J=8.5 Hz), 6.98 (2 H, d, J=8.5 Hz), 4.98 (2 H, s), 4.53 (1 H, m), 3.57 (3 H, s), 2.96-3.06 (2 H, m), 1.71 (4 H, s), 1.31 (6 H, s), 1.30 (6 H, s).

6.20 Example 5

This example illustrates the preparation of (S)-3-(oxazol-5-yl)-3-(4-((5,5,8,8-tetramethyl-5,6,7,8-tetrahydronaphthalen-2-yl)methoxy)phenyl)propanoic acid (5).

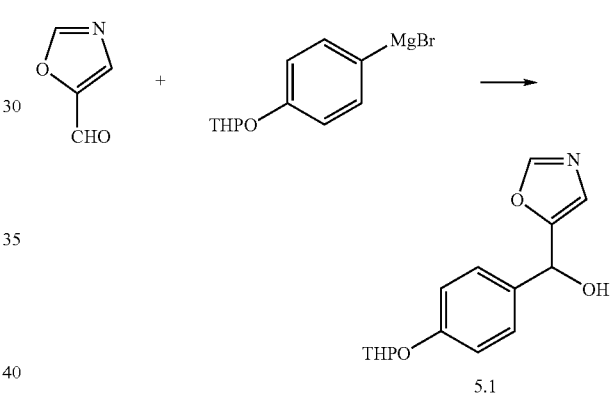

Oxazol-5-yl(4-(tetrahydro-2H-pyran-2-yloxy)phenyl)methanol (5.1). 4-(2-Tetrahydro-3H-pyranoxy)phenylmagnesium bromide (120 mL, 0.5 M in THF, 60 mmol) was added dropwise to a solution of oxazole-4-carbaldehyde (4.85 g, 50 mmol) in THF (90 mL) at −78° C. After stirring at −78° C. for 21 hours, the reaction was quenched with saturated NH$_4$Cl (aq) and warmed to room temperature. The mixture was extracted with EtOAc (500 mL), the organic phase was washed with water and brine, dried over anhydrous sodium sulfate, filtered, and concentrated under reduced pressure to give 17 g of the crude product 5.1, which was used in the next reaction without further purification.

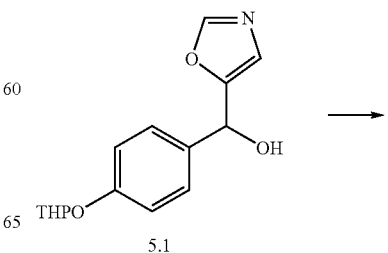

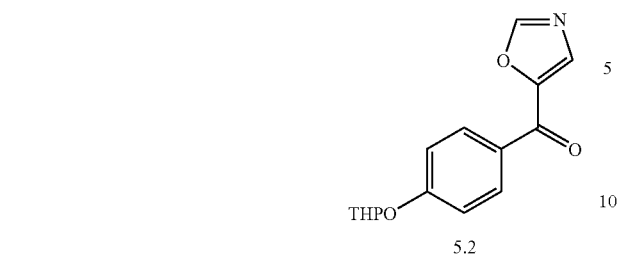

5.2

Oxazol-5-yl(4-(tetrahydro-2H-pyran-2-yloxy)phenyl)methanone (5.2). Dess-Martin periodinane (25 g, 60 mmol) was added to a solution of 5.1 (17 g crude, ~50 mmol) in DCM (200 mL). After 1 hour, the reaction mixture was concentrated with silica gel and chromatographed (silica gel, 1:2 EtOAc/hexane) to obtain compound 5.2 (5.74 g, 21 mmol). MS ESI (pos.) m/e: 274.1 (M+H).

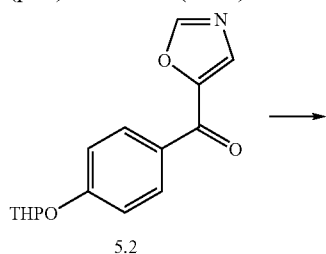

5.2

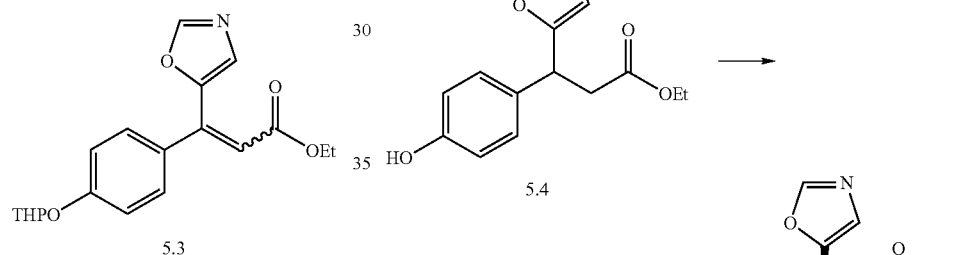

5.3

Ethyl 3-(oxazol-5-yl)-3-(4-(tetrahydro-2H-pyran-2-yloxy)phenyl)acrylate (5.3). To a solution of lithium bis(trimethylsilyl)amide (31.5 mmol, 1 M in THF) was added ethyl trimethylsilylacetate (31.5 mmol) dropwise at −78° C. After 20 minutes at −78° C., a solution of 5.2 (21 mmol) in THF (60 mL) was added dropwise and the reaction was maintained at −78° C. for 1.5 hours. The reaction was quenched saturated NH$_4$Cl (aq) and warmed to room temperature. The mixture was extracted with EtOAc (500 mL), the organic phase was washed with water and brine, dried over anhydrous sodium sulfate, filtered, and concentrated with silica gel under reduced pressure. The residue was chromatographed (silica gel, 1:1 EtOAc/hexane) to afford compound 5.3 (4.83 g, 14 mmol). MS ESI (pos.) m/e 344.2 (M+H).

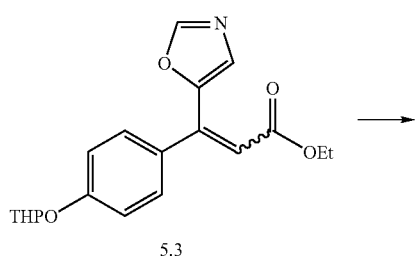

5.3

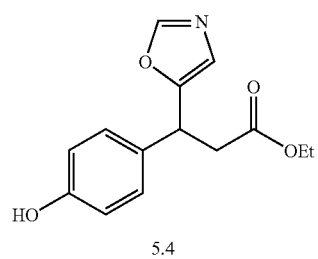

5.4

Ethyl 3-(4-hydroxyphenyl)-3-(oxazol-5-yl)propanoate (5.4). TFA (10 mL) was added to a solution of 5.3 (14 mmol) in dry DCM (100 mL) and stirred at room temperature for 2 hours. To the reaction mixture was slowly added solid NaHCO$_3$ with stirring. The reaction was then washed with saturated NaHCO$_3$ (2×), dried over Na$_2$SO$_4$, and concentrated under reduced pressure. The residue was then re-dissolved in EtOH, stirred with Pd—C (1.48 g, 0.7 mmol) under hydrogen at room temperature for 14 hours. The Pd—C was removed by filtration through celite with EtOAc as eluant. After concentration, the residue was chromatographed (silica gel, 1:1 EtOAc/hexane) to afford compound 5.4 (1.3 g, 5 mmol). MS ESI (pos.) m/e 262.1 (M+H).

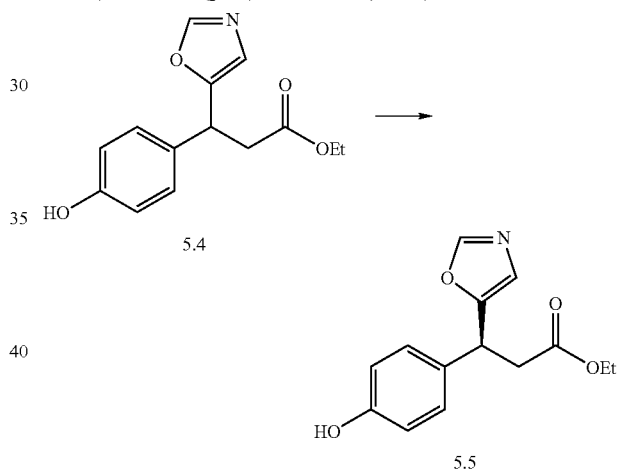

5.4

5.5

(S)-ethyl 3-(4-hydroxyphenyl)-3-(oxazol-5-yl)propanoate (5.5). Racemic compound 5.4 (1.3 g, 5 mmol) was separated on a semi-preparatory chiral CHIRALCEL OJ-H column (30×250 mm), using 20% i-PrOH in hexane as eluant. Eluant containing the peak with greater retention time was concentrated and compound 5.5 (620 mg, 2.38 mmol) was obtained as off-white solid. The absolute configuration was assigned by analogy to other GPR40 agonist compounds. MS ESI (pos.) m/e 262.1 (M+H).

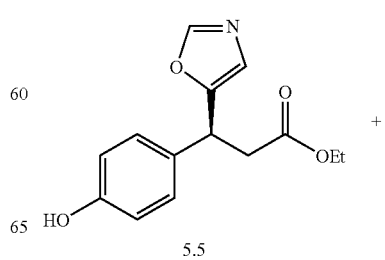

5.5

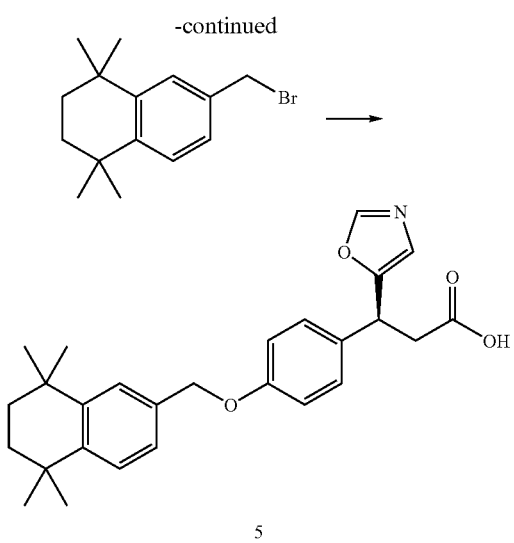

5

(S)-3-(Oxazol-5-yl)-3-(4-((5,5,8,8-tetramethyl-5,6,7,8-tetrahydronaphthalen-2-yl)methoxy)phenyl)propanoic acid (5). A mixture of 5.5 (0.1 mmol), 6-(bromomethyl)-1,1,4,4-tetramethyl-1,2,3,4-tetrahydronaphthalene (0.12 mmol) and cesium carbonate (0.15 mmol) in DMF (2 mL) was stirred at room temperature for 3 hours. To the reaction mixture was added LiOH in water (1 mL, 1N solution), and the reaction was stirred at 50° C. for 3 hours. The mixture was filtered and purified by reverse phase HPLC to give 5 (12 mg, 0.03 mmol) after lyophilization. MS ESI (pos.) m/e 434.2 (M+H). $^1$H NMR (500 MHz) (CDCl$_3$) δ 7.94 (s, 1H); 7.31-7.41 (m, 3H); 7.22 (d, J=8.5 Hz, 2H); 6.99 (d, J=8.5 Hz, 2H); 6.87 (s, 1H); 4.99 (s, 2H); 4.58 (t, J=7.9 Hz, 1H); 3.14 (dd, J=16.5, 7.6 Hz, 1H); 2.99 (dd, J=16.5, 7.6 Hz, 1H); 1.72 (s, 4H); 1.31 (s, 12H).

6.21 Example 6

Synthesis of (S)-3-(Isoxazol-3-yl)-3-(4-((5,5,8,8-tetramethyl-5,6,7,8-tetrahydronaphthalen-2-yl)methoxy)phenyl)propanoic acid (6)

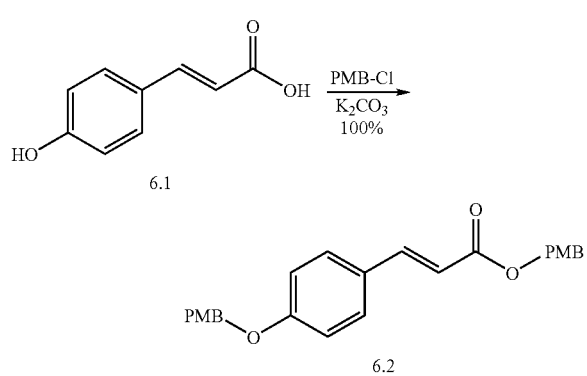

(E)-4-Methoxybenzyl 3-(4-(4-methoxybenzyloxy)phenyl)acrylate (6.2). Potassium carbonate (21 g, 152 mmol) was added to a mixture of 4-hydroxycinnamic acid 6.1 (6.25 g, 38.1 mmol) and p-methoxy benzyl chloride (10.35 mL, 76 mmol) in DMF (100 mL). The mixture was stirred at 80° C. for five hours. After cooling, the mixture was poured into water (700 mL). The solid was collected by filtration, washed with water and dried to give 6.2 (15 g). MS ESI (pos.) m/e: 405 (M+H). $^1$HNMR (CDCl$_3$) δ 7.68 (d, 1H), 7.47 (d, 2H), 7.38 (m, 4H), 6.95 (m, 6H), 6.35 (d, 1H), 5.20 (s, 2H), 5.03 (s, 2H), 3.84 (s, 3H), 3.83 (s, 3H).

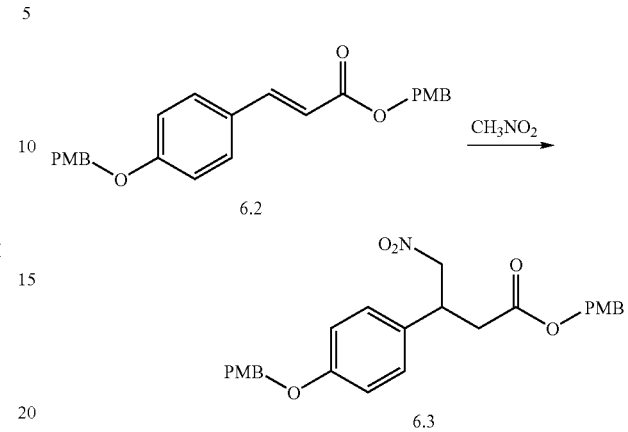

4-Methoxybenzyl 3-(4-(4-methoxybenzyloxy)phenyl)-4-nitrobutanoate (6.3). 1,1,3,3-tetramethylguanidine (0.31 mL, 2.48 mmol) was added to 6.2 (5 g, 12.4 mmol) in nitromethane (20 mL). The mixture was stirred at room temperature for 3 hours, at 50° C. for 3 hours, and at 100° C. for 8 hours. Nitromethane was removed under vacuum and the crude product was purified by flash chromatography to give 6.3 (4.5 g). MS ESI (pos.) m/e: 466 (M+H).

$^1$HNMR (CDCl$_3$) δ 7.37 (d, 2H), 7.19 (d, 2H), 7.12 (d, 2H), 6.92 (m, 6H), 5.01 (s, 2H), 4.97 (s, 2H), 4.68 (m, 1H), 4.59 (m, 1H), 3.96 (m, 1H), 3.84 (s, 3H), 3.82 (s, 3H), 2.77 (m, 2H).

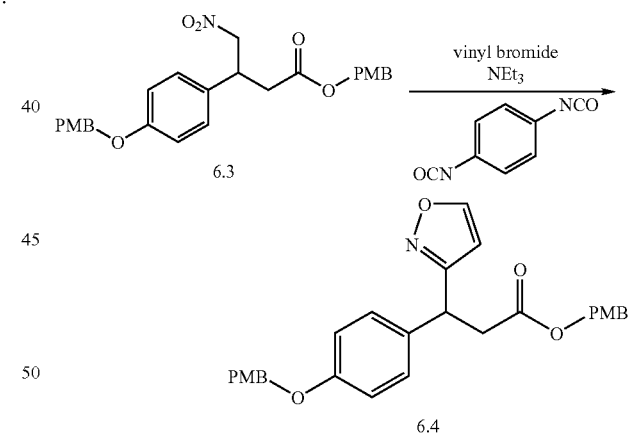

4-Methoxybenzyl 3-(4-(4-methoxybenzyloxy)phenyl)-3-(isoxazol-3-yl)propanoate (6.4). Triethylamine (1 mL) was added to a mixture of 6.3 (1.89 g, 4.1 mmol), vinyl bromide (32.5 mL, 1.0 M solution in THF) and 1,4-phenylene diisocyanate (2.3 g, 14.35 mmol). The mixture was stirred at 80° C. for 8 hours. After cooling, the solid was removed from the mixture by filtration, and the filtrate was concentrated and purified by flash chromatography to give 6.4 (3 g). MS ESI (pos.) m/e: 474 (M+H). $^1$HNMR (CDCl$_3$) δ 8.28 (d, 1H), 7.37 (d, 2H), 7.18 (m, 4H), 6.92 (m, 6H), 6.07 (d, 1H), 5.02 (s, 2H), 4.97 (s, 2H), 4.59 (t, 1H), 3.84 (s, 3H), 3.82 (s, 3H), 3.33 (dd, 1H), 3.00 (dd, 1H).

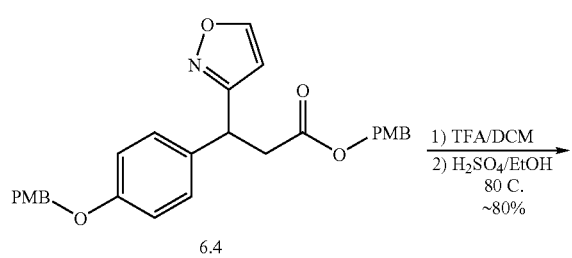

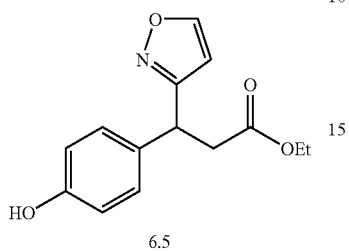

Ethyl 3-(4-hydroxyphenyl)-3-(isoxazol-3-yl)propanoate (6.5). TFA (10 mL) was added to 6.4 (940 mg) in DCM (10 mL). The mixture was stirred at room temperature for 1.5 hours. TFA and DCM were removed under vacuum, and the residue was treated with EtOH (50 mL). The insoluble solid was removed by filtration. To the filtrate was added concentrated sulfuric acid (2 drops). The mixture was stirred at 80° C. overnight. After concentration, the crude product was purified by flash chromatography to give 6.5 (410 mg). MS ESI (pos.) m/e: 262 (M+H). $^1$HNMR (CDCl$_3$) δ 8.29 (d, 1H), 7.12 (d, 2H), 6.76 (d, 2H), 6.10 (d, 1H), 4.56 (t, 1H), 4.10 (q, 2H), 3.27 (dd, 1H), 2.97 (dd, 1H), 1.19 (t, 3H). The racemic compound 6.5 was separated into two enantiomers 6.6 and 6.7 using chiral preparative AD-H column (8% IPA/92% hexanes). The stereochemistry of 6.6 and 6.7 was assigned arbitrarily.

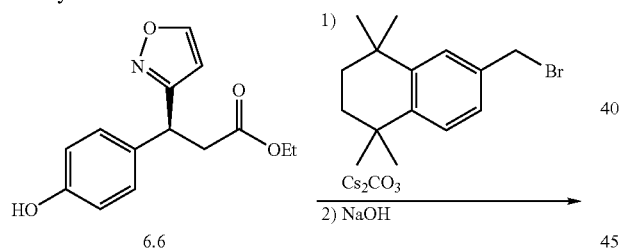

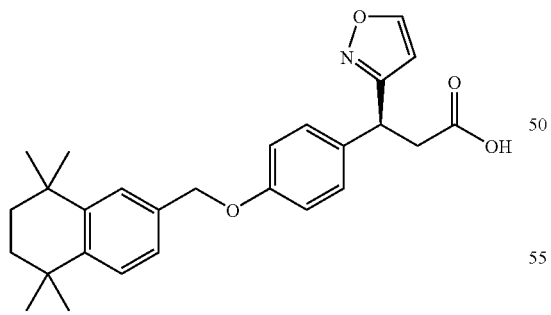

(S)-3-(Isoxazol-3-yl)-3-(4-((5,5,8,8-tetramethyl-5,6,7,8-tetrahydronaphthalen-2-yl)methoxy)phenyl)propanoic acid (6). Cesium carbonate (14 mg, 0.042 mmol) was added into a mixture of 6.6 (10 mg, 0.038 mmol) and 6-(bromomethyl)-1,1,4,4-tetramethyl-1,2,3,4-tetrahydronaphthalene (11 mg, 0.038 mmol) in DMSO (0.5 mL). The mixture was stirred at room temperature for 2 hours and at 35° C. for 4 hours. After cooling, the mixture was treated with EtOAc (5 mL) and brine (5 mL). The organic layer was separated, washed with brine twice, dried and concentrated. The crude product was treated with THF (1 mL), MeOH (1 mL), water (0.5 mL) and NaOH (0.05 mL, 10N). The mixture was stirred at room temperature for 4 hours. The organic solvent was blown away by nitrogen and the aqueous was acidified by HCl (0.18 mL, 3N). The aqueous was extracted with DCM. The organic layer was dried, concentrated and purified by flash chromatography to give 6 (15 mg). MS ESI (pos.) m/e: 434 (M+H). $^1$HNMR (CDCl$_3$) δ 8.30 (d, 1H), 7.35 (m, 2H), 7.19 (m, 3H), 6.96 (d, 2H), 6.09 (d, 1H), 4.97 (s, 2H), 4.57 (t, 1H), 3.37 (dd, 1H), 2.99 (dd, 1H), 1.71 (s, 4H), 1.30 (s, 12H).

6.22 Example 7

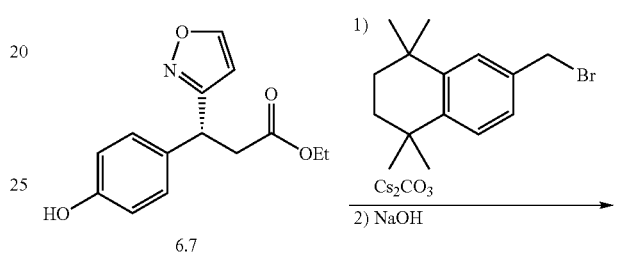

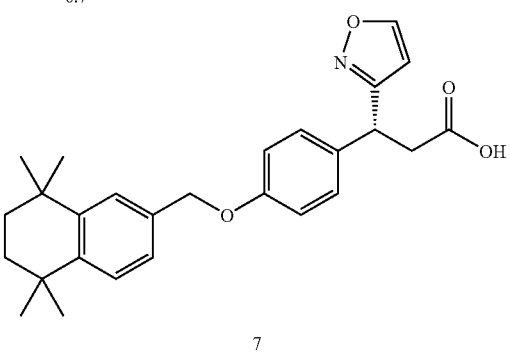

(R)-3-(Isoxazol-3-yl)-3-(4-((5,5,8,8-tetramethyl-5,6,7,8-tetrahydronaphthalen-2-yl)methoxy)phenyl)propanoic acid (7). Compound 7 was synthesized using the procedure above for preparing Example 6 using compound 6.7. MS ESI (pos.) m/e: 434 (M+H). $^1$HNMR (CDCl$_3$) δ 8.30 (d, 1H), 7.35 (m, 2H), 7.19 (m, 3H), 6.96 (d, 2H), 6.09 (d, 1H), 4.97 (s, 2H), 4.57 (t, 1H), 3.37 (dd, 1H), 2.99 (dd, 1H), 1.71 (s, 4H), 1.30 (s, 12H).

6.23 Example 8

Synthesis of (3S)-3-(1-Methyl-1H-imidazol-2-yl)-3-(4-(1-(5,5,8,8-tetramethyl-5,6,7,8-tetrahydronaphthalen-2-yl)ethoxy)phenyl)propanoic acid (8)

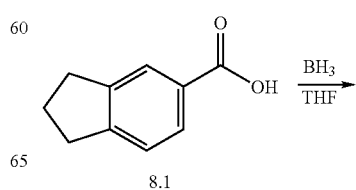

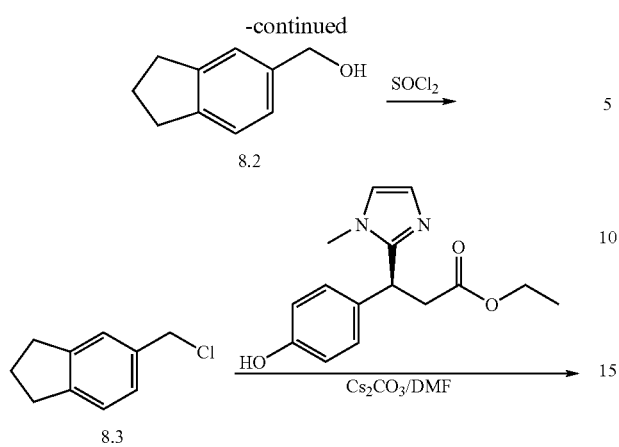

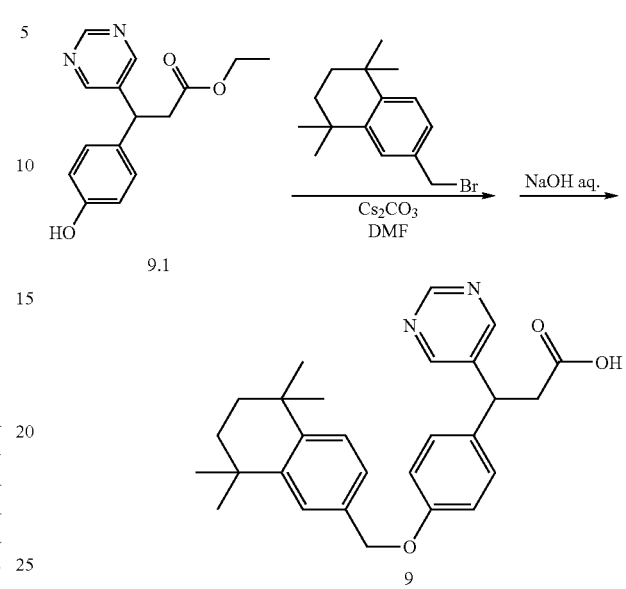

(2,3-Dihydro-1H-inden-5-yl)methanol (11) To a solution of 8.1 (1.0 g, 6.17 mmol) in THF was slowly dripped $BH_3 \cdot THF$ (30 mL, 1.0 M in THF) at 0° C. The reaction mixture was stirred at this temperature for 2 hours and then quenched with water. The mixture was poured into water, and extracted with EtOAc. The crude product was chromatographed on a silica gel column to afford the alcohol 8.2. $^1$HNMR (DMSO-$d_6$) δ 7.17-7.15 (m, 2H), 7.05 (d, 1H, J=7.57 Hz), 5.04 (t, 1H, J=5.87 Hz), 4.45 (d, 2H, J=5.63 Hz), 2.84 (m, 4H), 2.01 (m, 2H).

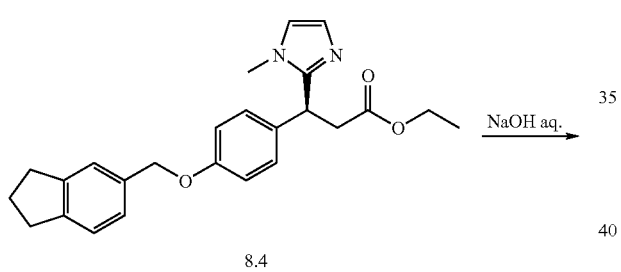

(3S)-3-(1-Methyl-1H-imidazol-2-yl)-3-(4-(1-(5,5,8,8-tetramethyl-5,6,7,8-tetrahydronaphthalen-2-yl)ethoxy)phenyl)propanoic acid (8) This compound was prepared by procedure analogous to that described in Example 16 starting with intermediate 8.2 which was converted to chloride 8.3 and then reacted with the imidazole phenol M12 shown in the reaction scheme and followed be removal of the ester group. MS ESI (pos.) m/e: 377.2 (M+H).

$^1$HNMR (MeOH-$d_4$) δ 7.52-7.48 (d, 2H), 7.26 (s, 1H), 7.23-7.15 (m, 4H), 7.02 (d, 2H, J=8.80 Hz), 5.04 (s, 2H), 4.95 (m, 1H), 3.84 (s, 3H), 3.37 (m, 1H), 3.19 (m, 1H), 2.89 (t, 4H, J=7.34 Hz), 2.08 (m, 2H).

6.24 Example 9

(R/S)-3-Pyrimidin-5-yl-3-[4-(5,5,8,8-tetramethyl-5,6,7,8-tetrahydro-naphthalen-2-ylmethoxy)-phenyl]-propionic acid (9). Compound 79.1 was prepared using the procedure in Method 12 used to prepare M12.5 using pyrimidine-5-carboxaldehyde in place of 1-methyl-2-imidazolecarboxaldehyde. Compound 9 was obtained from compound 9.1 by following the general procedure A. MS ESI (neg.) M/E: 443 (M−H). $^1$HNMR (DMSO-$d_6$) δ 8.9 (s, 1H), 8.7 (s, 2H), 7.25 (m, 4H), 7.1 (d, 1H), 6.8 (d, 1H), 4.9 (s, 2H), 4.3 (m, 1H), 3.1 (dd, 1H), 3.0 (dd, 1H), 1.55 (s, 4H), 1.15 (s, 12H).

6.25 Example 10

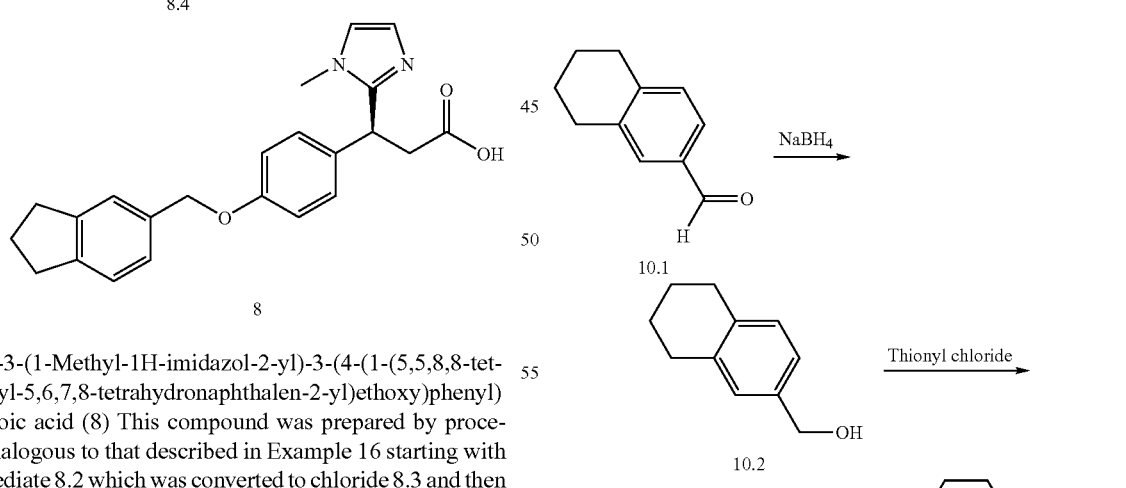

Compound 10.1 was reduced to 10.2 using a procedure very similar to that described in JOC, 43, (1978), 2167. 10.2 was converted to 10.3 by simply treating it with thionyl chloride at room temperature.

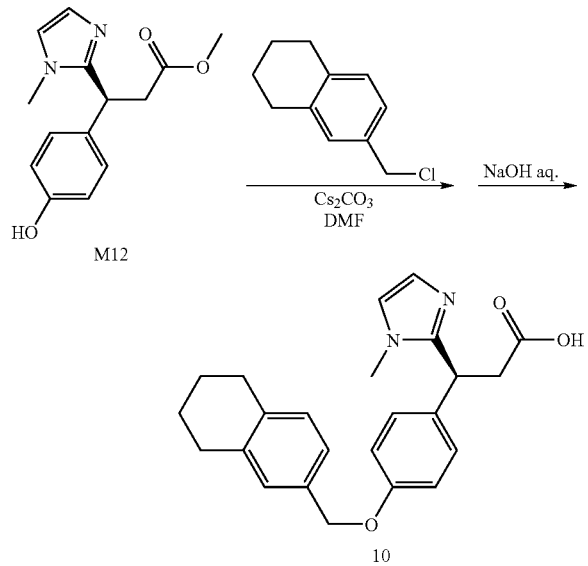

(S)-3-(1-Methyl-1H-imidazol-2-yl)-3-[4-(5,6,7,8-tetrahydro-naphthalen-2-ylmethoxy)-phenyl]-propionic acid (10). Compound 10 was obtained from compound M12 and 10.3 by following the general procedure A. MS ESI (neg.) M/E: 389 (M−H). ¹HNMR (DMSO-d₆) δ 7.6 (s, 1H), 7.5 (s, 1H), 7.2 (d, 2H), 7.1-6.9 (overlapping signals, 5H), 4.9 (s, 2H), 4.8 (m, 1H), 3.7 (s, 1H), 3.3 (dd, 1H), 3.0 (dd, 1H).

6.26 Example 11

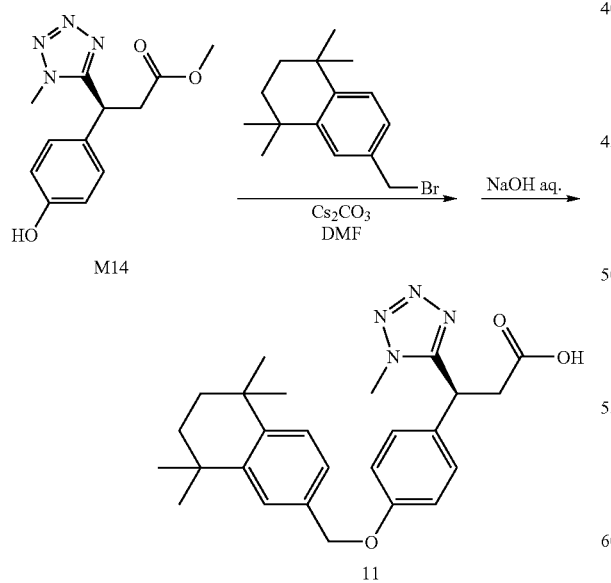

(S)-3-(1-Methyl-1H-tetrazol-5-yl)-3-[4-(5,5,8,8-tetramethyl-5,6,7,8-tetrahydro-naphthalen-2-ylmethoxy)-phenyl]-propionic acid (11). Compound 11 was obtained from compound M14 by following the general procedure A. MS ESI (neg.) M/E: 447 (M−H). ¹HNMR (DMSO-d₆) δ 7.3 (2s, 2H), 7.2 (d, 2H), 7.1 (d, 1H), 7.05 (d, 1H), 6.85 (d, 2H), 4.9 (s, 2H), 4.6 (m, 1H), 3.8 (s, 3H), 3.2 (dd, 1H), 2.8 (dd, 1H), 1.55 (s, 4H), 1.1 (s, 12H).

6.27 Example 12

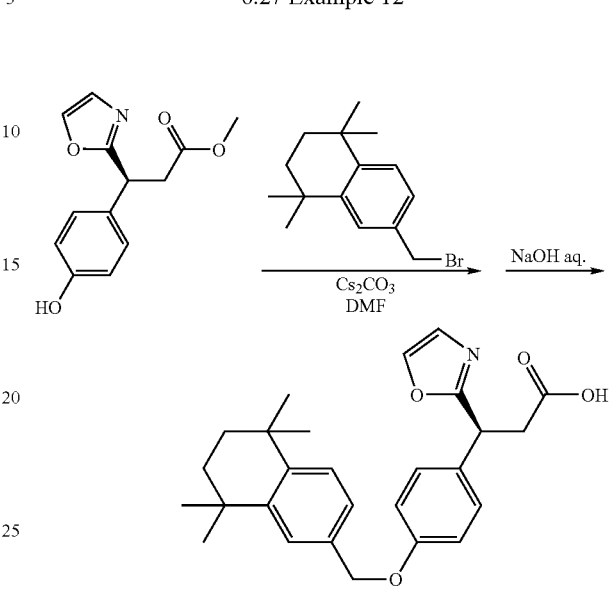

(S)-3-Oxazol-2-yl-3-[4-(5,5,8,8-tetramethyl-5,6,7,8-tetrahydro-naphthalen-2-ylmethoxy)-phenyl]-propionic acid (12). Compound 12 was obtained from compound 12.1 (resolved M11) by following the general procedure A. MS ESI (neg.) M/E: 432 (M−H). ¹HNMR (MeOH-d₄) δ 7.8 (s, 1H), 7.3 (m, 2H), 7.2 (m, 3H), 7.1 (s, 1H), 6.95 (d, 2H), 5.0 (s, 2H), 4.6 (m, 1H), 3.8 (s, 3H), 3.25 (dd, 1H), 2.9 (dd, 1H), 1.7 (s, 4H), 1.3 (s, 12H).

6.28 Examples 13 and 14

Synthesis of carboxylic acids (13) and (14)

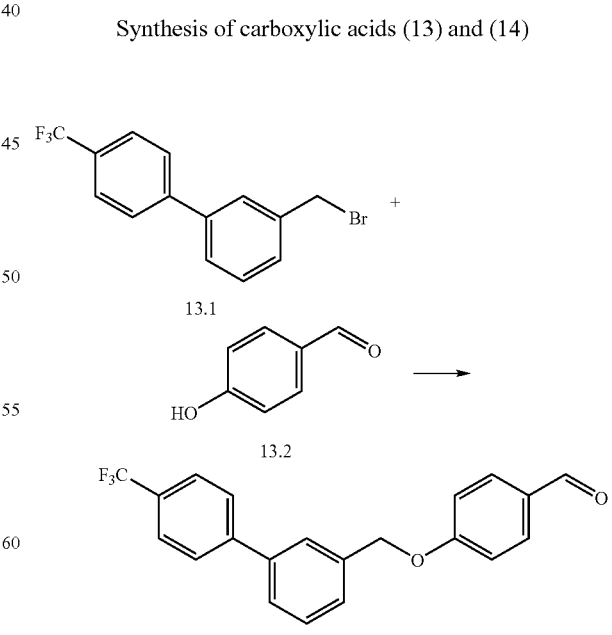

Aldehyde (13.3). The benzyl bromide 13.1 (10.24 g, 32.5 mmol) and 4-hydroxybenzaldehyde 13.2 (3.97 g, 32.5 mmol)

were dissolved in 300 mL of acetone. K$_2$CO$_3$ (8.9 g, 65 mmol) was then added. After 18 hours at room temperature, the reaction mixture was filtered through a plug of silica and concentrated afford 13.3 (11.4 g, 32 mmol, 98% yield). MS ESI (pos.) m/e: 357 (M+H)$^+$.

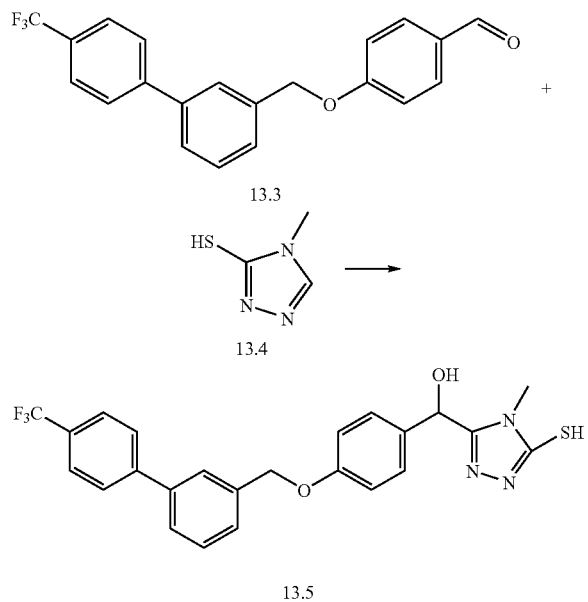

Alcohol (13.5). 3-Mercapto-4-methyl-1,2,4-triazole (468 mg, 4.07 mmol) was dissolved in 100 mL of THF and the solution was cooled to −78° C. under a nitrogen atmosphere. 2.5 M n-BuLi (4.07 mL, 10.18 mmol) was added over one minute. After 5 minutes, a solution of aldehyde 13.3 (1.45 g, 4.07 mmol) in 8 mL THF was added over 5 minutes. After 2 hours, the reaction mixture was poured onto 100 mL saturated NH$_4$Cl$_{(aq)}$ solution and subsequently diluted with 100 mL EtOAc. The organic layer was washed with water (1×250 mL), brine (1×250 mL) and dried with MgSO$_4$. The organic layer was filtered and concentrated under reduced pressure. The crude material was flashed through silica with 40% EtOAc/Hex to afford 13.5 (1.44 g, 3.06 mmol, 75% yield). MS ESI (pos.) m/e: 472 (M+H)$^+$.

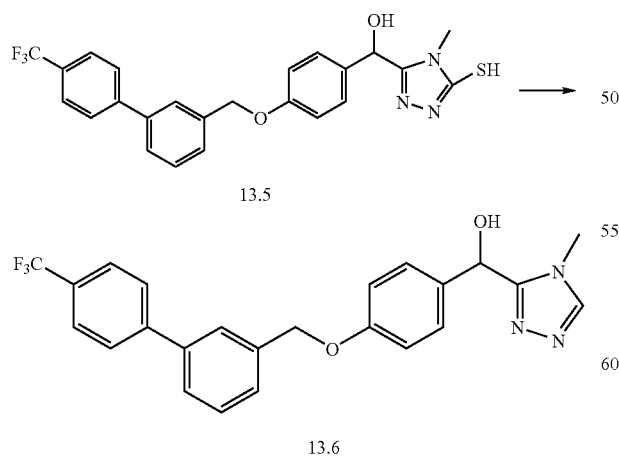

Alcohol (13.6). Alcohol 13.5 (1.44 g, 3.06 mmol) was dissolved in 50 mL of 4:1 THF/water. To this mixture was added NaNO$_2$ (422 mg, 6.12 mmol) followed by dropwise addition of concentrated HNO$_3$ (0.38 mL, 6.12 mmol). The reaction was stirred for 1 hour and then was diluted with 400 mL of EtOAc. The organic layer was washed with NaHCO$_{3(aq)}$ (2×150 mL), brine (1×150 mL), dried with MgSO$_4$, and filtered. The organic layer was concentrated under reduced pressure to afford 13.6 (1.34 g crude material). MS ESI m/e: 440 (M+H)$^+$.

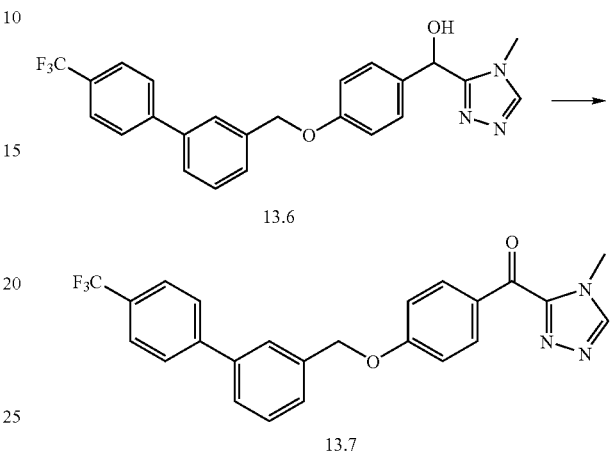

Ketone (13.7). Alcohol 13.6 (1.34 g crude) was dissolved in 50 mL of THF and Dess-Martin (15 mL, 0.3 M, 4.5 mmol) was added. After 18 hours, the mixture was diluted with EtOAc and then washed with NaSO$_3$(aq) (2×150 mL), brine (1×150 mL), and dried with MgSO$_4$ and filtered. The organic layer was concentrated under reduced to afford ketone 13.7 (1.34 g crude). MS ESI (pos.) m/e: 438 (M+H)$^+$.

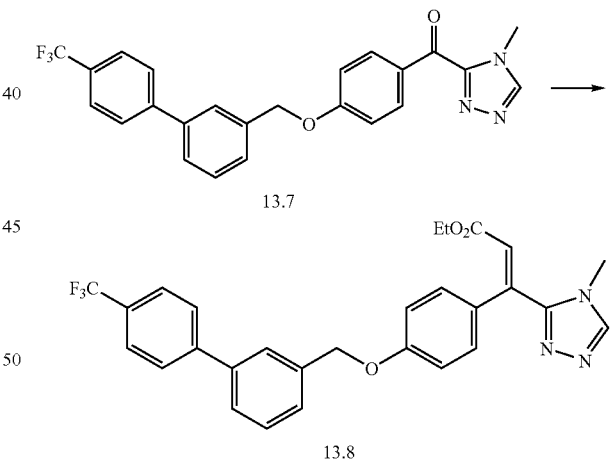

Ethyl ester (13.8). LHMDS (3 mL, 1 M, 3.00 mmol) was diluted with 25 mL of THF and cooled to −78° C. Then, ethyltrimethylsilylacetate (0.47 mL, 2.57 mmol) was added dropwise and the mixture was allowed to warm to −50° C. over 1.5 hours. The mixture was cooled to −78° C. and the ketone 13.7 (934 mg, 2.14 mmol) was added in 20 mL THF. After 1 hour, the mixture was poured onto 100 mL saturated NH$_4$Cl (aq) solution and subsequently diluted with 250 mL of EtOAc. The organic layer was separated and washed with brine (1×150 mL). The organic layer was dried with MgSO$_4$, filtered and concentrated under reduced pressure to afford 13.8 as a crude material. MS ESI (pos.) m/e: 508 (M+H)$^+$.

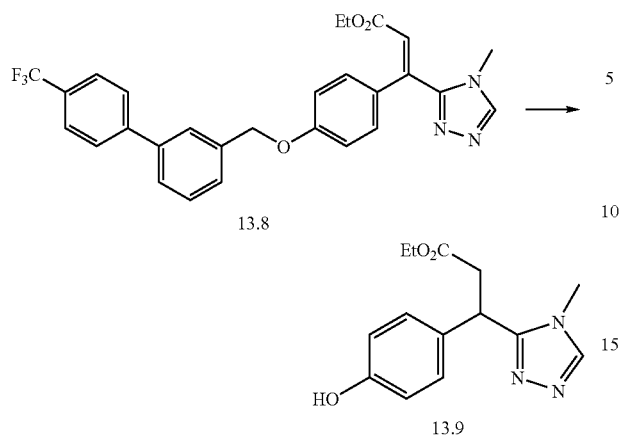

1,2,4-(4-Methyltriazole) (13.9). The ester 13.8 (~2.14 mmol) was dissolved in 50 mL of EtOAc then wet Pd/C (1.77 g) was added. The mixture was flushed with nitrogen, and a hydrogen balloon was attached. After 14 hours, the mixture was filtered through a small plug of silica, and the material was concentrated under reduced pressure. The residue was prepared by HPLC C18 chromatography to afford phenol 13.9 (400 mg, 1.45 mmol) as a white solid. The material was dissolved in MeOH and the enantiomers were separated on a Chiral AD-H column. 180 mg of each enantiomer was obtained. MS ESI (pos.) m/e: 276 (M+H)+.

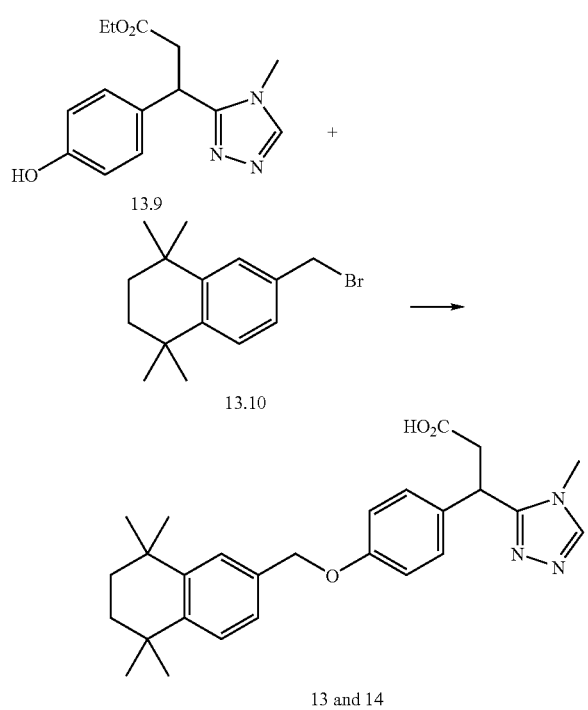

13 and 14

Carboxylic Acids (13 and 14). Benzyl bromide 13.10 (58 mg, 0.19 mmol) and phenol 13.9 (either of the separated enantiomers) (47 mg, 0.17 mmol) were dissolved in DMF (3 mL) and treated with $Cs_2CO_3$ (277 mg, 0.86 mmol). The reaction was stirred at room temperature for 16 hours and then diluted with EtOAc (50 mL) and washed with water (1×50 mL), brine (1×50 mL), then dried with $MgSO_4$, filtered, and concentrated to a residue. The residue was dissolved in THF/ MeOH/water, 3:1:1, and 10 equivalents 2N $LiOH_{(aq)}$ was added. The reaction was stirred for 12 hours and then concentrated to a residue. The residue was purified by HPLC C18 column chromatography (ACN/Water/TFA). Eluent containing compound 13 or 14 (depending on the enantiomer of 13.9 used) was lyophilized to afford a white solid (40 mg, 52%).

$^1$H NMR (500 MHz) ($DMSO_{D6}$) δ 8.50 (s, 1H); 7.35 (d, J=1.6 Hz, 1H); 7.32 (d, J=8.8 Hz, 1H); 7.16-7.19 (m, 3H); 6.96 (d, J=9.4 Hz, 2H); 4.97 (s, 2H); 4.56 (dd, J=6.1, 9.4 Hz, 1H); 3.44 (s, 3H); 3.24 (dd, J=9.4, 17.2 Hz, 1H); 2.84 (dd, J=6.1, 17.2 Hz, 1H); 1.64 (s, 4H); 1.24 (s, 6H); 1.23 (s, 6H). MS ESI (pos.) m/e: 448.1 (M+H)+.

6.29 Example 15

Synthesis of 3-(4,5-Dihydroisoxazol-3-yl)-3-(4-((5,5,8,8-tetramethyl-5,6,7,8-tetrahydronaphthalen-2-yl)methoxy)phenyl)propanoic acid (15)

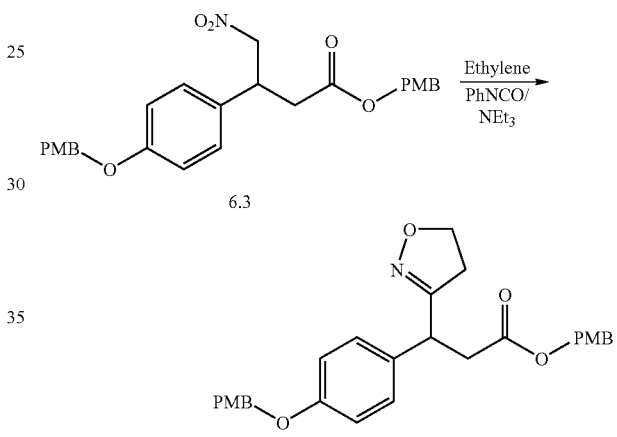

4-Methoxybenzyl 3-(4-(4-methoxybenzyloxy)phenyl)-3-(4,5-dihydroisoxazol-3-yl)propanoate (15.1). Ethylene was bubbled into a mixture of 6.3 (235 mg, 0.5 mmol, see Example 6) in benzene (2 mL) for 20 minutes. Phenyl isocyanate (0.22 mL, 2 mmol) and TEA (3 drops) were then added. The mixture was stirred at room temperature for 2 days. The solid was removed by filtration and washed by benzene. The filtrate was concentrated and purified by flash chromatography to give 15.1 (200 mg). MS ESI (pos.) m/e: 476 (M+H).

$^1$HNMR ($CDCl_3$) δ 7.37 (d, 2H), 7.21 (d, 2H), 7.16 (d, 2H), 6.92 (m, 6H), 5.05 (dd, 2H), 4.98 (s, 2H), 4.25 (m, 2H), 4.10 (t, 1H), 3.84 (s, 3H), 3.82 (s, 3H), 3.24 (dd, 1H), 2.79 (m, 3H).

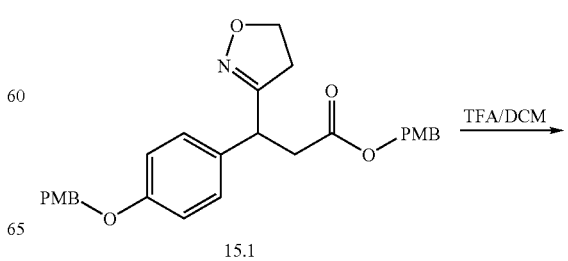

-continued

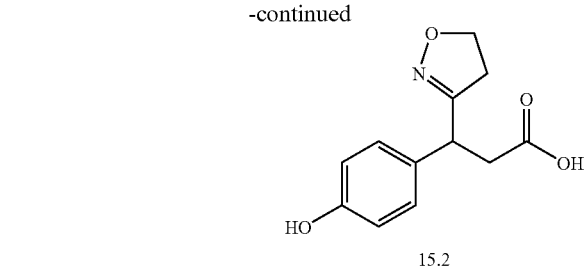

15.2

3-(4,5-Dihydroisoxazol-3-yl)-3-(4-hydroxyphenyl)propanoic acid (15.2). TFA (1 mL) was added to 15.1 (100 mg) in DCM (1 mL). The mixture was stirred at room temperature for 40 hours. TFA and DCM were removed under vacuum, and the residue was treated with EtOH (50 mL). The insoluble solid was removed by filtration. The filtrate was concentrated to give 15.2 (50 mg), which was used in the next step without further purification. MS ESI (pos.) m/e: 236 (M+H).

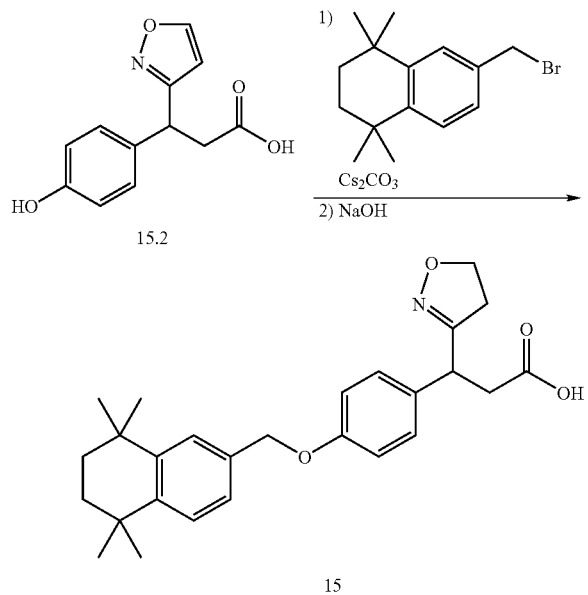

15

3-(4,5-Dihydroisoxazol-3-yl)-3-(4-((5,5,8,8-tetramethyl-5,6,7,8-tetrahydronaphthalen-2-yl)methoxy)phenyl)propanoic acid (15). Cesium carbonate (108 mg, 0.33 mmol) was added into a mixture of 15.2 (25 mg, 0.11 mmol) and 6-(bromomethyl)-1,1,4,4-tetramethyl-1,2,3,4-tetrahydronaphthalene (76 mg, 0.27 mmol) in DMSO (1 mL). The mixture was stirred at 45° C. for 3 hours. After cooling, the mixture was treated with EtOAc (5 mL) and brine (5 mL). The organic layer was separated, washed with brine twice, dried and concentrated. The crude product was treated with THF (1 mL), MeOH (1 mL), water (0.5 mL) and NaOH (0.05 mL, 10N). The mixture was stirred at room temperature for 4 hours. The organic solvent was blown away by nitrogen, and the aqueous layer was acidified by HCl (0.18 mL, 3N). The aqueous layer was extracted with DCM. The organic layer was dried, concentrated and purified by flash chromatography to give 15 (15 mg). MS ESI (pos.) m/e: 436 (M+H).

$^1$NMR (CDCl$_3$) δ 7.35 (m, 2H), 7.19 (m, 3H), 6.96 (d, 2H), 4.97 (s, 2H), 4.28 (m, 2H), 4.07 (t, 1H), 3.28 (dd, 1H), 2.79 (m, 3H), 1.71 (s, 4H), 1.30 (s, 12H).

6.30 Example 16

Synthesis of (S)-3-(4-((8,8-Dimethyl-5,6,7,8-tetrahydronaphthalen-2-yl)methoxy)phenyl)-3-(1-methyl-1H-imidazol-2-yl)propanoic acid (16)

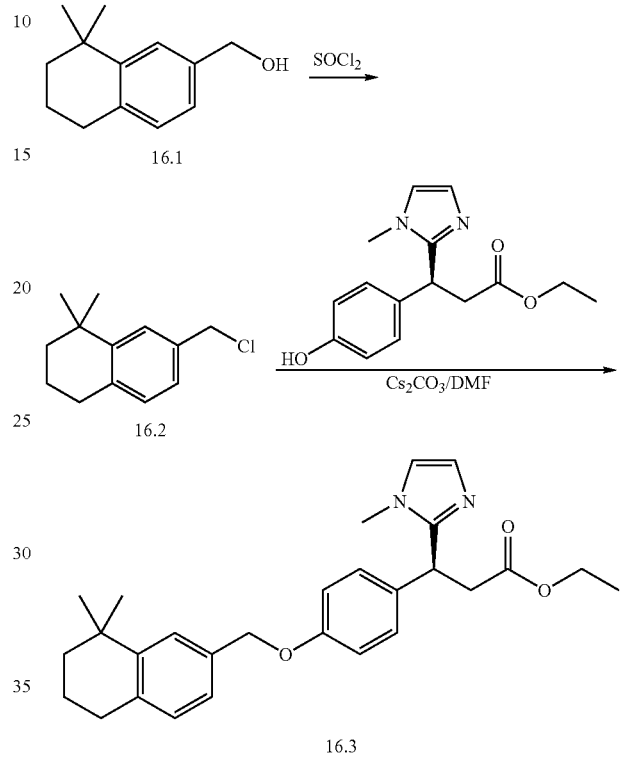

Starting material 16.1 was prepared according to the published procedure of Endo, Y. et al. (J. Med. Chem. 1998, 41, 1476-1496). To a solution of 16.1 (150 mg, 0.78 mmol) in CHCl$_3$ (5 mL) was added SOCl$_2$ (3 mL). The solution was heated at reflux for 3 hours. The solvent and excess SOCl$_2$ were removed under reduced pressure. The residue, crude 16.2 was pumped to dryness for half an hour under vacuum and redissolved in DMF (5 mL). Cs$_2$CO$_3$ (1.3 g, 4 mmol), and the imidazole phenol M12 shown in the reaction scheme (0.21 g, 0.77 mmol) were added as shown in the reaction scheme. The reaction mixture was left to stir at room temperature overnight, quenched with saline, extracted with EtOAc, and chromatographed on a silica gel column with 20-80% EtOAc/hexane to afford the ester 16.3.

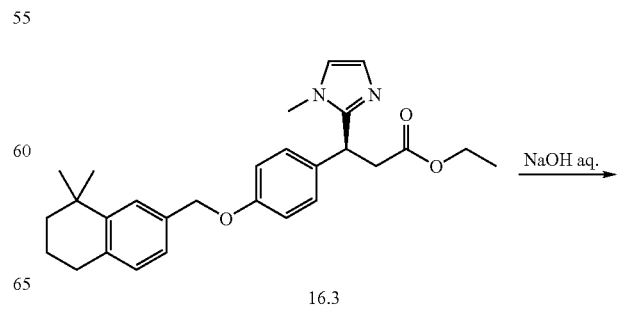

16.3

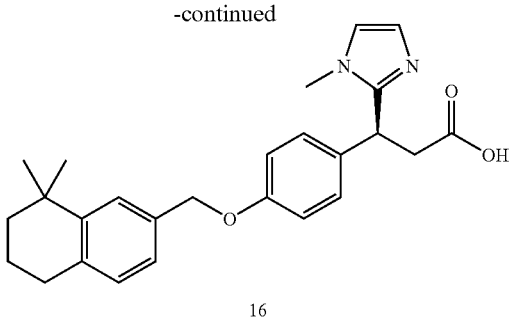

16

(S)-3-(4-((8,8-Dimethyl-5,6,7,8-tetrahydronaphthalen-2-yl)methoxy)phenyl)-3-(1-methyl-1H-imidazol-2-yl)propanoic acid (16). The ester 16.3 was dissolved in THF (3 mL) and MeOH (3 mL). To the solution was added 2N NaOH aqueous (3 mL), and the reaction was left overnight. The mixture was neutralized with AcOH (0.5 mL), filtered, and directly purified with $C_{18}$ reverse-phase HPLC eluting with 10-90% ACN/$H_2O$ containing 0.1% TFA. The product fractions were lyophilized to afford 16. MS ESI (pos.) m/e: 419.2 (M+H). $^1$HNMR (MeOH-$d_4$) δ 7.52 (d, 2H, J=10.76 Hz), 7.37 (s, 1H), 7.22 (d, 2H, J=8.80 Hz), 7.09 (d, 1H, J=7.83 Hz), 7.03 (d, 3H, J=8.56 Hz), 5.03 (s, 2H), 4.95 (m, 1H), 3.84 (s, 3H), 3.37 (m, 1H), 3.19 (m, 1H), 2.76 (t, 2H, J=6.36 Hz), 1.82 (m, 2H), 1.69 (m, 2H), 1.27 (s, 6H).

6.31 Example 17

Synthesis of (3S)-3-(1-Methyl-1H-imidazol-2-yl)-3-(4-(1-(5,5,8,8-tetramethyl-5,6,7,8-tetrahydronaphthalen-2-yl)ethoxy)phenyl)propanoic acid (17)

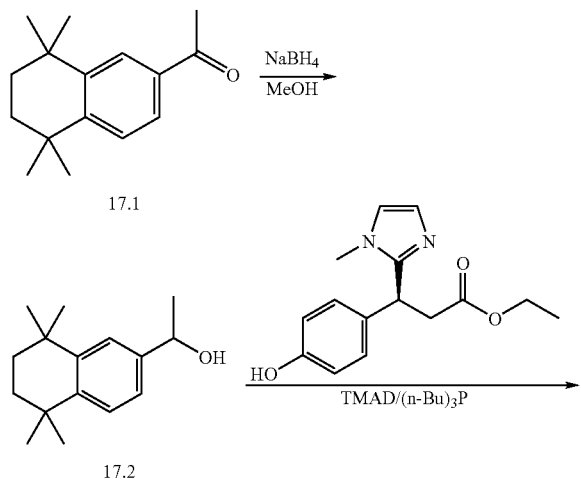

1-(5,5,8,8-Tetramethyl-5,6,7,8-tetrahydronaphthalen-2-yl)ethanol (17.2) To a solution of 17.1 (1.0 g, 4.34 mmol) in MeOH (20 mL) was added NaBH$_4$ (0.41 g, 10.8 mmol) at 0° C. The reaction was left at room temperature overnight. The solvent was then removed under reduced pressure. The residue was extracted with EtOAc/$H_2O$. The crude product was chromatographed with 0-20% EtOAc/hexane to afford 17.2. $^1$HNMR (DMSO-$d_6$) δ 7.26 (d, 1H), 7.24 (d, 1H), 7.06 (dd, 1H), 4.99 (d, 1H), 4.64 (m, 1H), 1.64 (s, 4H), 1.29 (d, 3H), 1.24 (m, 12H).

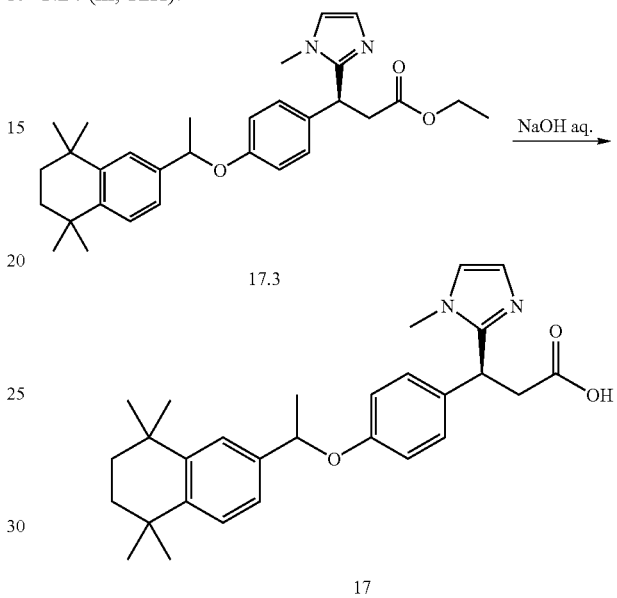

17

(3S)-3-(1-Methyl-1H-imidazol-2-yl)-3-(4-(1-(5,5,8,8-tetramethyl-5,6,7,8-tetrahydronaphthalen-2-yl)ethoxy)phenyl)propanoic acid (17) To a mixture of the imidazole phenol compound M12 shown in the reaction scheme (200 mg, 0.73 mmol), 17.2 (370 mg, 1.59 mmol), and tributylphosphine (0.54 mL, 2.19 mmol) in THF (8 mL) was added N,N,N',N'-tetramethylazodicarboxamide (TMAD) (0.38 g, 2.21 mmol) after bubbling with Ar for 2 minutes. The reaction mixture was stirred at room temperature overnight, quenched with saline, extracted with EtOAc, and chromatographed on a silica gel column to afford the ester 17.3. The ester was hydrolyzed by procedure analogous to that described for Example 16. MS ESI (pos.) m/e: 461.2 (M+H).

$^1$HNMR (MeOH-$d_4$) δ 7.50-7.46 (m, 2H), 7.29-7.26 (m, 2H), 7.14-7.10 (m, 3H), 6.91 (d, 2H, J=8.81 Hz), 5.34 (m, 1H), 4.90 (m, 1H), 3.81 (ss, 3H), 3.31 (m, 1H), 3.16 (m, 1H), 1.69 (s, 4H), 1.58 (d, 3H, J=6.35 Hz), 1.31 (m, 1H), 1.27-1.16 (m, 12H).

6.32 Example 18

Synthesis of (S)-3-(4-((8,8-Diethyl-5,5-dimethyl-5,6,7,8-tetrahydronaphthalen-2-yl)methoxy)phenyl)-3-(1-methyl-1H-imidazol-2-yl)propanoic acid (18)

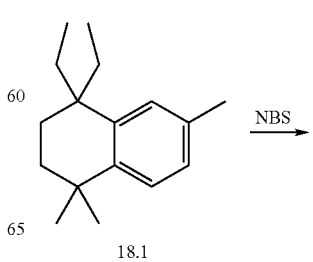

-continued

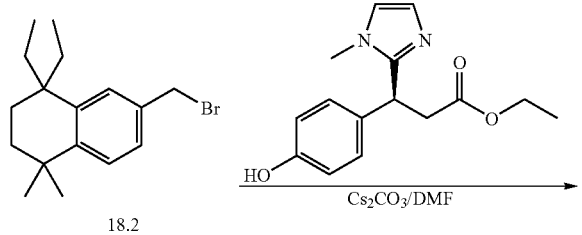

18.2

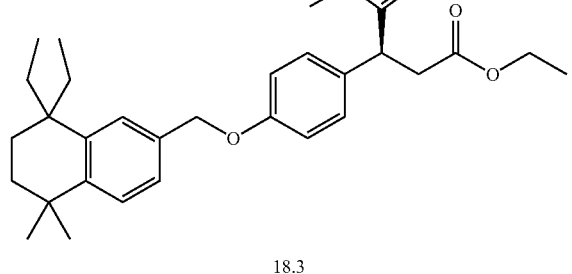

18.3

6-(Bromomethyl)-4,4-diethyl-1,1-dimethyl-1,2,3,4-tetrahydronaphthalene (18.2) Starting material 18.1 was prepared according to the published procedure of Kim, C. et al. (*Tetrahedron. Lett.* 1994, 35 (19), 3017-3020). A mixture of 18.1 (0.5 g, 2.17 mmol), NBS (0.58 g, 3.25 mmol), and dibenzoyl peroxide (53 mg) in $CCl_4$ (10 mL) was heated at reflux for 5 hours. The reaction was cooled, and the precipitate was filtered out. The solvent was removed providing crude 18.2, which was used directly in the next step.

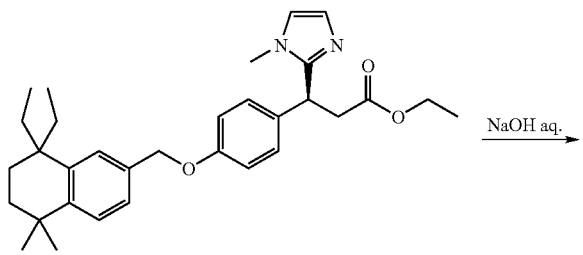

18.3

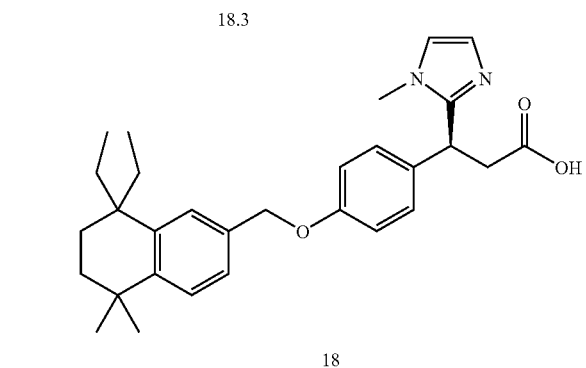

18

(S)-3-(4-((8,8-Diethyl-5,5-dimethyl-5,6,7,8-tetrahydronaphthalen-2-yl)methoxy)phenyl)-3-(1-methyl-1H-imidazol-2-yl)propanoic acid (18) Compound 18 was prepared using a procedure analogous to that described in Example 16 starting with the imidazole phenol compound M12 shown in the reaction scheme and 18.2. MS ESI (pos.) m/e: 475.1 (M+H).

$^1$HNMR (MeOH-$d_4$) δ 7.47 (dd, 2H, J=11.7, 2.2 Hz), 7.32 (d, 1H, J=8.1 Hz), 7.09-7.20 (m, 4H), 7.01-6.94 (m, 2H), 5.03 (s, 2H), 4.95-4.88 (m, 1H), 3.83 (s, 3H), 3.34 (m, 1H), 3.14 (m, 1H), 1.73-1.52 (m, 6H), 1.59-1.47 (m, 2H), 1.24 (s, 6H), 0.68 (t, 6H, J=7.3 Hz).

6.33 Example 19

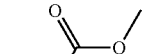

19.1

19

(S)-3-(4-((5,5,8,8-Tetramethyl-5,6,7,8-tetrahydronaphthalen-2-yl)methoxy)phenyl)hex-4-ynoic acid (19). Compound 19.1 is obtained by the procedure of Example 1 set forth in US 2006/0004012 which is hereby incorporated by reference. Compound 19.1 is reacted with 6-bromomethyl-1,1,4,4-tetramethyl-1,2,3,4-tetrahydro-naphthalene (available from Maybridge) by following the method of Example 3 set forth in US 2006/0004012 which is hereby incorporated by reference.

6.34 Example 20

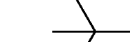

20.1

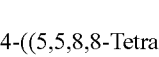

20

(R)-3-(4-((5,5,8,8-Tetramethyl-5,6,7,8-tetrahydronaphthalen-2-yl)methoxy)phenyl)hex-4-ynoic acid (20). By changing the resolving agent used in Example 19 to (1R,2S)-1-amino-2-indanol, compound 20.1 is obtained by the procedure of Example 1 set forth in US 2006/0004012 which is hereby incorporated by reference. Compound 20.1 is reacted with 6-bromomethyl-1,1,4,4-tetramethyl-1,2,3,4-tetrahydronaphthalene (available from Maybridge) by following the method of Example 3 set forth in US 2006/0004012 which is hereby incorporated by reference.

6.35 Example 21

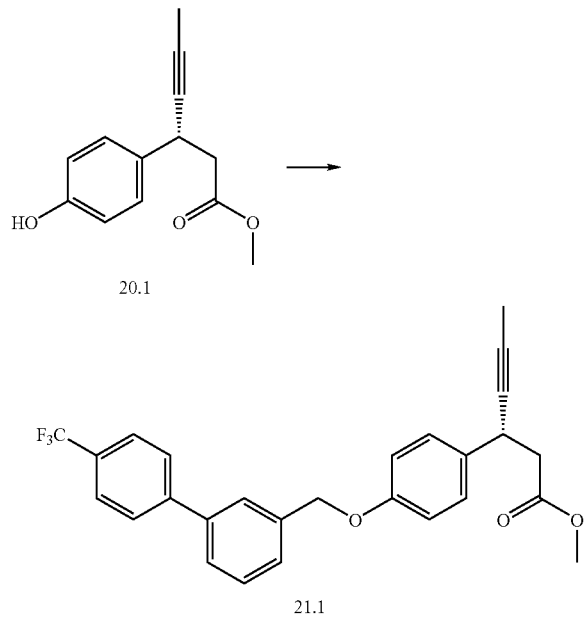

Methyl (3R)-3-(4-(((4'-(trifluoromethyl)-1,1'-biphenyl-3-yl)methyl)oxy)phenyl)-4-hexynoate (21.1). Compound 20.1 is reacted with 3-(4-trifluoromethylphenyl)-benzyl chloride (obtained by the procedure of Example 2 set forth in US 2006/0004012 which is hereby incorporated by reference) by following the method of Example 3 set forth in US 2006/0004012 which is hereby incorporated by reference.

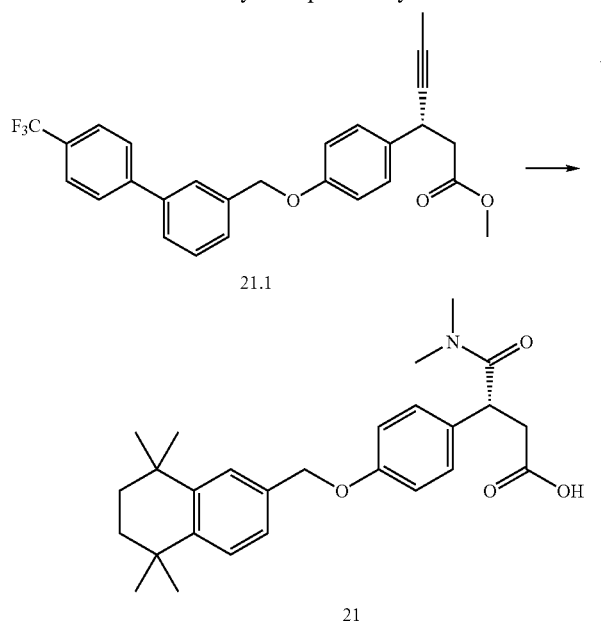

(R)-4-(Dimethylamino)-4-oxo-3-(4-((5,5,8,8-tetramethyl-5,6,7,8-tetrahydronaphthalen-2-yl)methoxy)phenyl) butanoic acid (21). Compound 21 is converted to the title compound following the procedure of Example 22.

6.36 Example 22

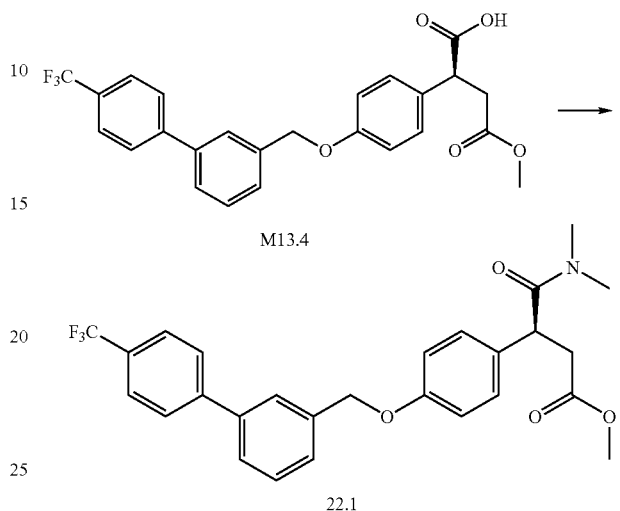

Methyl (3S)-4-(dimethylamino)-4-oxo-3-(4-(((4'-(trifluromethyl)-1,1'-biphenyl-3-yl)methyl)oxy)phenyl)butanoate (22.1). Acid M13.4 (3.5 g, 7.64 mmol) was dissolved in 50 mL of DCM. To this mixture was added 1-hydroxybenzotriazole hydrate (2.17 g, 16.04 mmol), N-(3-methylaminopropyl)-N'-ethylcarbondiimide hydrochloride (2.93 g, 15.28 mmol), and 2 M dimethylamine in THF (7.7 mL, 15.28 mmol). The reaction was stirred for 8 hours and diluted with 400 mL of EtOAc. The organic layer was washed with 2N HCl$_{(aq)}$ (2×50 mL), NaHCO$_{3(aq)}$ (1×50 mL), and brine (1×50 mL), dried with MgSO$_4$, and filtered. The organic layer was concentrated under reduced pressure, and the residue was flashed through silica with 15% EtOAc/DCM. The combined fractions were concentrated under reduced pressure to afford 22.1 (3.4 g, 7.03 mmol) as a colorless oil.

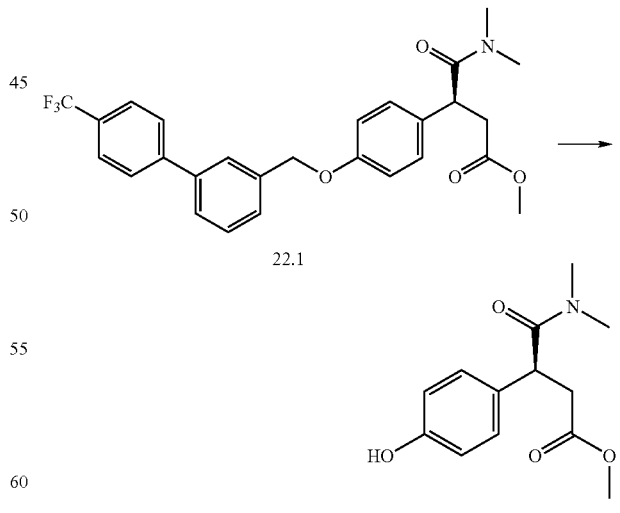

(S)-Methyl 4-(dimethylamino)-3-(4-hydroxyphenyl)-4-oxobutanoate (22.2). Dimethylamide 22.1 (2.1 g, 4.23 mmol) was dissolved in 50 mL of EtOAc, and nitrogen was bubbled through the solution for 5 minutes. 1 g of palladium on carbon (5 wt. %, wet contains 50% water) was added, and a hydrogen balloon was attached. After 8 hours, the mixture was filtered through a plug of silica with 10% MeOH in EtOAc. The organic layer was concentrated under reduced pressure and partitioned between ACN (100 mL) and hexane (50 mL). The ACN layer was washed with hexane (4×50 mL). The ACN layer was concentrated under reduced pressure to afford (S)-methyl 4-(dimethylamino)-3-(4-hydroxyphenyl)-4-oxobutanoate 22.2 (1.0 g, 3.98 mmol) as a colorless oil. MS ESI (pos.) m/e: 252.4 (M+H)+.

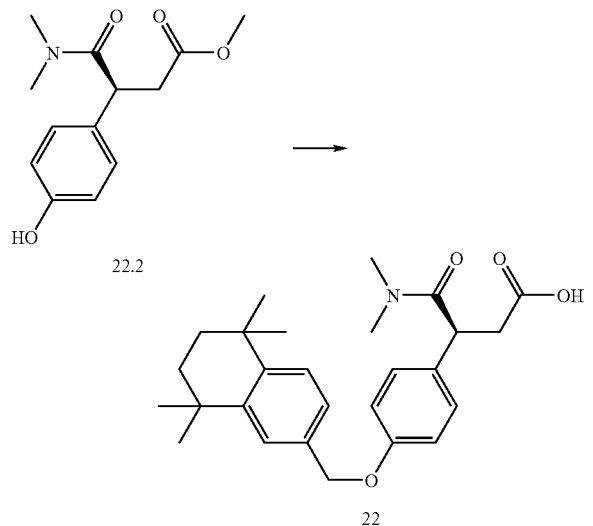

22

(S)-4-(Dimethylamino)-4-oxo-3-(4-((5,5,8,8-tetramethyl-5,6,7,8-tetrahydronaphthalen-2-yl)methoxy)phenyl)butanoic acid (22). The phenol 22.2 (315 mg, 1.26 mmol) is dissolved in 5 mL of DMF and 6-bromomethyl-1,1,4,4-tetramethyl-1,2,3,4-tetrahydro-naphthalene (available from Maybridge) (1.38 mmol) is added followed by cesium carbonate (600 mg, 1.88 mmol). The reaction is stirred for 14 hours and diluted with 250 mL of EtOAc. The organic layer is washed with 1N HCl (aq) (50 mL), saturated NaHCO₃ (aq) (50 mL), and brine (2×50 mL). The organic layer is dried with MgSO₄, filtered, and concentrated under reduced pressure. The residue is dissolved in 15 mL THF and 0.111 N NaOH (aq) (16 mL, 1.78 mmol) and MeOH (10 mL) is added. The solution is stirred for 8 hours and concentrated to remove the organic solvent. The slurry is diluted with water (50 mL) and DCM (300 mL). The mixture is adjusted with 2 N HCl (aq) to a pH of 2 and then extracted with DCM (3×75 mL). The combined organic layers are dried with Na₂SO₄ and concentrated under reduced pressure. The residue is purified by flash chromatography to yield compound 22.

6.37 Example 23

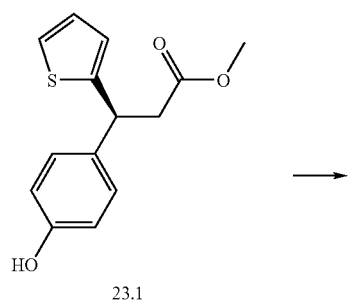

23.1

-continued

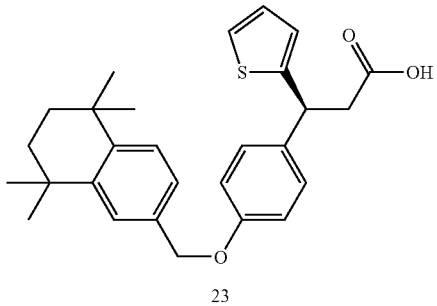

23

(S)-3-(4-((5,5,8,8-Tetramethyl-5,6,7,8-tetrahydronaphthalen-2-yl)methoxy)phenyl)-3-(thiophen-2-yl)propanoic acid (23). The racemate of compound 23.1 (obtained by the procedure of Example 52 set forth in US 2006/0004012 which is hereby incorporated by reference) is separated by chiral HPLC using methods known to those skilled in the art to provide compound 23.1. Compound 23.1 is reacted with 6-bromomethyl-1,1,4,4-tetramethyl-1,2,3,4-tetrahydro-naphthalene (available from Maybridge) by following the method of example 3 set forth in US 2006/0004012 which is hereby incorporated by reference to obtain compound 23.

6.38 Example 24

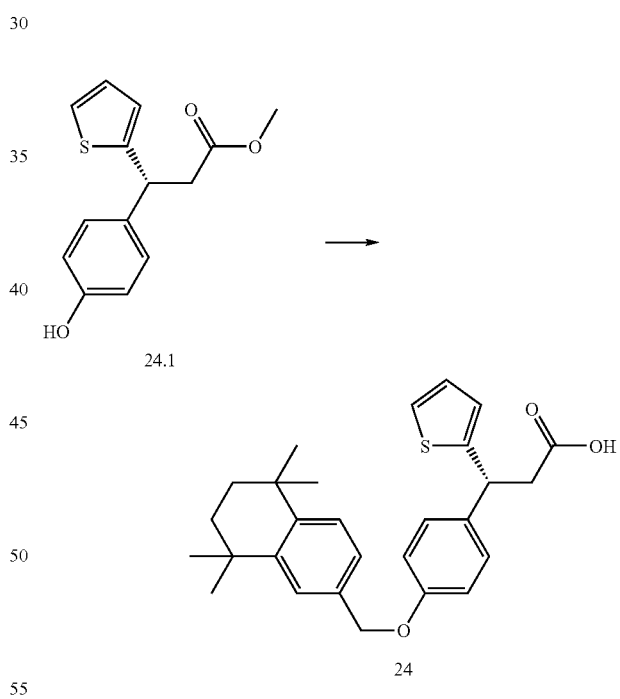

24

(R)-3-(4-((5,5,8,8-Tetramethyl-5,6,7,8-tetrahydronaphthalen-2-yl)methoxy)phenyl)-3-(thiophen-2-yl)propanoic acid (24). The racemate of compound 24.1 (obtained by the procedure of Example 52 set forth in US 2006/0004012 which is hereby incorporated by reference) is separated by chiral HPLC using methods known to those skilled in the art to provide compound 24.1. Compound 24.1 is reacted with 6-bromomethyl-1,1,4,4-tetramethyl-1,2,3,4-tetrahydro-naphthalene (available from Maybridge) by following the method of example 3 set forth in US 2006/0004012 which is hereby incorporated by reference.

6.39 Example 25

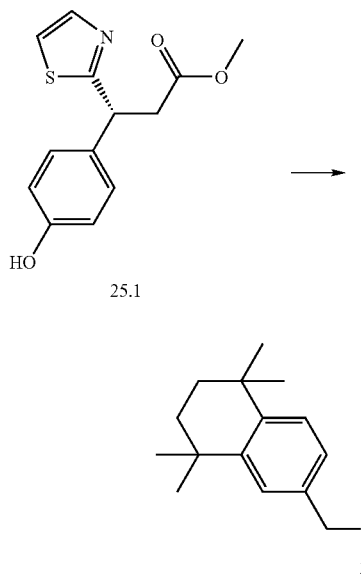

(R)-3-(4-((5,5,8,8-Tetramethyl-5,6,7,8-tetrahydronaphthalen-2-yl)methoxy)phenyl)-3-(thiazol-2-yl)propanoic acid 25). The racemate of compound 25.1 (obtained by the procedure of Example 53 set forth in US 2006/0004012 which is hereby incorporated by reference) is separated by chiral HPLC using methods known to those skilled in the art to provide compound 25.1. Compound 25.1 is reacted with 6-bromomethyl-1,1,4,4-tetramethyl-1,2,3,4-tetrahydro-naphthalene (available from Maybridge) by following the method of Example 3 set forth in US 2006/0004012 which is hereby incorporated by reference to obtain compound 25.

6.40 Example 26

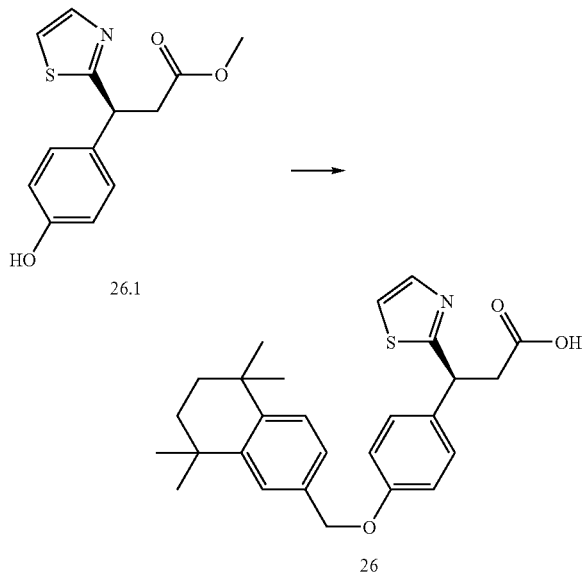

(S)-3-(4-((5,5,8,8-Tetramethyl-5,6,7,8-tetrahydronaphthalen-2-yl)methoxy)phenyl)-3-(thiazol-2-yl)propanoic acid (26). The racemate of compound 26.1 (obtained by the procedure of Example 53 set forth in US 2006/0004012 which is hereby incorporated by reference) is separated by chiral HPLC using methods known to those skilled in the art to provide compound 26.1. Compound 26.1 is reacted with 6-bromomethyl-1,1,4,4-tetramethyl-1,2,3,4-tetrahydro-naphthalene (available from Maybridge) by following the method of example 3 set forth in US 2006/0004012 which is hereby incorporated by reference to obtain the title compound.

6.41 Example 27

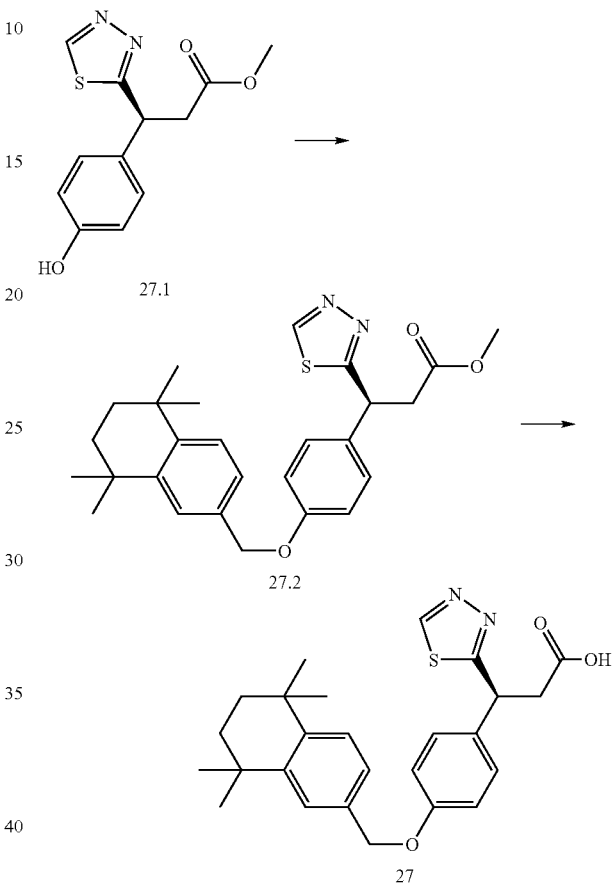

3-(4-((5,5,8,8-Tetramethyl-5,6,7,8-tetrahydronaphthalen-2-yl)methoxy)phenyl)-3-(1,3,4-thiadiazol-2-yl)propanoic acid (27). Compound M15 is separated by chiral HPLC using methods known to those skilled in the art to provide compound 27.1. Compound 27.1 is reacted with 6-bromomethyl-1,1,4,4-tetramethyl-1,2,3,4-tetrahydro-naphthalene (available from Maybridge) by following the method of Example 3 set forth in US 2006/0004012 which is hereby incorporated by reference to obtain ester 27.2. Ester 27.2 is converted to compound 27 using the methods described herein.

6.42 Example 28

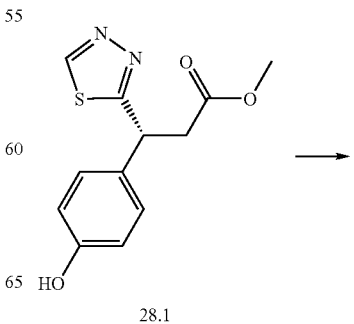

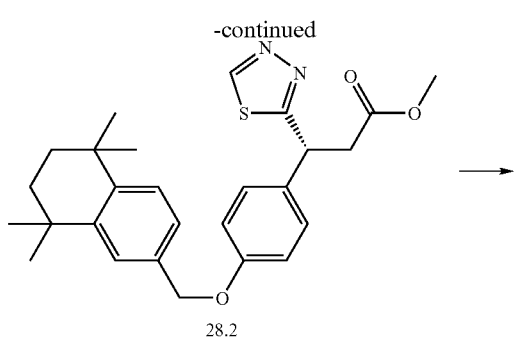

28.2

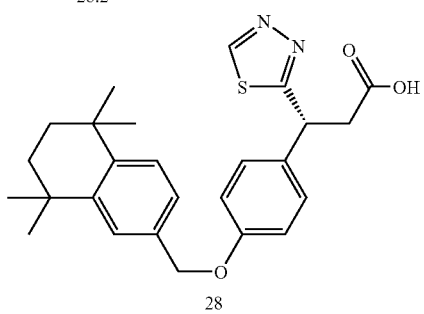

28

3-(4-((5,5,8,8-Tetramethyl-5,6,7,8-tetrahydronaphthalen-2-yl)methoxy)phenyl)-3-(1,3,4-thiadiazol-2-yl)propanoic acid (28). Compound M15 is separated by chiral HPLC using methods known to those skilled in the art to provide compound 28.1. Compound 28.1 is reacted with 6-bromomethyl-1,1,4,4-tetramethyl-1,2,3,4-tetrahydro-naphthalene (available from Maybridge) by following the method of Example 3 set forth in US 2006/0004012 which is hereby incorporated by reference to obtain ester 28.2. Ester 28.2 is converted to compound 28 using the methods described herein.

6.43 Example 29

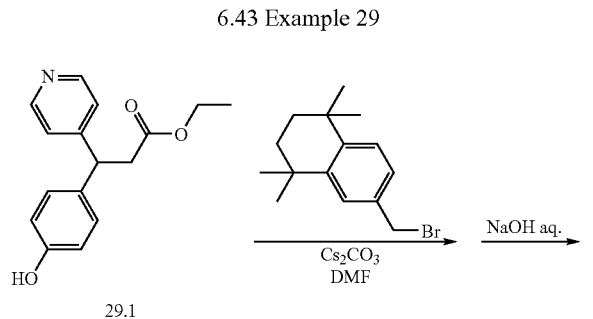

29.1

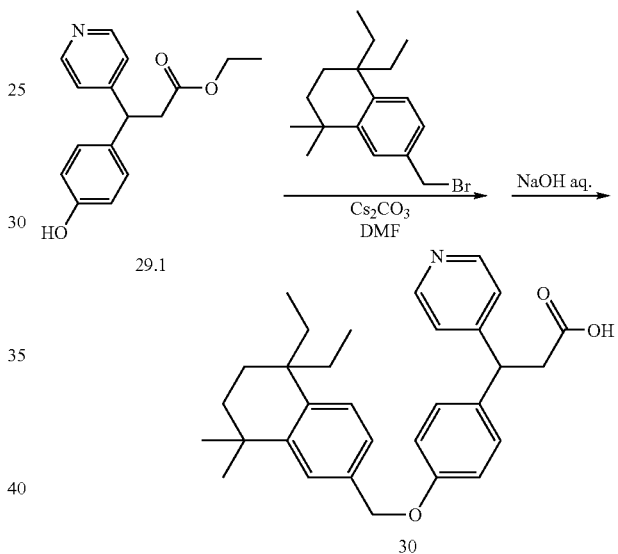

29

(R/S)-3-Pyridin-4-yl-3-[4-(5,5,8,8-tetramethyl-5,6,7,8-tetrahydro-naphthalen-2-ylmethoxy)-phenyl]-propionic acid (29). Compound 29.1 was prepared using the procedure in Method 12 used to prepare M12.5 using pyridine-4-carboxaldehyde in place of 1-methyl-2-imidazolecarboxaldehyde. Compound 29 is obtained from compound 29.1 by following the general procedure A.

6.44 Example 30

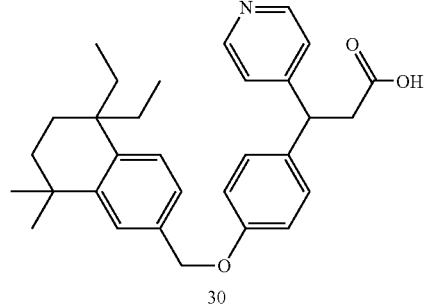

30

(R/S)-3-[4-(8,8-Diethyl-5,5-dimethyl-5,6,7,8-tetrahydro-naphthalen-2-ylmethoxy)-phenyl]-3-pyridin-4-yl-propionic acid (30). Compound 30 is obtained from compound 29.1 and 18.2 by following the general procedure A.

6.45 Example 31

Synthesis of (R)-3-(4-fluorophenyl)-3-(4-((5,5,8,8-tetramethyl-5,6,7,8-tetrahydronaphthalen-2-yl)methoxy)phenyl)propanoic acid (31)

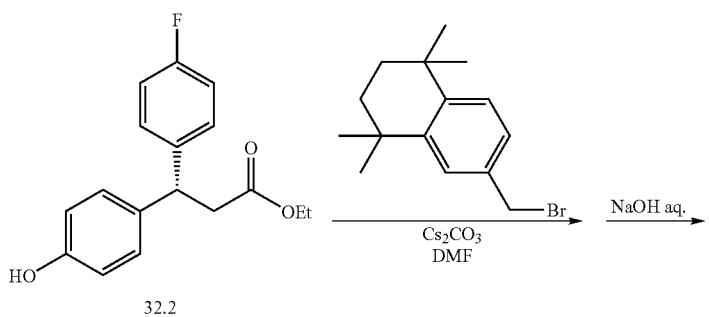

32.2

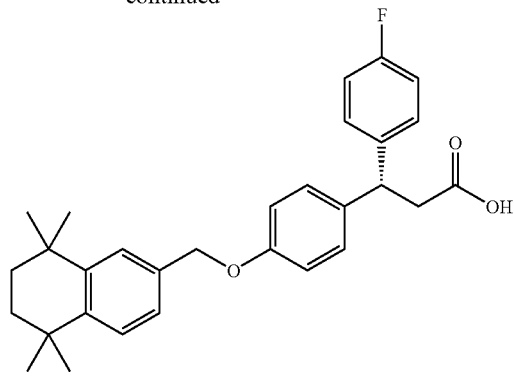

31

(R)-3-(4-Fluorophenyl)-3-(4-((5,5,8,8-tetramethyl-5,6,7,8-tetrahydronaphthalen-2-yl)methoxy)phenyl)propanoic acid (31). Compound 31 was obtained from compound 32.2 by following the general procedure E. LC-MS ESI (neg.) M/E: 459 (M−H). $^1$HNMR (500 MHz, CDCl$_3$, ppm) δ 7.35-7.37 (m, 2H), 7.19-7.23 (m, 3H), 7.16 (d, 2H, J=10 Hz), 6.94-7.02 (m, 4H), 4.98 (s, 2H), 4.50 (t, 1H J=10 Hz), 3.06 (ddd, 2H, J=5 Hz, 10 Hz, 10 Hz), 1.72 (s, 4H), 1.32 (s, 6H), 1.31 (s, 6H).

6.46 Example 32

Synthesis of (S)-3-(4-fluorophenyl)-3-(4-((5,5,8,8-tetramethyl-5,6,7,8-tetrahydronaphthalen-2-yl)methoxy)phenyl)propanoic acid (32)

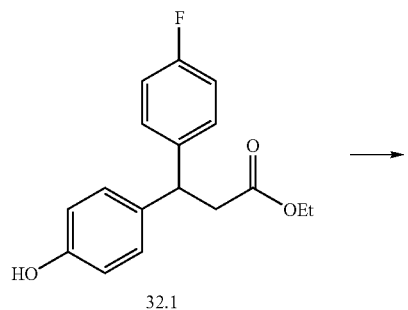

32.1

→

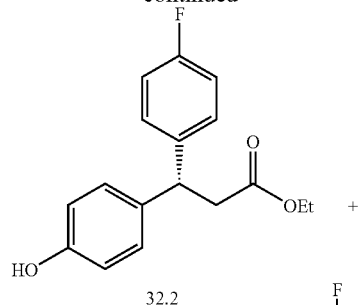

32.2 +

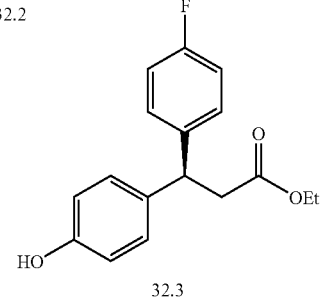

32.3

Compound 32.1 was prepared using the procedure of Example 45.2 set forth in US 2006/0004012 which is hereby incorporated by reference. 32.2 and 32.3 were separated from racemic material 32.1 using a prep chiral AD column using 10% isopropanol in hexane as eluent. Both compounds (R)-ethyl 3-(4-fluorophenyl)-3-(4-hydroxyphenyl)propanoate 32.2 (the first peak on AD column, shorter retention time) and (S)-ethyl 3-(4-fluorophenyl)-3-(4-hydroxyphenyl)propanoate 32.3 (the second peak on AD column, longer retention time) were obtained as white solid.

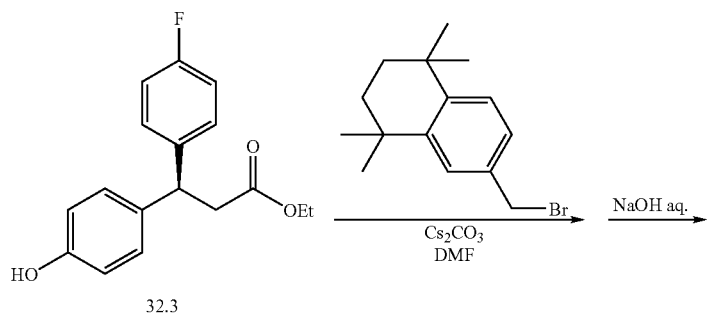

32.3

-continued

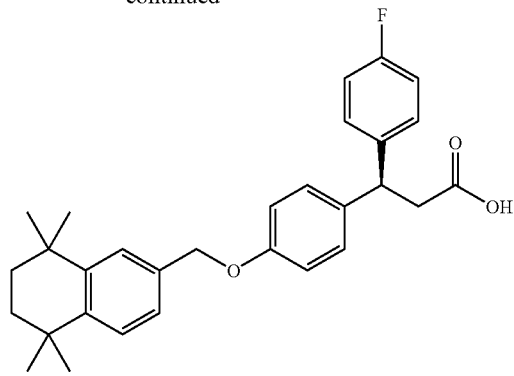

32

(S)-3-(4-Fluorophenyl)-3-(4-((5,5,8,8-tetramethyl-5,6,7,8-tetrahydronaphthalen-2-yl)methoxy)phenyl)propanoic acid (32). Compound 32 was obtained from compound 32.3 by following the general procedure E. LC-MS ESI (neg.) M/E: 459 (M−H). $^1$HNMR (500 MHz, CDCl$_3$, ppm) δ 7.35-7.37 (m, 2H), 7.19-7.23 (m, 3H), 7.16 (d, 2H, J=10 Hz), 6.94-7.02 (m, 4H), 4.98 (s, 2H), 4.50 (t, 1H J=10 Hz), 3.06 (ddd, 2H, J=5 Hz, 10 Hz, 10 Hz), 1.72 (s, 4H), 1.32 (s, 6H), 1.31 (s, 6H).

6.47 Example 33

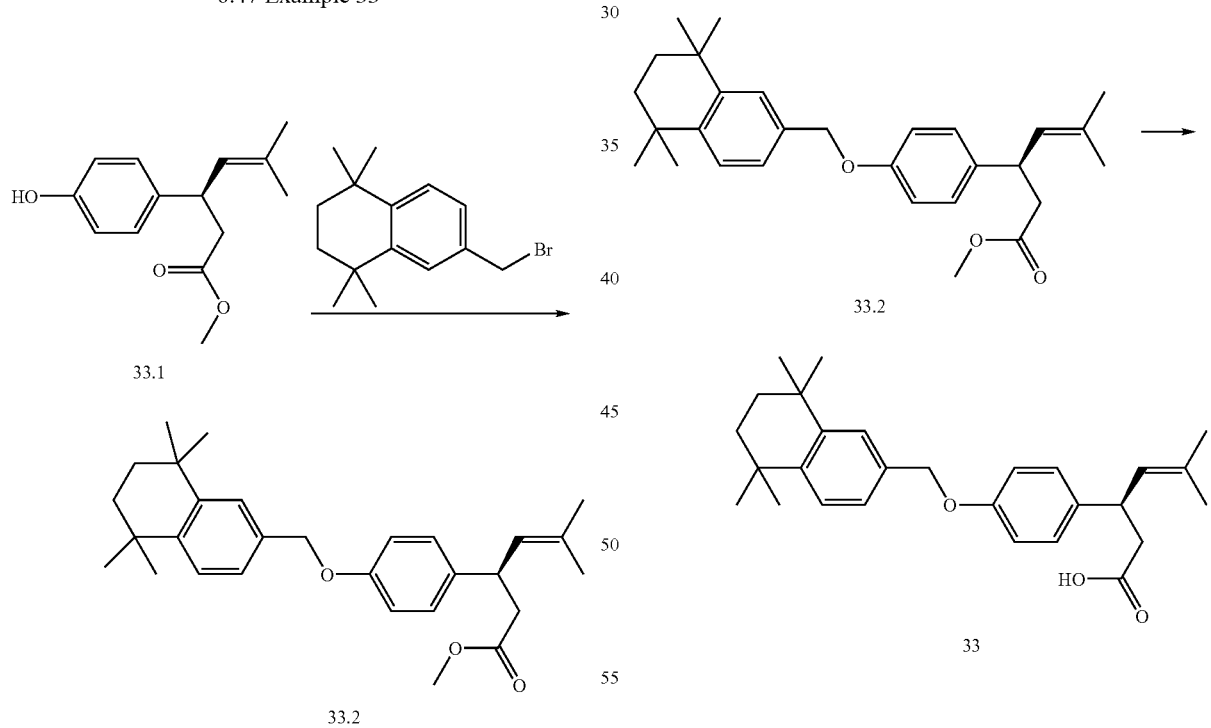

R)-Methyl 5-methyl-3-(4-((5,5,8,8-tetramethyl-5,6,7,8-tetrahydronaphthalen-2-yl)methoxy)phenyl)hex-4-enoate (33.2). The racemate of compound 33.1 (obtained by the procedure of Example 33 set forth in US 2006/0004012 which is hereby incorporated by reference) is separated by chiral HPLC using methods known to those skilled in the art to provide compound 33.1. A mixture of compound 33.1 (0.18 mmol), 6-bromomethyl-1,1,4,4-tetramethyl-1,2,3,4-tetrahydro-naphthalene (0.2 mmol; available from Maybridge) and cesium carbonate (0.27 mmol) in DMF (4 mL) is stirred at room temperature overnight. The reaction mixture is diluted with water and extracted into EtOAc. The separated organic layer is washed with brine and dried over sodium sulfate. After evaporation of the solvent, the residue is purified by column chromatography (silica gel; EtOAc/hexane) to yield compound 33.2.

(R)-5-Methyl-3-(4-((5,5,8,8-tetramethyl-5,6,7,8-tetrahydronaphthalen-2-yl)methoxy)phenyl)hex-4-enoic acid (33). A mixture of compound 33.2 (0.15 mmol) and sodium hydroxide (0.8 mmol) in water (1 mL) and EtOH (3 mL) is stirred at room temperature overnight. EtOH is removed under reduced pressure, and the remaining solution acidified with 1N HCl to pH 3-5 and then diluted with EtOAc (70 mL), washed with saturated brine, dried over anhydrous Na$_2$SO$_4$, concentrated under reduced pressure, and purified by column chromatography (silica gel; 1:9 MeOH/DCM) to yield compound 33.

6.48 Example 34

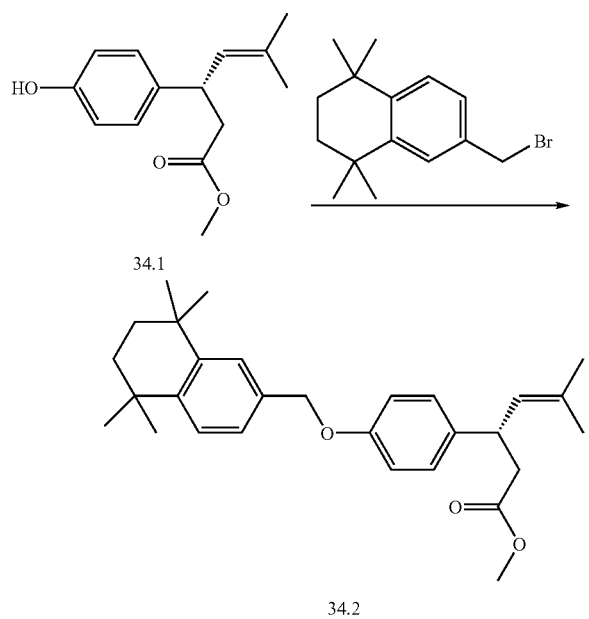

34.1

34.2

(S)-Methyl 5-methyl-3-(4-((5,5,8,8-tetramethyl-5,6,7,8-tetrahydronaphthalen-2-yl)methoxy)phenyl)hex-4-enoate (34.2). The racemate of compound 34.1 (obtained by the procedure of Example 33 set forth in US 2006/0004012 which is hereby incorporated by reference) is separated by chiral HPLC using methods known to those skilled in the art to provide compound 34.1. A mixture of compound 34.1 (0.18 mmol), 6-bromomethyl-1,1,4,4-tetramethyl-1,2,3,4-tetrahydro-naphthalene (0.2 mmol; available from Maybridge) and cesium carbonate (0.27 mmol) in DMF (4 mL) is stirred at room temperature overnight. The reaction mixture is diluted with water and extracted into EtOAc. The separated organic layer is washed with brine and dried over sodium sulfate. After evaporation of the solvent the residue is purified by column chromatography (silica gel; EtOAc/hexane) to yield compound 34.2.

34.2

34

(S)-5-Methyl-3-(4-((5,5,8,8-tetramethyl-5,6,7,8-tetrahydronaphthalen-2-yl)methoxy)phenyl)hex-4-enoic acid (34). Compound 34 is prepared from 34.2 by the procedure of Example 33.

6.49 Example 35

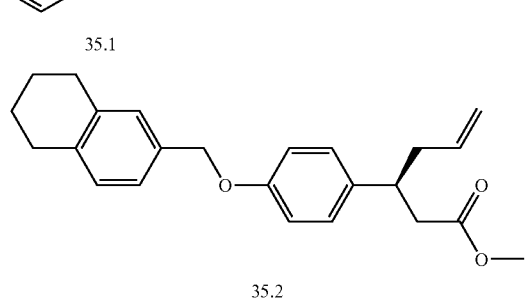

35.1

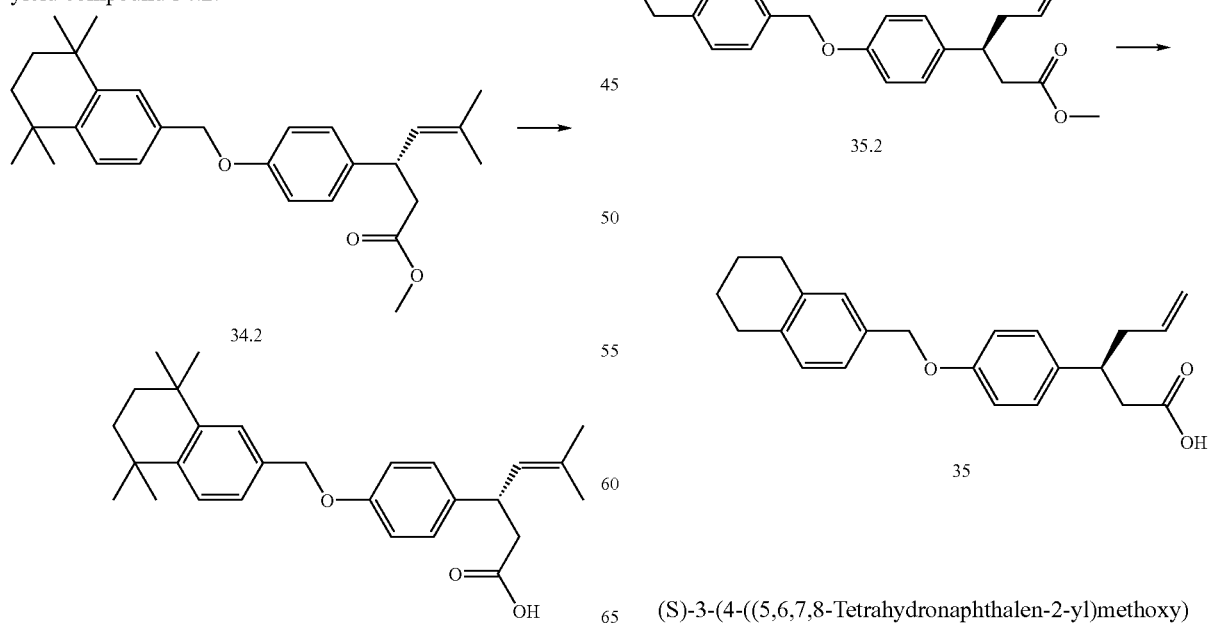

35.2

(S)-Methyl 3-(4-((5,6,7,8-tetrahydronaphthalen-2-yl)methoxy)phenyl)hex-5-enoate (35.2). The racemate of compound 35.1 (obtained by the procedure of Example 34 set forth in US 2006/0004012 which is hereby incorporated by reference) is separated by chiral HPLC using methods known to those skilled in the art to provide compound 35.1. Compound 35.1 is reacted with 6-bromomethyl-1,2,3,4-tetrahydro-naphthalene (prepared using the procedure of Example 103) by the procedure of Example 33 to yield compound 35.2.

35.2

35

(S)-3-(4-((5,6,7,8-Tetrahydronaphthalen-2-yl)methoxy)phenyl)hex-5-enoic acid (35). Compound 35 is prepared from compound 35.2 by the procedure of Example 33.

6.50 Example 36

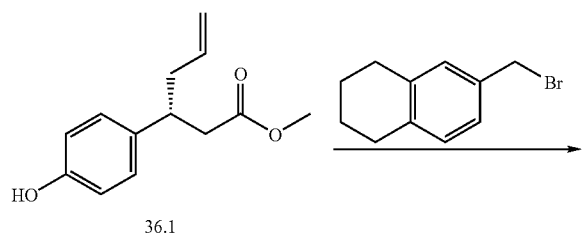

36.1

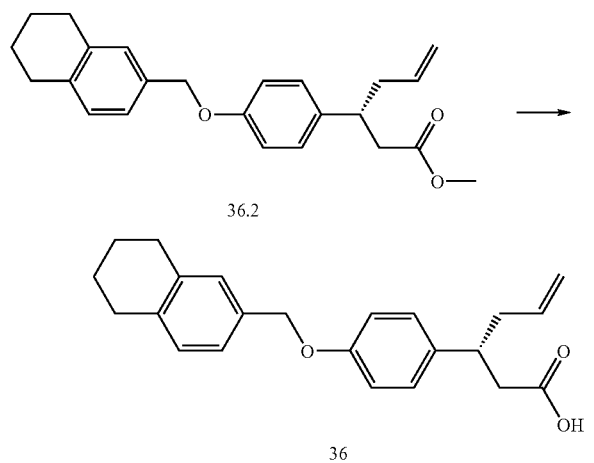

36.2

(R)-Methyl 3-(4-((5,6,7,8-tetrahydronaphthalen-2-yl)methoxy)phenyl)hex-5-enoate (36.2). The racemate of compound 36.1 (obtained by the procedure of Example 34 set forth in US 2006/0004012 which is hereby incorporated by reference) is separated by chiral HPLC using methods known to those skilled in the art to provide compound 36.1. Compound 36.1 is reacted with 6-bromomethyl-1,2,3,4-tetrahydro-naphthalene by the procedure of Example 33 to yield compound 36.2.

36

(R)-3-(4-((5,6,7,8-Tetrahydronaphthalen-2-yl)methoxy)phenyl)hex-5-enoic acid (36). Compound 36 is prepared from compound 36.2 using the procedure of Example 33.

6.51 Example 37

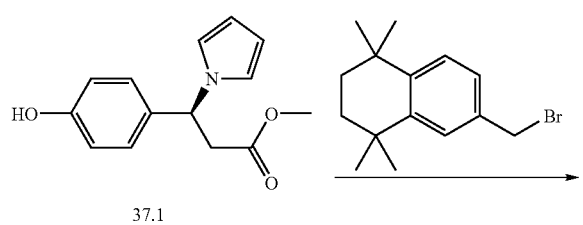

37.1

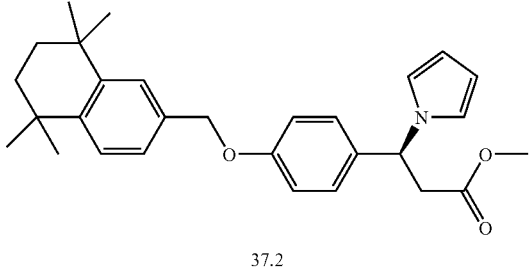

37.2

(S)-Methyl 3-(1H-pyrrol-1-yl)-3-(4-((5,5,8,8-tetramethyl-5,6,7,8-tetrahydro-naphthalen-2-yl)methoxy)phenyl)propanoate (37.2). Compound 37.1 is prepared from (S)-3-amino-3-(4-hydroxyphenyl)propanoic acid (available from Chem-Impex Intl, Inc.) using the procedure of Example 57 set forth in US 2006/0004012 which is hereby incorporated by reference. Alkylation according to the procedure of Example 33 provides the title compound 37.2.

37.2

37

(S)-3-(1H-Pyrrol-1-yl)-3-(4-((5,5,8,8-tetramethyl-5,6,7,8-tetrahydronaphthalen-2-yl)methoxy)phenyl)propanoic acid (37). Compound 37 is prepared from 37.2 by the procedure of Example 33.

6.52 Example 38

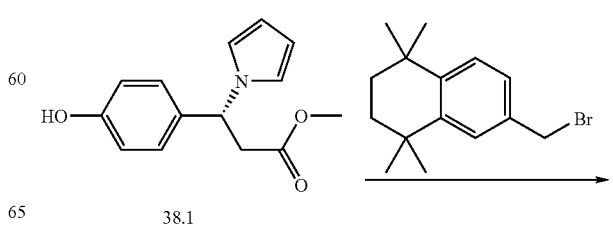

38.1

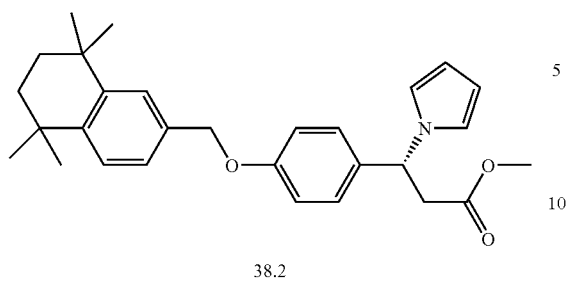

38.2

(R)-Methyl 3-(1H-pyrrol-1-yl)-3-(4-((5,5,8,8-tetramethyl-5,6,7,8-tetrahydro-naphthalen-2-yl)methoxy)phenyl)propanoate (38.2). Compound 38.1 is prepared from (R)-3-amino-3-(4-hydroxyphenyl)propanoic acid (available from Chem-Impex Intl, Inc.) using the procedure of Example 57 set forth in US 2006/0004012 which is hereby incorporated by reference. Alkylation according to the procedure of Example 33 provides the title compound 38.2.

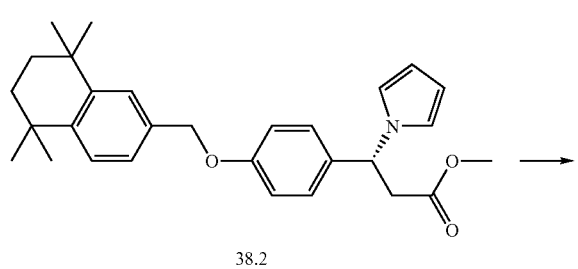

38.2

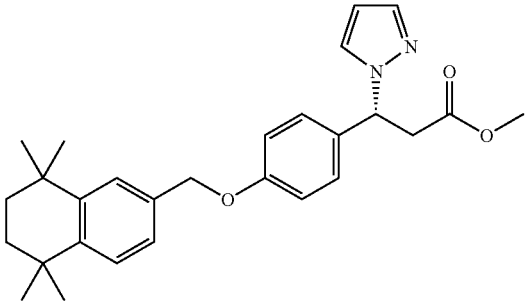

39.2

(R)-Methyl 3-(1H-pyrazol-1-yl)-3-(4-((5,5,8,8-tetramethyl-5,6,7,8-tetrahydro-naphthalen-2-yl)methoxy)phenyl)propanoate (39.2). The racemate of 39.1 (obtained by the procedure of Example 58 set forth in US 2006/0004012 which is hereby incorporated by reference) is separated by chiral HPLC using methods known to those skilled in the art to provide compound 39.1. Compound 39.2 is prepared from 39.1 by the procedure of Example 33.

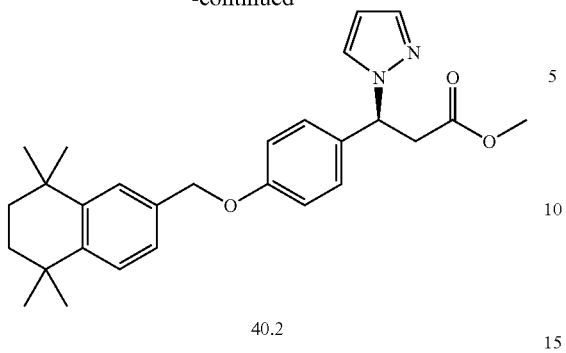

40.2

(S)-Methyl 3-(1H-pyrazol-1-yl)-3-(4-((5,5,8,8-tetramethyl-5,6,7,8-tetrahydro-naphthalen-2-yl)methoxy)phenyl)propanoate (40.2). The racemate of 40.1 (obtained by the procedure of Example 58 set forth in US 2006/0004012 which is hereby incorporated by reference) is separated by chiral HPLC using methods known to those skilled in the art to provide compound 40.1. Compound 40.2 is prepared from 40.1 by the procedure of Example 33.

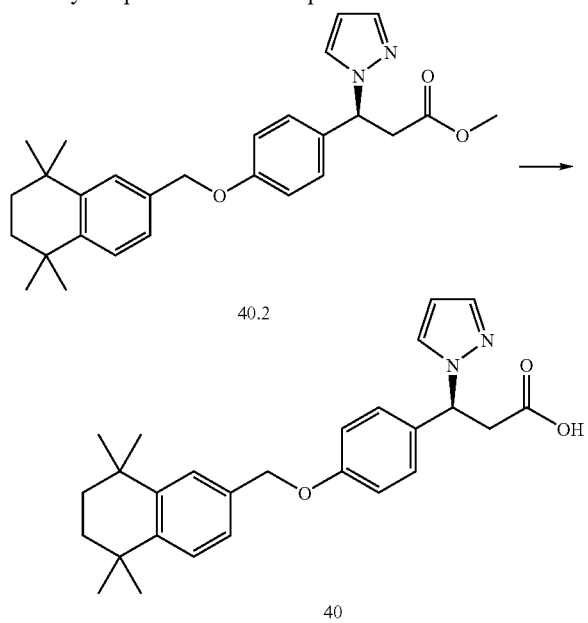

40

(S)-3-(1H-Pyrazol-1-yl)-3-(4-((5,5,8,8-tetramethyl-5,6,7,8-tetrahydronaphthalen-2-yl)methoxy)phenyl)propanoic acid (40). Compound 40 is prepared from compound 40.2 by the procedure of Example 33.

6.55 Example 41

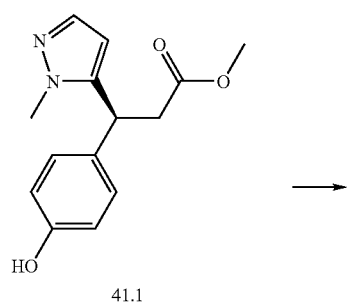

41.1

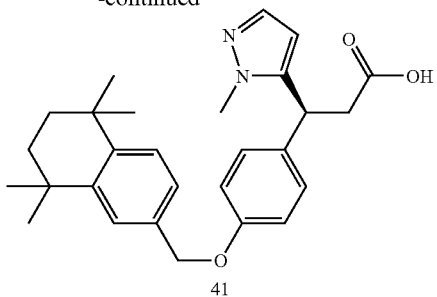

41

(S)-3-(1-methyl-1H-pyrazol-5-yl)-3-(4-((5,5,8,8-tetramethyl-5,5,7,8-tetrahydronaphthalen-2-yl)methoxy)phenyl)propanoic acid (41). The racemate of compound 41.1 (obtained as a mixture of regioisomers by the procedure of Example 63 set forth in US 2006/0004012 which is hereby incorporated by reference) is separated by chiral HPLC using methods known to those skilled in the art to provide compound 41.1. Compound 41.1 is reacted with 6-bromomethyl-1,1,4,4-tetramethyl-1,2,3,4-tetrahydro-naphthalene (available from Maybridge) to give a mixture of regioisomeric products which are separated and hydrolyzed by following the method of Example 63 set forth in US 2006/0004012 which is hereby incorporated by reference.

6.56 Example 42

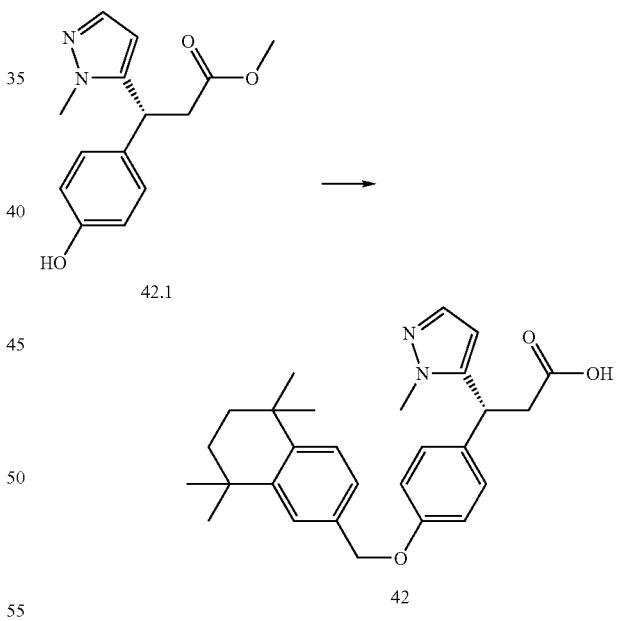

42

(R)-3-(1-methyl-1H-pyrazol-5-yl)-3-(4-((5,5,8,8-tetramethyl-5,6,7,8-tetrahydronaphthalen-2-yl)methoxy)phenyl)propanoic acid (42). The racemate of compound 42.1 (obtained as a mixture of regioisomers by the procedure of Example 63 set forth in US 2006/0004012 which is hereby incorporated by reference) is separated by chiral HPLC using methods known to those skilled in the art to provide compound 42.1. Compound 42.1 is reacted with 6-bromomethyl-1,1,4,4-tetramethyl-1,2,3,4-tetrahydro-naphthalene (available from Maybridge) to give a mixture of regioisomeric products which are separated and hydrolyzed by following the method of Example 63 set forth in US 2006/0004012 which is hereby incorporated by reference.

6.57 Example 43

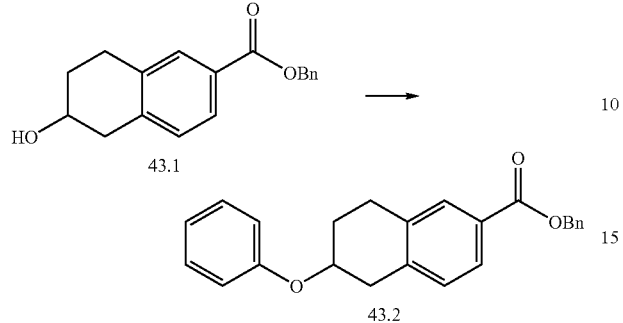

Benzyl 6-phenoxy-5,6,7,8-tetrahydronaphthalene-2-carboxylate (43.2). To a mixture of compound 43.1 (1.0 g, 3.54 mmol) (43.1 is prepared according to the procedure of Fisher, M. J. et al. (Example 39 of U.S. Pat. No. 5,618,843 which is hereby incorporated by reference herein in its entirety and for all purposes as if specifically set forth herein), phenol (0.49 g, 5.21 mmol), and tri-n-butylphosphine (1.62 mL, 6.57 mmol) in THF (20 mL) is added TMAD (1.14 g, 6.63 mmol) after bubbling Ar for 3 minutes. The reaction mixture is stirred at room temperature overnight, quenched with saline, extracted with EtOAc, and chromatographed on a silica gel column to afford compound 43.2.

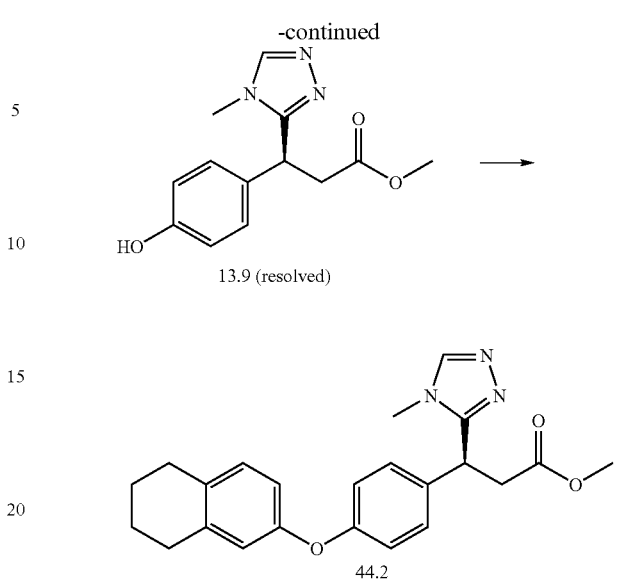

(3S)-3-(4-Methyl-4H-1,2,4-triazol-3-yl)-3-(4-((6-phenoxy-5,6,7,8-tetrahydronaphthalen-2-yl)methoxy)phenyl) propanoic acid (43) This compound is made following a procedure analogous to that of Example 45 below to afford compound 43.

6.58 Example 44

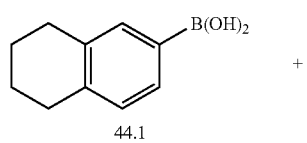

+

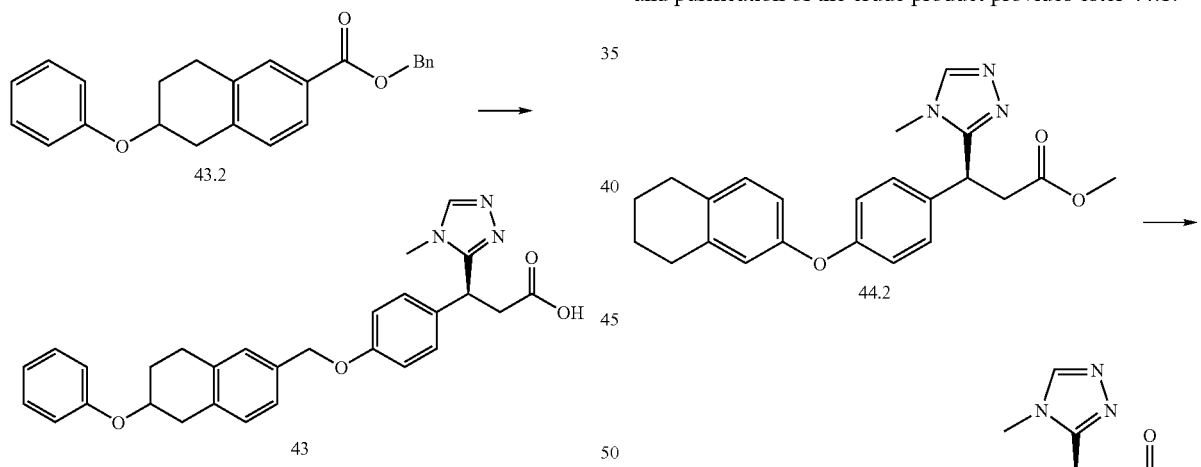

(S)-Methyl 3-(4-methyl-4H-1,2,4-triazol-3-yl)-3-(4-(5,6,7,8-tetrahydronaphthalen-2-yloxy)phenyl)propanoate (44.2). Boronic acid 44.1 is reacted with 13.9 (resolved using chiral chromatography as known to those skilled in the art) using the procedure of Example 42 set forth in US 2006/0004012 which is hereby incorporated by reference. Isolation and purification of the crude product provides ester 44.1.

(S)-3-(4-Methyl-4H-1,2,4-triazol-3-yl)-3-(4-(5,6,7,8-tetrahydronaphthalen-2-yloxy)phenyl)propanoic acid (44). A solution of 44.2 in THF/MeOH (1:1, 2 mL), is treated with 2N NaOH aqueous solution (1 mL) and stirred overnight at room temperature. The reaction mixture is acidified with aqueous 2N HCl and extracted with EtOAc to obtain 44, which is purified by preparative HPLC, eluting with 5~95% ACN in water containing 0.1% TFA.

6.59 Example 45

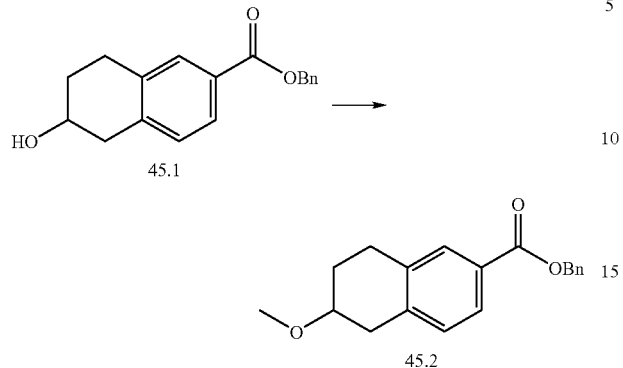

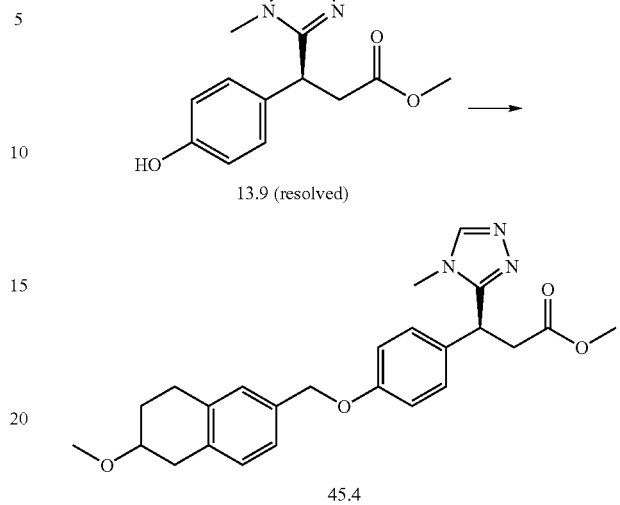

Benzyl 6-methoxy-5,6,7,8-tetrahydronaphthalene-2-carboxylate (45.2). Starting material 45.1 is prepared according to the procedure of Fisher, M. J. et al. (Example 39 of U.S. Pat. No. 5,618,843 which is hereby incorporated by reference in its entirety and for all purposes as is specifically set forth herein). To a solution of 45.1 (1.0 g, 3.54 mmol) in THF (20 mL), is added NaH (170 mg, 4.25 mmol, 60% in mineral oil) at 0° C. 30 Minutes later, MeI (0.33 mL, 5.34 mmol) is added, and the reaction is left at room temperature overnight, quenched with saline, extracted with EtOAc, and purified on a silica gel column to afford the ester 45.2.

(3S)-Methyl 3-(4-((6-methoxy-5,6,7,8-tetrahydronaphthalen-2-yl)methoxy)phenyl)-3-(4-methyl-4H-1,2,4-triazol-3-yl)propanoate (45.4) To a mixture of 45.3 (210 mg, 1.09 mmol), compound 13.9 (200 mg, 0.73 mmol) (resolved using chiral chromatography as known to those skilled in the art), and tri-n-butylphosphine (0.54 mL, 2.19 mmol) in THF (8 mL) is added TMAD (0.38 g, 2.21 mmol) after bubbling Ar for 2 minutes. The reaction mixture is stirred at room temperature overnight, quenched with saline, extracted with EtOAc, and chromatographed on a silica gel column to afford compound 45.4.

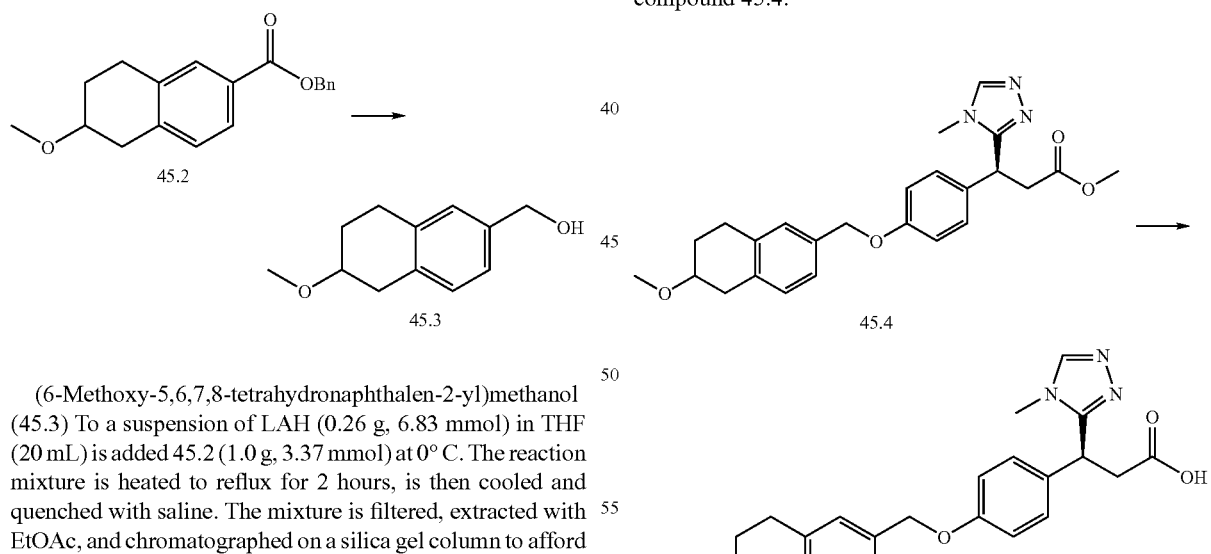

(6-Methoxy-5,6,7,8-tetrahydronaphthalen-2-yl)methanol (45.3) To a suspension of LAH (0.26 g, 6.83 mmol) in THF (20 mL) is added 45.2 (1.0 g, 3.37 mmol) at 0° C. The reaction mixture is heated to reflux for 2 hours, is then cooled and quenched with saline. The mixture is filtered, extracted with EtOAc, and chromatographed on a silica gel column to afford the alcohol 45.3.

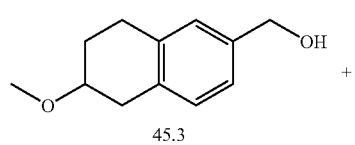
+

(3S)-3-(4-((6-Methoxy-5,6,7,8-tetrahydronaphthalen-2-yl)methoxy)phenyl)-3-(4-methyl-4H-1,2,4-triazol-3-yl)propanoic acid (45). A solution of 45.4 in THF/MeOH (1:1, 2 mL), is treated with 2N NaOH aqueous solution (1 mL) and stirred for overnight at room temperature. The reaction mixture is acidified with aqueous 2N HCl and extracted with EtOAc to obtain 45, which is purified by preparative HPLC, eluting with 5-95% ACN in water containing 0.1% TFA.

6.60 Example 46

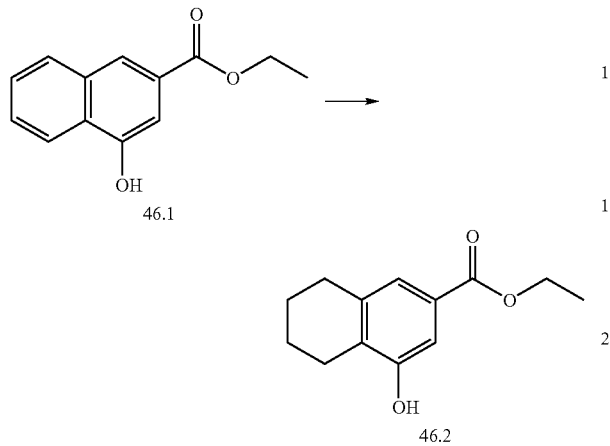

Napthalenecarboxylic acid, 5,6,7,8-tetrahydro-4-hydroxy-ethyl ester (46.2). The 2-napthalenecarboxylic acid, 5,6,7,8-terahydro-4-hydroxy-ethyl ester is formed according to the method of Kasibhatla et al. (*J. Med. Chem.,* 44, 613, (2001)) A mixture of ethyl-1-hydroxy-3-napthylcarboxylate 46.1 (3.0 g, 13.8 mmol) and 20% Pd(OH)$_2$/C (1.0 g, wet) in 200 mL of MeOH is stirred under a 1 atm of H$_2$ until TLC confirms the consumption of the starting material. The catalyst is filtered through celite, and the filtrate is concentrated in vacuo. The residue is purified by column chromatography (silica, EtOAc/Hexane), to afford 2-napthalenecarboxylic acid, 5,6,7,8-terahydro-4-hydroxy-ethyl ester 46.2.

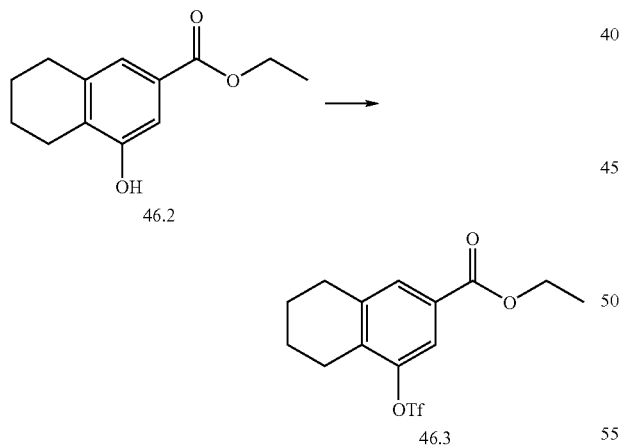

Ethyl 4-(trifluoromethylsulfonyloxy)-5,6,7,8-tetrahydronaphthalene-2-carboxylate (46.3). The Triflate is formed according to the method of Kasibhatla et al. (*J. Med. Chem.,* 44, 613, (2001)). A solution of 2-napthalenecarboxylic acid, 5,6,7,8-tetrahydro-4-hydroxy-ethyl ester 46.2 (2.5 g, 11.3 mmol) in 40 mL of pyridine is cooled to 0° C. and slowly treated with trifluoromethanesulfonic anhydride (2.1 mL, 12.5 mmol). On warming to room temperature, the mixture is further stirred until TLC confirms the consumption of the starting material. The solvent is evaporated, and the residue is diluted with 100 mL of water and extracted with ether. The combined organic layers are dried (MgSO$_4$) and concentrated under reduced pressure to yield the title compound

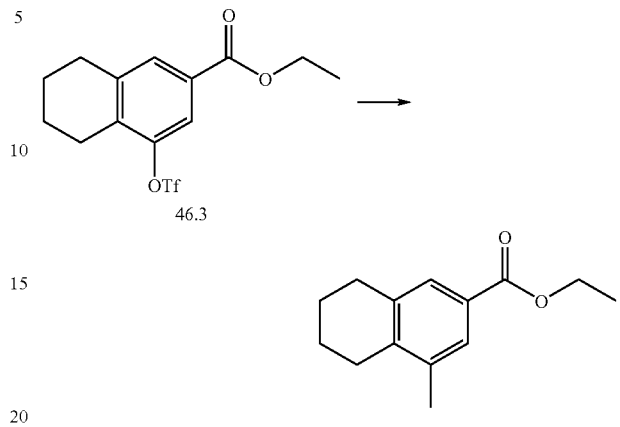

Ethyl 4-methyl-5,6,7,8-tetrahydronaphthalene-2-carboxylate (46.4). The ester is formed according to the method of Molander et al. (*J. Org. Chem.* 68, 5534, (2003)). To a stirring suspension of potassium methyltrifluoroborate (629.0 mg, 5.2 mmol) Cs$_2$CO$_3$ (5.0 g, 15.5 mmol), PdCl$_2$(dppf).CH$_2$Cl$_2$ (46.0 mg, 0.057 mmol), and triflate (46.3) (2.0 g, 5.7 mmol) in 50 mL THF is added water (5 mL) under an argon atmosphere. Stirring the mixture at reflux until TLC confirms the consumption of the starting material. The mixture is cooled to room temperature, and is diluted with water and extracted with ether. The combined organic layers are dried (MgSO$_4$) and concentrated under reduced pressure. The residue is purified by column chromatography (silica, EtOAc/Hexane), to afford ester 46.4.

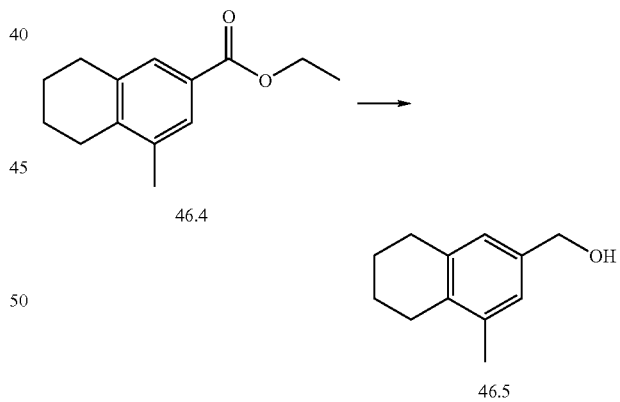

(4-Methyl-5,6,7,8-tetrahydronaphthalen-2-yl)methanol (46.5). To a stirring solution of the ester 46.4 (1.5 g, 6.9 mmol) in anhydrous THF (40 mL) is added dropwise a solution of LiAlH$_4$ in THF (1.0 M, 13.7 mL, 13.7 mmol) at 0° C. The mixture is stirred until TLC confirms the consumption of the starting material. The reaction is slowly quenched with water (10 mL) at 0° C., 1N NaOH aqueous solution (50 mL) and another portion of water (10 mL). The mixture is filtered and the filtrate is extracted with EtOAc (3×100 mL), dried over MgSO$_4$ and concentrated in vacuo. The residue is purified by column chromatography (silica, EtOAc/Hexane), to afford alcohol 46.5.

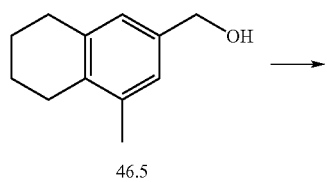

46.5

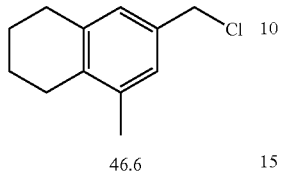

46.6

7-(Chloromethyl)-5-methyl-1,2,3,4-tetrahydronaphthalene (46.6). Alcohol 46.5 (1.0 g, 5.7 mmol) is dissolved in anhydrous DCM (50 mL). Thionyl chloride (619 μL, 8.5 mmol) is slowly added dropwise to the solution. The resulting mixture is stirred until TLC confirms consumption of the starting material. The organic solvent is removed in vacuo. The residue is purified by column chromatography (silica, EtOAc/Hexane), to afford chloride 46.6.

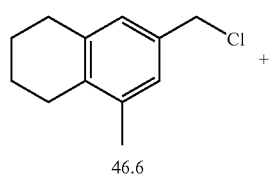

46.6

+

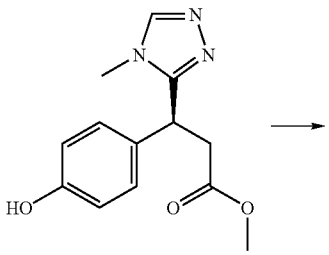

13.9 (resolved)

→

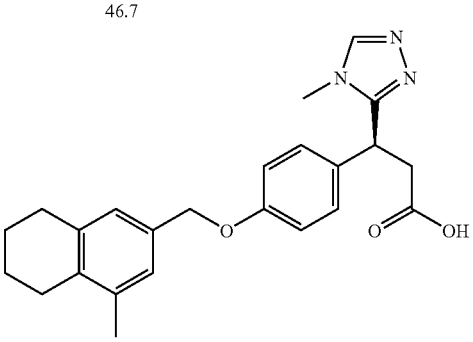

46.7

(S)-Methyl 3-(4-methyl-4H-1,2,4-triazol-3-yl)-3-(4-((4-methyl-5,6,7,8-tetrahydronaphthalen-2-yl)methoxy)phenyl) propanoate (46.7). To a stirred solution of 46.6 (100 mg, 0.38 mmol) in DMF (5 mL) at 23° C. is added resolved 13.9 (89.4 mg, 0.46 mmol) (13.9 is resolved using chiral chromatography as known to those skilled in the art) followed by Cs₂CO₃ (150 mg, 4.6 mmol). The resulting mixture is stirred until TLC confirms the consumption of the starting material. The reaction is then diluted with EtOAc (30 mL), washed with water and brine, dried over MgSO₄ and concentrated in vacuo. The residue is purified by column chromatography (silica, EtOAc/Hexane), to afford ester 46.7.

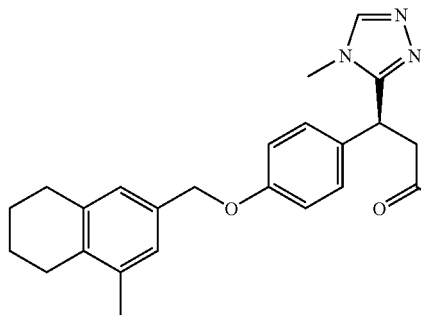

46.7

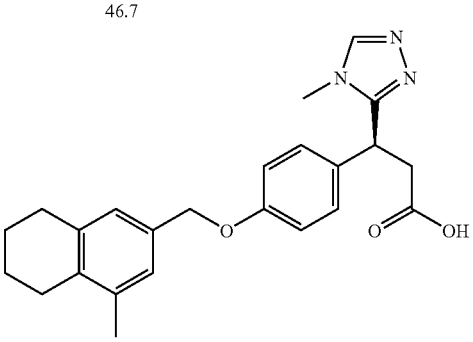

46

(S)-3-(4-Methyl-4H-1,2,4-triazol-3-yl)-3-(4-((4-methyl-5,6,7,8-tetrahydronaphthalen-2-yl)methoxy)phenyl)propanoic acid (46). To a stirred solution of 46.7 (150 mg, 3.6 mmol) in THF/EtOH (6 mL, 3/1, v/v) was added 1N LiOH (aq) (2 mL). The reaction mixture is stirred at 23° C. until TLC confirms consumption of the starting material. The organic solvent is removed in vacuo. 1N HCl is added to neutralize the mixture to pH 7. The mixture is extracted with EtOAc (2×10 mL), concentrated in vacuo. The residue is purified by column chromatography (silica, MeOH/DCM), to afford acid 46.

6.61 Example 47

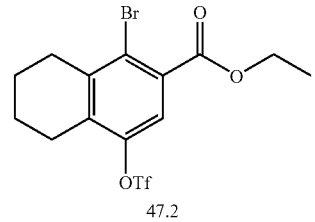

47.1

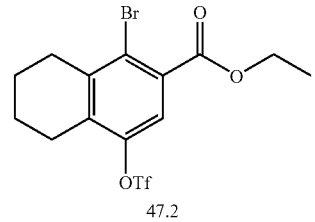

47.2

Ethyl 1-bromo-4-(trifluoromethylsulfonyloxy)-5,6,7,8-tetrahydronaphthalene-2-carboxylate (47.2). The triflate is formed according to the method of Kasibhatla et al. (*J. Med.*

Chem., 44, 613, (2001)). A solution of alcohol 47.1 (2.5 g, 8.4 mmol) in 40 mL of pyridine is cooled to 0° C. and slowly treated with trifluoromethanesulfonic anhydride (1.70 mL, 10.0 mmol). On warming to room temperature, the mixture is further stirred until TLC confirms consumption of the starting material. The solvent is evaporated, and the residue is diluted with 50 mL of water and extracted with ether. The combined organic layers are dried (MgSO$_4$) and concentrated under reduced pressure to yield the title compound 47.2.

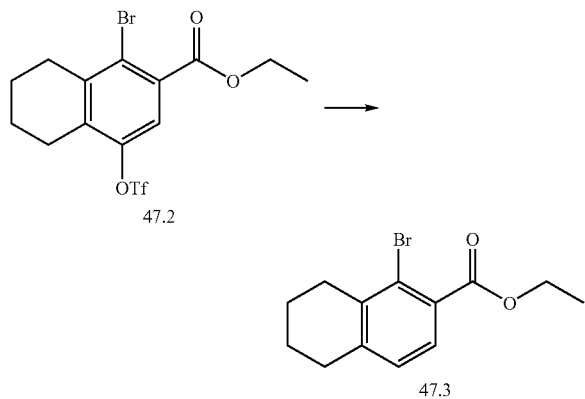

1-Bromo-5,6,7,8-tetrahydronaphthalene-2-carboxylate (47.3). The bromide is formed according to the method of Kasibhatla et al. (J. Med. Chem., 44, 613, (2001)). A solution of triflate 47.2 (2.2 g, 5.1 mmol) in 40 mL of DMF under nitrogen is stirred and tetrakis(triphenylphosphone) palladium (294 mg, 0.26 mmol) and tributyltin hydride (1.65 mL, 6.1 mmol) are added. The mixture is stirred until TLC confirms consumption of the starting material. After cooling to room temperature, the mixture is diluted with EtOAc (30 mL), washed with water and brine, dried over MgSO$_4$ and concentrated in vacuo. The residue is purified by column chromatography (silica, EtOAc/Hexane), to afford ester 47.3.

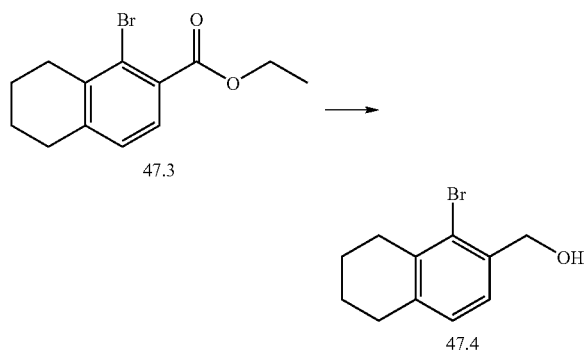

(1-Bromo-5,6,7,8-tetrahydronaphthalen-2-yl)methanol (47.4). The alcohol 47.4 is formed according to the method of Basabe et al. (Tetrahedron, 46, 9173, (2003)). To a stirring solution of the ester 47.3 (1.5 g, 5.3 mmol) in dry DCM (40 mL) at −78° C., is added dropwise a solution of DIBALH in toluene (1.5 M, 7.1 mL, 10.6 mmol). The mixture is stirred until TLC confirms consumption of the starting material. The reaction is slowly quenched with a solution of Na/K tartrate (10 mL). The mixture is further stirred for 2 hours. The aqueous layer is extracted with EtOAc (3×50 mL), dried over MgSO$_4$ and concentrated in vacuo. The residue is purified by column chromatography (silica, EtOAc/Hexane), to afford alcohol 47.4.

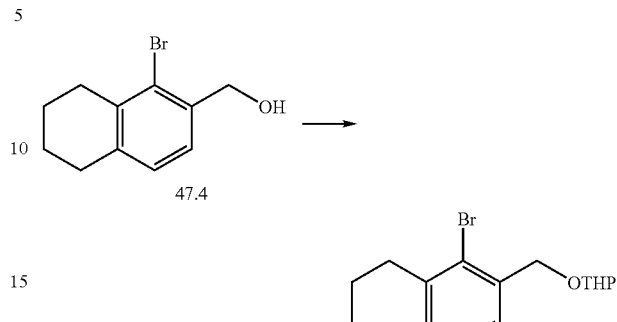

2-((1-Bromo-5,6,7,8-tetrahydronaphthalen-2-yl)methoxy)-tetrahydro-2H-pyran (47.5). To a stirring solution of alcohol 47.4 (1.0 g, 4.1 mmol) in DCM at 23° C., is added 3,4-dihydro-2H-pyran (757 µL, 8.3 mmol) followed by PPTS (catalytic). The mixture is stirred until TLC confirms consumption of the starting material. The mixture is concentrated in vacuo. The residue is purified by column chromatography (silica, EtOAc/Hexane), to afford the THP protected alcohol 47.5.

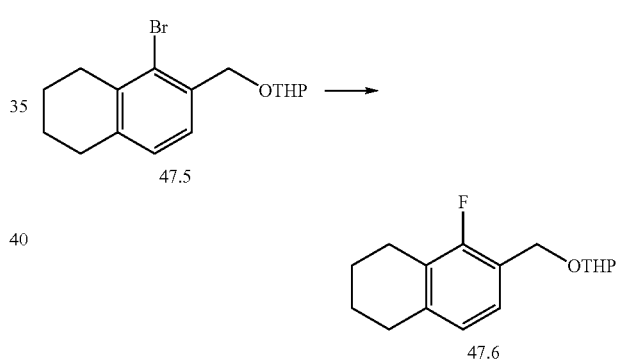

2-((1-Fluoro-5,6,7,8-tetrahydronaphthalen-2-yl)methoxy)-tetrahydro-2H-pyran (47.6). To stirring solution of bromide 47.5 (1.0 g, 3.1 mmol) in THF at −78° C. is added n-BuLi (1.6 M, 2.11 mL, 3.4 mmol), and stirring is continued for 1 hour. N-Fluorobenzene sulfonimide (3.7 mmol) is added and the mixture is allowed to warm to 23° C. Water is added to quench the reaction. The aqueous layer is extracted with EtOAc (3×100 mL), and the organic layer is dried over MgSO$_4$ and concentrated in vacuo. The residue is purified by column chromatography (silica, EtOAc/Hexane), to afford fluoride 47.6.

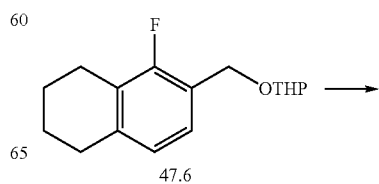

-continued

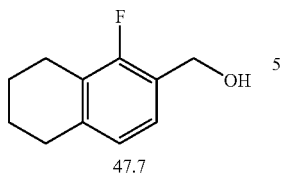

(1-Fluoro-5,6,7,8-tetrahydronaphthalen-2-yl)methanol (47.7). To a stirring solution of 47.6 (0.75 g, 2.8 mmol) in EtOH (25 mL) at 23° C., is added PPTS (catalytic). The mixture is stirred until TLC confirms consumption of the starting material. The mixture is concentrated in vacuo. The residue is purified by column chromatography (silica, EtOAc/Hexane), to afford alcohol 47.7.

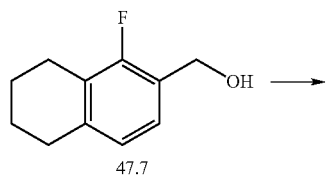

6-(Chloromethyl)-5-fluoro-1,2,3,4-tetrahydronaphthalene (47.8). The alcohol 47.7 (0.5 g, 2.77 mmol) is dissolved in anhydrous DCM (50 mL). Thionyl chloride (302 μL, 4.2 mmol) is slowly added dropwise to the above solution. The resulting mixture is stirred until TLC confirms the consumption of the starting material. The organic solvent is removed in vacuo. The residue is purified by column chromatography (silica, EtOAc/Hexane), to afford chloride 47.8.

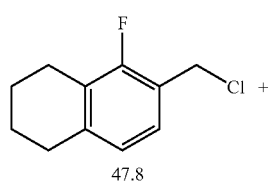

-continued

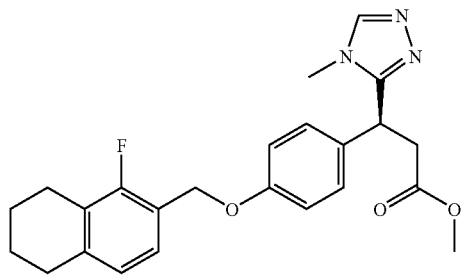

(S)-Methyl 3-(4-((1-fluoro-5,6,7,8-tetrahydronaphthalen-2-yl)methoxy)phenyl)-3-(4-methyl-4H-1,2,4-triazol-3-yl)propanoate (47.9). To a stirred solution of resolved 13.9 (0.1 g, 0.38 mmol) (13.9 is resolved using chiral chromatography ask known to those skilled in the art) in DMF (5 mL) at 23° C., is added 47.8 (91.2 mg, 0.46 mmol) followed by Cs₂CO₃ (150 mg, 0.46 mmol). The resulting mixture is stirred until TLC confirms consumption of the starting material. The reaction is then diluted with EtOAc (30 mL), washed with water and brine, dried over MgSO₄ and concentrated in vacuo. The residue is purified by column chromatography (silica, EtOAc/Hexane), to afford ester 47.9.

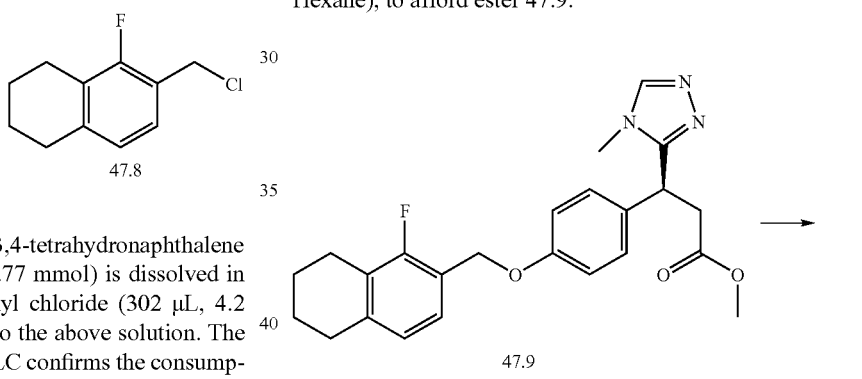

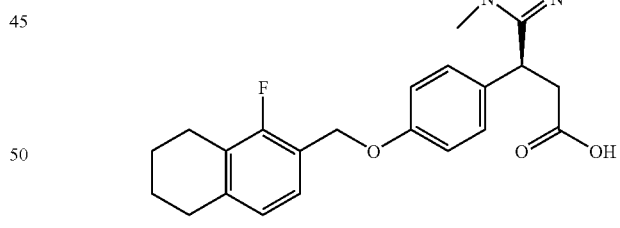

(S)-3-(4-((1-Fluoro-5,6,7,8-tetrahydronaphthalen-2-yl)methoxy)phenyl)-3-(4-methyl-4H-1,2,4-triazol-3-yl)propanoic acid (47). To a stirred solution of 47.9 (100 mg, 0.24 mmol) in THF/EtOH (6 mL, 3/1, v/v) is added 1N LiOH (aq) (2 mL). The reaction mixture is stirred at 23° C. until TLC confirms consumption of the starting material. The organic solvent is removed in vacuo. 1N HCl is added to neutralize the mixture to pH 7. The mixture is extracted with EtOAc (2×10 mL), concentrated in vacuo. The residue is purified by column chromatography (silica, MeOH/DCM), to afford acid 47.

6.62 Example 48

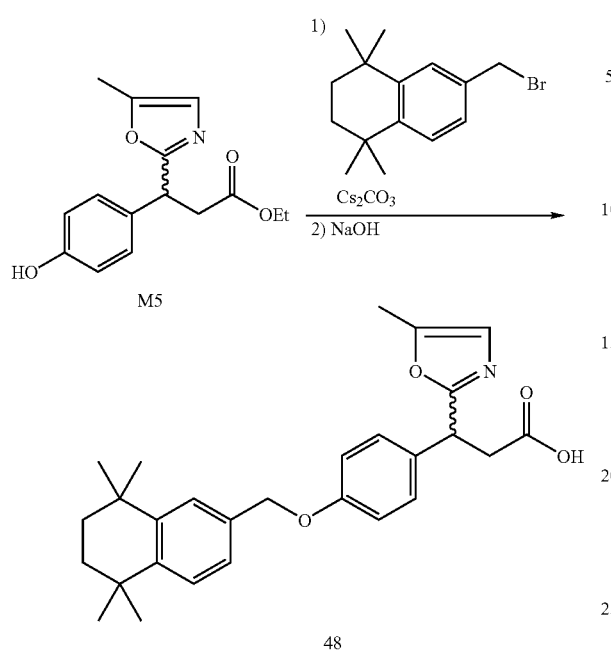

Synthesis of Compound 48. Compound 48 is synthesized using the procedure for preparing Example 6 using compound M5. Separation of the enantiomers of starting material M5 is accomplished using the procedure described herein and reacted with the benzyl bromide to provide the R and S enantiomers of 48. Alternatively, a racemic mixture of 48 can be separated on a chiral column to afford the individual enantiomers.

6.63 Example 49

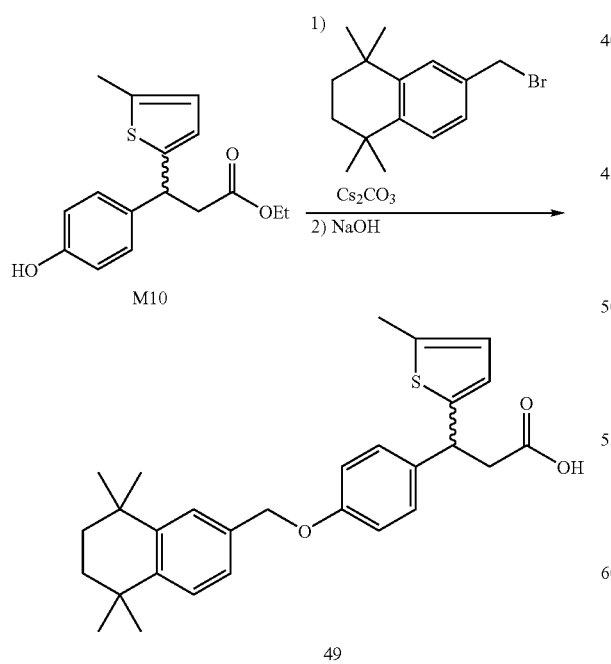

Synthesis of Compound 51. Compound 49 is synthesized using the procedure for preparing Example 6 using compound M10. Separation of the enantiomers of starting material M10 is accomplished using the procedure described herein and reacted with the benzyl bromide to provide the R and S enantiomers of 49. Alternatively, a racemic mixture of 49 can be separated on a chiral column to afford the individual enantiomers.

6.64 Example 50

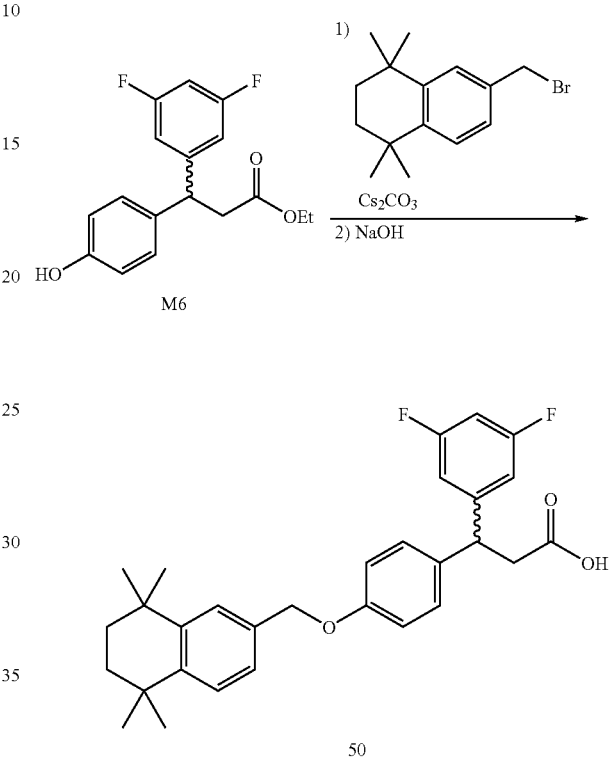

Synthesis of Compound 50. Compound 50 is synthesized using the procedure for preparing Example 6 using compound M6. Separation of the enantiomers of starting material M6 is accomplished using the procedure described herein and reacted with the benzyl bromide to provide the R and S enantiomers of 50. Alternatively, a racemic mixture of 50 can be separated on a chiral column to afford the individual enantiomers.

6.65 Example 51

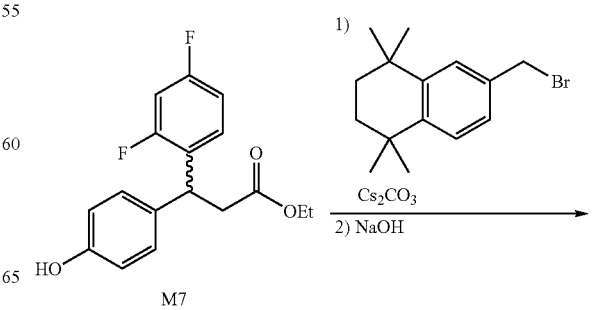

-continued

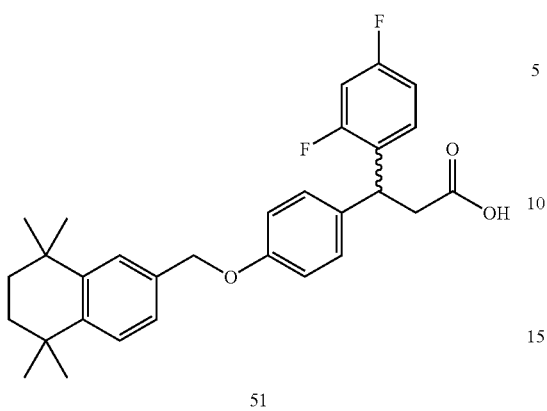

51

Synthesis of Compound 51. Compound 51 is synthesized using the procedure for preparing Example 6 using compound M7. Separation of the enantiomers of starting material M7 is accomplished using the procedure described herein and reacted with the benzyl bromide to provide the R and S enantiomers of 51. Alternatively, a racemic mixture of 51 can be separated on a chiral column to afford the individual enantiomers.

6.66 Example 52

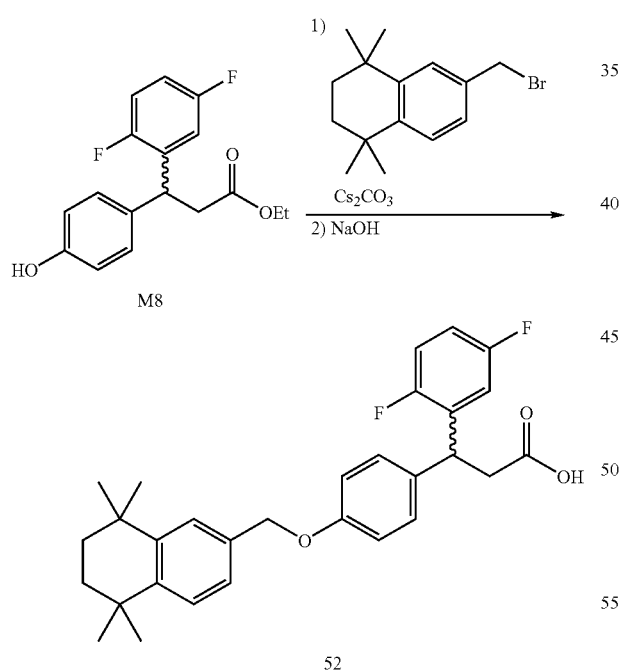

52

Synthesis of Compound 52. Compound 52 is synthesized using the procedure for preparing Example 6 using compound M8. Separation of the enantiomers of starting material M8 is accomplished using the procedure described herein and reacted with the benzyl bromide to provide the R and S enantiomers of 52. Alternatively, a racemic mixture of 52 can be separated on a chiral column to afford the individual enantiomers.

6.67 Example 53

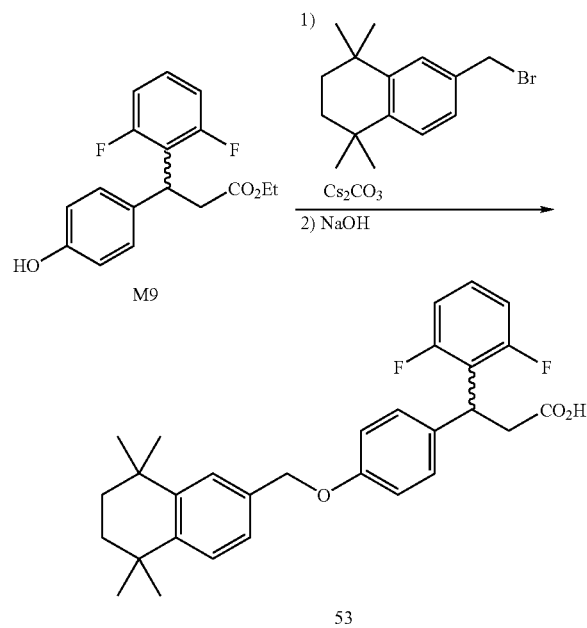

53

Synthesis of Compound 53. Compound 53 is synthesized using the procedure for preparing Example 6 using compound M9. Separation of the enantiomers of starting material M9 is accomplished using the procedure described herein and reacted with the benzyl bromide to provide the R and S enantiomers of 53. Alternatively, a racemic mixture of 53 can be separated on a chiral column to afford the individual enantiomers.

6.68 Example 54

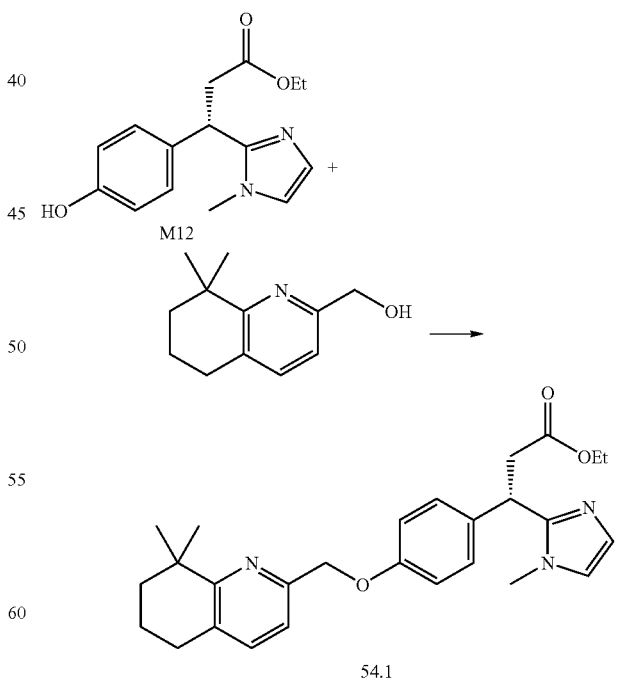

54.1

(S)-Ethyl 3-(4-((8,8-dimethyl-5,6,7,8-tetrahydroquinolin-2-yl)methoxy)phenyl)-3-(1-methyl-1H-imidazol-2-yl)propanoate (54.1). To a solution of (8,8-dimethyl-5,6,7,8-tetrahydroquinolin-2-yl)methanol (191 mg, 1 mmol; prepared according to D. Guay et al, Bioorg. Med. Chem. Lett. 1998, 8, 453-458), triphenylphosphine (288 mg, 1.1 mmol) and compound M12 (274 mg, 1 mmol) in THF (0.5 mL), is added slowly diethyl azodicarboxylate (174 mg, 1 mmol) at room temperature. The reaction mixture is stirred at room temperature for 30 minutes before loading on a silica gel cartridge and chromatographing (silica gel, 1:4 EtOAc/hexane) to afford compound 54.1.

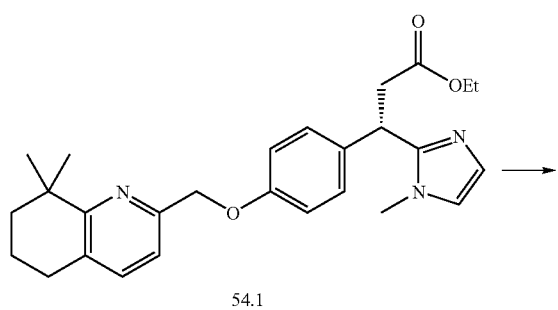

54.1

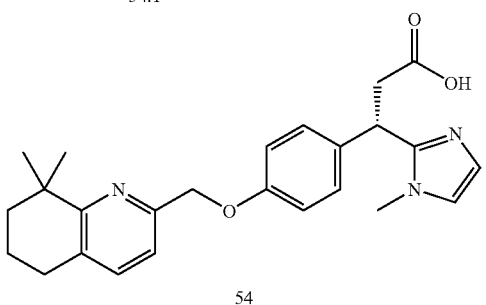

54

(S)-3-(4-((8,8-Dimethyl-5,6,7,8-tetrahydroquinolin-2-yl) methoxy)phenyl)-3-(1-methyl-1H-imidazol-2-yl)propanoic acid (54). 10% NaOH (aq) (1 mL) is added to a solution of compound 54.1 (45 mg, 0.1 mmol) in EtOH (2 mL). The reaction mixture is stirred at room temperature for 4 hours. 1N HCl is added to neutralize the mixture to pH 6-7. The mixture is extracted with EtOAc (2×20 mL), washed with water and brine, dried over $Na_2SO_4$, filtered and concentrated under reduced pressure. The residue is flash chromatographed (silica gel, 0-10% MeOH in DCM) to afford the compound 54.

6.69 Examples 55 and 56

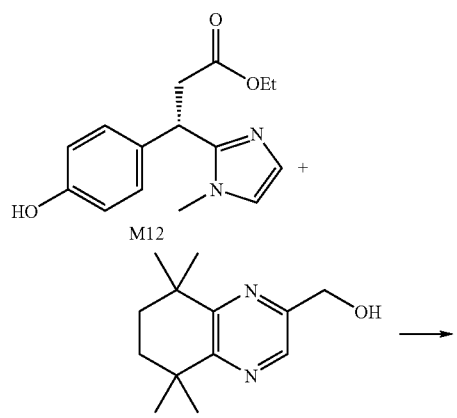

M12

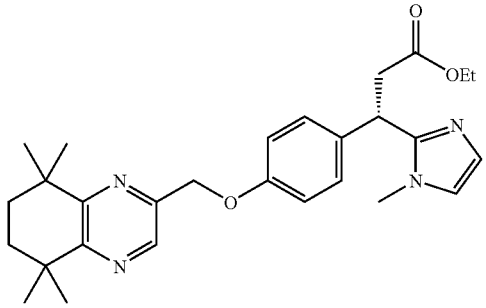

55

(S)-Ethyl 3-(1-methyl-1H-imidazol-2-yl)-3-(4-((5,5,8,8-tetramethyl-5,6,7,8-tetrahydroquinoxalin-2-yl)methoxy) phenyl)propanoate (55). To a solution of (5,5,8,8-Tetramethyl-5,6,7,8-tetrahydroquinoxalin-2-yl)methanol (220 mg, 1 mmol; prepared according to K. Kikuchi et al, J. Med. Chem. 2000, 43, 409-419), triphenylphosphine (288 mg, 1.1 mmol) and compound M12 (274 mg, 1 mmol) in THF (0.5 mL), is added slowly diethyl azodicarboxylate (174 mg, 1 mmol) at room temperature. The reaction mixture is stirred at room temperature for 30 minutes before loading on a silica gel cartridge and chromatographing (silica gel, 1:4 EtOAc/ hexane) to afford the compound 55.

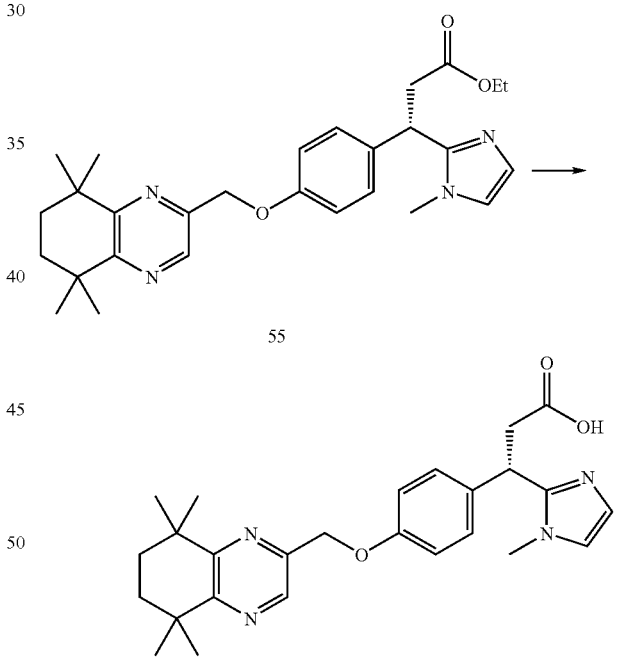

55

56

(S)-3-(1-Methyl-1H-imidazol-2-yl)-3-(4-((5,5,8,8-tetramethyl-5,6,7,8-tetrahydroquinoxalin-2-yl)methoxy)phenyl)propanoic acid (56). 10% $NaOH_{(aq)}$ (1 mL) is added to a solution of compound 55 (47 mg, 0.1 mmol) in EtOH (2 mL). The reaction mixture is stirred at room temperature for 4 hours. 1N HCl is added to neutralize the mixture to pH 6-7. The mixture is extracted with EtOAc (2×20 mL), washed with water and brine, dried over $Na_2SO_4$, filtered and concentrated under reduced pressure. The residue is flash chromatographed (silica gel, 0-10% MeOH in DCM) to afford compound 56.

6.70 Example 57

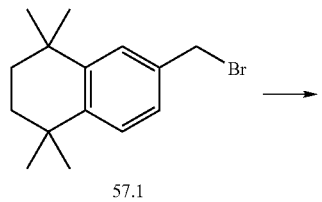

57.1

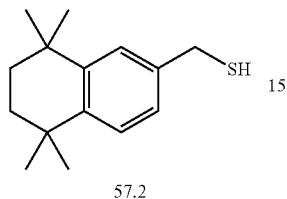

57.2

(5,5,8,8-Tetramethyl-5,6,7,8-tetrahydronaphthalen-2-yl)methanethiol (57.1). 6-Bromomethyl-1,1,4,4-tetramethyl-1,2,3,4-tetrahydronaphthalene 57.1 (available from Maybridge) is converted directly to the compound 57.2 by the published method of Yoon (*Synthesis* 1995, 373-75).

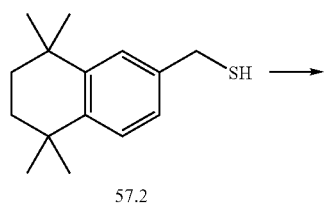

57.2

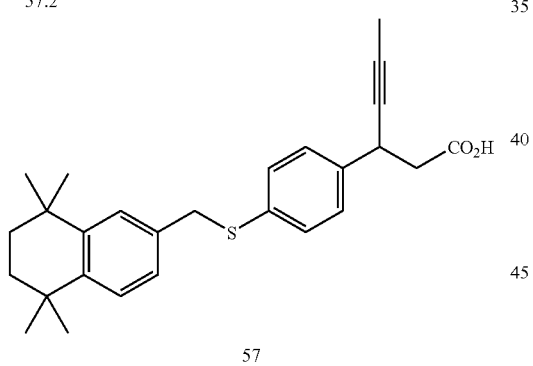

57

(+/−)-3-(4-((5,5,8,8-Tetramethyl-5,6,7,8-tetrahydronaphthalen-2-yl)methylthio)phenyl)hex-4-ynoic acid (57). Thiol 57.2 is converted to the title compound 57 according by a method analogous to that disclosed in Example 28 set forth in US 2006/0004012 which is hereby incorporated by reference.

6.71 Example 58

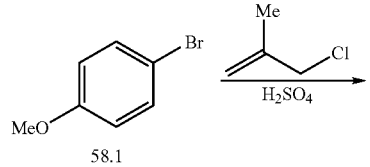 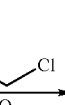

58.1

-continued

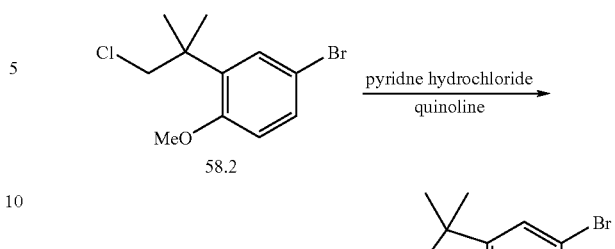

58.2

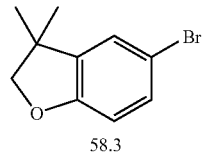

58.3

5-Bromo-3,3-dimethyl-2,3-dihydrobenzofuran (58.3). Compound 58.3 is synthesized using a literature procedure (*J. Med. Chem.* 1987, 30, 1474-1482).

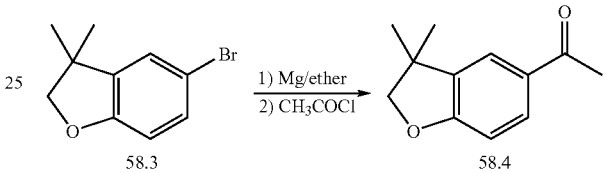

58.3  58.4

1-(3,3-Dimethyl-2,3-dihydrobenzofuran-5-yl)ethanone (58.4). Compound 58.4 is synthesized using a literature procedure (*J. Med. Chem.* 1998, 41, 3753-3757).

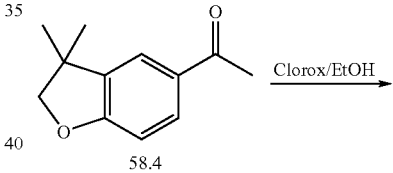

58.4

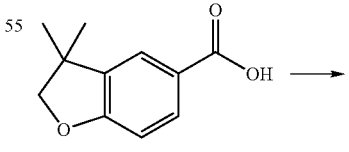

58.5

3,3-Dimethyl-2,3-dihydrobenzofuran-5-carboxylic acid (58.5). Compound 58.5 is synthesized using a literature procedure (*J. Med. Chem.* 1997, 40, 3567-3583).

58.5

58.6

153

(3,3-Dimethyl-2,3-dihydrobenzofuran-5-yl)methanol (58.6). Compound 58.6 is prepared using the procedure of Example 2.2 set forth in US 2006/0004012 which is hereby incorporated by reference.

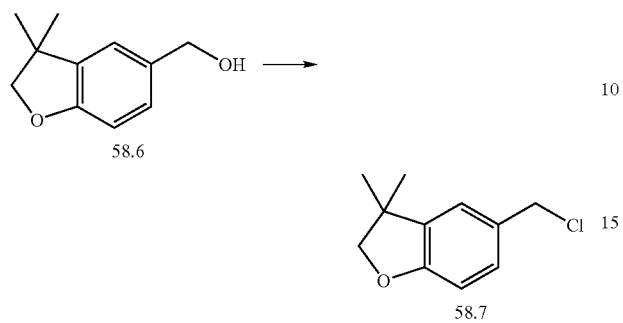

5-(Bromomethyl)-3,3-dimethyl-2,3-dihydrobenzofuran (58.7). Compound 58.7 is prepared using the procedure of Example 2.3 set forth in US 2006/0004012 which is hereby incorporated by reference.

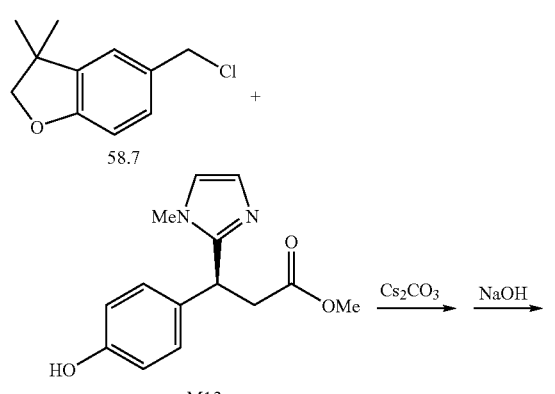

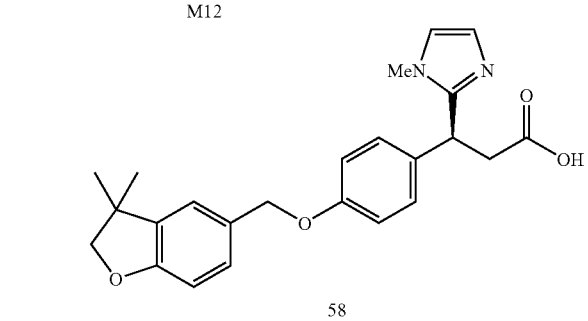

(S)-3-(4-((3,3-Dimethyl-2,3-dihydrobenzofuran-5-yl)methoxy)phenyl)-3-(1-methyl-1H-imidazol-2-yl)propanoic acid (58). Compound 58 is obtained from compound 58.7 and M12 (see Method 12) using the general procedure A.

6.72 Example 59

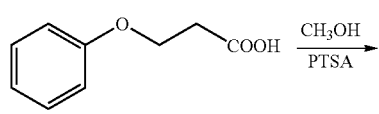

154

-continued

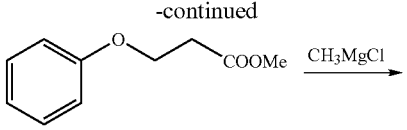

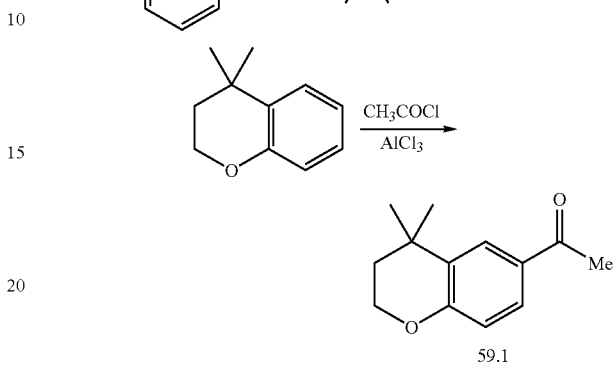

1-(4,4-Dimethylchroman-6-yl)ethanone (59.1). Compound 59.1 is synthesized using a literature procedure (*J. Med. Chem.* 1985, 28, 116-124).

4,4-Dimethylchroman-6-carboxylic acid (59.2). Compound 59.2 is synthesized using a literature procedure (*J. Med. Chem.* 1997, 40, 3567-3583).

(4,4-Dimethylchroman-6-yl)methanol (59.3). Compound 59.3 is prepared using the procedure of Example 2.2 set forth in US 2006/0004012 which is hereby incorporated by reference.

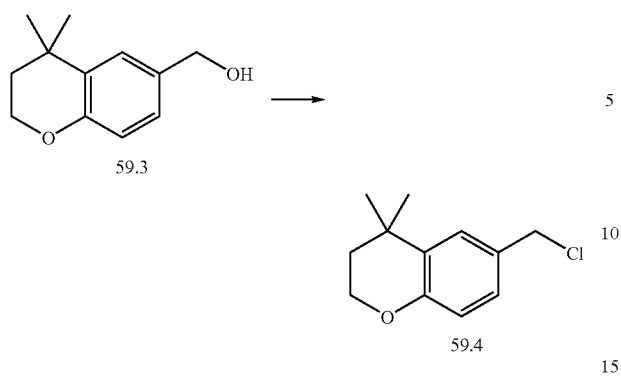

6-(Bromomethyl)-4,4-dimethylchroman (59.4). Compound 59.4 is prepared using the procedure of Example 2.3 set forth in US 2006/0004012 which is hereby incorporated by reference.

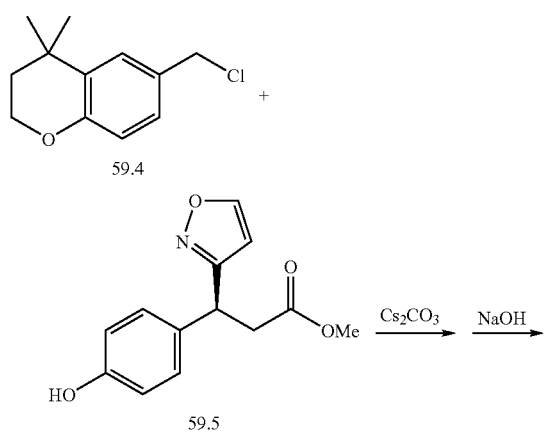

(S)-3-(4-((4,4-dimethylchroman-6-yl)methoxy)phenyl)-3-(isoxazol-3-yl)propanoic acid (59). Compound 59 is obtained from compound 59.4 and 59.5 (methyl ester 59.5 is prepared using the same procedure used to prepare ethyl ester 6.6 using methanol instead of ethanol) (see Example 6) using the procedure of Example 6.

6.73 Example 60

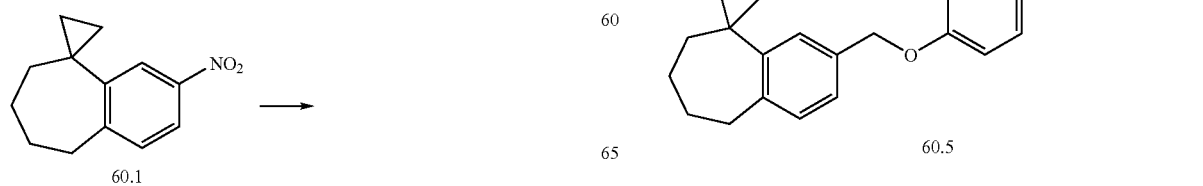

Benzyl Alcohol (60.4). Compound 60.4 is obtained using methods known to those skilled in the art (JACS 1972, 94(9), 3143-3148). Compound 60.1 is reduced with $SnCl_2$ to provide the corresponding aniline. The aniline is transformed to the aryl iodide 60.2 by treating with $NaNO_2$ and HCl in the presence of KI. The iodide 60.2 is converted to the corresponding acid 60.3 by lithium halogen exchange with s-BuLi followed by trapping with DMF. The acid 60.3 is reduced with borane to provide the benzyl alcohol 60.4.

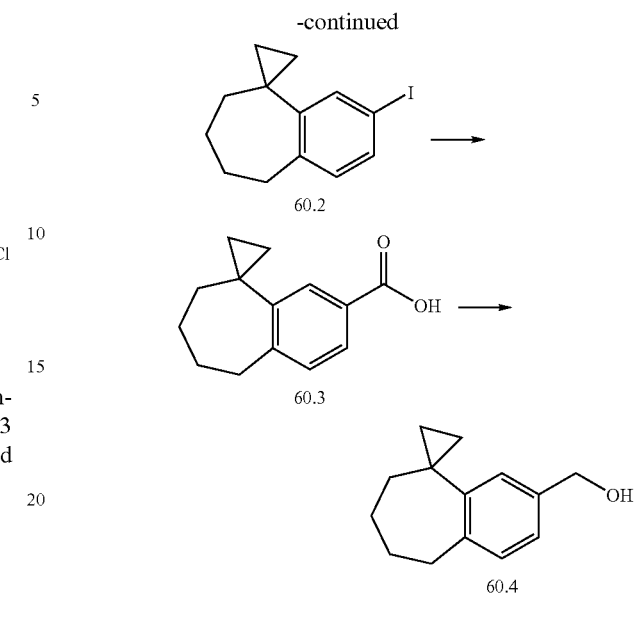

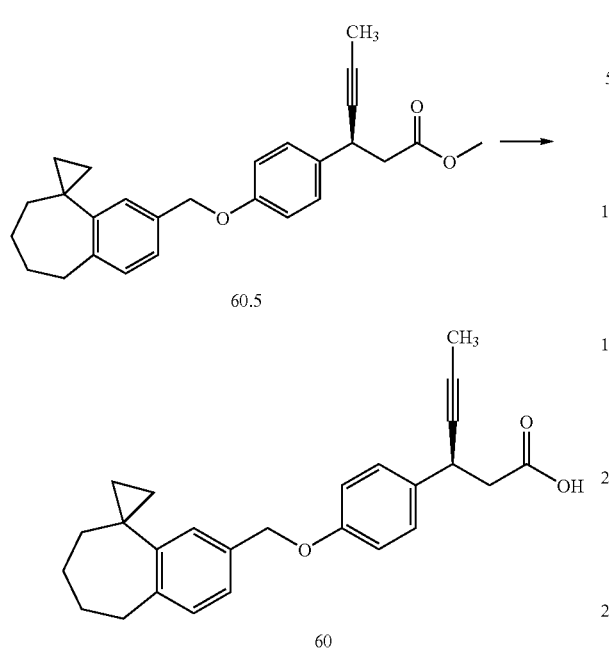

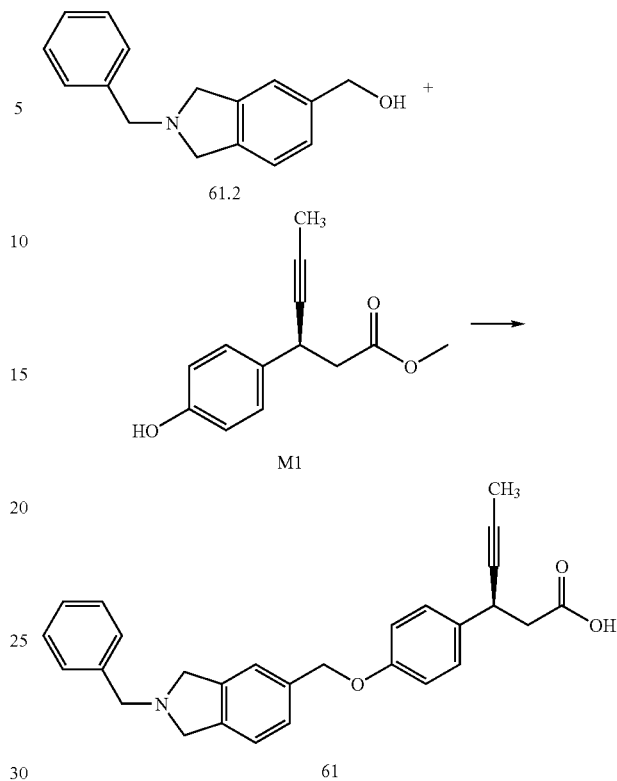

(S)-3-(4-((2-Benzylisoindolin-5-yl)methoxy)phenyl)hex-4-ynoic acid (60). Compound 60.4 and M1 are reacted under Mitsunobu conditions and the resulting ester 60.5 is hydrolyzed by a method analogous to that disclosed in Example 16 to provide 60.

6.74 Example 61

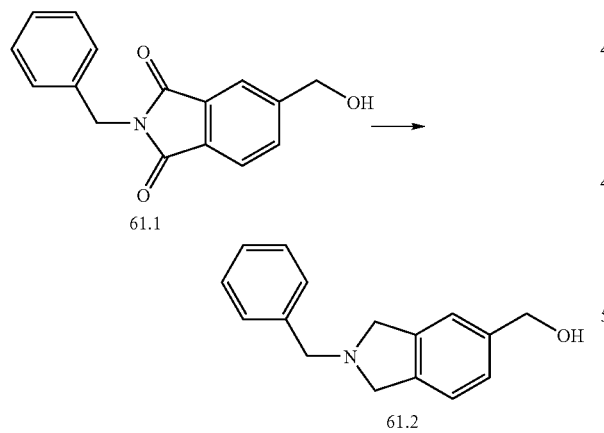

(2-Benzylisoindolin-5-yl)methanol (61.2). 61.1 is prepared according to the published method of Miyachi (*Bioorganic & Medicinal Chemistry Letters* 2005, 15, 4427-4431). To a stirred 20 mL THF solution of AM.1 (2.67 g, 10 mmol), is added dropwise IN LiAlH₄ 30 mL over 30 minutes at 0° C. under N₂. After completion, the solution is heated at reflux for 2 hours. The solution is cooled to room temperature, quenched with saturated NH₄Cl, extracted with DCM, dried over MgSO₄, concentrated under reduced pressure, and the residue purified by flash chromatography with EtOAc and hexanes as the mobile phase to obtain 61.2.

(S)-3-(4-((2-benzylisoindolin-5-yl)methoxy)phenyl)hex-4-ynoic acid (61). Compound 61.2 and M1 are reacted under Mitsunobu conditions and the resulting ester hydrolyzed by a method analogous to that disclosed in Example 16.

6.75 Example 62

Synthesis of (S)-3-(4-((3-bromo-5,5,8,8-tetramethyl-5,6,7,8-tetrahydronaphthalen-2-yl)methoxy)phenyl)-3-(1-methyl-1H-imidazol-2-yl)propanoic acid (62)

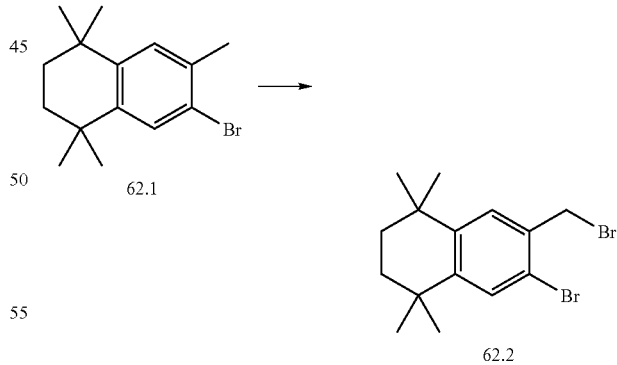

6-Bromo-7-(bromomethyl)-1,1,4,4-tetramethyl-1,2,3,4-tetrahydronaphthalene (62.2). The mixture of 6-bromo-7-methyl-1,1,4,4-tetramethyl-1,2,3,4-tetrahydronaphthalene (4.20 g, 15 mmol), NBS (3.20 g, 18 mmol), 2,2'-azobisisobutyronitrile (0.3 g, 1.8 mmol) and CCl₄ (120 mL) was heated at reflux for 16 hours. The mixture was concentrated under reduced pressure to about 50 mL. The reaction was then filtered, and the solid was washed with Et₂O (20 mL). The combined organic solution was then concentrated under vacuum to generate crude product. Crude 62.2 was generated as a brown oil and used directly in the next step without further purification.

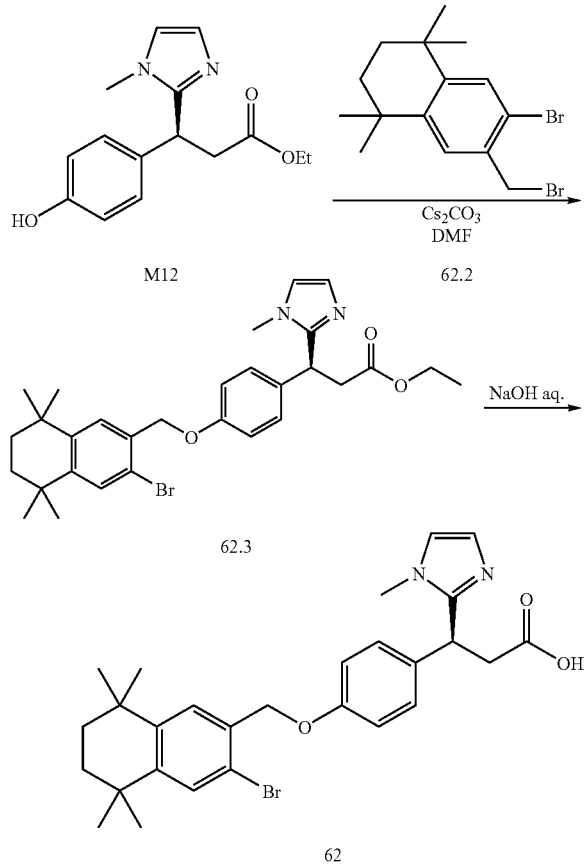

62

(S)-3-(4-((3-Bromo-5,5,8,8-tetramethyl-5,6,7,8-tetrahydronaphthalen-2-yl)methoxy)phenyl)-3-(1-methyl-1H-imidazol-2-yl)propanoic acid (62). Compound 62.3 was obtained from compound M12 and 62.2 following the general procedure E and isolated as a general intermediate. Compound 62 was obtained from compound 62.3 by following the general procedure E. LC-MS ESI (neg.) M/E: 523 (M–H). $^1$HNMR (500 MHz, MeOH-$d_4$, ppm) δ 7.52 (s, 1H), 7.43 (s, 1H), 7.18-7.21 (m, 4H), 6.96-7.20 (m, 2H), 5.07 (s, 2H), 4.73 (dd, 1H J=5 Hz, 10 Hz), 3.65 (s, 3H), 3.27 (dd, 1H, J=5 Hz, 10 Hz), 2.98 (dd, 1H, J=5 Hz, 10 Hz), 1.70 (s, 4H), 1.28 (s, 6H), 1.22 (s, 6H).

6.76 Example 63

Synthesis of (S)-3-(4-((3-cyclopropyl-5,5,8,8-tetramethyl-5,6,7,8-tetrahydronaphthalen-2-yl)methoxy)phenyl)-3-(1-methyl-1H-imidazol-2-yl)propanoic acid (63)

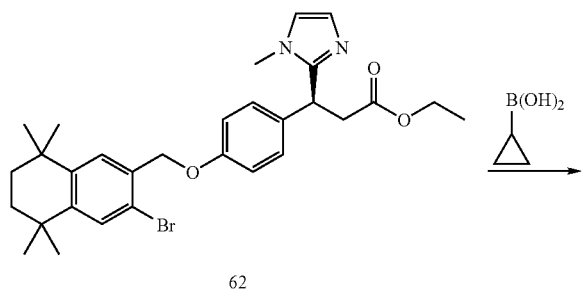

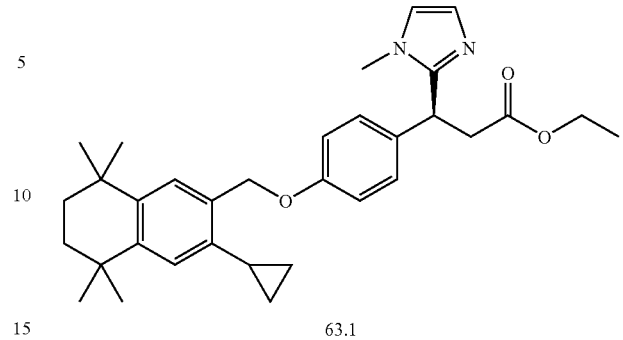

63.1

(S)-Ethyl 3-(1-methyl-1H-imidazol-2-yl)-3-(4-((3,5,5,8,8-pentamethyl-5,6,7,8-tetrahydronaphthalen-2-yl)methoxy)phenyl)propanoate (63.1). The mixture of compound 62 (166 mg, 0.3 mmol), cyclopropyl boronic acid (129 mg, 1.5 mmol), $K_3PO_4$ (212 mg, 1 mmol), Pd(OAc)$_2$ (26 mg, 0.12 mmol), Sphos (100 mg, 0.24 mmol) and dioxane (3 mL) was purged with nitrogen, and then heated at 100° C. overnight. The reaction mixture was directly purified by CombiFlash. The compound 63.1 was generated as a colorless oil. LC-MS ESI (pos.) M/E: 515 (M+H).

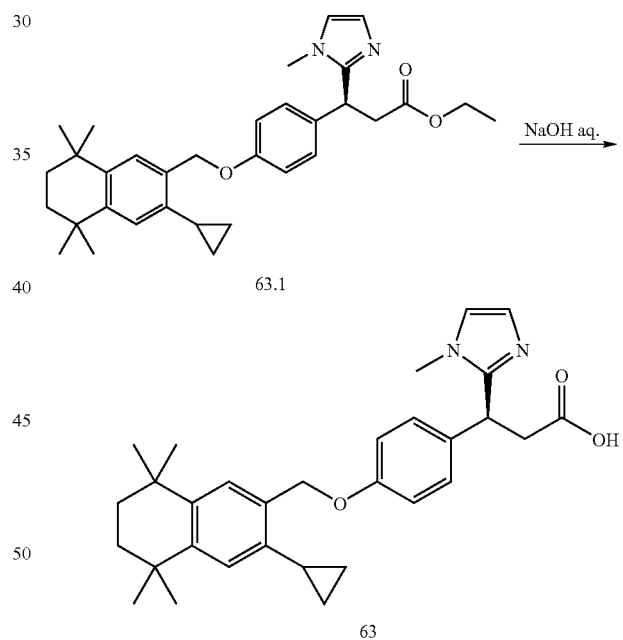

63

(S)-3-(4-((3-Cyclopropyl-5,5,8,8-tetramethyl-5,6,7,8-tetrahydronaphthalen-2-yl)methoxy)phenyl)-3-(1-methyl-1H-imidazol-2-yl)propanoic acid (63). Compound 63 was obtained from compound 63.1 by following the general procedure E. LC-MS ESI (neg.) M/E: 485 (M–H).

$^1$HNMR (500 MHz, MeOH-$d_4$, ppm) δ 7.53 (s, 1H), 7.51 (s, 1H), 7.29 (s, 1H), 7.23-7.25 (m, 2H), 7.05-7.07 (m, 2H), 7.01 (s, 1H), 5.22 (s, 2H), 4.97 (dd, 1H J=5 Hz, 10 Hz), 3.85 (s, 3H), 3.26 (dd, 1H, J=10 Hz, 15 Hz), 3.19 (dd, 1H, J=10 Hz, 20 Hz), 1.96 (m, 1H), 1.69 (s, 4H), 1.26 (s, 6H), 1.23 (s, 6H), 0.87-0.90 (m, 2H), 0.62-0.65 (m, 2H).

6.77 Example 64

Synthesis of (S)-3-(4-((3-methyl-5,5,8,8-tetramethyl-5,6,7,8-tetrahydronaphthalen-2-yl)methoxy)phenyl)-3-(1-methyl-1H-imidazol-2-yl)propanoic acid (64)

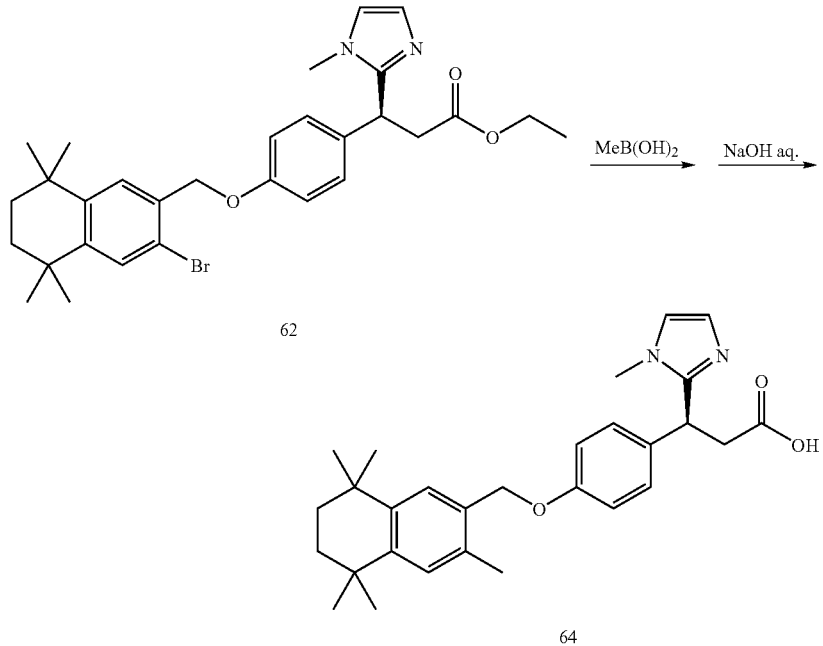

(S)-3-(4-((3-Methyl-5,5,8,8-tetramethyl-5,6,7,8-tetrahydronaphthalen-2-yl)methoxy)phenyl)-3-(1-methyl-1H-imidazol-2-yl)propanoic acid (64). Compound 64 was obtained from compound 62 and methyl boronic acid by following the same procedure used for compound 63. LC-MS ESI (neg.) M/E: 459 (M–H). $^1$HNMR (500 MHz, MeOH-$d_4$, ppm) δ 7.53 (s, 1H), 7.51 (s, 1H), 7.27 (s, 1H), 7.22-7.24 (m, 2H), 7.15 (s, 1H), 7.04-7.07 (m, 2H), 5.03 (s, 2H), 4.97 (dd, 1H J=5 Hz, 10 Hz), 3.85 (s, 3H), 3.36 (dd, 1H, J=10 Hz, 20 Hz), 3.19 (dd, 1H, J=10 Hz, 20 Hz), 2.30 (s, 3H), 1.70 (s, 4H), 1.28 (s, 6H), 1.24 (s, 6H).

6.78 Example 65

Synthesis of (S)-3-(4-((3-ethyl-5,5,8,8-tetramethyl-5,6,7,8-tetrahydronaphthalen-2-yl)methoxy)phenyl)-3-(1-methyl-1H-imidazol-2-yl)propanoic acid (65)

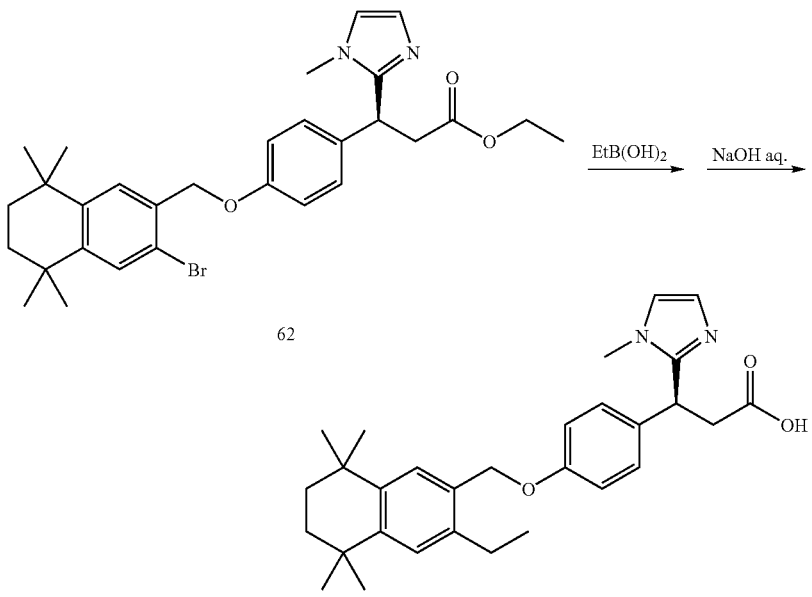

(S)-3-(4-((3-Ethyl-5,5,8,8-tetramethyl-5,6,7,8-tetrahydronaphthalen-2-yl)methoxy)phenyl)-3-(1-methyl-1H-imidazol-2-yl)propanoic acid (65). Compound 65 was obtained from compound 65 and ethyl boronic acid by following the same procedure as used for compound 63. LC-MS ESI (neg.) M/E: 473 (M–H). $^1$HNMR (500 MHz, MeOH-d$_4$, ppm) δ 7.53 (s, 1H), 7.51 (s, 1H), 7.29 (s, 1H), 7.22-7.26 (m, 2H), 7.19 (s, 1H), 7.03-7.07 (m, 2H), 5.05 (s, 2H), 4.97 (dd, 1H J=5 Hz, 10 Hz), 3.86 (s, 3H), 3.36 (dd, 1H, J=10 Hz, 15 Hz), 3.20 (dd, 1H, J=10 Hz, 20 Hz), 2.66 (q, 2H, J=10 Hz), 1.71 (s, 4H), 1.29 (s, 6H), 1.25 (s, 6H), 1.22 (t, 3H, J=10 Hz).

6.79 Example 66

Synthesis of (R/S)-3-(1-methyl-1H-imidazol-2-yl)-3-[4-(4,4,7,7-tetramethyl-4,5,6,7-tetrahydro-benzo[b]thiophen-2-ylmethoxy)-phenyl]-propionic acid (66)

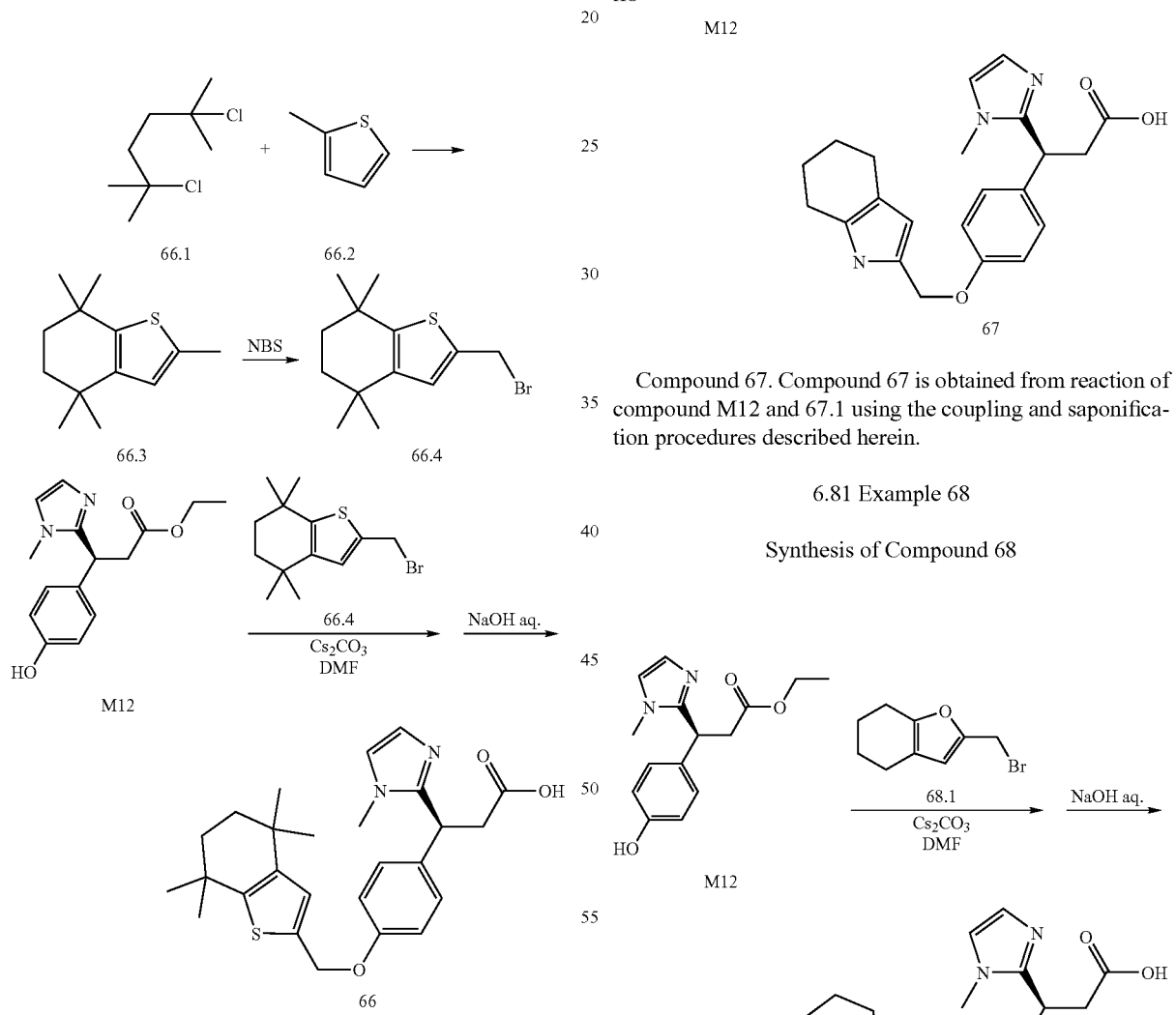

(R/S)-3-(1-Methyl-1H-imidazol-2-yl)-3-[4-(4,4,7,7-tetramethyl-4,5,6,7-tetrahydro-benzo[b]thiophen-2-ylmethoxy)-phenyl]-propionic acid (66). Compound 66.3 is obtained by the reaction of 2-methylthiophene 66.2 with 2,5-dichloro-2,5-dimethyl-hexane 66.1 according to the procedure of Faul et al, JOC, 66, 5772 (2000) or WO 96/13478. Compound 66.4 is obtained by the reaction of 66.3 with NBS and AIBN. Compound 66 is obtained from compound M12 and 66.4 using the coupling and saponification procedures described herein.

6.80 Example 67

Synthesis of Compound 67

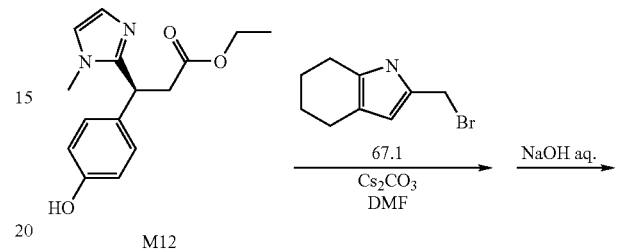

Compound 67. Compound 67 is obtained from reaction of compound M12 and 67.1 using the coupling and saponification procedures described herein.

6.81 Example 68

Synthesis of Compound 68

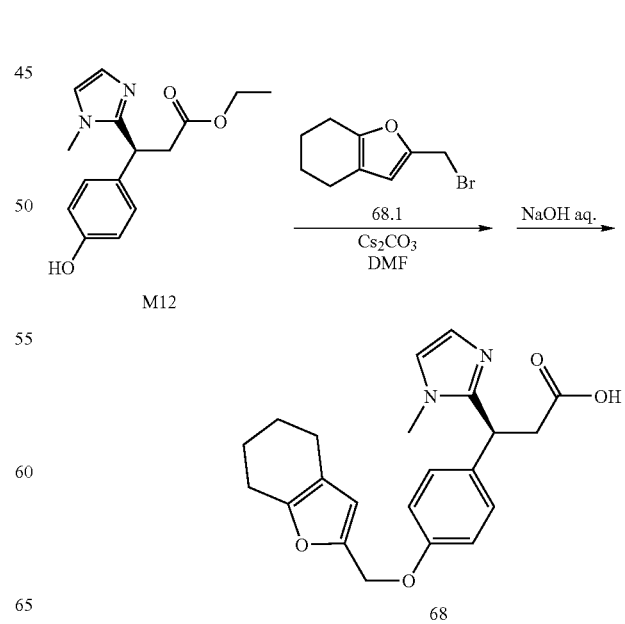

Compound 68. Compound 68 is obtained from reaction of compound M12 and 68.1 using the coupling and saponification procedures described herein.

6.82 Example 69

Synthesis of Compound 69

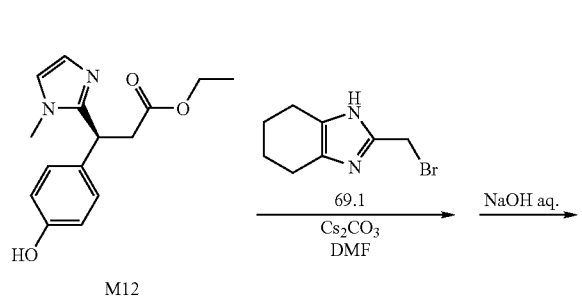

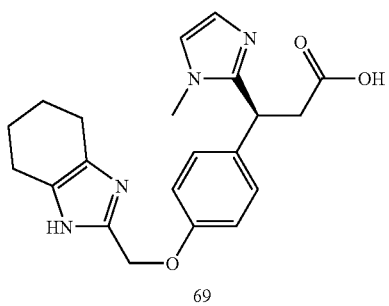

Compound 69. Compound 69 is obtained from reaction of compound M12 and 69.1 using the coupling and saponification procedures described herein.

6.83 Example 70

Synthesis of Compound 70

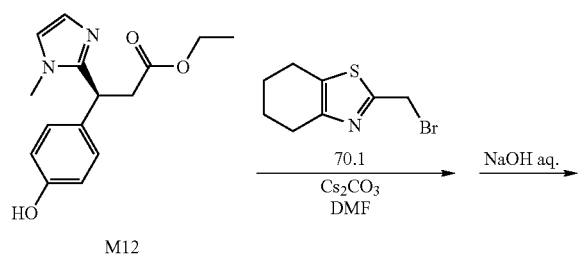

Compound 70. Compound 70 is obtained from reaction of compound M12 and 70.1 using the coupling and saponification procedures described herein.

6.84 Example 71

Synthesis of Compound 71

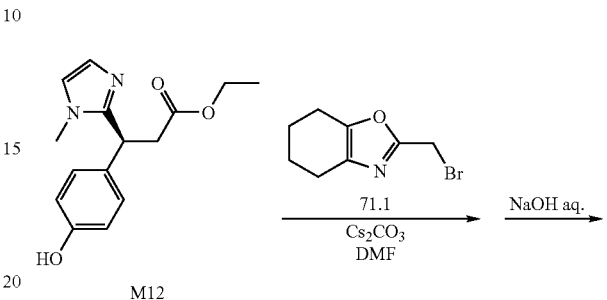

Compound 71. Compound 71 is obtained from reaction of compound M12 and 71.1 using the coupling and saponification procedures described herein.

6.85 Example 72

Synthesis of (S)-3-(4-((8,8-diethyl-5,5-dimethyl-5,6,7,8-tetrahydronaphthalen-2-yl)methoxy)phenyl)-3-(isoxazol-3-yl)propanoic acid (72)

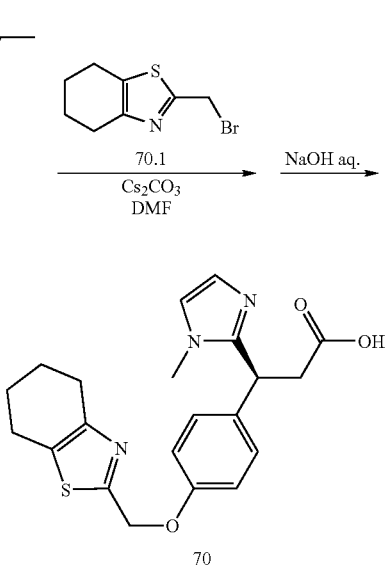

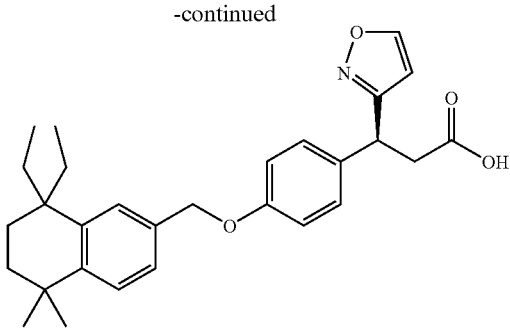

72

Starting from 18.2 and 59.5 (methyl ester was prepared using the same procedure used to prepare ethyl ester 6.6 using methanol instead of ethanol), compound 72 was prepared using a procedure analogous to that described in Example 16. MS ESI (pos.) m/e: 462.1 (M+H). ¹H NMR (MeOH-d₄) δ 8.50 (s, 1H), 7.34 (d, 1H, J=8.07 Hz), 7.21-7.15 (m, 4H), 6.94 (d, 2H, J=8.80 Hz), 6.28 (d, 1H, J=1.71 Hz), 5.02 (s, 2H), 4.57 (t, 1H, J=7.82 Hz), 3.20 (dd, 1H, J1=8.07 Hz, J2=8.07 Hz), 2.94 (dd, 1H, J1=7.33 Hz, J2=8.80 Hz), 1.73 (m, 6H), 1.55 (m, 2H), 1.27 (s, 6H), 0.72 (t, 6H, J=7.58 Hz).

5.86 Example 73

Synthesis of (S)-3-(4-((8,8-diethyl-5,5-dimethyl-5,6,7,8-tetrahydronaphthalen-2-yl)methoxy)phenyl)-3-(1-methyl-1H-tetrazol-5-yl)propanoic acid (73)

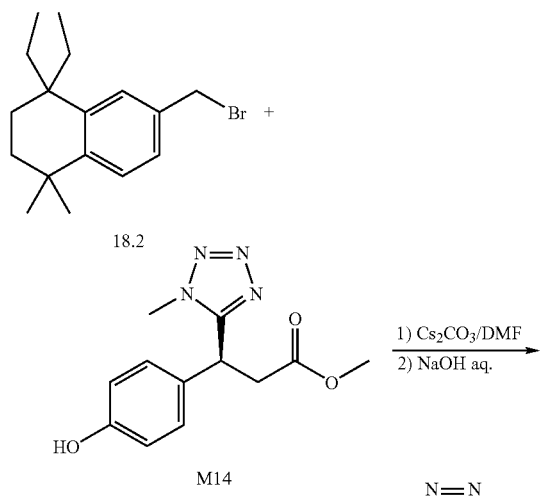

Starting from 18.2 and M14, compound 73 was prepared using a procedure analogous to that described in Example 16. MS ESI (pos.) m/e: 477.2 (M+H). ¹H NMR (MeOH-d₄) δ 7.35 (d, 1H, J=8.07 Hz), 7.21-7.19 (m, 3H), 7.16 (dd, 1H, J1=1.71 Hz, J2=8.07 Hz), 6.97 (d, 2H, J=8.80 Hz), 5.04 (s, 2H), 4.74 (dd, 1H, J1=5.62 Hz, J2=9.78 Hz), 3.91 (s, 3H), 3.42 (m, 1H), 3.03 (m, 1H), 1.71 (m, 6H), 1.54 (m, 2H), 1.27 (s, 6H), 0.70 (t, 6H, J=5.13 Hz).

6.86 Example 74

Synthesis of 3-(4,5-dihydroisoxazol-3-yl)-3-(4-((5,5,8,8-tetramethyl-5,6,7,8-tetrahydronaphthalen-2-yl)methoxy)phenyl)propanoic acid

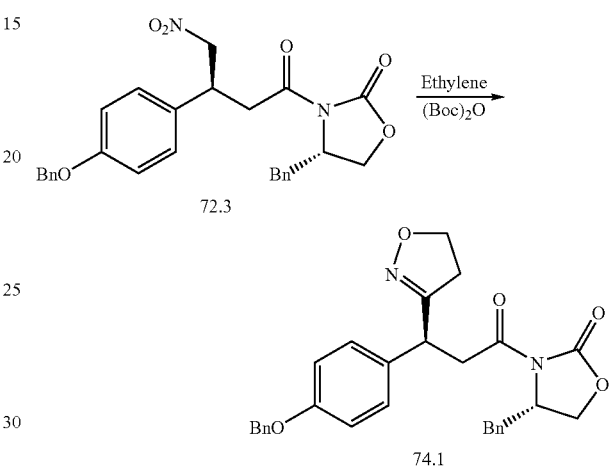

(S)-4-Benzyl-3-((S)-3-(4-(benzyloxy)phenyl)-3-(4,5-dihydroisoxazol-3-yl)propanoyl)oxazolidin-2-one (74.1). Ethylene was bubbled into 72.3 (882 mg, 1.86 mmol) in 40 mL ACN at room temperature for 20 minutes. (Boc)₂O (610 mg, 2.79 mmol) was added at room temperature, followed by the addition of DMAP (23 mg, 0.19 mmol). The mixture was stirred at room temperature for 6 hours. After HPLC indicated that all the 72.3 was consumed, the reaction mixture was taken into EtOAc (500 mL) and saturated sodium bicarbonate (400 mL). The organic layer was separated, washed with brine, dried, and concentrated under vacuum. The crude product was purified by flash chromatography to give 74.1 800 mg). MS ESI (pos.) m/e: 485 (M+H).

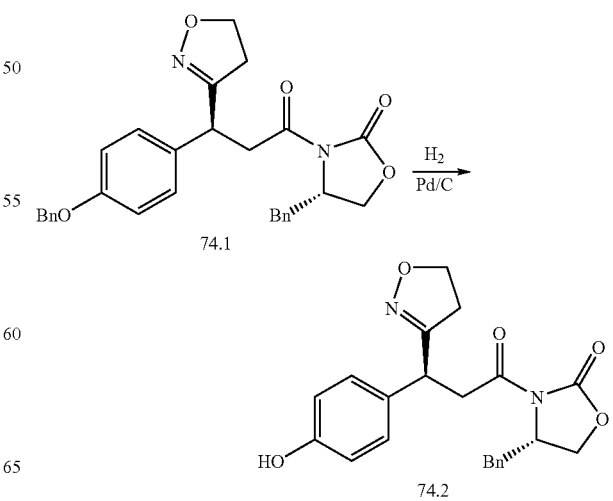

(S)-4-Benzyl-3-((S)-3-(4-hydroxyphenyl)-3-(4,5-dihydroisoxazol-3-yl)propanoyl)oxazolidin-2-one (74.2). Compound 74.1 (136 mg) and a catalytic amount of Pd/C in EtOH (2 mL) was stirred at room temperature under 1 atm of H₂ for 2.5 hours. The catalyst was removed by filtration, and the filtrate was concentrated to give 74.2 (100 mg). MS ESI (pos.) m/e: 395 (M+H).

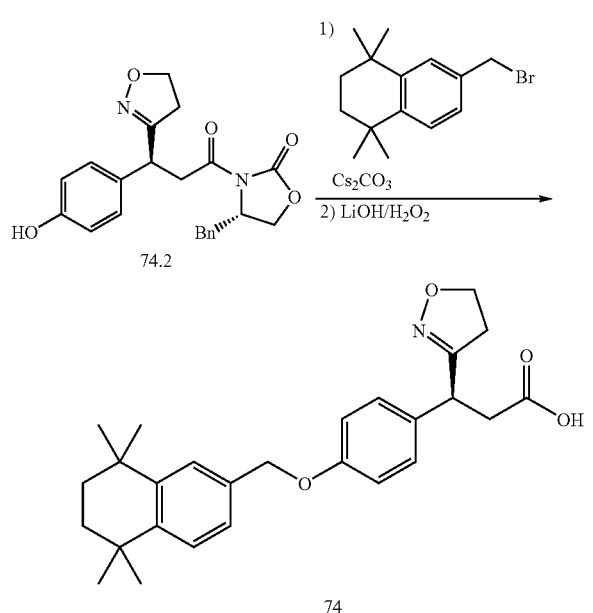

3-(4,5-Dihydroisoxazol-3-yl)-3-(4-((5,5,8,8-tetramethyl-5,6,7,8-tetrahydronaphthalen-2-yl)methoxy)phenyl)propanoic acid (74). Compound 74 was synthesized using the procedure above for preparing compound 15. MS ESI (pos.) m/e: 436 (M+H). ¹HNMR (CDCl₃) δ 7.35 (m, 2H), 7.19 (m, 3H), 6.96 (d, 2H), 4.97 (s, 2H), 4.28 (m, 2H), 4.07 (t, 1H), 3.28 (dd, 1H), 2.79 (m, 3H), 1.71 (s, 4H), 1.30 (s, 12H).

5.86 Example 75

Synthesis of (S)-3-(4-((5,5-dimethyl-5,6,7,8-tetrahydronaphthalen-2-yl)methoxy)phenyl)-3-(1-methyl-1H-imidazol-2-yl)propanoic acid (75)

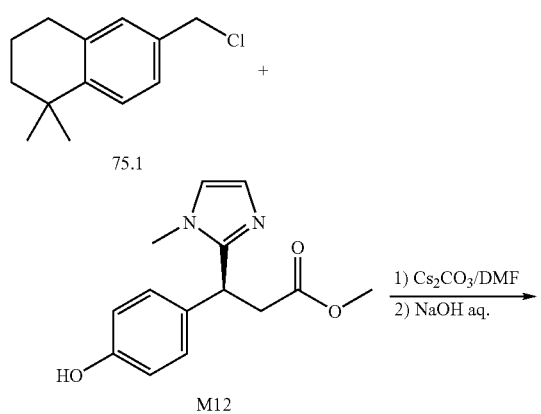

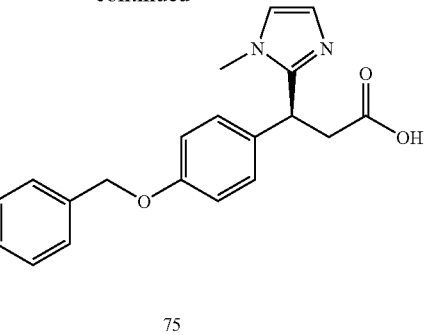

Starting from 75.1 and M12, compound 75 was prepared using a procedure analogous to that described in Example 16. Material 75.1 was prepared according to the similar published procedure of Endo, Y. et al. (*J. Med. Chem.* 1998, 41, 1476-1496). MS ESI (pos.) m/e: 419.2 (M+H). ¹H NMR (MeOH-d₄) δ 7.51 (dd, 2H, J1=1.95 Hz, J2=11.9 Hz), 7.34 (d, 1H, J=8.06 Hz), 7.22 (m, 2H), 7.16 (d, 1H, J=8.32 Hz), 7.07 (s, 1H), 7.03 (m, 2H), 5.01 (s, 2H), 4.95 (m, 1H), 3.85 (s, 3H), 3.37 (m, 1H), 3.21 (m, 1H), 2.76 (t, 2H, J=6.35 Hz), 1.82 (m, 2H), 1.70 (m, 2H), 1.29 (s, 6H).

5.86 Example 76

Synthesis of Compound 76

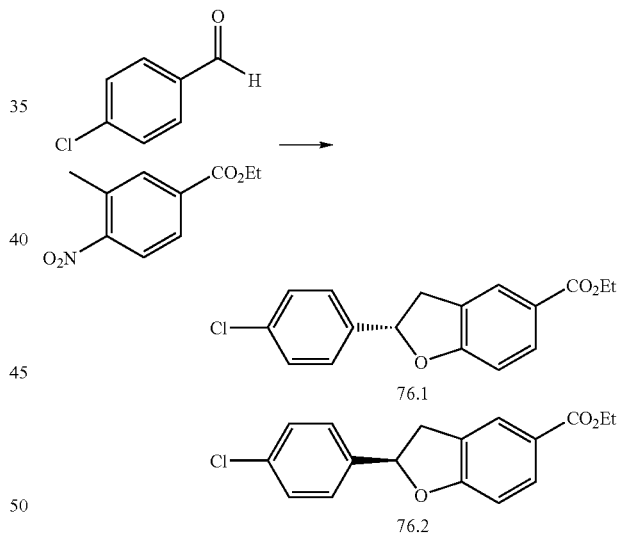

Compound 76.1. To a flask containing ethyl 3-methyl-4-nitrobenzoate (3.56 g, 17.0 mmol)(commercially available from Alfa Aesar), 4-chlorobenzaldehyde (2.0 g, 14.2 mmol), and 1M Bu₄NF in THF (25.6 mL, 25.6 mmol), was added NEt(i-Pr)₂ (5.6 mL, 34.1 mmol). The mixture was heated to reflux overnight. The reaction was concentrated in vacuo and the residue was purified by flash chromatography (SiO₂ gel 60, eluted with 0 to 20% EtOAc in hexanes). Fractions containing the desired product were combined and concentrated to provide a yellow solid (1.093 g, 25%). The enantiomers were resolved by chiral HPLC (Chiralcel OD-H column, 10% IPA/hexane, 220 nm) to afford 76.1 (0.525 g, 12.0% yield, 8.33 minutes) and 76.2 (0.520 g, 12.0% yield, 16.1 minutes). The absolute configurations were assigned arbitrarily. ¹H NMR spectroscopy analysis was consistent with the desired products.

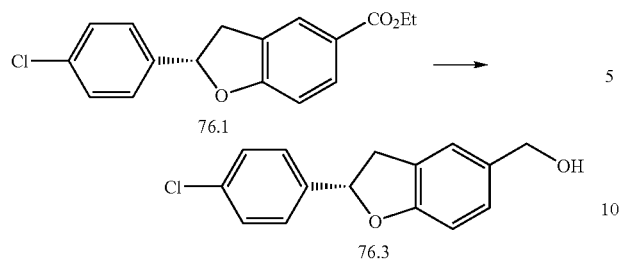

Compound 76.3. A flask containing 76.1 (0.800 g, 2.64 mmol) in THF (40 mL) was cooled to −78° C. and DIBALH was then slowly added. The reaction was stirred at −78° C. for one hour and then allowed to warm to room temperature. The reaction was carefully quenched with an aqueous saturated solution of Rochelle's salt and then extracted with EtOAc, dried over sodium sulfate, filtered, and concentrated to provide 76.3 (0.79 g, 3.03 mmol, 92% yield).

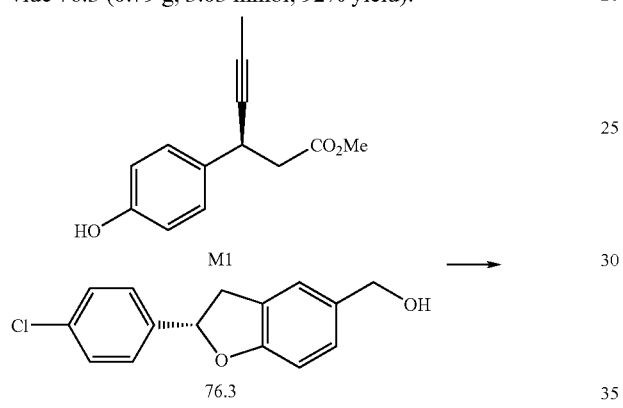

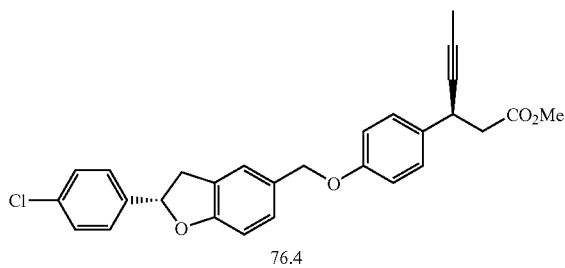

Compound 76.4. To M1 (50 mg, 0.23 mmol), 76.3 (60 mg 0.23 mmol), and triphenylphosphine (60 mg, 0.23 mmol) in THF was added DEAD (46 µL, 0.25 mmol). The resulting reaction mixture was then stirred overnight. The reaction was concentrated and purified by flash chromatography (SiO$_2$ gel 60, eluted with 0 to 20% EtOAc in hexanes). Fractions containing the desired product were combined and concentrated to provide 76.4 (30 mg, 28% yield).

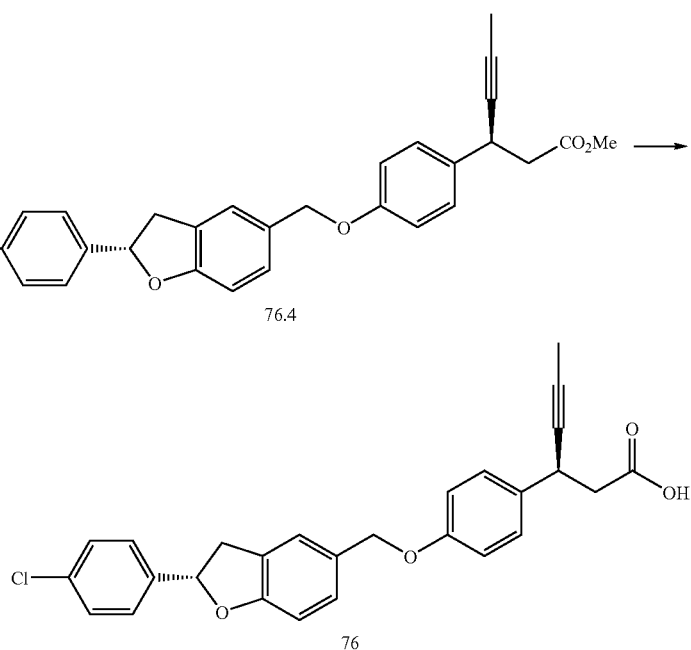

(S)-3-(4-(((S)-2-(4-Chlorophenyl)-2,3-dihydrobenzofuran-5-yl)methoxy)phenyl)hex-4-ynoic acid (76). Compound 76 was synthesized using the procedure above for preparing Example 6 using compound 76.4. $^1$HNMR (CDCl$_3$) δ 7.35-7.20 (8H, m), 6.94 (2H, d, J=8.6 Hz), 6.87 (1H, d, J=8.3 Hz), 5.76 (1H, m), 4.96 (2H, s), 3.65 (1H, dd, J=9.5, 15.7 Hz), 3.18 (1H, dd, J=8.1, 15.9 Hz), 2.82 (1H, dd, J=8.6, 15.9 Hz), 2.73 (1H, dd, J=6.6, 15.9 Hz), 1.85 (3H, d, J=2.0 Hz).

5.87 Examples 77

Synthesis of Compound 77

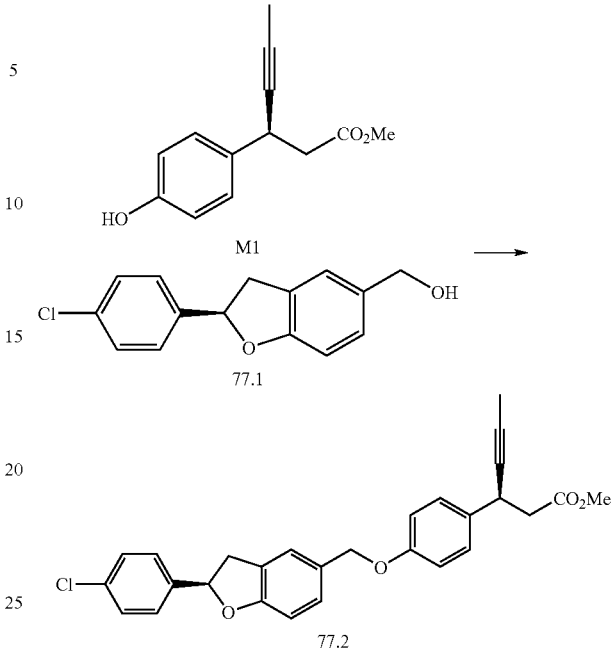

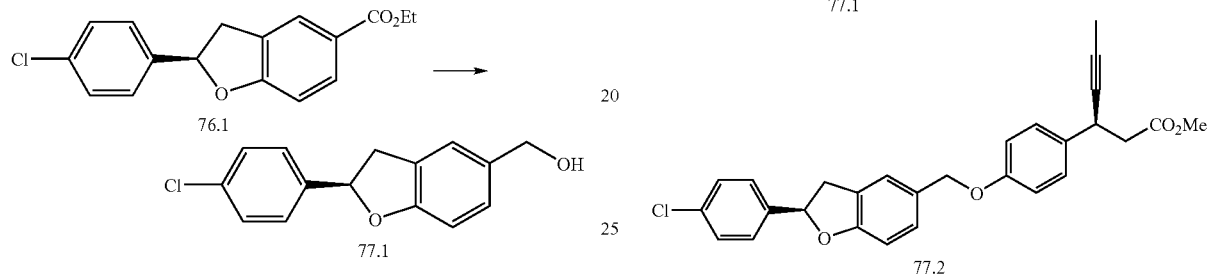

Compound 77.1. A flask containing 76.2 (0.800 g, 2.64 mmol) in THF (40 mL) was cooled to −78° C. and then DIBALH was added slowly. The reaction was stirred at −78° C. for one hour and then warmed to room temperature. The reaction was carefully quenched with an aqueous saturated solution of Rochelle's salt and then extracted with EtOAc, dried over sodium sulfate, filtered, and concentrated to provide 76.3 (0.79 g, 3.03 mmol, 92% yield).

Compound 77.2. To M1 (50 mg, 0.23 mmol), 77.1 (60 mg 0.23 mmol), and triphenylphosphine (60 mg, 0.23 mmol) in THF was added DEAD (46 μL, 0.25 mmol) and allowed to stir overnight. The reaction was concentrated and purified by flash chromatography (SiO$_2$ gel 60, eluted with 0 to 20% EtOAc in hexanes). Fractions containing the desired product were combined and concentrated to provide 77.2 (30 mg, 28% yield).

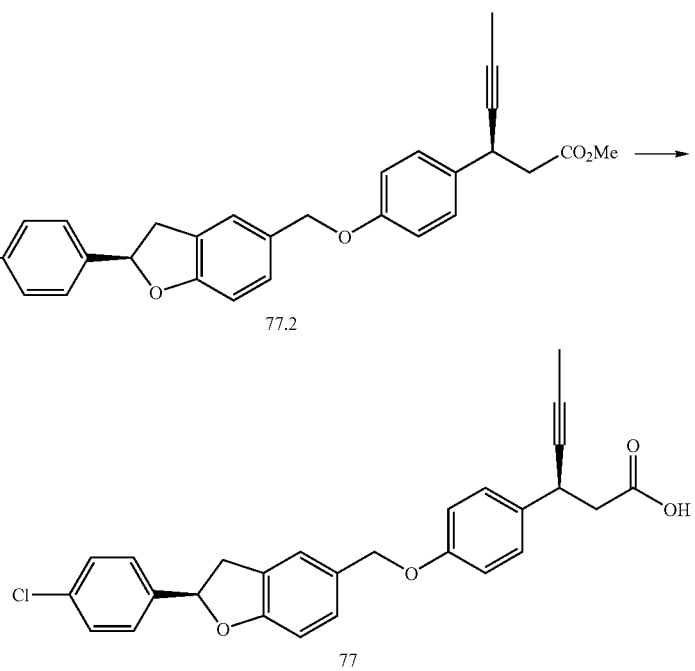

(S)-3-(4-(((R)-2-(4-Chlorophenyl)-2,3-dihydrobenzofuran-5-yl)methoxy)phenyl)hex-4-ynoic acid (77). Compound 77 was synthesized using the procedure above for preparing Example 6 using compound 77.2. ¹HNMR (CDCl₃) δ 7.35-7.20 (8H, m), 6.94 (2H, d, J=8.6 Hz), 6.87 (1H, d, J=8.3 Hz), 5.76 (1H, m), 4.96 (2H, s), 3.65 (1H, dd, J=9.5, 15.7 Hz), 3.18 (1H, dd, J=8.1, 15.9 Hz), 2.82 (1H, dd, J=8.6, 15.9 Hz), 2.73 (1H, dd, J=6.6, 15.9 Hz), 1.85 (3H, d, J=2.0 Hz).

5.86 Examples 78

Synthesis of Compound 78

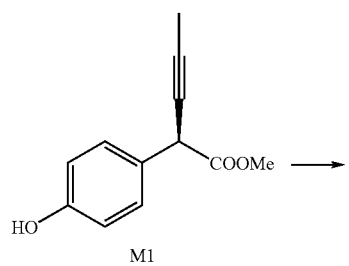

M1

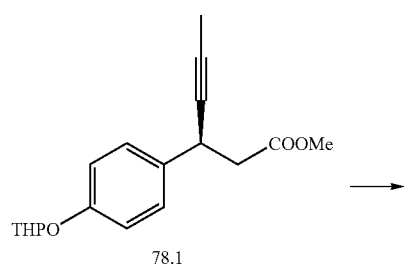

78.1

Compound 78.1. To stirred solution of phenol M1 (2.0 g, 9.2 mmol, 1 eq., MW 218.25) in DCM at 23° C. was added 3,4-dihydro-2H-pyran (1.7 mL, 18.4 mmol, 2 eq., MW 84.12) followed by PPTS (catalytic, MW 251.31). The resulting mixture was stirred for 16 hours and concentrated in vacuo. The residue was then purified by flash chromatography (SiO₂ gel 60, eluted with 0 to 20% EtOAc in hexanes). Fractions containing the desired product were combined and concentrated to provide 78.1 as a colorless oil (2.6 g, 94%). MS ESI (pos.) m/e: 325.1 (M+Na)⁺, 320.2 (M+H₂O)⁺.

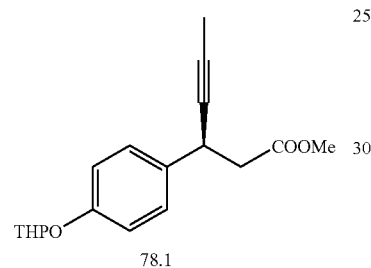

78.1

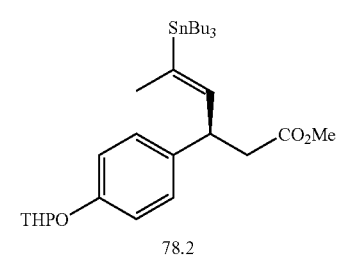

78.2

Compound 78.2. To a stirred solution of 78.1 (1.00 g, 3.3 mmol, MW 302.37) in THF at 23° C. was added PdCl₂(PPh₃)₂ (232.0 mg, 0.30 mmol, MW 701.89) followed by Bu₃SnH (964.0 µL, 3.6 mmol, MW 291.05). After the addition, the solution turned black. After a further 2 minutes, the mixture was concentrated in vacuo. The residue was then purified by flash chromatography (SiO₂ gel 60, eluted with 0 to 20% EtOAc in hexanes). Fractions containing the desired product were combined and concentrated to provide a colorless oil (760.0 mg, 39%). ¹H NMR spectroscopy analysis was consistent with the desired product.

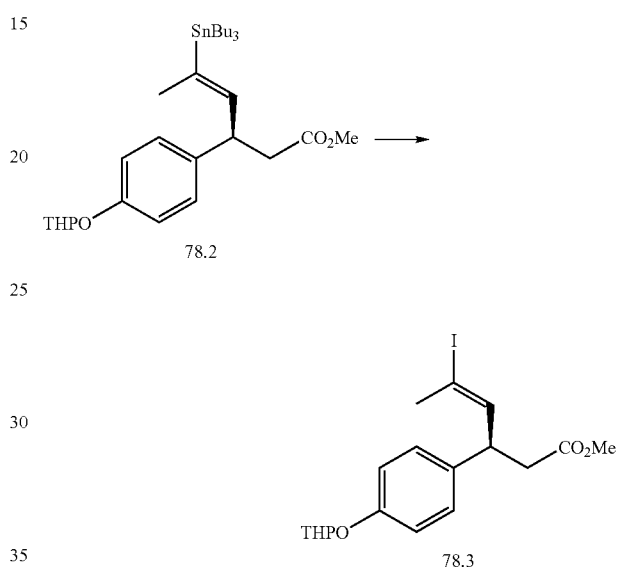

78.2

78.3

Compound 78.3. To a stirred solution of 78.2 (760.0 mg, 1.2 mmol, 1 eq., MW 593.42) in THF (45 mL) at −78° C., was added iodine (357.0 mg, 1.4 mmol, 1.1 eq., MW 253.81) in THF (5 mL) dropwise. After the addition was complete, a saturated solution of NaS₂O₃ and NaHCO₃ were added at the same time to quench the reaction. EtOAc was added to the mixture, and the resulting mixture was washed with NaHCO₃ (aq) (2×100 mL) and brine (1×100 mL). The organic layer was dried over MgSO₄ and filtered. The organic layer was concentrated in vacuo. The residue was then purified by flash chromatography (SiO₂ gel 60, eluted with 0 to 20% EtOAc in hexanes). Fractions containing the desired product were combined and concentrated to provide 78.3 as a colorless oil (440 mg, 80%). MS ESI (pos.) m/e: 453.0 (M+Na)⁺, 448.1 (M+H₂O)⁺.

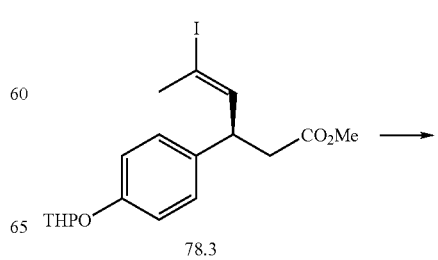

78.3

-continued

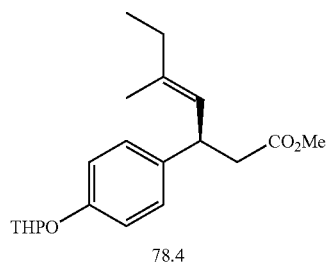
78.4

Compound 78.4. To a stirred solution of 78.3 (440.0 mg, 1.02 mmol, 1 eq., MW 430.29) in THF (30 mL) at 0° C., was added Pd(PPh$_3$)$_4$ (118 mg, 0.10 mmol, 0.1 eq., MW 1155.58) followed by dropwise addition of Et$_2$Zn (1.22 mL, 1.22 mmol, 1.2 eq., 1.0 M). The reaction was warmed to room temperature. After 30 minutes, TLC showed that the reaction was complete. Water (10 mL) was added to quench the reaction. The mixture was extracted with EtOAc (2×50 mL), dried with MgSO$_4$, and filtered. The organic layer was concentrated in vacuo. The residue was then purified by flash chromatography (SiO$_2$ gel 60, eluted with 0 to 20% EtOAc in hexanes). Fractions containing the desired product were combined and concentrated to provide 78.4 as a colorless oil (320 mg, 94%).

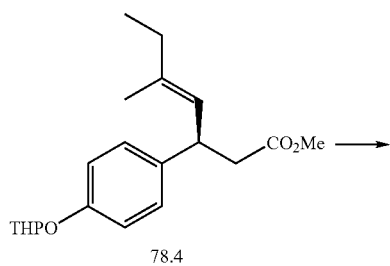
78.4

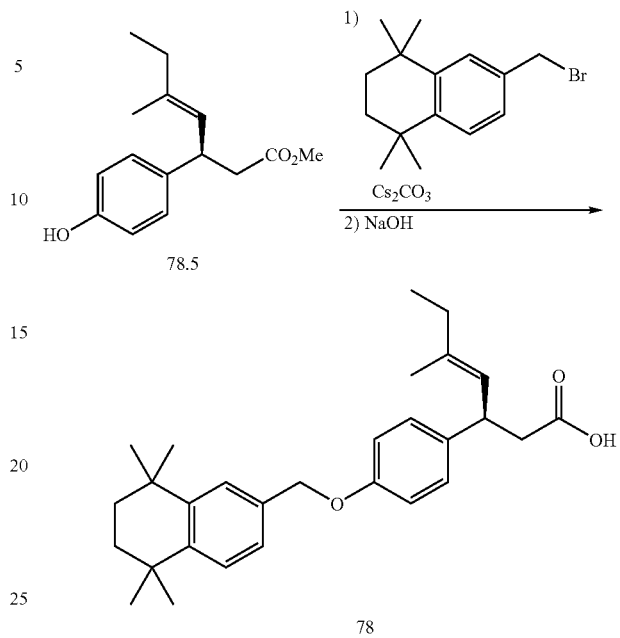

Compound 78.5. To a stirred solution of 78.4 (320.0 mg, 0.96 mmol, MW 332.44) in EtOH (10 mL) at 23 C, was added PPTS (catalytic). Stirring was continued for 12 hours. The reaction was concentrated in vacuo. The residue was then purified by flash chromatography (SiO$_2$ gel 60, eluted with 0 to 20% EtOAc in hexanes). Fractions containing the desired product were combined and concentrated to provide a colorless oil. The desired product was contaminated (~5%) with a further olefinic product. This impurity was removed by further purification on silica gel containing 10% AgNO$_3$ eluting with 0 to 20% EtOAc in hexanes. The combined fractions were concentrated under reduced pressure to afford phenol 78.5 (203 mg, 85%) as a colorless oil.

(R,E)-5-Methyl-3-(4-((5,5,8,8-tetramethyl-5,6,7,8-tetrahydronaphthalen-2-yl)methoxy)phenyl)hept-4-enoic acid (78). Compound 78 was synthesized using the procedure above for preparing Example 6 using compound 78.5. MS ESI (neg.) m/e: 867 (2M–H), 433 (M–H). $^1$HNMR (CDCl$_3$) δ 7.35-7.33 (2H, m), 7.23-7.17 (3H, m), 6.94 (2H, d, J=8.2 Hz), 5.27 (1H, dd, J=9.4, 1.2 Hz), 4.97 (2H, s), 4.04 (1H, m), 2.77-2.71 (1H, dd, J=15.0, 7.1 Hz), 2.65-2.59 (1H, dd, J=8.2, 15.0 Hz), 2.00 (2H, q, J=7.3 Hz), 1.71-1.69 (7H, m), 1.30 (12H, s), 0.98 (3H, t, J=7.3 Hz).

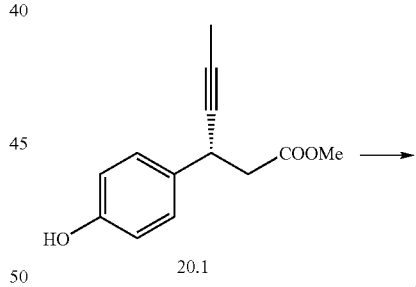
20.1

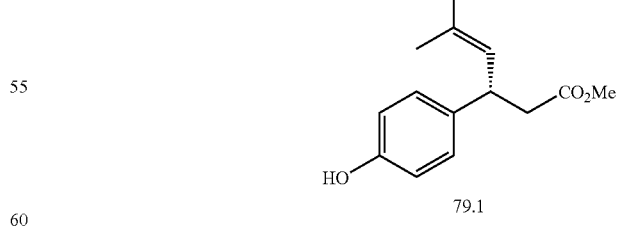
79.1

Compound 79.1. By changing the resolving agent used in Example 19 to (1R,2S)-1-amino-2-indanol, compound 20.1 was obtained by the procedure of Example 1 set forth in US 2006/0004012 which is hereby incorporated by reference. Compound 79.1 was synthesized using the procedure above for preparing Example 78 using compound 20.1.

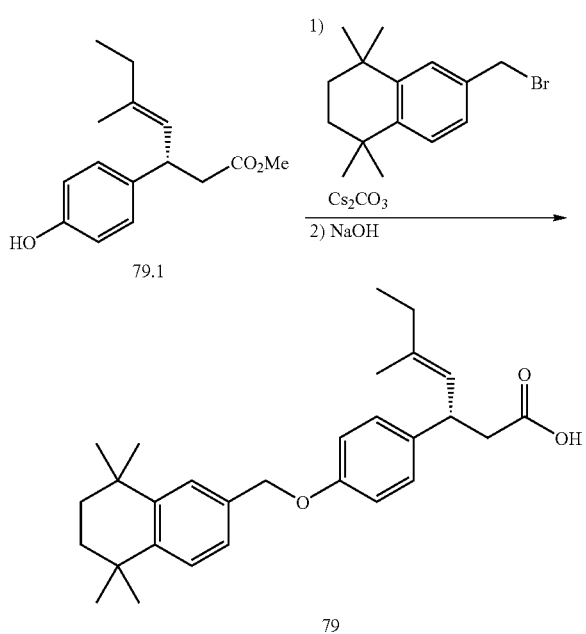

(S,E)-5-Methyl-3-(4-((5,5,8,8-tetramethyl-5,6,7,8-tetrahydronaphthalen-2-yl)methoxy)phenyl)hept-4-enoic acid (79). Compound 79 was synthesized using the procedure above for preparing Example 6 using compound 79.1. MS ESI (neg.) m/e: 867 (2M−H), 433 (M−H). $^1$HNMR (CDCl$_3$) δ 7.37-7.35 (2H, m), 7.24-7.20 (3H, m), 6.96 (2H, d, J=8.2 Hz), 5.29 (1H, dd, J=9.4, 1.2 Hz), 4.98 (2H, s), 4.06 (1H, m), 2.78-2.72 (1H, dd, J=15.0, 7.1 Hz), 2.66-2.60 (1H, dd, J=8.2, 15.0 Hz), 2.01 (2H, q, J=7.3 Hz), 1.72-1.70 (7H, m), 1.31 (12H, s), 1.00 (3H, t, J=7.3 Hz).

6.87 Example 80

((S)-3-(1-Methyl-1H-imidazol-2-yl)-3-(4-((1,1,3,3-tetramethyl-2,3-dihydro-1H-inden-5-yl)methoxy)phenyl)propanoic acid (80)

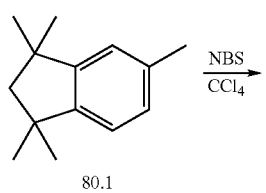

5-(Bromomethyl)-1,1,3,3-tetramethyl-2,3-dihydro-1H-indene (80.2) 1,1,3,3,5-Pentamethylindane (80.1) can be prepared according to the method given in U.S. Pat. No. 4,551,573. A mixture of 80.1 (100 mg, 0.53 mmol), N-bromosuccinimide (NBS) (114 mg, 0.64 mmol), and dibenzoyl peroxide (13 mg, 0.05 mmol) in CCl$_4$ (5 mL) was heated to reflux for 4 hours. The reaction was cooled, and the precipitate was filtered out. The solvent was removed to afford crude 80.2, which was used directly in the next step.

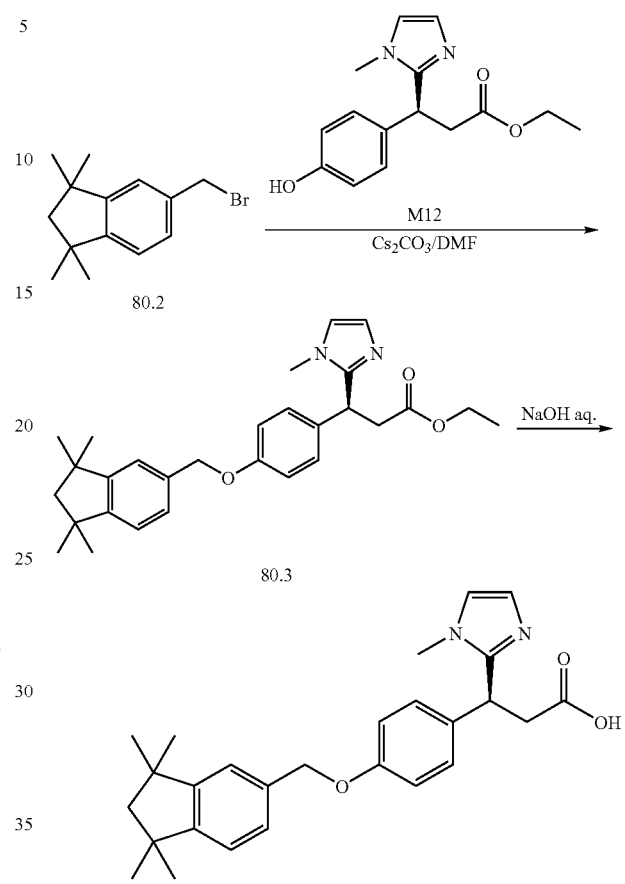

(S)-3-(1-Methyl-1H-imidazol-2-yl)-3-(4-((1,1,3,3-tetramethyl-2,3-dihydro-1H-inden-5-yl)methoxy)phenyl)propanoic acid (80) Compound 80 was prepared using a procedure analogous to that described in Example 16 starting with the imidazole phenol M12 shown in the reaction scheme and 80.2. MS ESI (pos.) m/e: 433.1 (M+H). $^1$HNMR (MeOH-d$_4$) δ 7.52 (d, 1H, J=1.96 Hz), 7.49 (d, 1H, J=1.96 Hz), 7.24-7.11 (m, 5H), 7.05-7.02 (m, 2H), 5.06 (s, 2H), 4.97-4.93 (m, 1H), 3.84 (s, 3H), 3.41-3.34 (m, 1H), 3.20-3.16 (m, 1H), 1.94 (s, 2H), 1.30 (s, 12H).

6.88 Example 81

(S)-3-(4-((5,5-dimethyl-8-oxo-5,6,7,8-tetrahydronaphthalen-2-yl)methoxy)phenyl)-3-(1-methyl-1H-imidazol-2-yl)propanoic acid (81)

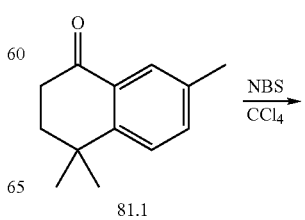

-continued

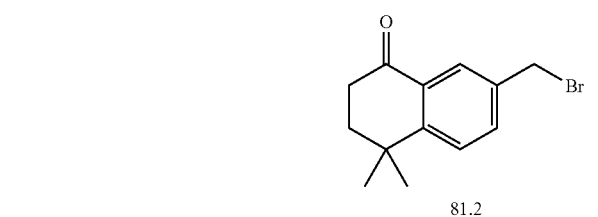

81.2

7-(Bromomethyl)-4,4-dimethyl-3,4-dihydronaphthalen-1 (2H)-one (81.2). Compound 81.1 can be prepared according to the method of Blaskovich (*Bioorg. Med. Chem. Lett.* 2003, 13, 2083-85). Intermediate 81.2 was prepared using a procedure analogous to that described in Example 80 starting with 81.1 The crude product was directly used in the next step.

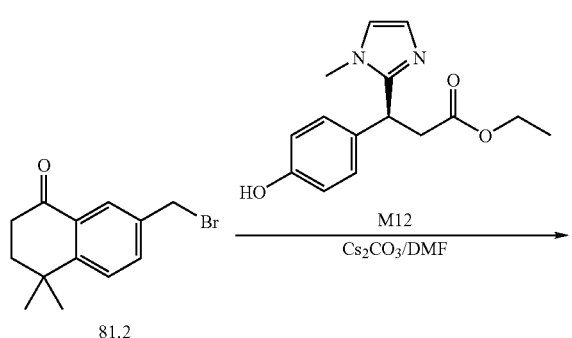

81.2

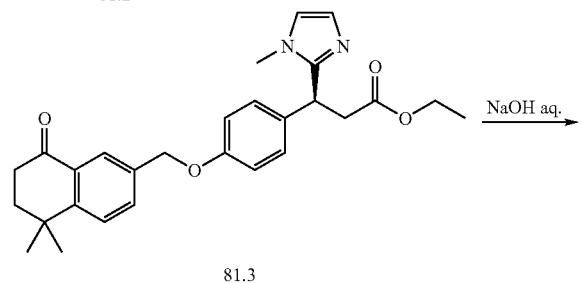

81.3

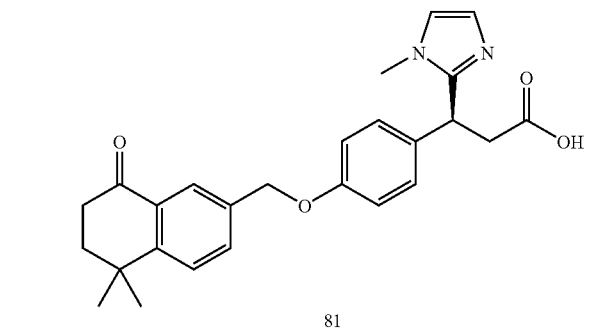

81

(S)-3-(4-((5,5-Dimethyl-8-oxo-5,6,7,8-tetrahydronaphthalen-2-yl)methoxy)phenyl)-3-(1-methyl-1H-imidazol-2-yl)propanoic acid (81) Compound 81 was prepared using a procedure analogous to that described in Example 16 starting with the imidazole phenol M12 shown in the reaction scheme and 81.2. MS ESI (pos.) m/e: 433.1 (M+H). $^1$HNMR (CDCl$_3$-d) δ 7.98 (s, 1H), 7.65-7.47 (m, 4H), 7.21 (d, 2H, J=8.80 Hz), 7.03 (d, 2H, J=8.40 Hz), 5.11 (s, 2H), 4.95-4.89 (m, 1H), 3.82 (s, 3H), 3.39-3.35 (m, 1H), 3.18-3.14 (m, 1H), 2.73 (s, 2H, J=6.35 Hz), 2.04 (t, 2H, J=6.35 Hz), 1.40 (s, 6H).

Example 82

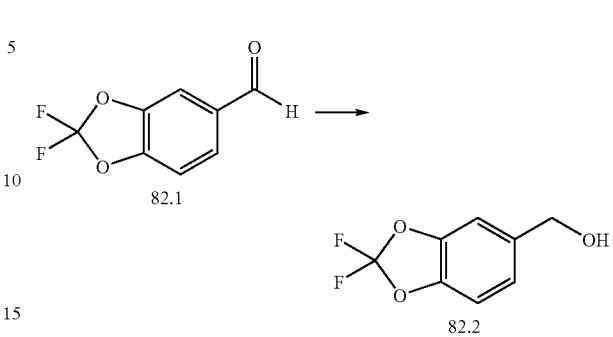

2,2-Difluorobenzo[d][1,3]dioxol-5-yl)methanol (82.2). Sodium borohydride (0.58 g, 15.4 mmol) was added in portions to a cold solution of 82.1 (1.00 mL, 7.63 mmol) in dry MeOH (12.0 mL). The mixture was stirred at 0° C. for 1 hour and then stirred at room temperature for 3 hours. The reaction was carefully quenched with cold water and then extracted three times with ether. The combined organic extracts were dried over MgSO$_4$, filtered, and concentrated under reduced pressure. The residue was then purified by flash chromatography (SiO$_2$ gel 60, eluted with 0 to 50% EtOAc in hexanes). Fractions containing the product 82.2 were combined and concentrated to provide the product as a colorless oil (0.90 g, 63%). $^1$H NMR (500 MHz) (CDCl$_3$) δ 7.08 (1H, m), 7.03, (2H, m), 4.62 (2H, s), 2.51, (1H, s).

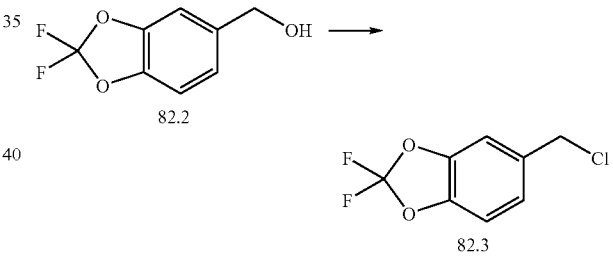

5-(Chloromethyl)-2,2-difluorobenzo[d][1,3]dioxole (82.3). Thionyl chloride (0.53 mL, 7.27 mmol) was added dropwise to a cold solution of 82.2 (0.90 g, 4.79 mmol) in dry DCM (10 mL). The mixture was allowed to warm to room temperature. After 19 hours, the mixture was concentrated and then purified by flash chromatography (SiO$_2$ gel 60, eluted with 0 to 30% EtOAc in hexanes). Fractions containing the desired product 82.3 were combined and concentrated to provide the product as a colorless oil (0.90 g, 63%). $^1$H NMR (500 MHz) (CDCl$_3$) δ 7.00 (2H, m), 6.88, (1H, d, J=8.1 Hz), 4.43 (2H, s).

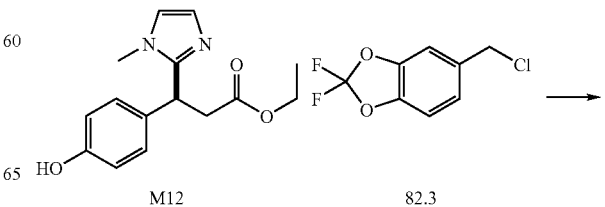

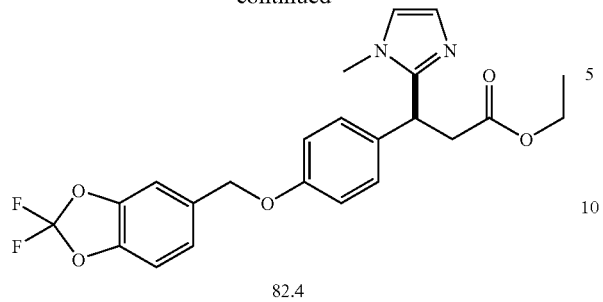

82.4

(S)-Ethyl 3-(4-((2,2-difluorobenzo[d][1,3]dioxol-5-yl)methoxy)phenyl)-3-(1-methyl-1H-imidazol-2-yl)propanoate (82.4). Compound 82.4 was prepared by a method analogous to that of General procedure A for 5.15.1. MS ESI (pos.) m/e: 445.1 (M+H)$^+$.

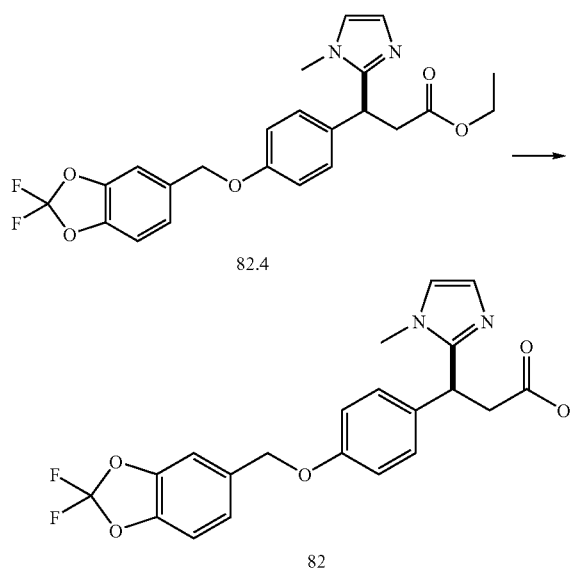

82

(S)-3-(4-((2,2-difluorobenzo[d][1,3]dioxol-5-yl)methoxy)phenyl)-3-(1-methyl-1H-imidazol-2-yl)propanoic acid (82). Compound 82 was prepared by a method analogous to that of General Procedure A for 5.15.1. MS ESI (neg.) m/e: 417.1 (M−H). $^1$H NMR (500 MHz) (DMSO-d$_6$) δ 7.48 (1H, s), 7.40 (1H, d, J=8.2 Hz), 7.28 (1H, d, J=8.2 Hz), 7.12 (2H, d, J=7.9 Hz), 6.98 (1H, s), 6.92 (2H, d, J=7.9 Hz), 6.79 (1H, s), 5.04 (2H, s), 4.50 (1H, m), 3.42 (3H, m), 3.15 (1H, dd, J=16.3, 9.0 Hz), 2.73 (1H, dd, J=16.2, 5.8).

Example 83

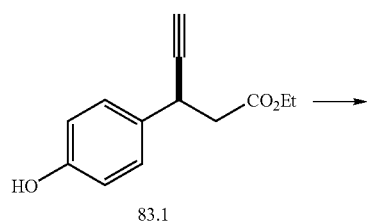

83.1

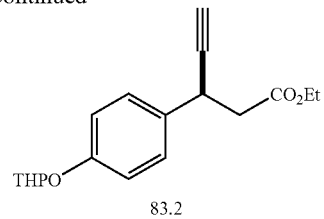

83.2

Ethyl (3S)-3-(4-(tetrahydro-2H-pyran-2-yloxy)phenyl)-4-pentynoate (83.2). Compound 83.1 was prepared by a method based on that reported in *Biochemistry* 1989, 28, 3833-3842. To stirred solution of phenol 83.1 (1.0 g, 4.6 mmol, 1 eq., MW 218.25) in DCM at 23° C. was added 3,4-dihydro-2H-pyran (839 μL, 9.2 mmol, 2 eq., MW 84.12) followed by PPTS (catalytic, MW 251.31). The resulting mixture was stirred for 16 hours and concentrated in vacuo. The residue was then purified by flash chromatography (SiO$_2$ gel 60, eluted with 0 to 20% EtOAc in hexanes). Fractions containing the desired product were combined and concentrated to a colorless oil (1.3 g, 94%). MS ESI (pos.) m/e: 325.1 (M+Na)$^+$, 320.2 (M+H$_2$O)$^+$.

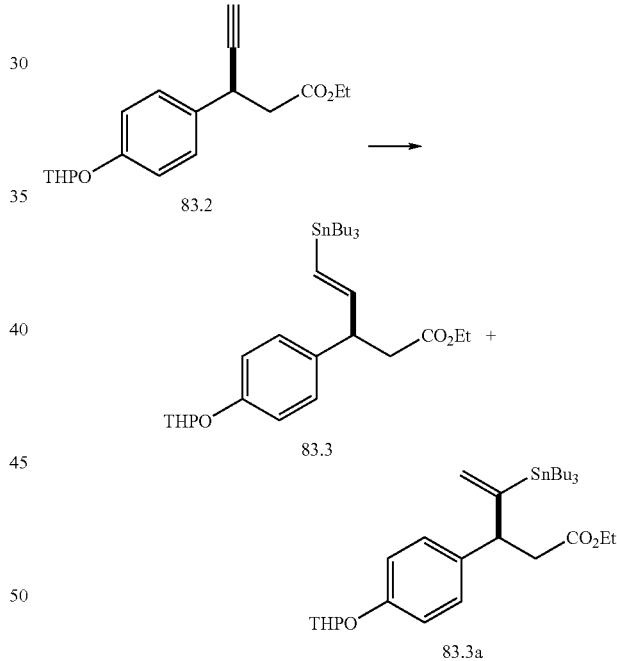

Ethyl (3S)-3-(4-(tetrahydro-2H-pyran-2-yloxy)phenyl)-5-(tributylstannanyl)-4-pentenoate (83.3). To a stirred solution of 83.2 (80.0 mg, 0.26 mmol, MW 302.37) in THF at 23° C. was added PdCl$_2$(PPh$_3$)$_2$ (18.6 mg, 0.026 mmol, MW 701.89) followed by Bu$_3$SnH (84.0 μL, 0.32 mmol, MW 291.05). After the addition, the solution turned black. After a further 2 minutes, the mixture was concentrated in vacuo. The residue was then purified by flash chromatography (SiO$_2$ gel 60, eluted with 0 to 20% EtOAc in hexanes). Fractions containing the desired product 83.3 were combined and concentrated to provide a colorless oil (96.0 mg). $^1$H NMR spectroscopy showed the product to be a 3:1 ratio of 83.3:83.3a respectively.

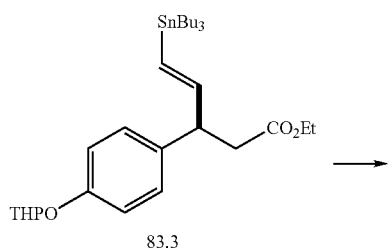

83.3

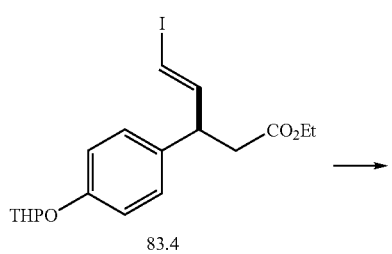

83.4

Ethyl (3S,4E)-5-iodo-3-(4-(tetrahydro-2H-pyran-2-yloxy)phenyl)-4-pentenoate (83.4). To a stirred solution of 83.3/83.3a (96.0 mg, 0.16 mmol, 1 eq., MW 593.42) in THF (5 mL) at −78° C. was added iodine (45.0 mg, 0.18 mmol, 1.1 eq., MW 253.81) in THF (2 mL) dropwise. After the addition was complete, a saturated solution of $NaS_2O_3$ and $NaHCO_3$ were added at the same time to quench the reaction. EtOAc was added to the mixture, and the resulting mixture was washed with $NaHCO_3$ (aq) (2×50 mL) and brine (1×50 mL). The organic layer was dried over $MgSO_4$ and filtered. The organic layer was concentrated in vacuo. The residue was then purified by flash chromatography ($SiO_2$ gel 60, eluted with 0 to 20% EtOAc in hexanes). Fractions containing the desired product were combined and concentrated to a colorless oil (66 mg, 58% over 2 steps). MS ESI (pos.) m/e: 453.0 $(M+Na)^+$, 448.1 $(M+H_2O)^+$.

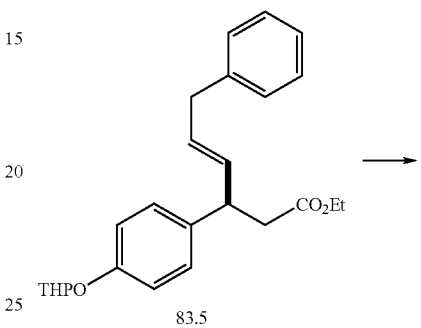

(3R,E)-Ethyl 6-phenyl-3-(4-(tetrahydro-2H-pyran-2-yloxy)phenyl)hex-4-enoate (83.5). To a stirred solution of 83.4 (571.9 mg, 1.33 mmol, 1 eq., MW 430.29) in THF (15 mL) at 23° C. was added $Pd(PPh_3)_4$ (153.6 mg, 0.133 mmol, 0.1 eq., MW 1155.58) followed by dropwise addition of benzylzinc bromide solution (3.2 mL, 1.6 mmol, 1.2 eq., 0.5 M). After 17.5 hours, water (10 mL) was added to quench the reaction. The mixture was extracted with EtOAc (2×50 mL), dried with $MgSO_4$, and filtered. The organic layer was concentrated in vacuo. The residue was then purified by flash chromatography ($SiO_2$ gel 60, eluted with 0 to 20% EtOAc in hexanes). Fractions containing the desired product were combined and concentrated providing a colorless oil that was used without further purification.

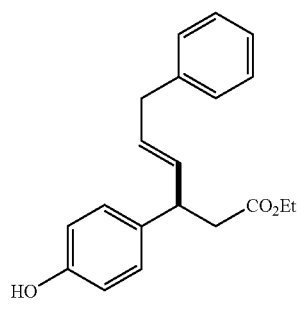

(R,E)-Ethyl 3-(4-hydroxyphenyl)-6-phenylhex-4-enoate (83.6). To a stirred solution of 83.5 (405.8 mg, 1.03 mmol, MW 394.50) in EtOH (11 mL) at 23° C. was added PPTS (catalytic). Stirring was continued for 16 hours. The reaction was concentrated in vacuo. The residue was then purified by flash chromatography ($SiO_2$ gel 60, eluted with 0 to 20% EtOAc in hexanes). Fractions containing the desired product were combined and concentrated providing a colorless oil. The desired product was contaminated (~5%) with a further olefinic product (believed to contain a terminal double bond) and was used without further purification.

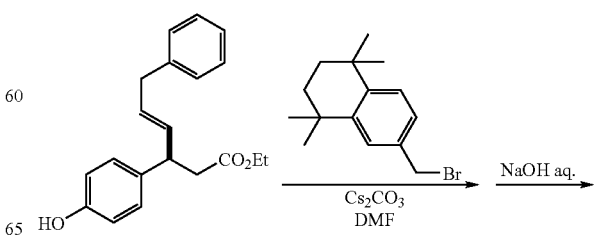

-continued

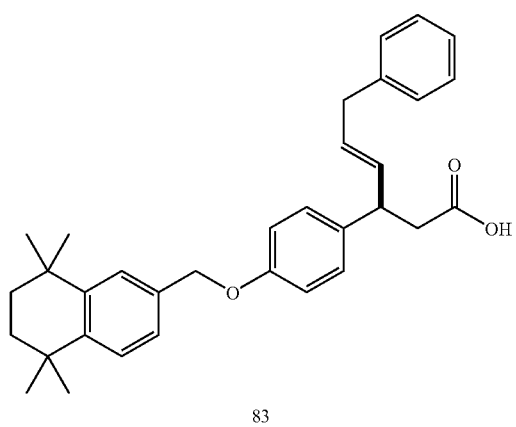

83

(R,E)-6-Phenyl-3-(4-((5,5,8,8-tetramethyl-5,6,7,8-tetrahydronaphthalen-2-yl)methoxy)phenyl)hex-4-enoic acid (83). Compound 83 was prepared by a method analogous to that of General Procedure A for 5.15.1. MS ESI (neg.) m/e: 481.3 (M−H). $^1$H NMR (400 MHz) (CDCl$_3$) δ 7.25 (2H, s), 7.19 (2H, t, J=7.4 Hz), 7.14 (6H, m), 6.87 (2H, d, J=8.6 Hz), 5.64 (2H, m), 4.88 (2H, s), 3.80 (1H, m), 3.27 (2H, d, J=5.5 Hz), 2.67 (2H, m), 1.62 (4H, s), 1.21 (12H, s).

Example 84

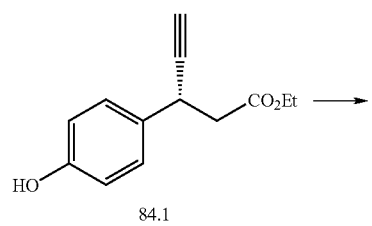

84.1

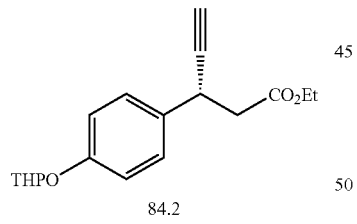

84.2

Ethyl (3S)-3-(4-(tetrahydro-2H-pyran-2-yloxy)phenyl)-4-pentynoate (84.2). Compound 84.1 was prepared by a method based on that reported in *Biochemistry* 1989, 28, 3833-3842. To stirred solution of phenol 84.1 (1.0 g, 4.6 mmol, 1 eq., MW 218.25) in DCM at 23° C. was added 3,4-dihydro-2H-pyran (839 µL, 9.2 mmol, 2 eq., MW 84.12) followed by PPTS (catalytic, MW 251.31). The resulting mixture was stirred for 16 hours and concentrated in vacuo. The residue was then purified by flash chromatography (SiO$_2$ gel 60, eluted with 0 to 20% EtOAc in hexanes). Fractions containing the desired product were combined and concentrated to a colorless oil (1.3 g, 94%). MS ESI (pos.) m/e: 325.1 (M+Na)$^+$, 320.2 (M+H$_2$O)$^+$.

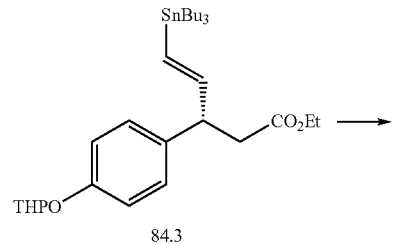

Ethyl (3S)-3-(4-(tetrahydro-2H-pyran-2-yloxy)phenyl)-5-(tributylstannanyl)-4-pentenoate (84.3). To a stirred solution of 84.2 (80.0 mg, 0.26 mmol, MW 302.37) in THF at 23° C. was added PdCl$_2$(PPh$_3$)$_2$ (18.6 mg, 0.026 mmol, MW 701.89) followed by Bu$_3$SnH (84.0 µL, 0.32 mmol, MW 291.05). After the addition, the solution turned black. After a further 2 minutes, the mixture was concentrated in vacuo. The residue was then purified by flash chromatography (SiO$_2$ gel 60, eluted with 0 to 20% EtOAc in hexanes). Fractions containing the desired product 84.3 were combined and concentrated providing a colorless oil (96.0 mg). $^1$H NMR spectroscopy showed the product to be a 3:1 ratio of 84.3:84.3a respectively.

Ethyl (3S,4E)-5-iodo-3-(4-(tetrahydro-2H-pyran-2-yloxy)phenyl)-4-pentenoate (84.4). To a stirred solution of 84.3/84.3a (96.0 mg, 0.16 mmol, 1 eq., MW 593.42) in THF (5 mL) at −78° C. was added iodine (45.0 mg, 0.18 mmol, 1.1 eq., MW 253.81) in THF (2 mL) dropwise. After the addition was complete, a saturated solution of NaS$_2$O$_3$ and NaHCO$_3$ were added at the same time to quench the reaction. EtOAc was added to the mixture, and the resulting mixture was washed with NaHCO$_3$ (aq) (2×50 mL) and brine (1×50 mL). The organic layer was dried over MgSO$_4$ and filtered. The organic layer was concentrated in vacuo. The residue was then purified by flash chromatography (SiO$_2$ gel 60, eluted with 0 to 20% EtOAc in hexanes). Fractions containing the desired product were combined and concentrated providing the product as a colorless oil (66 mg, 58% over 2 steps). MS ESI (pos.) m/e: 453.0 (M+Na)$^+$, 448.1 (M+H$_2$O)$^+$.

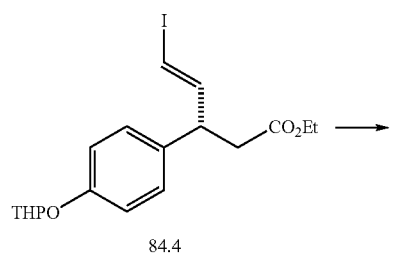

84.4

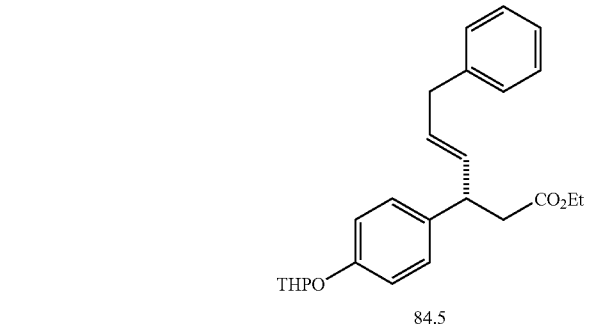

84.5

(3S,E)-Ethyl 6-phenyl-3-(4-(tetrahydro-2H-pyran-2-yloxy)phenyl)hex-4-enoate (84.5). To a stirred solution of 84.4 (321.9 mg, 0.748 mmol, 1 eq., MW 430.29) in THF (19 mL) at 23° C. was added Pd(PPh$_3$)$_4$ (86.8 mg, 0.075 mmol, 0.1 eq., MW 1155.58) followed by dropwise addition of benzyl zinc bromide solution (1.8 mL, 0.90 mmol, 1.2 eq., 0.5 M) After 3 hours, water (10 mL) was added to quench the reaction. The mixture was extracted with EtOAc (2×50 mL), dried with MgSO$_4$, and filtered. The organic layer was concentrated in vacuo. The residue was then purified by flash chromatography (SiO$_2$ gel 60, eluted with 0 to 20% EtOAc in hexanes). Fractions containing the desired product were combined and concentrated providing the product as a colorless oil that was used without further purification.

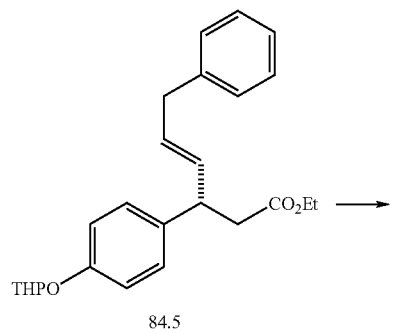

84.5

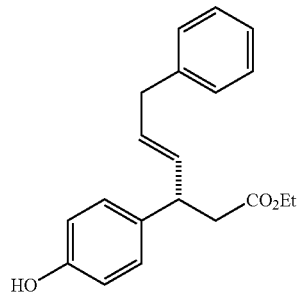

84.6

(S,E)-Ethyl 3-(4-hydroxyphenyl)-6-phenylhex-4-enoate (84.6). To a stirred solution of 84.4 (156.9 mg, 0.398 mmol, MW 394.50) in EtOH (5 mL) at 23° C. was added PPTS (catalytic). Stirring was continued for 16 hours. The reaction was concentrated in vacuo. The residue was then purified by flash chromatography (SiO$_2$ gel 60, eluted with 0 to 20% EtOAc in hexanes). Fractions containing the desired product were combined and concentrated providing a colorless oil. The desired product was contaminated (~5%) with a further olefinic product (believed to contain a terminal double bond) and was used without further purification.

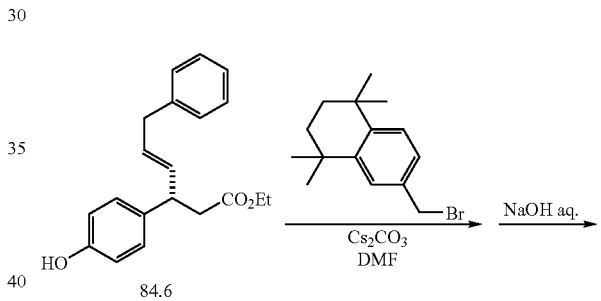

84.6

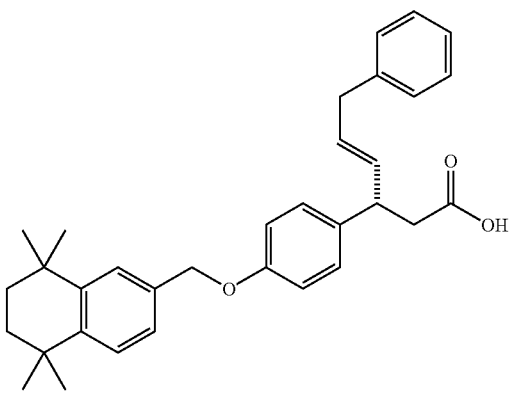

84

(S,E)-6-Phenyl-3-(4-((5,5,8,8-tetramethyl-5,6,7,8-tetrahydronaphthalen-2-yl)methoxy)phenyl)hex-4-enoic acid (84) Compound 84 was prepared by a method analogous to that of General Procedure A for 5.15.1. (MS ESI (neg.) m/e: 481.3 (M−H). $^1$H NMR (400 MHz) (CDCl$_3$) δ 7.25 (2H, s), 7.19 (2H, t, J=6.7 Hz), 7.15 (6H, m), 6.87 (2H, d, J=8.6 Hz), 5.64 (2H, m), 4.88 (2H, s), 3.80 (1H, m), 3.28 (2H, d, J=5.5 Hz), 2.67 (2H, m), 1.62 (4H, s), 1.21 (12H, s).

6.89 Example 85

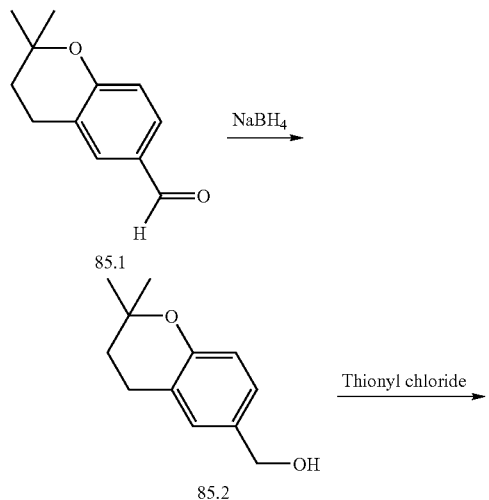

Compound 85.1 (commercially available from Maybridge) was reduced to 85.2 using a procedure very similar to that described in JOC, 43, (1978), 2167. 85.2 was converted to 85.3 by simply treating it with thionyl chloride at room temperature.

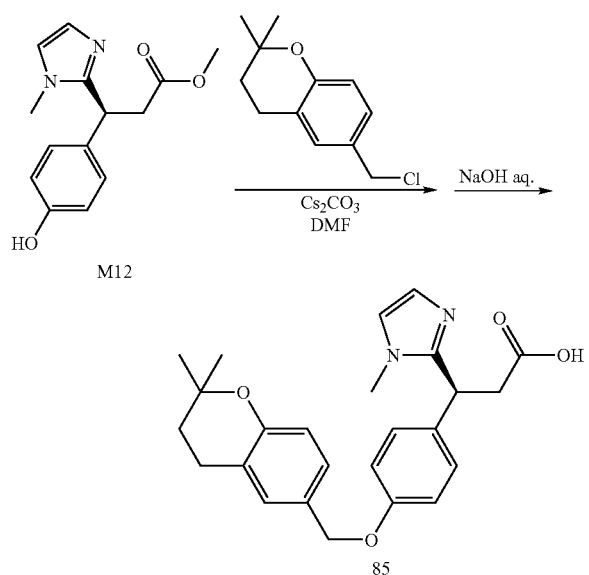

(S)-3-(4-((2,2-Dimethyl-3,4-dihydro-2H-chromen-7-yl)methoxy)phenyl)-3-(1-methyl-1H-imidazol-2-yl)propanoic acid (85). Compound 85 was obtained from compound M12 and 85.3 by following General Procedure A. MS ESI (neg.) M/E: 419 (M–H).

6.90 Example 86

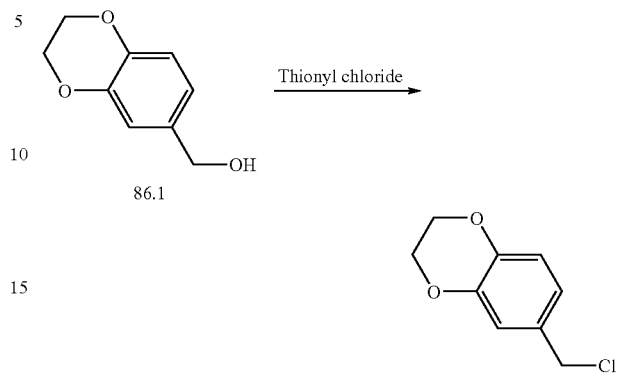

86.1 (commercially available from Maybridge) was converted to 86.2 by treating it with thionyl chloride at room temperature.

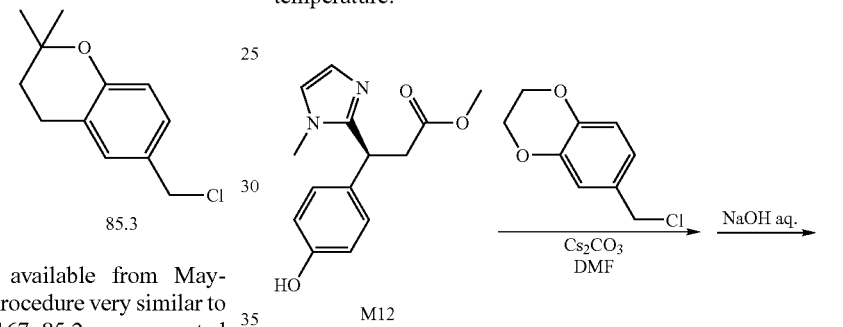

(S)-3-(4-((2,3-Dihydrobenzo[b][1,4]dioxin-6-yl)methoxy)phenyl)-3-(1-methyl-1H-imidazol-2-yl)propanoic acid (86). Compound 86 was obtained from compound M12 and 86.2 by following the general procedure A. MS ESI (neg.) M/E: 393 (M–H). $^1$HNMR (DMSO-$d_6$) δ 7.6 (s, 1H), 7.5 (s, 1H), 7.2 (d, 2H), 6.9 (d, 2H), 6.85-6.75 (overlapping signals, 3H), 4.9 (s, 2H), 4.8 (m, 1H), 4.2 (s, 4H), 3.7 (s, 3H), 3.3 (dd, 1H), 3.0 (dd, 1H).

Cell-based Aequorin Assay

Cell-based aequorin assays were employed to characterize the modulatory activity of compounds on the GPR40 signaling pathway. In an exemplary assay, CHO cells were stably transfected with both GPR40 and Aequorin (Euroscreen). Cells were detached from the tissue culture dish with 2 mL of trypsin (0.25% (w/v)). Trypsinization was halted with 28 mL of Hanks Buffered Salt Solution containing 20 mM Hepes (H/HBSS) and 0.01% fatty acid-free human serum albumin (HSA). Coelantrazine is added to 1 ug/mL, and the cells were incubated for 2 hours at room temperature. Compounds were dissolved in DMSO for preparation of 10 mM stock solutions.

Compounds were diluted in H/HBSS containing 0.01% HSA. Serial dilutions of the test compounds were prepared to determine dose response.

Aequorin luminescence measurements were made using an EG&G Berthold 96-well luminometer, and the response was measured over a 20 second interval after cells and compounds were mixed. The maximum relative light units was plotted to determine dose response. The $EC_{50}$ (effective concentration to reach 50% maximal response) was determined from the dose response plot.

Table 1 presents representative data ($EC_{50}$ values) obtained for exemplary compounds of the invention for the relative activation of human GPR40.

The stereoisomers in Table 1 are as specified, i.e., S-enantiomers or R-enantiomers, and if not specified, or if shown with wavy bonds, are mixtures of S-enantiomers and R-enantiomers. In addition, the present invention provides the S-enantiomers, the R-enantiomers, and mixtures of both S-enantiomers and R-enantiomers including racemates of each compound prepared according to the synthetic methods described herein or adapted with the necessary minor modifications from these methods.

Insulin Secretion Assay

Human islets were isolated from cadaveric donors. Islets were treated with trypsin (0.25% (w/v) and cells were seeded in 96-well plates containing 3,000 cells per well. Cells were cultured in Roswell Park Memorial Institute (RMPI) media containing 10% fetal bovine serum.

For determination of insulin secretion, media was removed from islet cells and replaced with Krebs-Ringer bicarbonate buffer containing 10 mM HEPES (KRBH) and 2 mM glucose. After one hour incubation, media was replaced with KRBH containing 11.2 mM glucose and test compounds. Insulin released into the medium from the islet cells was measured using scintillation proximity assay (SPA). The compounds of Examples 4 and 9 stimulated insulin secretion from islet cells with $EC_{50}$ values of less than 1 uM.

For determination of insulin secretion from rodent islets, C57/B16 mice are euthanized with carbon dioxide gas. The pancreatic bile duct is clamped proximal to the duodenum and then cannulated. H/HBSS containing 0.75 mg/mL collagenase XI (Sigma) is then infused into the pancreas through the cannula. The pancreas is excised and then incubated at 37° C. for 13 minutes to complete enzymatic digestion. The collagenase digestion is quenched in H/HBSS containing 1% BSA and washed once in the same buffer. Islets can be purified using density gradient centrifugation using Histopaque (Sigma) and are hand-picked under a stereomicroscope.

Islets are cultured overnight in Roswell Park Memorial Institute (RMPI) media containing 10% fetal bovine serum and 50 uM beta-mercaptoethanol. Following overnight culture, islets are incubated in KRBH containing 2.8 mM glucose for one hour.

For determination of insulin secretion, islets are incubated in DMEM containing 12.5 mM glucose and test compounds for one hour. Insulin released into the culture medium from the islets is measured using an insulin ELISA.

TABLE 1

| No. | Structure[a] | Relative $EC_{50}$[b] |
|---|---|---|
| 1 | 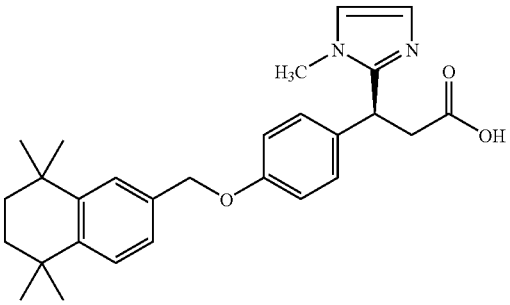 | +++ |
| 2 | 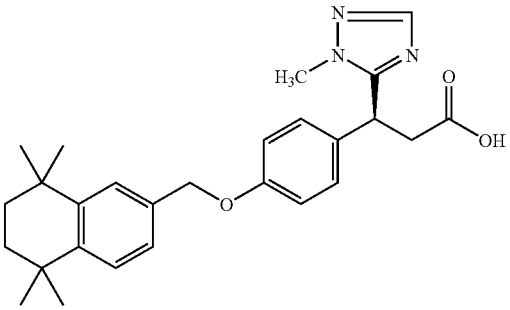 | +++ |

Aequorin Assay Using Human GPR40

TABLE 1-continued

Aequorin Assay Using Human GPR40

| No. | Structure[a] | Relative EC$_{50}$[b] |
|---|---|---|
| 3 | | ++++ |
| 4 | | +++ |
| 5 | | +++ |
| 6 | | ++++ |

TABLE 1-continued

Aequorin Assay Using Human GPR40

| No. | Structure[a] | Relative EC$_{50}$[b] |
|---|---|---|
| 7 | | ++ |
| 8 | | ++ |
| 9 | | ++ |
| 10 | | +++ |
| 11 | | ++++ |

TABLE 1-continued
Aequorin Assay Using Human GPR40
| No. | Structure[a] | Relative EC$_{50}$[b] |
|---|---|---|
| 12 | 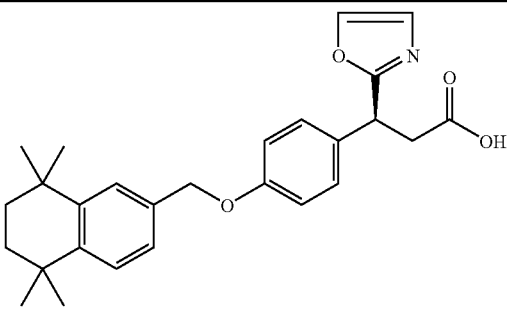 | +++ |
| 13 | 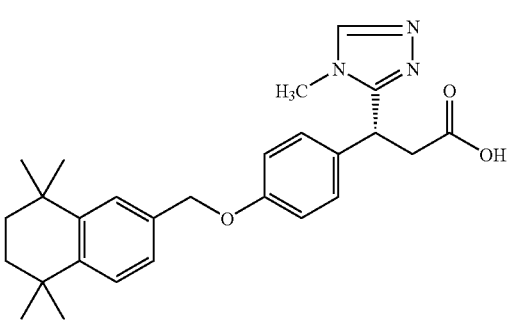 | + |
| 14 | 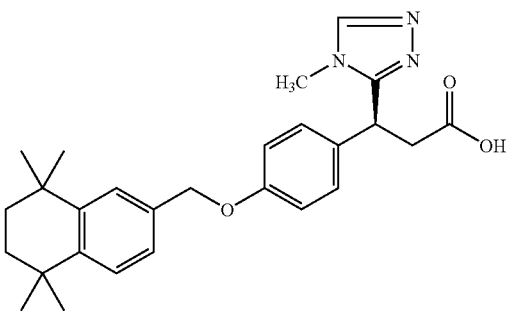 | +++ |
| 15 | 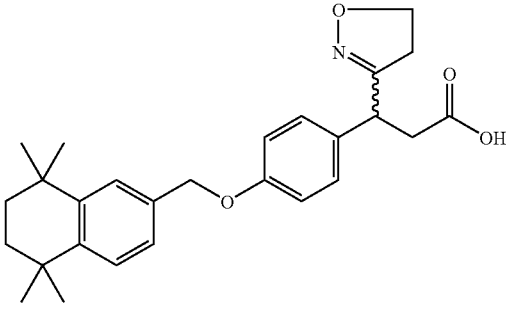 | +++ |
| 16 | 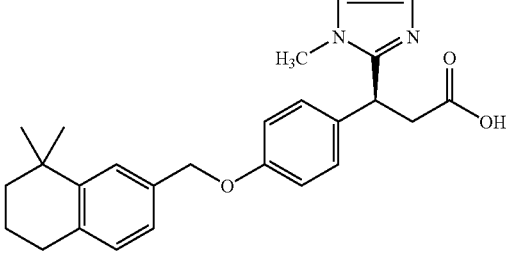 | +++ |

TABLE 1-continued

Aequorin Assay Using Human GPR40

| No. | Structure[a] | Relative EC$_{50}$[b] |
|---|---|---|
| 17 | | + |
| 18 | | +++ |
| 19 | | ++ |
| 20 | | ++ |

TABLE 1-continued
Aequorin Assay Using Human GPR40
| No. | Structure[a] | Relative EC$_{50}$[b] |
|---|---|---|
| 21 | 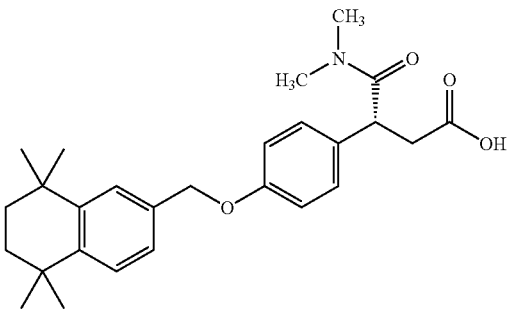 | A[d] |
| 22 | 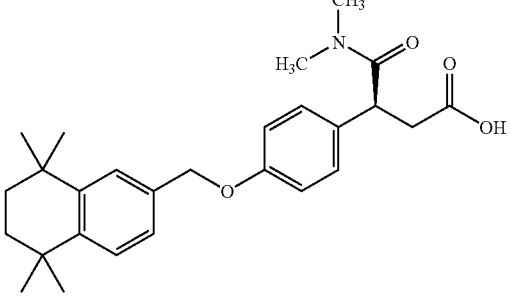 | A[d] |
| 23 | 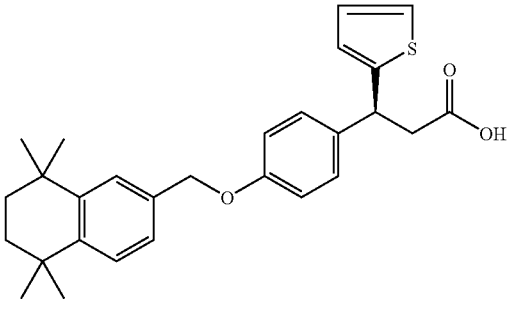 | A[d] |
| 24 | 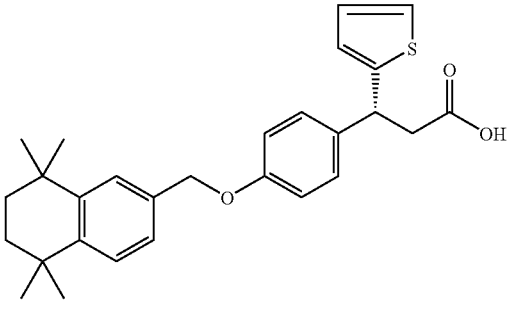 | A[d] |

TABLE 1-continued

Aequorin Assay Using Human GPR40

| No. | Structure[a] | Relative EC$_{50}$[b] |
|---|---|---|
| 25 | | A[d] |
| 26 | | A[d] |
| 27 | | A[d] |
| 28 | | A[d] |

TABLE 1-continued
Aequorin Assay Using Human GPR40
| No. | Structure[a] | Relative EC$_{50}$[b] |
|---|---|---|
| 29 | 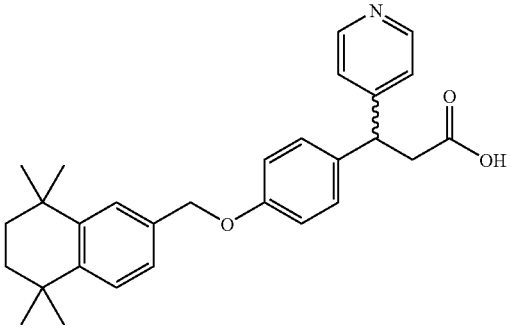 | A[d] |
| 30 | 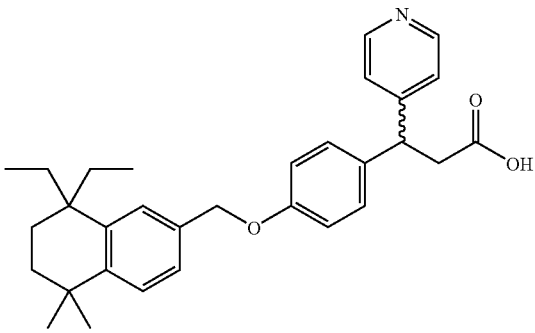 | A[d] |
| 31 | 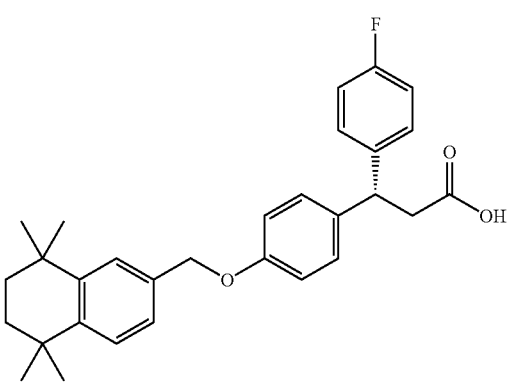 | ++ |
| 32 | 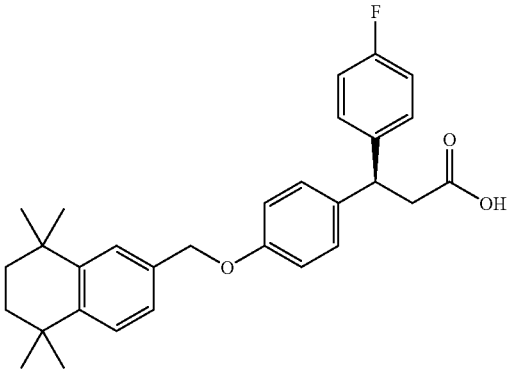 | +++ |

TABLE 1-continued

Aequorin Assay Using Human GPR40

| No. | Structure[a] | Relative EC$_{50}$[b] |
|---|---|---|
| 33 | | A[d] |
| 34 | | A[d] |
| 35 | | A[d] |
| 36 | | A[d] |
| 37 | | A[d] |

TABLE 1-continued

Aequorin Assay Using Human GPR40

| No. | Structure[a] | Relative EC$_{50}$[b] |
|---|---|---|
| 38 | | A[d] |
| 39 | | A[d] |
| 40 | | A[d] |
| 41 | | A[d] |

TABLE 1-continued
Aequorin Assay Using Human GPR40
| No. | Structure[a] | Relative EC$_{50}$[b] |
|---|---|---|
| 42 | 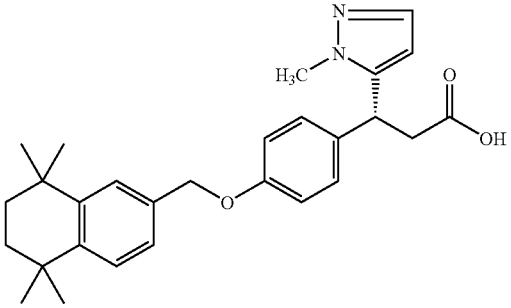 | A[d] |
| 43 | 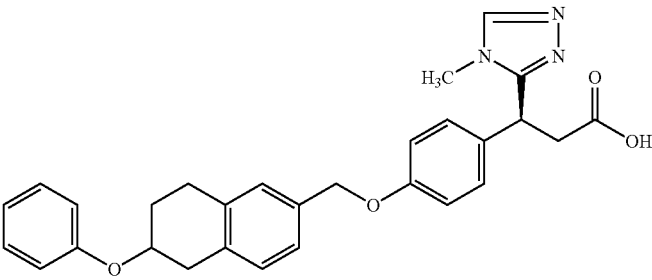 | A[d] |
| 44 | 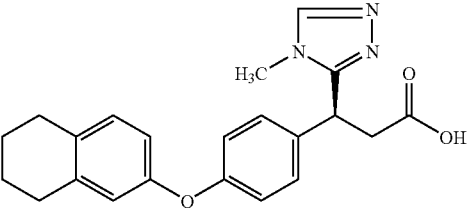 | A[d] |
| 45 | 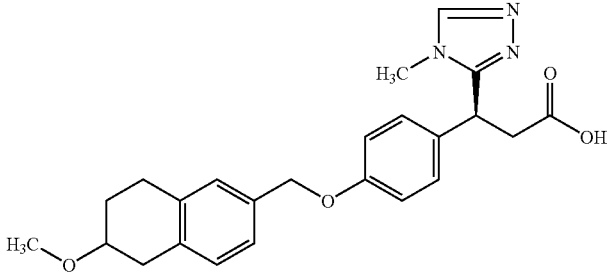 | A[d] |
| 46 | 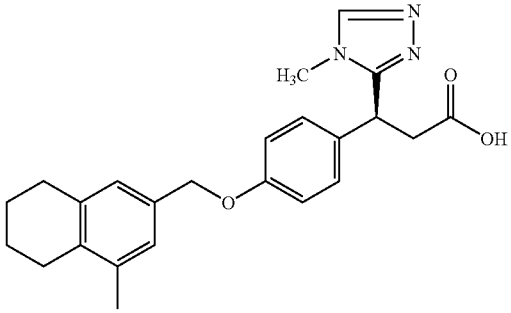 | A[d] |

TABLE 1-continued
Aequorin Assay Using Human GPR40
| No. | Structure[a] | Relative EC$_{50}$[b] |
|---|---|---|
| 47 | 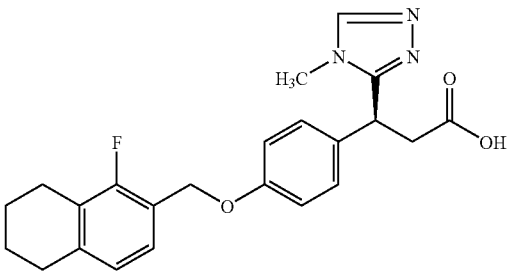 | A[d] |
| 48 | 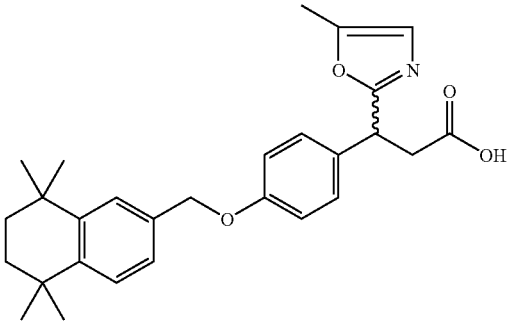 | A[d] |
| 49 | 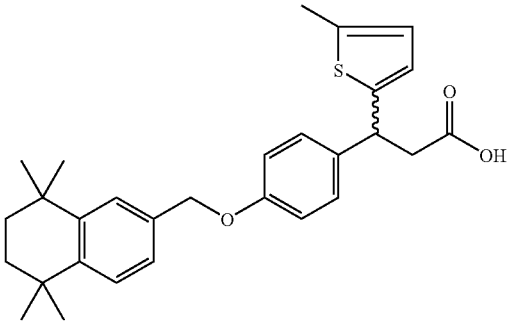 | A[d] |
| 50 | 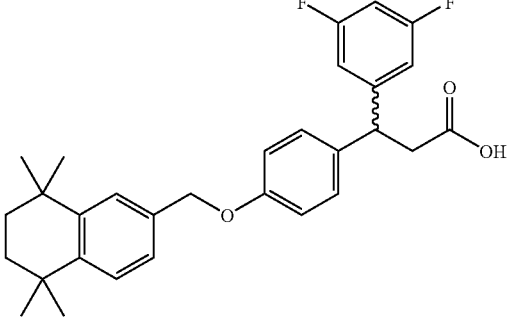 | A[d] |

TABLE 1-continued

Aequorin Assay Using Human GPR40

| No. | Structure[a] | Relative EC$_{50}$[b] |
|---|---|---|
| 51 | | A[d] |
| 52 | | A[d] |
| 53 | | A[d] |
| 54 | | A[d] |

TABLE 1-continued

Aequorin Assay Using Human GPR40

| No. | Structure[a] | Relative EC$_{50}$[b] |
|---|---|---|
| 56 | | A[d] |
| 57 | | A[d] |
| 58 | | A[d] |
| 59 | | A[d] |
| 60 | | A[d] |

TABLE 1-continued
Aequorin Assay Using Human GPR40
| No. | Structure[a] | Relative EC$_{50}$[b] |
|---|---|---|
| 61 | 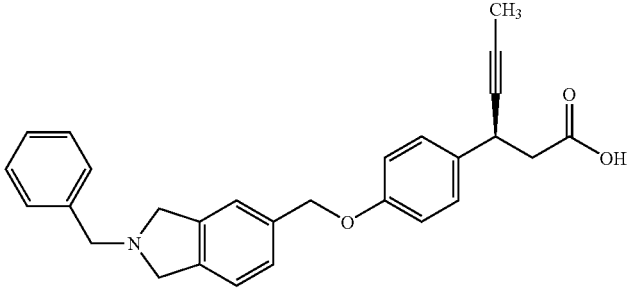 | A[d] |
| 62 | 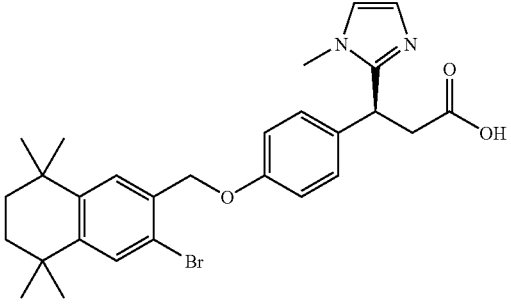 | +++ |
| 63 | 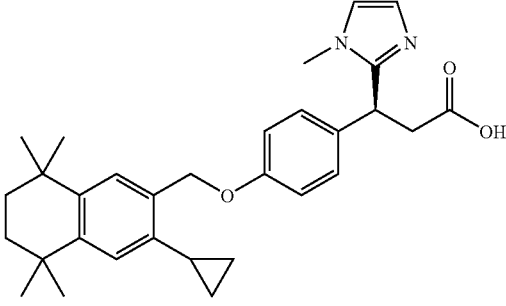 | + |
| 64 | 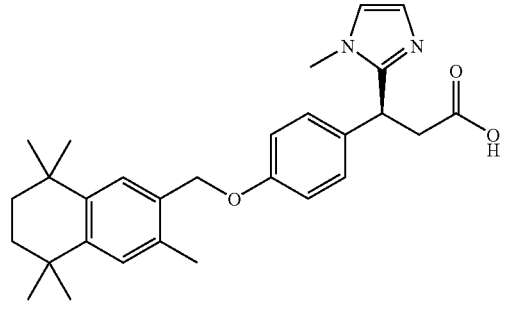 | +++ |

TABLE 1-continued

Aequorin Assay Using Human GPR40

| No. | Structure[a] | Relative EC$_{50}$[b] |
|---|---|---|
| 65 | | +++ |
| 66 | | A[d] |
| 67 | | A[d] |
| 68 | | A[d] |
| 69 | | A[d] |

TABLE 1-continued
Aequorin Assay Using Human GPR40
| No. | Structure[a] | Relative EC$_{50}$[b] |
|---|---|---|
| 70 | 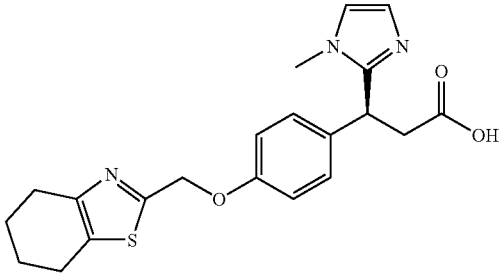 | A[d] |
| 71 | 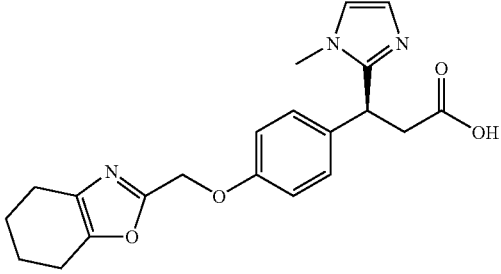 | A[d] |
| 72 | 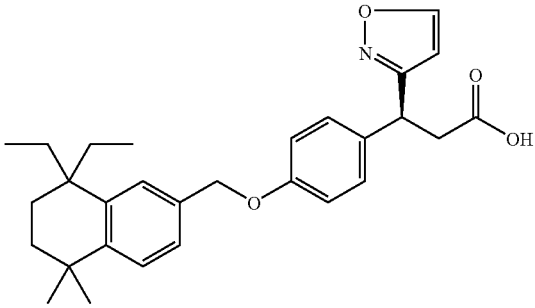 | ++++ |
| 73 | 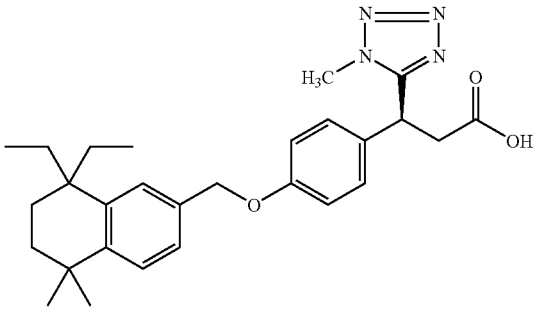 | +++/++++ |
| 74 | 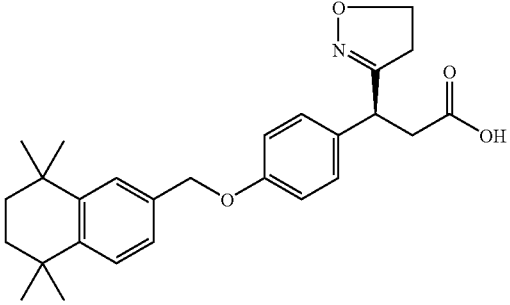 | ++++ |

TABLE 1-continued

Aequorin Assay Using Human GPR40

| No. | Structure[a] | Relative EC$_{50}$[b] |
|---|---|---|
| 75 | | +++ |
| 76 | | ++++ |
| 77 | | ++++ |
| 78 | | +++ |

TABLE 1-continued

Aequorin Assay Using Human GPR40

| No. | Structure[a] | Relative EC$_{50}$[b] |
|---|---|---|
| 79 | | ++ |
| 80 | | +++ |
| 81 | | ++ |
| 82 | | +++ |

TABLE 1-continued

Aequorin Assay Using Human GPR40

| No. | Structure[a] | Relative EC$_{50}$[b] |
|---|---|---|
| 83 | | ++ |
| 84 | | ++ |
| 85 | | ++ |

TABLE 1-continued

Aequorin Assay Using Human GPR40

| No. | Structure[a] | Relative $EC_{50}$[b] |
|---|---|---|
| 86 | 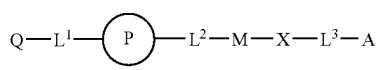 | ++ |

[a]When present, the "" bond indicates a mixture of stereoisomers are present in the exemplary compound.
[b]$EC_{50}$ Ranges:
+ $EC_{50} > 10$ μM
++ $1$ μM $\leq EC_{50} \leq 10$ μM
+++ $0.1$ μM $\leq EC_{50} < 1$ μM
++++ $0.01$ μM $\leq EC_{50} < 0.1$ μM
+++++ $EC_{50} < 0.01$ μM
[c]Aequorin assay data from transiently transfected cell line.
[d]This compound is tested using the methods described herein and is found to have an $EC_{50}$ of less than or about 10 μM.

All publications and patent applications cited in this specification are herein incorporated by reference as if each individual publication or patent application were specifically and individually indicated to be incorporated by reference. Each publication and patent application cited herein is incorporated in its entirety as if fully set forth herein. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:
1. A compound having the formula I:

$$Q-L^1-\boxed{P}-L^2-M-X-L^3-A \qquad I$$

or a pharmaceutically acceptable salt, stereoisomer, or $C_1$-$C_6$ alkyl ester thereof; or a tautomer or a pharmaceutically acceptable salt, stereoisomer, or $C_1$-$C_6$ alkyl ester thereof; or a mixture thereof, wherein Q is hydrogen;
$L^1$ is a bond;

$\boxed{P}$ represents an optionally substituted benzo-fused ($C_5$-$C_8$)cycloalkane ring comprising a benzene ring fused to a ($C_5$-$C_8$) cycloalkane ring, wherein the benzene ring of the benzo-fused ($C_5$-$C_8$)cycloalkane ring is bonded to $L^2$;
$L^2$ is oxymethylene;
M is an optional substituted benzene ring;
X is $CR^1R^{1'}$;
$L^3$ is a ($C_1$-$C_5$)alkylene;
A is —$CO_2H$;
$R^1$ is cyano, aryl, heteroaryl, heterocycloalkyl, ($C_2$-$C_8$) alkenyl, ($C_3$-$C_8$)alkenyl, ($C_2$-$C_8$)alkynyl, ($C_3$-$C_8$)alkynyl, or —C(O)$NR^2R^3$;
$R^{1'}$ is hydrogen; and
$R^2$ and $R^3$ are independently selected from hydrogen, aryl, heteroaryl, ($C_1$-$C_8$)alkyl, ($C_2$-$C_8$)heteroalkyl, ($C_3$-$C_8$) cycloalkyl, or ($C_3$-$C_8$)heterocycloalkyl; or
optionally, $R^2$ and $R^3$ are combined to form a 4-, 5-, 6- or 7-membered ring containing the nitrogen atom to which they are attached comprising from 0 to 2 additional heteroatoms selected from N, O, or S;
wherein, $R^1$ is a group other than a group of the following formula:

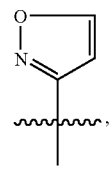

and further wherein, $R^1$ is a group of the following formula:

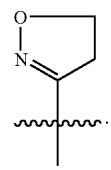

2. The compound of claim 1, wherein the compound has the formula II:

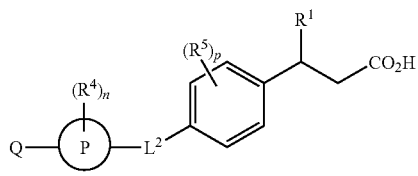

II or a pharmaceutically acceptable salt, stereoisomer, or $C_1$-$C_6$ alkyl ester thereof; or a tautomer or a pharmaceutically acceptable salt, stereoisomer, or $C_1$-$C_6$ alkyl ester thereof; or a mixture thereof, wherein Q is hydrogen;

$L^2$ is oxymethylene;

$R^1$ is selected from ($C_2$-$C_8$)alkynyl, aryl, heteroaryl, heterocycloalkyl, or —C(O)$NR^2R^3$;

$R^2$ and $R^3$ are independently selected from hydrogen or ($C_1$-$C_4$)alkyl;

$R^4$ is independently selected from substituted ($C_1$-$C_6$) alkyl, —R', —OR', =O, =NR', =N—OR', —NR'R", —SR', halogen, —OC(O)R', —C(O)R', —$CO_2$R', —CONR'R", —OC(O)NR'R", —NR"C(O)R', —NR'—C(O)NR"R''', —NR'—$SO_2$NR"R''', —NR"$CO_2$R', —NH—C($NH_2$)=NH, —NR'C($NH_2$)=NH, —NH—C($NH_2$)=NR', —SiR'R"R''', —S(O)R', —$SO_2$R', —$SO_2$NR'R", —NR"$SO_2$R, —CN, —($C_2$-$C_5$) alkynyl, —($C_2$-$C_5$)alkenyl, or —$NO_2$, where R', R" and R''' each independently refer to hydrogen, unsubstituted ($C_1$-$C_8$) alkyl or heteroalkyl, unsubstituted aryl, aryl substituted with one to three halogens, unsubstituted alkyl, alkoxy or thioalkoxy groups, halo($C_1$-$C_4$)alkyl, or aryl-($C_1$-$C_4$) alkyl groups;

$R^5$ is independently selected from ($C_1$-$C_6$)alkyl, halogen, ($C_1$-$C_6$)alkoxy, cyano, or nitro;

the subscript n is 0, 1, 2, 3, 4, 5, 6, 7, 8, 9, 10, 11, 12, 13, or 14; and the subscript p is 0, 1, 2, 3 or 4.

3. The compound of claim 2, wherein $R^4$ independently is selected from ($C_1$-$C_6$)alkyl, halogen, ($C_1$-$C_6$)alkoxy, cyano, or nitro.

4. The compound of claim 2, wherein the compound has the formula IIIA or IIIB:

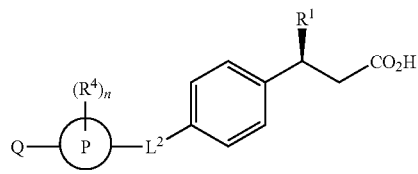

IIIA

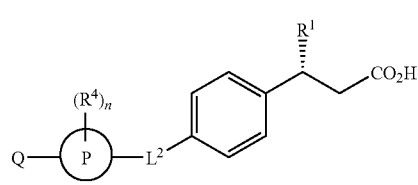

IIIB or a pharmaceutically acceptable salt, or $C_1$-$C_6$ alkyl ester thereof or a tautomer or a pharmaceutically acceptable salt, or $C_1$-$C_6$ alkyl ester thereof;

or a mixture thereof.

5. The compound of claim 1, wherein the compound has the formula IV:

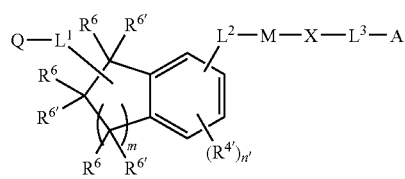

IV or a pharmaceutically acceptable salt, stereoisomer, or $C_1$-$C_6$ alkyl ester thereof; or a tautomer or a pharmaceutically acceptable salt, stereoisomer, or $C_1$-$C_6$ alkyl ester thereof; or a mixture thereof, wherein $R^{4'}$ is independently selected from substituted ($C_1$-$C_6$) alkyl, —R', —OR', =O, =NR', =N—OR', —NR'R", —SR', halogen, —OC(O)R', —C(O)R', —$CO_2$R', —CONR'R", —OC(O)NR'R", —NR"C(O)R', —NR'—C(O)NR"R''', —NR'—$SO_2$NR"R''', —NR"$CO_2$R', —NH—C($NH_2$)=NH, —NR'C($NH_2$)=NH, —NH—C($NH_2$)=NR', —SiR'R"R''', —S(O)R', —$SO_2$R', —$SO_2$NR'R", —NR"$SO_2$R, —CN, —($C_2$-$C_5$)alkynyl, —($C_2$-$C_5$)alkenyl, or —$NO_2$, where R', R" and R''' each independently refer to hydrogen, unsubstituted ($C_1$-$C_8$) alkyl or heteroalkyl, unsubstituted aryl, aryl substituted with one to three halogens, unsubstituted alkyl, alkoxy or thioalkoxy groups, halo($C_1$-$C_4$)alkyl, or aryl-($C_1$-$C_4$) alkyl groups;

one of $R^6$ and $R^{6'}$ is $L^1$ or Q, and the others of $R^6$ and $R^{6'}$ are independently selected from H, ($C_1$-$C_6$)alkyl, halogen, ($C_1$-$C_6$)alkoxy, cyano, or nitro, wherein one of $R^6$ and one of $R^{6'}$ on adjacent or non-adjacent carbon atoms, or on the same carbon atom may join together to form a $C_5$-$C_8$ cycloalkane ring, or two of $R^6$ or two of $R^{6'}$, on adjacent or non-adjacent carbon atoms, may join together to form a $C_5$-$C_8$ cycloalkane ring;

the subscript n' is 0, 1, 2, or 3; and the subscript m is 1, 2, 3, or 4.

6. The compound of claim 5, wherein the compound has the formula V:

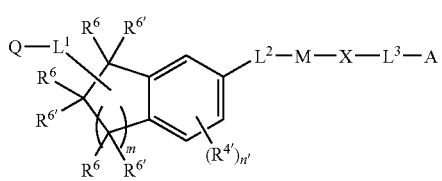

V or a pharmaceutically acceptable salt, stereoisomer, or $C_1$-$C_6$ alkyl ester thereof; or a tautomer or a pharmaceutically acceptable salt, stereoisomer, or $C_1$-$C_6$ alkyl ester thereof; or a mixture thereof.

7. The compound of claim 5, wherein the compound has the formula VI:

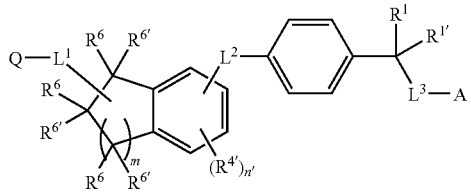

VI or a pharmaceutically acceptable salt, stereoisomer, or $C_1$-$C_6$ alkyl ester thereof; or a tautomer or a pharmaceutically acceptable salt, stereoisomer, or $C_1$-$C_6$ alkyl ester thereof; or a mixture thereof.

8. The compound of claim 5, wherein the subscript m is 1 or 2.

9. The compound of claim 5, wherein the subscript m is 1 or 2; the subscript n' is 0; and $R^1$ is selected from aryl, heteroaryl, heterocycloalkyl, ($C_2$-$C_8$)alkenyl, ($C_3$-$C_8$)alkenyl, ($C_2$-$C_8$)alkynyl, or ($C_3$-$C_8$)alkynyl.

10. The compound of claim 5, wherein $L^3$ is $CH_2$.

11. The compound of claim 5, wherein $R^6$ and $R^{6'}$ are independently selected from H and methyl and at least two of $R^6$ and $R^{6'}$ are methyl groups.

12. The compound of claim 5, wherein $R^6$ and $R^{6'}$ are independently selected from H and methyl and at least four of $R^6$ and $R^{6'}$ are methyl groups.

13. The compound of claim 1, wherein $R^1$ is selected from heteroaryl or heterocycloalkyl.

14. The compound of claim 13, wherein $R^1$ is selected from a substituted or unsubstituted imidazolyl, triazolyl, tetrazolyl, oxazolyl, pyrazolyl, pyrrolyl, thiazolyl, thiophenyl, furanyl, thiadiazolyl, pyridyl, or pyrimidinyl.

15. The compound of claim 1, wherein the compound has the formula of XIa, XIb, XIc, XId, XIe, XIf, XII, or XIm:

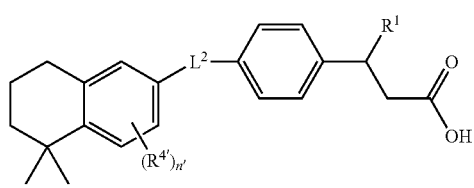

XIa

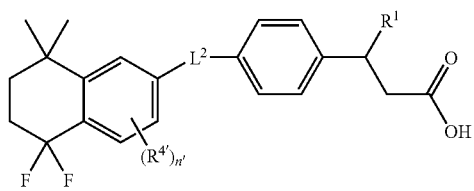

XIb

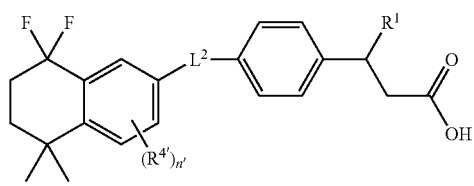

XIc

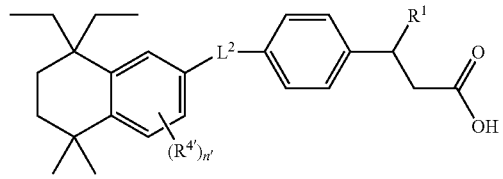

XId

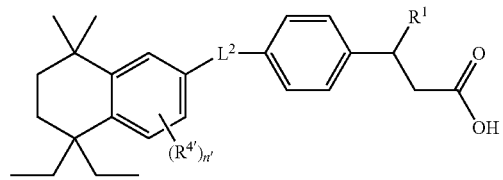

XIe

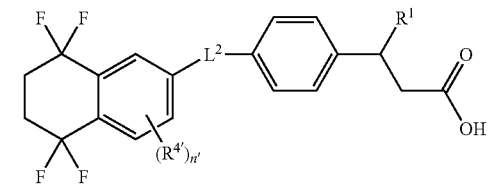

XIf

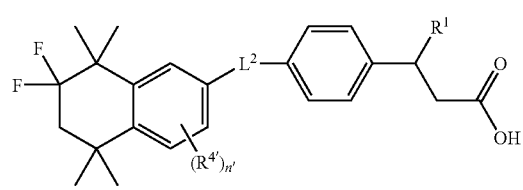

XII

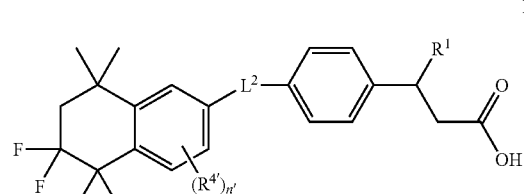

XIm or a pharmaceutically acceptable salt, or $C_1$-$C_6$ alkyl ester thereof; or a tautomer or a pharmaceutically acceptable salt, or $C_1$-$C_6$ alkyl ester thereof; or a mixture thereof, wherein
  $R^{4'}$ is independently selected from substituted ($C_1$-$C_6$) alkyl, —R', —OR', =O, =NR', =N—OR', —NR'R'', —SR', halogen, —OC(O)R', —C(O)R', —CO$_2$R', —CONR'R''', —OC(O)NR'R'', —NR''C(O)R', —NR'—C(O)NR''R''', —NR'—SO$_2$NR''R''', —NR''CO$_2$R', —NH—C(NH$_2$)=NH, —NR'C(NH$_2$)=NH, —NH—C(NH$_2$)=NR', —SiR'R''R''', —S(O)R', —SO$_2$R', —SO$_2$NR'R'', —NR'' SO$_2$R, —CN, —($C_2$-$C_5$)alkynyl, —($C_2$-$C_5$)alkenyl, or —NO$_2$, where R', R'' and R''' each independently refer to hydrogen, unsubstituted ($C_1$-$C_8$) alkyl or heteroalkyl, unsubstituted aryl, aryl substituted with one to three halogens, unsubstituted alkyl, alkoxy or thioalkoxy groups, halo($C_1$-$C_4$)alkyl, or aryl-($C_1$-$C_4$) alkyl groups;
  the subscript n' is 0, 1, 2, or 3; and
  $R^d$ is selected from optionally substituted $C_1$-$C_6$ alkyl or optionally substituted aryl.

16. A pharmaceutical composition, comprising: a pharmaceutically acceptable carrier, diluent, or excipient, and the compound of claim 1.

17. The compound of claim 1, wherein $L^3$ methylene.

18. The compound claim 1, wherein X is para to $L^2$.

* * * * *